United States Patent
Smith et al.

(10) Patent No.: US 11,773,094 B2
(45) Date of Patent: Oct. 3, 2023

(54) FARNESOID X RECEPTOR AGONISTS AND USES THEREOF

(71) Applicant: Metacrine, Inc., San Diego, CA (US)

(72) Inventors: Nicholas D. Smith, San Diego, CA (US); Steven P. Govek, San Diego, CA (US); Karensa L. Douglas, San Diego, CA (US); Andiliy G. Lai, San Diego, CA (US)

(73) Assignee: ORGANOVO, INC., San Diego, CA (US)

(*) Notice: Subject to any disclaimer, the term of this patent is extended or adjusted under 35 U.S.C. 154(b) by 0 days.

(21) Appl. No.: 17/349,757

(22) Filed: Jun. 16, 2021

(65) Prior Publication Data

US 2021/0395253 A1 Dec. 23, 2021

Related U.S. Application Data

(63) Continuation of application No. 16/573,993, filed on Sep. 17, 2019, now Pat. No. 11,084,817.

(60) Provisional application No. 62/881,560, filed on Aug. 1, 2019, provisional application No. 62/733,004, filed on Sep. 18, 2018, provisional application No. 62/733,006, filed on Sep. 18, 2018.

(51) Int. Cl.
| | | |
|---|---|---|
| C07D 471/14 | (2006.01) | |
| C07D 487/04 | (2006.01) | |
| C07D 417/14 | (2006.01) | |
| C07D 413/14 | (2006.01) | |

(52) U.S. Cl.
CPC ......... *C07D 471/14* (2013.01); *C07D 413/14* (2013.01); *C07D 417/14* (2013.01); *C07D 487/04* (2013.01)

(58) Field of Classification Search
CPC .................................................. C07D 471/14
USPC ...................................................... 514/210.2
See application file for complete search history.

(56) References Cited

U.S. PATENT DOCUMENTS

| | | |
|---|---|---|
| 6,645,980 B1 | 11/2003 | Cuny et al. |
| 8,212,006 B2 | 7/2012 | Downes et al. |
| 10,077,268 B2 | 9/2018 | Evans et al. |
| 10,301,268 B2 | 5/2019 | Evans et al. |
| 10,377,717 B2 | 8/2019 | Smith et al. |
| 10,626,081 B2 | 4/2020 | Smith et al. |
| 10,703,712 B2 | 7/2020 | Smith et al. |
| 10,927,082 B2 | 2/2021 | Smith et al. |
| 10,961,198 B2 | 3/2021 | Smith et al. |
| 11,084,817 B2 | 8/2021 | Smith et al. |
| 11,236,071 B1 | 2/2022 | Smith et al. |
| 2006/0009459 A1 | 1/2006 | Chakka et al. |
| 2006/0223879 A1 | 10/2006 | Downes et al. |
| 2008/0081824 A1 | 4/2008 | Zheng et al. |
| 2008/0280916 A1 | 11/2008 | Bilich et al. |
| 2012/0115869 A1 | 5/2012 | Crosignani et al. |
| 2014/0155247 A1 | 6/2014 | Aoyagi et al. |
| 2015/0258052 A1 | 9/2015 | Evans et al. |
| 2015/0342930 A1 | 12/2015 | Kinzel et al. |
| 2017/0066724 A1 | 3/2017 | Evans et al. |
| 2018/0000768 A1 | 1/2018 | Fang et al. |
| 2018/0116993 A1 | 5/2018 | Li et al. |
| 2020/0092932 A1 | 3/2020 | Youn et al. |
| 2020/0131129 A1 | 4/2020 | Smith et al. |
| 2020/0131142 A1 | 4/2020 | Smith et al. |
| 2020/0290973 A1 | 9/2020 | Smith et al. |
| 2021/0032195 A1 | 2/2021 | Smith et al. |
| 2021/0300875 A1 | 9/2021 | Smith et al. |
| 2021/0347736 A1 | 11/2021 | Smith et al. |
| 2022/0047553 A1 | 2/2022 | Song et al. |
| 2022/0054469 A1 | 2/2022 | Smith et al. |
| 2022/0056019 A1 | 2/2022 | Smith et al. |
| 2022/0081390 A1 | 3/2022 | Smith et al. |

FOREIGN PATENT DOCUMENTS

| | | |
|---|---|---|
| CN | 107126419 A | 9/2017 |
| FR | 2839974 A1 | 11/2003 |
| JP | 2006199656 A | 8/2006 |
| JP | 2007530582 A | 11/2007 |
| JP | 2010077109 A | 4/2010 |
| MY | 144229 A | 8/2011 |
| WO | WO-0069810 A1 | 11/2000 |
| WO | WO-0071518 A2 | 11/2000 |
| WO | WO-0185694 A2 | 11/2001 |
| WO | WO-0192226 A1 | 12/2001 |
| WO | WO-0224649 A1 | 3/2002 |
| WO | WO-0230927 A1 | 4/2002 |
| WO | WO-02098852 A2 | 12/2002 |
| WO | WO-2004009549 A2 | 1/2004 |
| WO | WO-2004026823 A1 | 4/2004 |
| WO | WO-2004009549 A3 | 6/2004 |
| WO | WO-2004045511 A2 | 6/2004 |
| WO | WO-2004046068 A2 | 6/2004 |

(Continued)

OTHER PUBLICATIONS

Bernstein. Crystal Structure Prediction and Polymorphism. ACA Transactions 39:14-23 (2004).
Braga et al. Making crystals from crystals: a green route to crystal engineering and polymorphism. J. Royal Soc. Chem. Commun 29:3635-3645 (2005).
Fu et al. Discovery of new non-steroidal FXR ligands via a virtual screening workflow based on Phase shape and induced fit docking. Bioorg Med Chem Lett 22(22):6848-6853 (2012).
Jones et al.: Pharmaceutical Cocrystals: An Emerging Approach to Physical Property Enhancement. MRS Bulletin 31:875-879 (2006).
PCT/US2019/051604 International Search Report and Written Opinion dated Dec. 4, 2019.

(Continued)

*Primary Examiner* — Taofiq A Solola
(74) *Attorney, Agent, or Firm* — WILSON SONSINI GOODRICH & ROSATI

(57) ABSTRACT

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

19 Claims, No Drawings

(56) References Cited

FOREIGN PATENT DOCUMENTS

| WO | WO-2004046162 A2 | 6/2004 |
|---|---|---|
| WO | WO-2004096771 A1 | 11/2004 |
| WO | WO-2005011655 A2 | 2/2005 |
| WO | WO-2004046162 A8 | 3/2005 |
| WO | WO-2005058822 A1 | 6/2005 |
| WO | WO-2005113522 A1 | 12/2005 |
| WO | WO-2007110237 A2 | 10/2007 |
| WO | WO-2008065500 A2 | 6/2008 |
| WO | WO-2009076747 A1 | 6/2009 |
| WO | WO-2009106991 A2 | 9/2009 |
| WO | WO-2010001869 A1 | 1/2010 |
| WO | WO-2011006935 A2 | 1/2011 |
| WO | WO-2011008915 A1 | 1/2011 |
| WO | WO-2012011081 A1 | 1/2012 |
| WO | WO-2012129495 A1 | 9/2012 |
| WO | WO-2014133414 A2 | 9/2014 |
| WO | WO-2015040425 A1 | 3/2015 |
| WO | WO-2015138969 A1 | 9/2015 |
| WO | WO-2015138986 A1 | 9/2015 |
| WO | WO-2016149111 A1 | 9/2016 |
| WO | WO-2017018751 A1 | 2/2017 |
| WO | WO-2017049172 A1 | 3/2017 |
| WO | WO-2017049173 A1 | 3/2017 |
| WO | WO-2017049176 A1 | 3/2017 |
| WO | WO-2017049177 A1 | 3/2017 |
| WO | WO-2017170182 A1 | 10/2017 |
| WO | WO-2018170165 A1 | 9/2018 |
| WO | WO-2018170166 A1 | 9/2018 |
| WO | WO-2018170167 A1 | 9/2018 |
| WO | WO-2018170173 A1 | 9/2018 |
| WO | WO-2018170182 A1 | 9/2018 |
| WO | WO-2018215002 A1 | 11/2018 |
| WO | WO-2020061112 A1 | 3/2020 |
| WO | WO-2020061113 A1 | 3/2020 |
| WO | WO-2020061114 A1 | 3/2020 |
| WO | WO-2020061115 A1 | 3/2020 |
| WO | WO-2020061116 A1 | 3/2020 |
| WO | WO-2020061117 A1 | 3/2020 |
| WO | WO-2020061118 A1 | 3/2020 |
| WO | WO-2021188688 A1 | 9/2021 |
| WO | WO-2021188692 A1 | 9/2021 |
| WO | WO-2021188695 A1 | 9/2021 |

OTHER PUBLICATIONS

PCT/US2019/051605 International Search Report and Written Opinion dated Dec. 4, 2019.
Stojancevic et al. The impact of farnesoid X receptor activation on intestinal permeability in inflammatory bowel disease. Can J Gastroenterol 26(9):631-637 (2012).
U.S. Appl. No. 17/152,548 Office Action dated Dec. 10, 2021.
Wang et al. Farnesoid X receptor antagonizes nuclear factor kappaB in hepatic inflammatory response. Hepatology 48(5):1632-1643 (2008).
Ali et al. Recent advances in the development of farnesoid X receptor agonists. Ann Transl Med 3(1):5 (2015).
Amidon et al. Colon-Targeted Oral Drug Delivery Systems: Design Trends and Approaches, AAPS PharmSciTech 16(4)731-741 (2015).
Beaulieu et al., Preparation of 2-amido benzoic acid compounds as viral polymerase inhibitors. Chemical Abstracts Service. XP002791354. Database accession No. 2009:771969 (2009).
Berge et al. Pharmaceutical Salts. Journal of Pharmaceutical Sciences 66(1):1-19 (Jan. 1977).
Boss et al., Preparation of N-benzyl N-piperidin-4-yl benzamides as inhibitors of parasitic aspartyl protease. Chemical Abstracts Service. XP002791357. Database accession No. 2005:570873 (2005).
Boss et al., Preparation of piperidines for the treatment of central nervous system disorders. Chemical Abstracts Service. XP002791361. Database accession No. 2004:80651 (2004).
Boss et al., Preparation of substituted amino-aza-cycloalkanes as anti-malarial agents. Chemical Abstracts Service. XP002791363. Database accession No. 2002:240729 (2002).

Boss et al., Achiral, cheap, and potent inhibitors of Plasmepsins I, Ii, and IV. ChemMedChem. 1(12):1341-1345 (2006).
Braeuer et al. Evolutionary chemistry approach toward finding novel inhibitors of the type 2 diabetes target glucose-6-phosphate translocase. CA, Chemical Abstracts Service, Columbus, Ohio, US, (2005), Database accession No. 2005:154377, URL: STN, XP002791358.
Brauer et al., Evolutionary chemistry approach toward finding novel inhibitors of the type 2 diabetes target glucose-6-phosphate translocase. Journal of Combinatorial Chemistry. 7(2):218-226 (2005).
Bromidge et al., Preparation of biaryl compounds having activity at the 5-HT5A receptor. Chemical Abstracts Service. XP002791359. Database accession No. 2004:965222 (2004).
Brough et al., Preparation of resorcinol N-Aryl amide compounds, for use as pyruvate dehydrogenase kinase inhibitors. Chemical Abstracts Service. XP002791352 Database accession No. 2015:512259 (2015).
Bundgaard. Design and Application of Prodrugs. Textbook of Drug Design and Development. Krosgaard-Larsen and Bundgaard. Chapters, pp. 113-191 (1991).
Bundgaard. Means to Enhance Penetration: Prodrugs as a Means to Improve the Delivery of Peptide Drugs. Advanced Drug Delivery Review 8:1-38 (1992).
Camilleri. Bile Acid diarrhea: prevalence, pathogenesis, and therapy. Gut Liver 9(3):332-339 (2015).
CAS Registry No. 1349456-93-4. CA Index Name: [1,1?-biphenyl]-2-carboxylicacid, 4?-[[[[2-[[acetyl[4-(1-piperidinylmethyl)phenyl]amino]methyl]cyclopropyl]carbonyl]amino]methyl]-3,3?-difluoro-, methyl ester. Entered STN: Dec. 6, 2011.
CAS Registry No. 485347-98-6; CA Index Name: acetamide,N-[2-(aminomethyl)-1H-benzimidazol-6-yl]-N-[[2-(phenylmethoxy)phenyl]methyl]- Entered STN: Feb. 4, 2003.
Chemical Abstract compound, STN express RN 1026708-50-8 (Entered STN: Jun. 9, 2008).
Chourasia et al. Pharmaceutical approaches to colon targeted drug delivery systems. J Pharm Pharm Sci. 6(1):33-66 (2003).
Costantino et al. Molecular Dynamics Simulation of the Ligand Binding Domain of Farnesoid X Receptor. Insights into Helix-12 Stability and Coactivator Peptide Stabilization in Response to Agonist Binding. J Med Chem 48:3251-3259 (2005).
Downes et al. A Chemical, Genetic, and Structural Analysis of the Nuclear Bile Acid Receptor FXR. Molecular Cell 11:1079-1092 (2003).
Erb et al. Sequential One-Pot Access to Molecular Diversity through Aniline Aqueous Borylation. J Organ Chem 79:10568-10580 (2014).
Fang et al. Intestinal FXR agonism promotes adipose tissue browning and reduces obesity and insulin resistance. Nat Med 21(2):159-165 (2015).
Fett et al., Preparation of oxadiazole and pyridazine derivatives as inhibitors of biosynthesis of triglycerides. Chemical Abstracts Service. XP002791353 Database accession No. 2012:125764 (2012).
Fu et al. Fibroblast growth factor 19 increases metabolic rate and reverses dietary and leptin-deficient diabetes. Endocrinology 145:2594-2603 (2004).
Gadaleta et al. Farnesoid X receptor activation inhibits inflammation and preserves the intestinal barrier in inflammatory bowel disease. Gut 60(4):463-472 (2011).
Gangloff et al. Synthesis of 3,5-disubstituted 1,2,4-oxadiazoles using tetrabutylammonium fluoride as a mild and efficient catalyst. Tetrahedron Letters 42(8):1441-1443 (2001).
Gege et al. Knocking on FXR's Door: The "Hammerhead"-Structure Series of FXR Agonists—Amphiphilic Isoxazoles with Potent In Vitro and In Vivo Activi-ties. Current Topics in Medicinal Chemistry 14:2143-2158 (2014).
Genin et al. Discovery of 6-(4-{[5-Cyclopropyl-3-(2,6-dichlorophenyl)isoxazol-4-yl]methoxy}piperidin-1-yl)-1-methyl-1H-indole-3-carboxylic Acid: A Novel FXR Agonist for the Treatment of Dyslipidemia. J Med Chem 58(24):9768-9772 (2015).
Hamada et al. Synthesis and antimicrobial evaluation of some heterocyclic chaicone derivatives. Molecules 16:2304-2312 (2011).

(56) References Cited

OTHER PUBLICATIONS

Hambruch et al. On the Pharmacology of Farnesoid X Receptor Agonists: Give me an "A", Like an "Acid". Nuclear Receptor Research 3:Article ID 101207 (2016).
Honorio et al. 3D QSAR Comparative molecular field analysis on nonsteroidal farnesoid X receptor activators. J Mol Graph Model 25:921-927 (2007).
Honorio et al. Hologram quantitative structure-activity relationships for a series of farnesoid X receptor activators. Bioorg Med Chem Letts 15:3119-3125 (2005).
Hu et al. Predicting biological Functions of Compounds based on Chemical-Chemical Interactions. PLoS One 6(12):e29491 (2011).
Inagaki et al. Regulation of antibacterial defense in the small intestine by the nuclear bile acid receptor. PNA USA 103:3920-3925 (2006).
Johnson et al., Preparation of arylheterocyclylamides as motilin antagonists. Chemical Abstracts Service. XP002791364. Database accession No. 2001:833284 (2001).
Jursic et al. Preparation of 5-substituted 2-methyl-1,3,4-oxadiazoles from 5-substituted tetrazoles and acetic anhydride. Synthetic Communications 24(11):1575-82 (1994).
Kim et al. Inhibitory Effects of Bile Acides and Synthetic Farnesoid X Receptor Agonists on Rotavirus Replication. J Virol 85(23):12570-12577 (2011).
Kumar et al. Colon targeted drug delivery systems—an overview. Curr Drug Deliv 5(3):186-198 (2008).
Lam et al. Bile acids inhibit duodenal secretin expression via orphan nuclear receptor small heterodimer partner (SHP). Am J Physol Gastrointest Liver Physiol 287:G90-G97 (2009).
Li et al. Microbiome remodelling leads to inhibition of intestinal farnesoid X receptor signalling and decreased obesity. Nat Commun 4:2384 (2013).
Li et al. Progress in the ligands and their complex structures of farnesoid X receptor. ACTA Pharmaceutica Sinica 47(6):704-715 (2012) (English Abstract).
Ling et al., Preparation of 3-(benzoylamino)propionic acid derivatives as glucagon antagonists/inverse agonists. Chemical Abstracts Service. XP002791365. Database accession No. 2000:824211 (2000).
Merk et al. Medicinal chemistry of farnesoid X receptor ligands: from agonists and antagonists to modulators. Future Med Chem 4(8):1015-1036 (2012).
Misawa et al. Discovery and structural development of small molecules that enhance transport activity of bile salt export pump mutant associated with progressive familial intrahepatic cholestasis type 2. Bioorg Med Chem 20:2940-2949 (2012).
Mokale et al. Synthesis and in-vivo hypolipidemic activity of some novel substituted phenyl isoxazol phenoxy acetic acid derivatives. Bioorg Med Chem Lett 24(9):2155-2158 (2014).
Mueller et al. Synthesis of plasmepsin II inhibitors—potential antimalarial agents. Molecules 8(7):556-564 (2003).
Mueller et al., Synthesis of plasmepsin II inhibitors as potential antimalarial agents. Chemical Abstracts Service. XP002791362. Database accession No. 2003:524478 (2003).
Nicolaou et al. Discovery and optimization of non-steroidal FXR agonists from natural product-like libraries. Org Biomol Chem 1:908-920 (2003).
O'Keefe et al., Preparation of amide and sulfonamidel igands for the estrogen receptor. Chemical Abstracts Service. XP002791360. Database accession No. 2004:267292 (2004).
Patel et al.Therapeutic opportunities in colon-specific drug-delivery systems. Crit Rev Ther Drug Carrier Syst. 24(2):147-202 (2007).
PCT/US2016/052270 International Search Report and Written Opinion dated Mar. 3, 2017.
PCT/US2018/022488 International Search Report and Written Opinion dated Jul. 30, 2018.
PCT/US2018/022488 Third Party Observation dated Jul. 15, 2019.
PCT/US2018/022489 International Search Report and Written Opinion dated Jul. 30, 2018.
PCT/US2018/022489 Third Party Observation dated Jul. 15, 2019.
PCT/US2018/022497 International Search Report and Written Opinion dated Jul. 30, 2018.
PCT/US2018/022497 Third Party Observation dated Jul. 15, 2019.
PCT/US2018/022513 International Search Report and Written Opinion dated Jul. 24, 2018.
PCT/US2018/022513 Third Party Observation dated Jul. 15, 2019.
PCT/US2019/051602 International Search Report and Written Opinion dated Dec. 4, 2019.
PCT/US2019/051603 International Search Report and Written Opinion dated Dec. 4, 2019.
PCT/US2019/051606 International Search Report and Written Opinion dated Dec. 4, 2019.
PCT/US2019/051607 International Search Report and Written Opinion dated Dec. 4, 2019.
PCT/US2019/051608 International Search Report and Written Opinion dated Dec. 4, 2019.
Poondra et al. Discovery of Indoline-Based, Natural-Product-like Compounds as Probes of Focal Adhesion Kinase Signaling Pathways. J Comb Chem 11(2):303-309 (2009).
Poondra et al., Discovery of Indoline-Based, Natural-Product-like Compounds as Probes of Focal Adhesion Kinase Signaling Pathways. Chemical Abstracts Service. XP002791355 Database accession No. 2009:61531 (2009).
Ramanathan et al. One-Pot Reactions for Synthesis of 2,5-Substituted Tetrazoles from Aryldiazonium Salts and Amidines. Organic Letters 17(23):5886-5889 (2015).
Reschly et al. Ligand specificity and evolution of liver X receptors. J Steroid Biochem Mol Biol 110(1-2):83-94 (2008).
Sanyal et al. Involvement of corepressor complex subunit GPS2 in transcriptional pathways governing human bile acid biosynthesis. PNAS USA 104(40):15665-15670 (2007).
Schuster et al. Pharmacophore-based discovery of FXR agonists. Part 1: Model development and experimental validation. Bioorg Med Chem 19:7168-7180 (2011).
Science IP—The CAS Search Service. Jul. 17, 2015 (316 pgs).
Shen et al. Synthesis and structure-activity relationships of thiadiazole-derivatives as potent and orally active peroxisome proliferator-activated receptors alpha/delta dual agonists. Bioorg Med Chem 16(6):3321-3341 (2008).
Steri et al. Antidiabetic sulfonylureas modulate farnesoid X receptor activation and target gene transcription. Future Med Chem 2(4):575-589 (2010).
Vallin et al. Efficient Chemoenzymatic Dynamic Kinetic Resolution of 1-Heteroaryl Ethanols. J Org Chem 74(24):9328-9336 (2009).
Van Den Mooter. Colon drug delivery. Expert Opin Drug Deliv. 3(1):111-125 (2006).
Widder et al. Section III: Prodrugs Kinetics. Method in Enzymology. 112:309-396 (1985).
Yang et al. Syntheses of nicotinamide riboside and derivatives: effective agents for increasing nicotinamide adenine dinucleotide concentrations in mammalian cells. J. Med. Chem. 50:6458-61 (2007).
Zheng et al., Preparation of substituted piperidines as modulators of chemokine receptor activity. Chemical Abstracts Service. XP002791356. Database accession No. 2008:419604 (2008).
PCT/US2021/022786 International Search Report and Written Opinion dated Jun. 15, 2021.
PCT/US2021/022790 International Search Report and Written Opinion dated Jun. 15, 2021.
PCT/US2021/022793 International Search Report and Written Opinion dated Jul. 16, 2021.
Price. The computational prediction of pharmaceutical crystal structures and polymorphism. Advanced Drug Delivery Reviews 56:301-319 (2004).

FARNESOID X RECEPTOR AGONISTS AND USES THEREOF

CROSS-REFERENCE

This application is a continuation of U.S. patent application Ser. No. 16/573,993, filed on Sep. 17, 2019, which claims the benefits of U.S. Provisional Application No. 62/881,560, filed on Aug. 1, 2019, U.S. Provisional Application No. 62/733,004, filed on Sep. 18, 2018, U.S. Provisional Application No. 62/733,006, filed on Sep. 18, 2018, all of which are herein incorporated by reference in their entirety.

FIELD OF THE INVENTION

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

BACKGROUND OF THE INVENTION

Farnesoid X receptor (FXR) is a nuclear receptor highly expressed in the liver, intestine, kidney, adrenal glands, and adipose tissue. FXR regulates a wide variety of target genes involved in the control of bile acid synthesis and transport, lipid metabolism, and glucose homeostasis. FXR agonism is a treatment modality for many metabolic disorders, liver diseases or conditions, inflammatory conditions, gastrointestinal diseases, or cell proliferation diseases.

SUMMARY OF THE INVENTION

In one aspect, described herein is a compound of Formula (F), or a pharmaceutically acceptable salt or solvate thereof:

Formula (I')

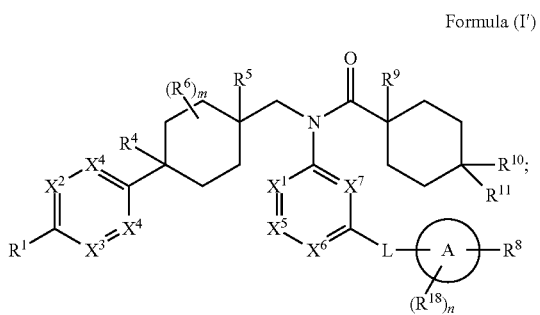

wherein:
ring A is a 5-membered heteroaryl that is oxazolyl, thiazolyl, pyrazolyl, furanyl, thienyl, pyrrolyl, imidazolyl, triazolyl, tetrazolyl, isoxazolyl, isothiazolyl, oxadiazolyl, or thiadiazolyl;
or ring A is a 6-membered heteroaryl that is pyridinyl, pyrimidinyl, pyrazinyl, pyridazinyl, or triazinyl;
$X^1$, $X^5$, $X^6$, and $X^7$ are each independently $CR^7$ or N; wherein at least one of $X^1$, $X^5$, $X^6$, and $X^7$ are $CR^7$;
$R^1$ is selected from H, halogen, —CN, —OH, —N($R^{17}$)$_2$, —NR$^{17}$S(=O)$_2$(C$_1$-C$_4$alkyl), —S(=O)$_2$N($R^{17}$)$_2$, —OC(=O)(C$_1$-C$_4$alkyl), —CO$_2$H, —CO$_2$(C$_1$-C$_4$alkyl), —C(=O)N($R^{17}$)$_2$, —NR$^{17}$C(=O)(C$_1$-C$_4$alkyl), —NR$^{17}$C(=O)O(C$_1$-C$_4$alkyl), —OC(=O)N($R^{17}$)$_2$, —NR$^{15}$C(=O)N($R^{17}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, and monocyclic C$_2$-C$_5$heterocycloalkyl;
$X^2$ is $CR^2$ or N;
$R^2$ is H, halogen, —CN, —OH, —N($R^{17}$)$_2$, —NR$^{17}$S(=O)$_2$(C$_1$-C$_4$alkyl), —S(=O)$_2$N($R^{17}$)$_2$, —OC(=O)(C$_1$-C$_4$alkyl), —CO$_2$H, —CO$_2$(C$_1$-C$_4$alkyl), —C(=O)N($R^{17}$)$_2$, —NR$^{17}$C(=O)(C$_1$-C$_4$alkyl), —NR$^{17}$C(=O)O(C$_1$-C$_4$alkyl), —OC(=O)N($R^{17}$)$_2$, —NR$^{17}$C(=O)N($R^{17}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, or monocyclic C$_2$-C$_5$heterocycloalkyl;
or $R^1$ and $R^2$ are taken together with the intervening atoms to form a fused 5- or 6-membered ring with 0-3 N atoms and 0-2 O or S atoms in the ring, wherein the fused 5- or 6-membered ring is optionally substituted with halogen or C$_1$-C$_4$alkyl;
$X^3$ is $CR^3$ or N;
$R^3$ is H, halogen, —CN, —OH, —N($R^{17}$)$_2$, —NR$^{17}$S(=O)$_2$(C$_1$-C$_4$alkyl), —OC(=O)(C$_1$-C$_4$alkyl), —CO$_2$H, —CO$_2$(C$_1$-C$_4$alkyl), —C(=O)N($R^{17}$)$_2$, —NR$^{17}$C(=O)(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, or C$_1$-C$_4$heteroalkyl;
each $X^4$ is independently CH, CF, or N;
$R^4$ is H, F, or —CH$_3$;
$R^5$ is H, F, or —CH$_3$;
or $R^4$ and $R^5$ are taken together to form a bridge that is —CH$_2$— or —CH$_2$CH$_2$—;
each $R^6$ is independently H, F, —OH, or —CH$_3$;
L is absent, —Y$^2$-L$^1$-, -L$^1$-Y$^2$—, cyclopropylene, cyclobutylene, or bicyclo[1.1.1]pentylene;
$Y^2$ is absent, —O—, —S—, —S(=O)—, —S(=O)$_2$—, —S(=O)$_2$NR$^{17}$—, —CH$_2$—, —CH=CH—, —C≡C—, —C(=O)—, —C(=O)O—, —OC(=O)—, —OC(=O)O—, —C(=O)NR$^{17}$—, —NR$^{17}$C(=O)—, —OC(=O)NR$^{17}$—, —NR$^{17}$C(=O)O—, —NR$^{17}$C(=O)NR$^{17}$—, —NR$^{17}$S(=O)$_2$—, or —NR$^{17}$—;
L$^1$ is absent or C$_1$-C$_4$alkylene;
each $R^7$ is independently selected from H, halogen, —CN, —OH, C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_3$-C$_6$cycloalkyl, and C$_1$-C$_4$heteroalkyl;
$R^8$ is C$_4$-C$_8$alkyl or C$_4$-C$_8$haloalkyl;
$R^9$ is H, F, or —CH$_3$;
$R^{10}$ is —OC(=O)N($R^{12}$)($R^{13}$), —N($R^{16}$)C(=O)$R^{14}$, or —N($R^{16}$)C(=O)O$R^{15}$;
$R^{11}$ is H, F, or —CH$_3$;
$R^{12}$ is —C$_1$-C$_6$alkyl-OR$^{17}$ or monocyclic C$_2$-C$_5$heterocycloalkyl optionally substituted with one or two oxo groups;
$R^{13}$ is H or C$_1$-C$_4$alkyl; or $R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N(C$_1$-C$_4$alkyl)$_2$, C$_1$-C$_6$alkyl, C$_1$-C$_6$alkoxy, —S(C$_1$-C$_4$alkyl), —S(=O)

($C_1$-$C_4$alkyl), —S(=O)$_2$($C_1$-$C_4$alkyl), —$C_1$-$C_4$alkyl-S(=O)$_2$($C_1$-$C_4$alkyl), —$C_1$-$C_6$alkyl-OR$^{17}$, and —O—$C_1$-$C_6$alkyl-OR$^{17}$;

R$^{14}$ is $C_1$-$C_6$alkyl, $C_3$-$C_6$cycloalkyl, or —$C_1$-$C_6$alkyl-OR$^{17}$;

R$^{15}$ is $C_1$-$C_6$alkyl, —$C_1$-$C_6$alkyl-OR$^{17}$, $C_3$-$C_6$cycloalkyl, or $C_2$-$C_6$heterocycloalkyl;

R$^{16}$ is H or $C_1$-$C_6$alkyl;

each R$^{17}$ is independently H or $C_1$-$C_6$alkyl;

each R$^{18}$ is independently halogen, —CN, —OH, —N(R$^{17}$)$_2$, —NR$^{17}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N(R$^{17}$)$_2$, —C(=O)($C_1$-$C_4$alkyl), —OC(=O)($C_1$-$C_4$alkyl), —CO$_2$H, —CO$_2$($C_1$-$C_4$alkyl), —NR$^{17}$C(=O)($C_1$-$C_4$alkyl), —C(=O)N(R$^{17}$)$_2$, —NR$^{17}$C(=O)O($C_1$-$C_4$alkyl), —OC(=O)N(R$^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, $C_3$-$C_6$cycloalkyl, monocyclic $C_2$-$C_6$heterocycloalkyl, phenyl, or monocyclic heteroaryl;

m is 0, 1, or 2; and n is 0, 1, or 2.

In some embodiments is a compound of Formula (F), or a pharmaceutically acceptable salt or solvate thereof, having the structure of Formula (Ia'):

Formula (Ia')

In some embodiments is a compound of Formula (F) or (Ia'), or a pharmaceutically acceptable salt or solvate thereof, wherein X$^1$ is N, and X$^5$, X$^6$, and X$^7$ are CH. In some embodiments is a compound of Formula (I') or (Ia'), or a pharmaceutically acceptable salt or solvate thereof, wherein X$^1$ and X$^6$ are N, and X$^5$ and X$^7$ are CH. In some embodiments is a compound of Formula (I') or (Ia'), or a pharmaceutically acceptable salt or solvate thereof, wherein X$^1$ and X$^7$ are N, and X$^5$ and X$^6$ are CH. In some embodiments is a compound of Formula (I') or (Ia'), or a pharmaceutically acceptable salt or solvate thereof, wherein X$^1$, X$^5$, X$^6$, and X$^7$ are CH.

In another aspect, described herein is a compound of Formula (I), or a pharmaceutically acceptable salt or solvate thereof:

Formula (I)

wherein:

ring A is a 5-membered heteroaryl that is oxazolyl, thiazolyl, pyrazolyl, furanyl, thienyl, pyrrolyl, imidazolyl, triazolyl, tetrazolyl, isoxazolyl, isothiazolyl, oxadiazolyl, or thiadiazolyl;

or ring A is a 6-membered heteroaryl that is pyridinyl, pyrimidinyl, pyrazinyl, pyridazinyl, or triazinyl;

X$^1$ is C(H), C(F), or N;

R$^1$ is selected from H, halogen, —CN, —OH, —N(R$^{17}$)$_2$, —NR$^{17}$S(=O)$_2$($C_1$-$C_4$alkyl), —S(=O)$_2$N(R$^{17}$)$_2$, —OC(=O)($C_1$-$C_4$alkyl), —CO$_2$H, —CO$_2$($C_1$-$C_4$alkyl), —C(=O)N(R$^{17}$)$_2$, —NR$^{17}$C(=O)($C_1$-$C_4$alkyl), —NR$^{17}$C(=O)O($C_1$-$C_4$alkyl), —OC(=O)N(R$^{17}$)$_2$, —NR$^{15}$C(=O)N(R$^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, and monocyclic $C_2$-$C_5$heterocycloalkyl;

X$^2$ is CR$^2$ or N;

R$^2$ is H, halogen, —CN, —OH, —N(R$^{17}$)$_2$, —NR$^{17}$S(=O)$_2$($C_1$-$C_4$alkyl), —S(=O)$_2$N(R$^{17}$)$_2$, —OC(=O)($C_1$-$C_4$alkyl), —CO$_2$H, —CO$_2$($C_1$-$C_4$alkyl), —C(=O)N(R$^{17}$)$_2$, —NR$^{17}$C(=O)($C_1$-$C_4$alkyl), —NR$^{17}$C(=O)O($C_1$-$C_4$alkyl), —OC(=O)N(R$^{17}$)$_2$, —NR$^{17}$C(=O)N(R$^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl;

or R$^1$ and R$^2$ are taken together with the intervening atoms to form a fused 5- or 6-membered ring with 0-3 N atoms and 0-2 O or S atoms in the ring, wherein the fused 5- or 6-membered ring is optionally substituted with halogen or $C_1$-$C_4$alkyl;

X$^3$ is CR$^3$ or N;

R$^3$ is H, halogen, —CN, —OH, —N(R$^{17}$)$_2$, —NR$^{17}$S(=O)$_2$($C_1$-$C_4$alkyl), —OC(=O)($C_1$-$C_4$alkyl), —CO$_2$H, —CO$_2$($C_1$-$C_4$alkyl), —C(=O)N(R$^{17}$)$_2$, —NR$^{17}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;

each X$^4$ is independently CH or N;

R$^4$ is H, F, or —CH$_3$;

R$^5$ is H, F, or —CH$_3$;

or R$^4$ and R$^5$ are taken together to form a bridge that is —CH$_2$— or —CH$_2$CH$_2$—; each R$^6$ is independently H, F, —OH, or —CH$_3$;

L is absent, —Y$^2$-L$^1$-, -L$^1$-Y$^2$—, cyclopropylene, cyclobutylene, or bicyclo[1.1.1]pentylene;

Y² is absent, —O—, —S—, —S(=O)—, —S(=O)₂—, —S(=O)₂NR¹⁷—, —CH₂—, —CH=CH—, —C≡C—, —C(=O)—, —C(=O)O—, —OC(=O)—, —OC(=O)O—, —C(=O)NR¹⁷—, —NR¹⁷C(=O)—, —OC(=O)NR¹⁷—, —NR¹⁷C(=O)O—, —NR¹⁷C(=O)NR¹⁷—, —NR¹⁷S(=O)₂—, or —NR¹⁷—;

L¹ is absent or C₁-C₄alkylene;

each R⁷ is independently selected from H, halogen, —CN, —OH, C₁-C₄alkyl, C₂-C₄alkenyl, C₂-C₄alkynyl, C₁-C₄alkoxy, C₁-C₄fluoroalkyl, C₁-C₄fluoroalkoxy, and C₁-C₄heteroalkyl;

R⁸ is C₄-C₈alkyl or C₄-C₈haloalkyl;

R⁹ is H, F, or —CH₃;

R¹⁰ is —OC(=O)N(R¹²)(R¹³), —N(R¹⁶)C(=O)R¹⁴, or —N(R¹⁶)C(=O)OR¹⁵;

R¹¹ is H, F, or —CH₃;

R¹² is —C₁-C₆alkyl-OR¹⁷ or monocyclic C₂-C₅heterocycloalkyl optionally substituted with one or two oxo groups;

R¹³ is H or C₁-C₄alkyl; or R¹² and R¹³ are taken together to form a 4-, 5-, or 6-membered heterocycloalkyl ring optionally containing an additional heteroatom selected from O, S, and N and optionally substituted with 1, 2, or 3 groups selected from —OH, —N(C₁-C₄alkyl)₂, C₁-C₆alkyl, C₁-C₆alkoxy, —S(C₁-C₄alkyl), —S(=O)(C₁-C₄alkyl), —S(=O)₂(C₁-C₄alkyl)₅-C₁-C₄alkyl-S(=O)₂(C₁-C₄alkyl), —C₁-C₆alkyl-OR¹⁷, and —O—C₁-C₆alkyl-OR¹⁷;

R¹⁴ is C₁-C₆alkyl or —C₁-C₆alkyl-OR¹⁷;

R¹⁵ is C₁-C₆alkyl, —C₁-C₆alkyl-OR¹⁷, or C₂-C₆heterocycloalkyl;

R¹⁶ is H or C₁-C₆alkyl;

each R¹⁷ is independently H or C₁-C₆alkyl;

each R¹⁸ is independently halogen, —CN, —OH, —N(R¹⁷)₂, —NR¹⁷S(=O)₂(C₁-C₄alkyl), —S(C₁-C₄alkyl), —S(=O)(C₁-C₄alkyl), —S(=O)₂(C₁-C₄alkyl), —S(=O)₂N(R¹⁷)₂, —C(=O)(C₁-C₄alkyl), —OC(=O)(C₁-C₄alkyl), —CO₂H, —CO₂(C₁-C₄alkyl), —NR¹⁷C(=O)(C₁-C₄alkyl), —C(=O)N(R¹⁷)₂, —NR¹⁷C(=O)O(C₁-C₄alkyl), —OC(=O)N(R¹⁷)₂, C₁-C₄alkyl, C₂-C₄alkenyl, C₂-C₄alkynyl, C₁-C₄alkoxy, C₁-C₄fluoroalkyl, C₁-C₄fluoroalkoxy, C₁-C₄heteroalkyl, C₃-C₆cycloalkyl, monocyclic C₂-C₆heterocycloalkyl, phenyl, or monocyclic heteroaryl;

m is 0, 1, or 2; and n is 0, 1, or 2.

In some embodiments is a compound of Formula (I), or a pharmaceutically acceptable salt or solvate thereof, having the structure of Formula (Ia):

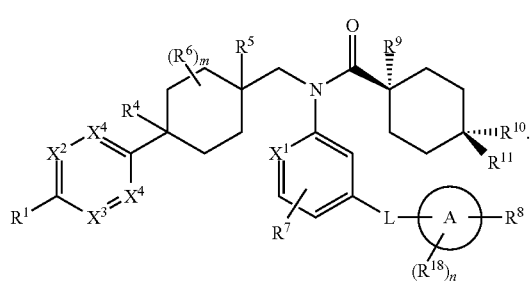

Formula (Ia)

In some embodiments is a compound of Formula (I'), (I), (Ia'), or (Ia), or a pharmaceutically acceptable salt or solvate thereof, wherein ring A is a 5-membered heteroaryl that is oxazolyl, thiazolyl, imidazolyl, or pyrazolyl; or ring A is a 6-membered heteroaryl that is pyridinyl or pyrimidinyl. In some embodiments is a compound of Formula (I'), (I), (Ia'), or (Ia), or a pharmaceutically acceptable salt or solvate thereof, wherein ring n is 0. In some embodiments is a compound of Formula (I'), (I), (Ia'), or (Ia), or a pharmaceutically acceptable salt or solvate thereof, wherein ring

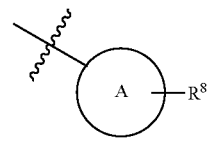

is

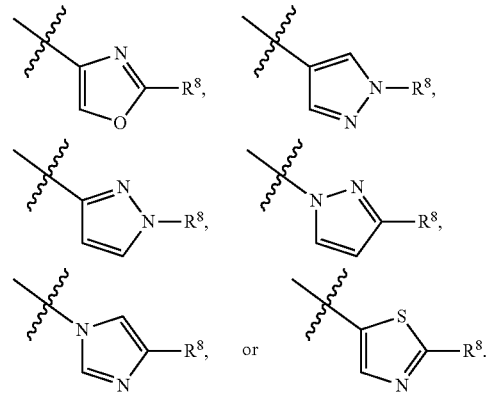

In some embodiments is a compound of Formula (I'), (I), (Ia'), or (Ia), or a pharmaceutically acceptable salt or solvate thereof, wherein R¹⁰ is —OC(=O)N(R¹²)(R¹³). In some embodiments is a compound of Formula (I'), (I), (Ia'), or (Ia), or a pharmaceutically acceptable salt or solvate thereof, wherein R¹² is —C₁-C₆alkyl-OR¹⁷. In some embodiments is a compound of Formula (I'), (I), (Ia'), or (Ia), or a pharmaceutically acceptable salt or solvate thereof, wherein R¹² is —CH₂CH₂OH, —CH₂CH₂CH₂OH, or —CH₂CH₂C(CH₃)₂OH. In some embodiments is a compound of Formula (I'), (I), (Ia'), or (Ia), or a pharmaceutically acceptable salt or solvate thereof, wherein R¹³ is H. In some embodiments is a compound of Formula (I'), (I), (Ia'), or (Ia), or a pharmaceutically acceptable salt or solvate thereof, wherein R¹² and R¹³ are taken together to form a 4-, 5-, or 6-membered heterocycloalkyl ring optionally containing an additional heteroatom selected from O, S, and N and optionally substituted with 1, 2, or 3 groups selected from —OH, —N(C₁-C₄alkyl)₂, C₁-C₆alkyl, C₁-C₆alkoxy, —S(=O)₂(C₁-C₄alkyl), —C₁-C₄alkyl-S(=O)₂(C₁-C₄alkyl), —C₁-C₆alkyl-OR¹⁷, and —O—C₁-C₆alkyl-OR¹⁷.

In another aspect, described herein is a compound of Formula (II), or a pharmaceutically acceptable salt or solvate thereof:

Formula (II)

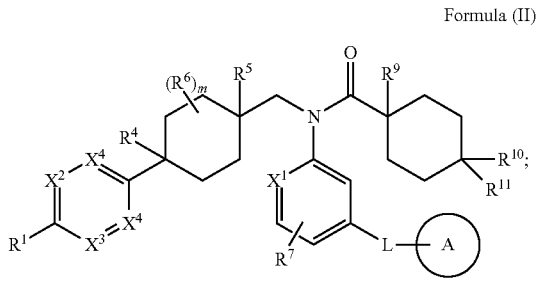

wherein:
ring A is

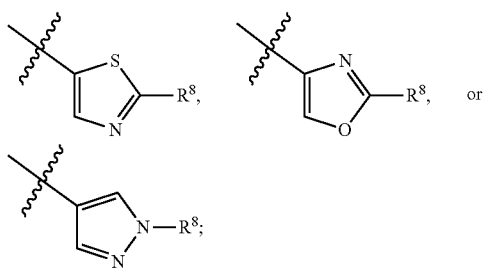

$X^1$ is CH or N;
$R^1$ is H, halogen, —CN, —OH, —N($R^{17}$)$_2$, —$NR^{17}$S(=O)$_2$($C_1$-$C_4$alkyl), —S(=O)$_2$N($R^{17}$)$_2$, —OC(=O)($C_1$-$C_4$alkyl), —$CO_2$H, —$CO_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, —$NR^{15}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl;
$X^2$ is $CR^2$ or N;
$R^2$ is H, halogen, —CN, —OH, —N($R^{17}$)$_2$, —$NR^{17}$S(=O)$_2$($C_1$-$C_4$alkyl), —S(=O)$_2$N($R^{17}$)$_2$, —OC(=O)($C_1$-$C_4$alkyl), —$CO_2$H, —$CO_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, —$NR^{17}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl;
or $R^1$ and $R^2$ are taken together with the intervening atoms to form a fused 5- or 6-membered ring with 0-3 N atoms and 0-2 O or S atoms in the ring, wherein the fused 5- or 6-membered ring is optionally substituted with halogen or $C_1$-$C_4$alkyl;
$X^3$ is $CR^3$ or N;
$R^3$ is H, halogen, —CN, —OH, —N($R^{17}$)$_2$, —$NR^{17}$S(=O)$_2$($C_1$-$C_4$alkyl), —OC(=O)($C_1$-$C_4$alkyl), —$CO_2$H, —$CO_2$($C_1$-$C_4$alkyl), —C(=O)N($R^{17}$)$_2$, —$NR^{17}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;
each $X^4$ is independently CH or N;

$R^4$ is H, F, or —$CH_3$;
$R^5$ is H, F, or —$CH_3$;
or $R^4$ and $R^5$ are taken together to form a bridge that is —$CH_2$— or —$CH_2CH_2$—;
each $R^6$ is independently H, F, —OH, or —$CH_3$;
$R^7$ is H, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;
L is absent, —$Y^2$-$L^1$-, -$L^1$-$Y^2$—, cyclopropylene, cyclobutylene, or bicyclo[1.1.1]pentylene;
$Y^2$ is absent, —O—, —S—, —S(=O)—, —S(=O)$_2$—, —S(=O)$_2$$NR^{17}$—, —$CH_2$—, —CH=CH—, —C≡C—, —C(=O)—, —C(=O)O—, —OC(=O)—, —OC(=O)O—, —C(=O)$NR^{17}$—, —$NR^{17}$C(=O)—, —OC(=O)$NR^{17}$—, —$NR^{17}$C(=O)O—, —$NR^{17}$C(=O)$NR^{17}$—, —$NR^{17}$S(=O)$_2$—, or —$NR^{17}$—;
$L^1$ is absent or $C_1$-$C_4$alkylene;
$R^8$ is $C_4$-$C_8$alkyl;
$R^9$ is H, F, or —$CH_3$;
$R^{10}$ is —OC(=O)N($R^{12}$)($R^{13}$), —N($R^{16}$)C(=O)$R^{14}$, or —N($R^{16}$)C(=O)$OR^{15}$;
$R^{11}$ is H, F, or —$CH_3$;
$R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N($C_1$-$C_4$alkyl)$_2$, $C_1$-$C_6$alkyl, and $C_1$-$C_6$alkoxy;
$R^{14}$ is $C_1$-$C_6$alkyl or —$C_1$-$C_6$alkyl-$OR^{17}$;
$R^{15}$ is $C_1$-$C_6$alkyl, —$C_1$-$C_6$alkyl-$OR^{17}$, or $C_2$-$C_6$heterocycloalkyl;
$R^{16}$ is H or $C_1$-$C_6$alkyl;
each $R^{17}$ is independently H or $C_1$-$C_6$alkyl; and
m is 0, 1, or 2.

In some embodiments is a compound of Formula (II), or a pharmaceutically acceptable salt or solvate thereof, having the structure of Formula (IIa):

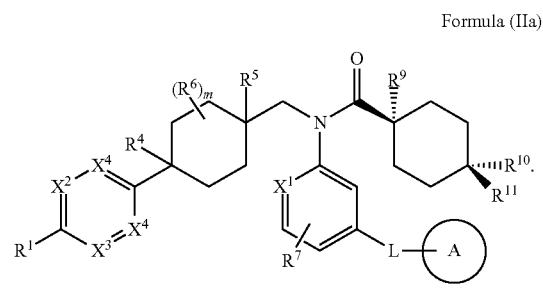

Formula (IIa)

In some embodiments is a compound of Formula (I'), (I), (Ia'), (Ia), (II), or (IIa), or a pharmaceutically acceptable salt or solvate thereof, wherein ring A is

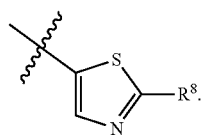

In some embodiments is a compound of Formula (I'), (I), (Ia'), (Ia), (II), or (IIa), or a pharmaceutically acceptable salt or solvate thereof, wherein ring A is

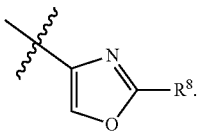

In some embodiments is a compound of Formula (I'), (I), (Ia'), (Ia), (II), or (IIa), or a pharmaceutically acceptable salt or solvate thereof, wherein ring A is

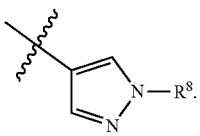

In some embodiments is a compound of Formula (I'), (I), (Ia'), (Ia), (II), or (IIa), or a pharmaceutically acceptable salt or solvate thereof, wherein $R^8$ is —C(CH$_3$)$_3$. In some embodiments is a compound of Formula (I), (Ia), (II), or (IIa), or a pharmaceutically acceptable salt or solvate thereof, wherein $X^1$ is N. In some embodiments is a compound of Formula (I), (Ia), (II), or (IIa), or a pharmaceutically acceptable salt or solvate thereof, wherein $X^1$ is CH. In some embodiments is a compound of Formula (I'), (I), (Ia'), (Ia), (II), or (IIa), or a pharmaceutically acceptable salt or solvate thereof, wherein $R^4$ is H and $R^5$ is H. In some embodiments is a compound of Formula (I'), (I), (Ia'), (Ia), (II), or (IIa), or a pharmaceutically acceptable salt or solvate thereof, wherein $R^4$ and $R^5$ are taken together to form a bridge that is —CH$_2$— or —CH$_2$CH$_2$—. In some embodiments is a compound of Formula (I'), (I), (Ia'), (Ia), (II), or (IIa), or a pharmaceutically acceptable salt or solvate thereof, wherein $R^4$ and $R^5$ are taken together to form a bridge that is —CH$_2$CH$_2$—. In some embodiments is a compound of Formula (I'), (I), (Ia'), (Ia), (II), or (IIa), or a pharmaceutically acceptable salt or solvate thereof, wherein $R^{10}$ is —OC(=O)N($R^{12}$)($R^{13}$). In some embodiments is a compound of Formula (I'), (I), (Ia'), (Ia), (II) or (IIa), or a pharmaceutically acceptable salt or solvate thereof, wherein $R^{12}$ and $R^{13}$ are taken together to form a 4-membered or 5-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (I'), (I), (Ia'), (Ia), (II) or (IIa), or a pharmaceutically acceptable salt or solvate thereof, wherein $R^{10}$ is

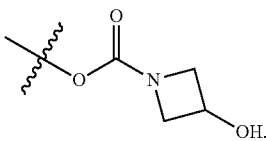 [SMILES: *OC(=O)N1CC(O)C1]

In some embodiments is a compound of Formula (I'), (I), (Ia'), (Ia), (II) or (IIa), or a pharmaceutically acceptable salt or solvate thereof, wherein $R^{10}$ is

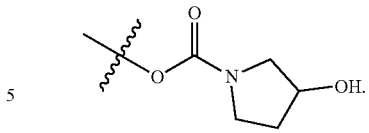

In some embodiments is a compound of Formula (I'), (I), (Ia'), (Ia), (II), or (IIa), or a pharmaceutically acceptable salt or solvate thereof, wherein $R^{10}$ is —N($R^{16}$)C(=O)$R^{14}$. In some embodiments is a compound of Formula (I'), (I), (Ia'), (Ia), (II), or (IIa), or a pharmaceutically acceptable salt or solvate thereof, wherein $R^{14}$ is C$_1$-C$_6$alkyl. In some embodiments is a compound of Formula (I'), (I), (Ia'), (Ia), (II), or (IIa), or a pharmaceutically acceptable salt or solvate thereof, wherein $R^{14}$ is —C$_1$-C$_6$alkyl-O$R^{17}$. In some embodiments is a compound of Formula (I'), (I), (Ia'), (Ia), (II), or (IIa), or a pharmaceutically acceptable salt or solvate thereof, wherein $R^{10}$ is —N($R^{16}$)C(=O)O$R^{15}$. In some embodiments is a compound of Formula (I'), (I), (Ia'), (Ia), (II), or (IIa), or a pharmaceutically acceptable salt or solvate thereof, wherein $R^{15}$ is C$_1$-C$_6$alkyl. In some embodiments is a compound of Formula (I'), (I), (Ia'), (Ia), (II), or (IIa), or a pharmaceutically acceptable salt or solvate thereof, wherein $R^{15}$ is —C$_1$-C$_6$alkyl-O$R^{17}$. In some embodiments is a compound of Formula (I'), (I), (Ia'), (Ia), (II), or (IIa), or a pharmaceutically acceptable salt or solvate thereof, wherein $R^{15}$ is C$_2$-C$_6$heterocycloalkyl. In some embodiments is a compound of Formula (I'), (I), (Ia'), (Ia), (II), or (IIa), or a pharmaceutically acceptable salt or solvate thereof, wherein $R^{16}$ is H. In some embodiments is a compound of Formula (I'), (I), (Ia'), (Ia), (II), or (IIa), or a pharmaceutically acceptable salt or solvate thereof, wherein one $X^4$ is CH and one $X^4$ is N. In some embodiments is a compound of Formula (I'), (I), (Ia'), (Ia), (II), or (IIa), or a pharmaceutically acceptable salt or solvate thereof, wherein each $X^4$ is CH. In some embodiments is a compound of Formula (I'), (I), (Ia'), (Ia), (II), or (IIa), or a pharmaceutically acceptable salt or solvate thereof, wherein $X^3$ is CH. In some embodiments is a compound of Formula (I'), (I), (Ia'), (Ia), (II), or (IIa), or a pharmaceutically acceptable salt or solvate thereof, wherein $X^2$ is C$R^2$. In some embodiments is a compound of Formula (I'), (I), (Ia'), (Ia), (II), or (IIa), or a pharmaceutically acceptable salt or solvate thereof, wherein $R^2$ is halogen, —CN, or C$_1$-C$_4$alkyl. In some embodiments is a compound of Formula (I'), (I), (Ia'), (Ia), (II), or (IIa), or a pharmaceutically acceptable salt or solvate thereof, wherein $R^2$ is C$_1$-C$_4$alkyl. In some embodiments is a compound of Formula (I'), (I), (Ia'), (Ia), (II), or (IIa), or a pharmaceutically acceptable salt or solvate thereof, wherein $R^1$ is C$_1$-C$_4$alkyl or C$_1$-C$_4$alkoxy. In some embodiments is a compound of Formula (I'), (I), (Ia'), (Ia), (II), or (IIa), or a pharmaceutically acceptable salt or solvate thereof, wherein $R^1$ is C$_1$-C$_4$alkoxy. In some embodiments is a compound of Formula (I'), (I), (Ia'), (Ia), (II), or (IIa), or a pharmaceutically acceptable salt or solvate thereof, wherein $R^1$ is —OCH$_3$. In some embodiments is a compound of Formula (I'), (I), (Ia'), (Ia), (II), or (IIa), or a pharmaceutically acceptable salt or solvate thereof, wherein L is absent. In some embodiments is a compound of Formula (I'), (I), (Ia'), (Ia), (II), or (IIa), or a pharmaceutically acceptable salt or solvate thereof, wherein m is 0. In some embodiments is a compound of Formula (I'), (I), (Ia'), (Ia), (II), or (IIa), or a pharmaceutically acceptable salt or solvate thereof, wherein $R^9$ is H. In some embodiments is a compound of Formula (I'), (I), (Ia'), (Ia), (II), or (IIa), or a pharmaceutically acceptable salt or solvate thereof, wherein $R^{11}$ is H. In some embodiments is a compound of Formula (I'), (I), (Ia'), (Ia), (II), or (IIa), or a pharmaceutically acceptable salt or solvate thereof, wherein each $R^7$ is H.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In another aspect, described herein is a method of treating a disease or condition in a mammal that would benefit from FXR agonism comprising administering a compound as described herein, or pharmaceutically acceptable salt or solvate thereof, to the mammal in need thereof. In some embodiments, the disease or condition is a metabolic condition. In some embodiments, the disease or condition is a liver condition.

In some embodiments, the compound is administered to the mammal by intravenous administration, subcutaneous administration, oral administration, inhalation, nasal administration, dermal administration, or ophthalmic administration.

In one aspect, described herein is a method of treating or preventing any one of the diseases or conditions described herein comprising administering a therapeutically effective amount of a compound described herein, or a pharmaceutically acceptable salt or solvate thereof, to a mammal in need thereof.

In one aspect, described herein is a method for the treatment or prevention of a metabolic or liver condition in a mammal comprising administering a therapeutically effective amount of a compound described herein, or a pharmaceutically acceptable salt or solvate thereof, to the mammal in need thereof. In other embodiments, the metabolic or liver condition is amenable to treatment with an FXR agonist. In some embodiments, the method further comprises administering a second therapeutic agent to the mammal in addition to the compound described herein, or a pharmaceutically acceptable salt or solvate thereof.

In one aspect, described herein is a method of treating or preventing a liver disease or condition in a mammal, comprising administering to the mammal a compound of Formula (I'), (I), (Ia'), (Ia), (II), or (IIa), or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is nonalcoholic steatohepatitis (NASH). In some embodiments, the non-alcoholic liver disease or condition is nonalcoholic steatohepatitis (NASH) and is accompanied by liver fibrosis. In some embodiments, the non-alcoholic liver disease or condition is nonalcoholic steatohepatitis (NASH) without liver fibrosis. In some embodiments, the non-alcoholic liver disease or condition is intrahepatic cholestasis or extrahepatic cholestasis.

In one aspect, described herein is a method of treating or preventing a liver fibrosis in a mammal, comprising administering to the mammal a compound of Formula (I'), (I), (Ia'), (Ia), (II), or (IIa), or a pharmaceutically acceptable salt or solvate thereof. In some embodiments, the mammal is diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the mammal is diagnosed with nonalcoholic steatohepatitis (NASH).

In one aspect, described herein is a method of treating or preventing a liver inflammation in a mammal, comprising administering to the mammal a compound of Formula (I'), (I), (Ia'), (Ia), (II), or (IIa), or a pharmaceutically acceptable salt or solvate thereof. In some embodiments, the mammal is diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the mammal is diagnosed with nonalcoholic steatohepatitis (NASH). In some embodiments, the liver inflammation is associated with inflammation in the gastrointestinal tract. In some embodiments, the mammal is diagnosed with inflammatory bowel disease.

In one aspect, described herein is a method of treating or preventing a gastrointestinal disease or condition in a mammal, comprising administering to the mammal a compound of Formula (I'), (I), (Ia'), (Ia), (II), or (IIa), or a pharmaceutically acceptable salt or solvate thereof. In some embodiments, the gastrointestinal disease or condition is necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, graft versus host disease, or any combination thereof. In some embodiments, the gastrointestinal disease is irritable bowel syndrome (IBS), irritable bowel syndrome with diarrhea (IBS-D), irritable bowel syndrome with constipation (IBS-C), mixed IBS (IBS-M), unsubtyped IBS (IBS-U), or bile acid diarrhea (BAD).

In one aspect, described herein is a method of treating or preventing a disease or condition in a mammal that would benefit from treatment with an FXR agonist, comprising administering to the mammal a compound of Formula (I'), (I), (Ia'), (Ia), (II), or (IIa), or a pharmaceutically acceptable salt or solvate thereof. In some embodiments, the methods described herein further comprise administering at least one additional therapeutic agent in addition to the compound of Formula (I'), (I), (Ia'), (Ia), (II), or (IIa), or a pharmaceutically acceptable salt or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound of Formula (I'), (I), (Ia'), (Ia), (II), or (IIa) described herein, or a pharmaceutically acceptable salt thereof. In various embodiments, each agent is administered in any order, including simultaneously.

In any of the embodiments disclosed herein, the mammal or subject is a human.

In some embodiments, compounds provided herein are administered to a human.

In some embodiments, compounds provided herein are orally administered.

In some embodiments, described herein is a method of treating or preventing a metabolic disorder in a subject, comprising: administering to a gastrointestinal tract of the subject a therapeutically effective amount of one or more of the compounds described herein, or a pharmaceutically acceptable salt or solvate thereof, thereby activating farnesoid X receptors (FXR) in the intestines, and treating or preventing a metabolic disorder in the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound. In some embodiments, the method reduces or prevents diet-induced weight gain. In some embodiments, the method increases a metabolic rate in the subject. In some embodiments, the increasing the metabolic rate comprises enhancing oxidative phosphorylation in the subject. In some embodiments, the method further comprises improving glucose and/or lipid homeostasis in the subject. In some embodiments, the method results in no substantial change in food intake and/or fat consumption in the subject. In some embodiments, the method results in no substantial change in appetite in the subject. In some embodiments, the metabolic disorder is selected from obesity, diabetes, insulin resistance, dyslipidemia or any combination thereof. In some embodiments, the metabolic disorder is non-insulin dependent diabetes mellitus. In some embodiments, the method protects against diet-induced weight gain, reduces inflammation, enhances thermogenesis, enhances insulin sensitivity in the liver, reduces hepatic steatosis, promotes activation of BAT, decreases blood glucose, increases weight loss, or any combination thereof. In some embodiments, the method enhances insulin sensitivity in the liver and promotes brown adipose tissue (BAT) activation. In some embodiments, the method further comprises administering to the subject an insulin sensitizing drug, an insulin secretagogue, an alpha-glucosidase inhibitor, a glucagon-like peptide (GLP) agonist, a dipeptidyl peptidase-4 (DPP-4) inhibitor, nicotinamide ribonucleoside, an analog of nicotinamide ribonucleoside, or combinations thereof.

In some embodiments, described herein is a method of treating or preventing inflammation in an intestinal region of a subject, comprising: administering to a gastrointestinal tract of the subject a therapeutically effective amount of one or more of the compounds described herein, or a pharmaceutically acceptable salt or solvate thereof, thereby activating FXR receptors in the intestines, and thereby treating or preventing inflammation in the intestinal region of the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the inflammation is associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis or any combination thereof. In some embodiments, the one or more FXR target genes comprises IBABP, OSTα, Perl, FGF15, FGF19, SHP or combinations thereof. In some embodiments, the method further comprises administering a therapeutically effective amount of an antibiotic therapy to the subject, wherein the method treats or prevents inflammation associated with pseudomembranous colitis in the subject. In some embodiments, the method further comprises administering to the subject a therapeutically effective amount of an oral corticosteroid, other anti-inflammatory or immunomodulatory therapy, nicotinamide ribonucleoside, an analog of nicotinamide ribonucleoside, or combinations thereof. In some embodiments, the method increases HSL phosphorylation and β3-adrenergic receptor expression. In some embodiments, a serum concentration of the compound in the subject remains below its $EC_{50}$ following administration of the compound.

In some embodiments, described herein is a method of treating or preventing a cell proliferation disease in a subject, comprising administering to a gastrointestinal tract of the subject a therapeutically effective amount of one or more of the compounds described herein or a pharmaceutically acceptable salt or solvate thereof. In some embodiments, the cell proliferation disease is an adenocarcinoma. In some embodiments, the adenocarcinoma is a colon cancer. In some embodiments, the treating the adenocarcinoma reduces the size of the adenocarcinoma, the volume of the adenocarcinoma, the number of adenocarcinomas, cachexia due to the adenocarcinoma, delays progression of the adenocarcinoma, increases survival of the subject, or combinations thereof. In some embodiments, the method further comprises administering to the subject an additional therapeutic compound selected from the group consisting of a chemotherapeutic, a biologic, a radiotherapeutic, or combinations thereof.

In some embodiments, described herein is a method of treating or preventing a liver disease or condition in a subject, comprising administering to the subject a therapeutically effective amount of one or more of the compounds described herein, or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is intrahepatic cholestasis or extrahepatic cholestasis.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for the treatment, prevention or amelioration of one or more symptoms of a disease or condition that would benefit from FXR agonism, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

The nuclear hormone receptor farnesoid X receptor (also known as FXR or nuclear receptor subfamily 1, group H, member 4 (NR1H4)) (OMIM: 603826) functions as a regulator for bile acid metabolism. FXR is a ligand-activated transcriptional receptor expressed in diverse tissues including the adrenal gland, kidney, stomach, duodenum, jejunum, ileum, colon, gall bladder, liver, macrophages, and white and brown adipose tissue. FXRs are highly expressed in tissues that participate in bile acid metabolism such as the liver, intestines, and kidneys. Bile acids function as endogenous ligands for FXR such that enteric and systemic release of bile acids induces FXR-directed changes in gene expression networks. Bile acids are the primary oxidation product of cholesterol, and in some cases, upon secretion into the intestines, are regulators of cholesterol absorption. The rate-limiting step for conversion of cholesterol into bile acids is catalyzed by cytochrome p450 enzyme cholesterol 7-α-hydroxylase (CYP7A1) and occurs in the liver. The cytochrome p450 enzyme sterol 12-α-hydroxylase (CYP8B1) mediates production of cholic acid and determines the relative amounts of the two primary bile acids, cholic acid and chenodeoxycholic acid. Activation of FXR can represses the transcription of CYP7A1 and CYP8B1 by increasing the expression level of the hepatic small heterodimer partner (SHP) (also known as nuclear receptor subfamily 0, group B, member 2; or NR0B2) and intestinal expression of fibroblast growth factor 15 (FGF15) in mice and fibroblast growth factor 19 (FGF19) in human. SHP represses the liver receptor homolog (LRH-1) and hepatocyte nuclear factor 4 alpha (HNFa4), transcription factors that regulate CYP7A1 and CYP8B1 gene expression. CYP8B1 repression by FXR can be species-specific and FXR activation may in some cases increase CYP8B1 expression in humans (Sanyal et al *PNAS,* 2007, 104, 15665). In some cases, FGF15/19 released from the intestine then activates the fibroblast growth factor receptor 4 in the liver, leading to activation of the mitogen-activated protein kinase (MAPK) signaling pathway which suppress CYP7A1 and CYP8B1.

In some embodiments, elevated levels of bile acids have been associated with insulin resistance. For example, insulin resistance sometimes leads to a decreased uptake of glucose from the blood and increased de novo glucose production in the liver. In some instances, intestinal sequestration of bile acids has been shown to improve insulin resistance by promoting the secretion of glucagon-like peptide-1 (GLP1) from intestinal L-cells. GLP-1 is an incretin derived from the transcription product of the proglucagon gene. It is released in response to the intake of food and exerts control in appetite and gastrointestinal function and promotes insulin secretion from the pancreas. The biologically active forms of GLP-1 include GLP-1-(7-37) and GLP-1-(7-36)$NH_2$, which result from selective cleavage of the proglucagon molecule. In such cases, activation of FXR leading to decreased production of bile acids correlates to a decrease in insulin resistance.

In some embodiments, the activation of FXR also correlates to the secretion of pancreatic polypeptide-fold such as peptide YY (PYY or PYY3-36). In some instances, peptide YY is a gut hormone peptide that modulates neuronal activity within the hypothalamic and brainstem, regions of the brain involved in reward processing. In some instances, reduced level of PYY correlates to increased appetite and weight gain.

In some instances, the activation of FXR indirectly leads to a reduction of plasma triglycerides. The clearance of triglycerides from the bloodstream is due to lipoprotein lipase (LPL). LPL activity is enhanced by the induction of its activator apolipoprotein CII, and the repression of its inhibitor apolipoprotein CIII in the liver occurs upon FXR activation.

In some cases, the activation of FXR further modulates energy expenditure such as adipocyte differentiation and function. Adipose tissue comprises adipocytes or fat cells. In some instances, adipocytes are further differentiated into brown adipose tissue (BAT) or white adipose tissue (WAT). The function of BAT is to generate body heat, while WAT functions as fat storing tissues.

In some instances, FXR is widely expressed in the intestine. In some cases, the activation of FXR has been shown to induce the expression and secretion of FGF19 (or FGF15 in mouse) in the intestine. FGF19 is a hormone that regulates bile acid synthesis as well as exerts an effect on glucose metabolism, lipid metabolism, and on energy expenditure. In some instances, FGF19 has also been observed to modulate adipocyte function and differentiation. Indeed, a study has shown that the administration of FGF19 to high-fat diet-fed mice increased energy expenditure, modulated adipocytes differentiation and function, reversed weight gain, and improved insulin resistance (see, Fu et al, "Fibroblast growth factor 19 increases metabolic rate and reverses dietary and leptin-deficient diabetes." *Endocrinology* 145: 2594-2603 (2004)).

In some cases, intestinal FXR activity has also been shown to be involved in reducing overgrowth of the microbiome, such as during feeding (Li el al., *Nat Commun* 4:2384, 2013). For example, a study had shown that activation of FXR correlated with increased expression of several genes in the ileum such as Ang2, iNos. and Il18, which have established antimicrobial actions (Inagaki et al., *Proc Natl Acad Sci USA* 103:3920-3925, 2006).

In some cases, FXR has been implicated in barrier function and immune modulation in the intestine. FXR modulates transcription of genes involved in bile salt synthesis, transport and metabolism in the liver and intestine, and in some cases has been shown to lead to improvements in intestinal inflammation and prevention of bacterial translocation into the intestinal tract (Gadaleta et al., *Gut.* 2011 April; 60(4):463-72).

In some cases, over production of bile acids or improper transport and re-cycling of bile acids can lead to diarrhea. FXR modulates transcription of genes involved in bile salt synthesis, transport and metabolism in the liver and intestine, and in some cases may lead to improvements in diarrhea Camilleri, *Gut Liver.* 2015 May; 9(3): 332-339.

G protein-coupled bile acid receptor 1 (also known as GPBAR2, GPCR19, membrane-type receptor for bile acids or M-BAR, or TGR5) is a cell surface receptor for bile acids. Upon activation with bile acid, TGR5 induces the production of intracellular cAMP, which then triggers an increase in triiodothyronine due to the activation of deiodinase (DIO2) in BAT, resulting in increased energy expenditure.

Hence in some embodiments, regulation of metabolic processes such as bile acid synthesis, bile-acid circulation, glucose metabolism, lipid metabolism, or insulin sensitivity is modulated by the activation of FXR. Furthermore, in some embodiments, dis-regulation of metabolic processes such as bile acid synthesis, bile-acid circulation, glucose metabolism, lipid metabolism, or insulin sensitivity results in metabolic diseases such as diabetes or diabetes-related conditions or disorders, alcoholic or non-alcoholic liver disease or condition, intestinal inflammation, or cell proliferative disorders.

Disclosed herein, in certain embodiments, are compounds that have activity as FXR agonists. In some embodiments, the FXR agonists described herein are structurally distinct from bile acids, other synthetic FXR ligands, and other natural FXR ligands.

In some embodiments, also disclosed herein are methods of treating or preventing a metabolic disorder, such as diabetes, obesity, impaired glucose tolerance, dyslipidemia, or insulin resistance by administering a therapeutically effective amount of an FXR agonist. In some instances, the compounds are administered to the GI tract of a subject.

In additional embodiments, disclosed herein are methods for treating or preventing alcoholic or non-alcoholic liver disease or conditions (e.g., cholestasis, primary biliary cirrhosis, steatosis, cirrhosis, alcoholic hepatitis, non-alcoholic steatohepatitis (NASH), non-alcoholic fatty liver disease (NAFLD), primary sclerosing cholangitis (PSC), or elevated liver enzymes) by administering a therapeutically effective amount of an FXR agonist to a subject in need thereof (e.g., via the GI tract). In additional embodiments, disclosed herein include methods for treating or preventing cholestasis, cirrhosis, primary biliary cirrhosis, non-alcoholic steatohepatitis (NASH), non-alcoholic fatty liver disease (NAFLD), or primary sclerosing cholangitis (PSC) by administering a therapeutically effective amount of an FXR agonist to a subject in need thereof. In some embodiments, disclosed herein include methods for treating or preventing cholestasis by administering a therapeutically effective amount of an FXR agonist to a subject in need thereof. In some embodiments, disclosed herein include methods for treating or preventing primary biliary cirrhosis by administering a therapeutically effective amount of an FXR agonist to a subject in need thereof. In some embodiments, disclosed herein include methods for treating or preventing NASH by administering a therapeutically effective amount of an FXR agonist to a subject in need thereof. In some embodiments, disclosed herein include methods for treating or preventing NAFLD by administering a therapeutically effective amount of an FXR agonist to a subject in need thereof.

In further embodiments, disclosed herein include methods for treating or preventing inflammation in the intestines and/or a cell proliferative disorder, such as cancer, by administering a therapeutically effective amount of an FXR agonist to a subject in need thereof (e.g., via the GI tract).

In still further embodiments, disclosed herein include FXR agonists that modulate one or more of the proteins or genes associated with a metabolic process such as bile acid synthesis, glucose metabolism, lipid metabolism, or insulin sensitivity, such as for example, increase in the activity of FGF19 (FGF15 in mouse), increase in the secretion of GLP-1, or increase in the secretion of PYY.

Metabolic Disorders

Disclosed herein, in certain embodiments, are methods of treating a metabolic disorder in a subject in need thereof. Also described herein include methods of preventing a metabolic disorder in a subject in need thereof. In some instances, these methods include administering to the subject in need thereof a therapeutically effective amount of one or more of the compounds disclosed herein. In some instances, the one or more compounds disclosed herein are absorbed in the gastrointestinal (GI) tract. In additional instances, the one or more disclosed compounds absorbed in the GI tract activates FXR receptors thereby treating or preventing a metabolic disorder in the subject.

In some embodiments, the disclosed compounds demonstrate systemic exposure. In some instances, the disclosed compounds have local exposure in the intestines, but limited exposure in the liver or systemically. In some embodiments, local exposure of the disclosed compounds in the intestines maybe demonstrated by regulation of FXR target genes in the intestines. In some embodiments, the target genes may include: SHP, FGF19 (FGF15), IBABP, $C_3$, OST $\alpha/\beta$. In some embodiments, exposure of the disclosed compounds is about 40%, 50%, 55%, 60%, 65%, 70%, 75%, 80%, 85%, 90%, 95%, 99%, 99.5%, or more in the intestines. In some instances, exposure of the disclosed compounds is about 0.5%, 1%, 5%, 10%, 15%, 20%, 25%, 30%, 40%, 50%, or less in the systemic circulation. In some embodiments, the exposure of the FXR agonists in the intestinal lumen reduces the chance of side effects which results from systemic action, thereby improving the safety profile of the therapy. In additional embodiments, the disclosed compounds enhance FXR target gene expression in the intestines. In additional embodiments, the disclosed compounds further modulate gene expressions in the FXR-mediated pathway, such as for example, FGF19 (FGF15) which inhibits CYP7A1 and CYP8B1 gene expression in the liver. In some instances, the disclosed compounds enhance gene expression in the FXR-mediated pathway. In other instances, the disclosed compounds reduce or inhibit gene expression in the FXR-mediated pathway. In some instances, enhancing is about 1%, 5%, 10%, 15%, 20%, 25%, 30%, 40%, 50%, 60%, 70%, 80%, 90%, 100%, 200%, 300%, 500%, 1,000%, 5,000%, 10,000%, 50,000%, 100,000%, 500,000%, or higher in gene expression in the intestines, liver, kidney, or other tissues relative to the gene expression in the absence of the disclosed compound. In some cases, reducing is about 100%, 90%, 80%, 70%, 60%, 50%, 40%, 30%, 25%, 20%, 15%, 10%, 5%, 1%, or less in gene expression in the intestines, liver, kidney, or other tissues relative to the gene expression in the absence of the disclosed compound.

In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound.

In some embodiments, metabolic disorder refers to any disorder that involves an alteration in the normal metabolism of carbohydrates, lipids, proteins, nucleic acids or a combination thereof. In some instances, a metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, oxyntomodulin, PYY or the like), or the neural control system (e.g., GLP-1 in the brain). Exemplary metabolic disorders include, but are not limited to, diabetes, insulin resistance, dyslipidemia, liver disease, inflammation related intestinal conditions, cell proliferative disorders, or the like.

Diabetes Mellitus and Diabetes-Related Conditions or Disorders

In some embodiments, disclosed herein are methods of treating a subject having diabetes mellitus or diabetes-related condition or disorder with administration of an FXR agonist described herein. In some instances, diabetes is type II diabetes or non-insulin-dependent diabetes mellitus (NIDDM). In some instances, diabetes-related conditions or disorders include obesity, impaired glucose tolerance, dyslipidemia, and insulin resistance. In some instances, diabetes-related conditions or disorders further include secondary complications such as atherosclerosis, stroke, fatty liver disease, blindness, gallbladder disease, or polycystic ovary disease. In some cases, an FXR agonist is administered for the treatment of type II diabetes, obesity, impaired glucose tolerance, dyslipidemia, insulin resistance, or secondary complications such as atherosclerosis, stroke, fatty liver disease, blindness, gallbladder disease, or polycystic ovary disease.

In some embodiments, a diabetic subject (e.g., a type II diabetic subject) is further characterized with a body mass index (BMI) of 25 or greater, 30 or greater, 35 or greater, 40 or greater, such as a BMI of 25 to 29, 30 to 34, or 35 to 40.

In some examples, an FXR agonist described herein reduces or prevents weight gain in a subject. In some instances, the weight gain is diet-induced weight gain. In other instances, the weight gain is non-diet-related, such as familial/genetic obesity or obesity resulting from medication. In some examples, such methods reduce or prevent weight gain in the subject by at least 5%, at least 10%, at least 15%, at least 20%, at least 30%, at least 40%, at least 50%, or more. In some instances, weight gain is reduced or prevented by about 5% to about 50%, by about 5% to about 25%, by about 10% to about 20%, or by about 10% to about 30%. In some cases, the reduction or prevention of weight gain is relative to the reduction or prevention of weight gain observed in a subject not treated with the FXR agonist.

Similarly, in some cases, the FXR agonist reduces the BMI of a subject. In some examples, such methods reduce the BMI of a subject by at least 5%, at least 10%, at least 15%, at least 20%, at least 25%, at least 30%, or more, relative to a subject not treated with the FXR agonist. In some instances, the subject is overweight but not obese. In other instances, the subject is neither overweight nor obese.

In some instances, administration of an FXR agonist results in a decrease in the amount of serum lipids. In some examples, the decrease in the amount of serum lipids is by at least 5%, at least 10%, at least 15%, at least 20%, at least 30%, at least 50%, at least 60%, at least 70%, at least 75%, or more. In some cases, the decrease in the amount of serum lipids is by about 5% to about 50%, by about 5% to about 25%, by about 10% to about 20%, by about 10% to about 70%, or by about 10% to about 30%. In some cases, the decrease in the amount of serum lipids is relative to the amount of serum lipids observed in a subject not treated with the FXR agonist.

In some examples, administration of an FXR agonist results in a decrease in triglyceride (e.g., hepatic triglyceride) level. In some instances, the decrease in triglyceride (e.g., hepatic triglyceride) level is by at least 5%, at least 10%, at least 15%, at least 20%, at least 30%, at least 50%, at least 60%, at least 70%, at least 75%, or more. In some instances, the decrease in triglyceride (e.g, hepatic triglyceride) level is by about 5% to about 50%, by about 5% to about 25%, by about 10% to about 20%, by about 10% to about 70%, or by about 10% to about 30%. In some cases, the decrease in triglyceride (e.g, hepatic triglyceride) level is relative to the triglyceride (e.g., hepatic triglyceride) level observed in a subject not treated with the FXR agonist.

In some examples, administration of an FXR agonist results in an increased insulin sensitivity to insulin in the liver. In some instances, the increase in insulin sensitivity is by at least 5%, at least 10%, at least 15%, at least 20%, at least 30%, at least 40%, at least 50%, or more. In some cases, the increase in insulin sensitivity is by about 5% to about 50%, by about 5% to about 25%, by about 10% to about 20%, or by about 10% to about 30%. In some cases, the increase in insulin sensitivity is relative to sensitivity observed in a subject not treated with the FXR agonist.

In some embodiments, administration of an FXR agonist results in a decrease in the amount of serum insulin in the subject. In some examples, the decrease in serum insulin is by at least 5%, at least 10%, at least 15%, at least 20%, at least 30%, at least 50%, at least 60%, at least 70%, at least 75%, or more. In some instances, serum insulin is decreased by about 5% to about 50%, by about 5% to about 25%, by about 10% to about 20%, by about 10% to about 70%, or by about 10% to about 30%. In some cases, the decrease in serum insulin level is relative to levels observed in a subject not treated with the FXR agonist.

In some embodiments, administration of an FXR agonist results in a decrease in the amount of serum glucose in the subject. In some examples, the decrease in serum glucose is by at least 5%, at least 10%, at least 15%, at least 20%, at least 30%, at least 50%, at least 60%, at least 70%, at least 75%, or more. In some instances, serum glucose is decreased by about 5% to about 50%, by about 5% to about 25%, by about 10% to about 20%, by about 10% to about 70%, or by about 10% to about 30%. In some cases, the decrease in serum glucose level is relative to levels observed in a subject not treated with the FXR agonist.

In some examples, an FXR agonist described herein increases browning of white adipose tissue in a subject. In some examples, the rate of increase of browning of white adipose tissue in the subject is by at least 5%, at least 10%, at least 15%, at least 20%, at least 30%, at least 40%, at least 50%, or more, relative to a subject not treated with the FXR agonist.

In some embodiments, administration of an FXR agonist does not result in substantial change in food intake and/or fat consumption in the subject. In some instances, food intake and/or fat consumption is reduced, such as by less than 15%, less than 10%, or less than 5%. In some embodiments, no substantial change in appetite in the subject results. In other embodiments, reduction in appetite is minimal as reported by the subject.

In some embodiments, administration of an FXR agonist results in an increase in the metabolic rate in the subject. In some instances, the FXR agonist increases the metabolic rate in a subject. In some cases, the metabolic rate in the subject is increased by at least 5%, at least 10%, at least 15%, at least 20%, at least 30%, at least 40%, at least 50%, at least 60%, at least 70%, at least 75%, or more. In some instances, the metabolic rate is increased by about 5% to about 50%, by about 5% to about 25%, by about 10% to about 20%, by about 10% to about 70%, or by about 10% to about 30%. In some cases, the increase in metabolic rate is relative to the rate observed in a subject not treated with the FXR agonist.

In some embodiments, the increase in metabolism results from enhanced oxidative phosphorylation in the subject, which in turn leads to increased energy expenditure in tissues (such as BAT). In such instances, the FXR agonist helps to increase the activity of BAT. In some examples, the activity of BAT is increased by at least 5%, at least 10%, at least 15%, at least 20%, at least 30%, at least 50%, at least 60%, at least 70%, at least 75%, or more. In some instances, the activity of BAT is increased by about 5% to about 50%, by about 5% to about 25%, by about 10% to about 20%, by about 10% to about 70%, or by about 10% to about 30%. In some cases, the increase in BAT activity is relative to the activity of BAT observed in a subject not treated with the FXR agonist.

Alcoholic and Non-Alcoholic Liver Disease or Condition

Disclosed herein include methods of preventing and/or treating alcoholic or non-alcoholic liver diseases or conditions. Exemplary alcoholic or non-alcoholic liver diseases or conditions include, but are not limited to cholestasis, cirrhosis, steatosis, alcoholic hepatitis, non-alcoholic steatohepatitis (NASH), non-alcoholic fatty liver disease (NAFLD), primary sclerosing cholangitis (PSC), elevated liver enzymes, and elevated triglyceride levels. In some embodiments, an FXR agonist is used in the prevention or treatment of alcoholic or non-alcoholic liver diseases. In some embodiments, an FXR agonist is used in the prevention or treatment of cholestasis, cirrhosis, steatosis, alcoholic hepatitis, non-alcoholic steatohepatitis (NASH), non-alcoholic fatty liver disease (NAFLD), or primary sclerosing cholangitis (PSC).

Cholestasis

In some embodiments, an FXR agonist disclosed herein is used in the treatment of cholestasis in a subject. Cholestasis is an impairment or cessation in the flow of bile, which in some cases, causes hepatotoxicity due to the buildup of bile acids and other toxins in the liver. In some instances, cholestasis is a component of many liver diseases, including cholelithiasis, cholestasis of pregnancy, primary biliary cirrhosis (PBC), and primary sclerosing cholangitis (PSC). In some instances, the obstruction is due to gallstone, biliary trauma, drugs, one or more additional liver diseases, or to cancer. In some cases, the enterohepatic circulation of bile acids enables the absorption of fats and fat-soluble vitamins from the intestine and allows the elimination of cholesterol, toxins, and metabolic by-products such as bilirubin from the liver. In some cases, activation of FXR induces expression of the canalicular bile transporters BSEP (ABCB11) and multi drug resistance-related protein 2 (MRP2; ABCC2, cMOAT), and represses genes involved in bile acid biosynthesis, such as for example sterol 12α-hydroxylase (CYP8B1) and CYP7A1.

In some examples, the FXR agonist reduces cholestasis in the subject by at least 5%, at least 10%, at least 15%, at least 20%, at least 30%, at least 40%, at least 50%, or more. In some cases, cholestasis is reduced by about 5% to about 50%, by about 5% to about 25%, by about 10% to about 20%, or by about 10% to about 30%. In some instances, the level of cholestasis is relative to the level of cholestasis in a subject not treated with the FXR agonist.

Primary Biliary Cirrhosis and Cirrhosis

In some embodiments, an FXR agonist disclosed herein is used in the treatment of primary biliary cirrhosis (PBC) in a subject. PBC is a liver disease that primarily results from autoimmune destruction of the bile ducts that transport bile acids (BAs) out of the liver, resulting in cholestasis. As PBC progresses, persistent toxic buildup of BAs causes progressive liver damage. Chronic inflammation and fibrosis can advance to cirrhosis. In some examples, the FXR agonist reduces PBC in the subject by at least 5%, at least 10%, at least 15%, at least 20%, at least 30%, at least 40%, at least 50%, or more. In some cases, PBC is reduced by about 5% to about 50%, by about 5% to about 25%, by about 10% to about 20%, or by about 10% to about 30%. In some instances, the level of PBC is relative to the level of PBC in a subject not treated with the FXR agonist.

In some embodiments, an FXR agonist disclosed herein reduces cirrhosis in a subject. In some examples, the FXR agonist reduces cirrhosis in the subject by at least 5%, at least 10%, at least 15%, at least 20%, at least 30%, at least 40%, at least 50%, or more. In some cases, cirrhosis is reduced by about 5% to about 50%, by about 5% to about 25%, by about 10% to about 20%, or by about 10% to about 30%. In some instances, the level of cirrhosis is relative to the level of cirrhosis in a subject not treated with the FXR agonist.

Non-Alcoholic Fatty Liver Disease and Non-Alcoholic Steatohepatitis

Non-alcoholic fatty liver disease (NAFLD) is associated with excessive fat in the liver (steatosis) and in some cases progresses to NASH, which is defined by the histologic hallmarks of inflammation, cell death, and fibrosis. In some instances, primary NASH is associated with insulin resistance, while secondary NASH is caused by medical or surgical conditions, or drugs such as, but not limited to, tamoxifen. In some cases, NASH progresses to advanced fibrosis, hepatocellular carcinoma, or end-stage liver disease requiring liver transplantation.

In some instances, NASH develops as a result of triglyceride (TGs) imbalance. For example, dysfunctional adipocytes secrete pro-inflammatory molecules such as cytokines and chemokines leading to insulin resistance and a failure of lipolysis suppression in the adipocytes. In some instances, this failure of lipolysis suppression leads to a release of free fatty acids (FFAs) into the circulation and uptake within the liver. In some cases, over accumulation of FFAs in the form of triglycerides (TGs) in lipid droplets leads to oxidative stress, mitochondrial dysfunction, and upregulation of pro-inflammatory molecules.

In some instances, activation of FXR inhibits triglyceride (TG)/fatty acid (FA) synthesis facilitated by suppressing sterol regulatory element-binding protein 1c (SREBP1c) via activation of SHP. In some cases, FXR additionally increases the clearance of TG by stimulating lipoprotein lipase (LPL) activity as well as the hepatic uptake of remnants and low-density lipoprotein by inducing syndecan 1 (SDC1) and the VLDL receptor (VLDLR).

In some embodiments, an FXR agonist disclosed herein is used in the treatment of non-alcoholic steatohepatitis (NASH). In some examples, the FXR agonist reduces NASH the subject by at least 5%, at least 10%, at least 15%, at least 20%, at least 30%, at least 40%, at least 50%, or more. In some cases, NASH is reduced by about 5% to about 50%, by about 5% to about 25%, by about 10% to about 20%, or by about 10% to about 30%. In some instances, the level of NASH is relative to the level of NASH in a subject not treated with the FXR agonist.

In some embodiments, an FXR agonist disclosed herein is used in the treatment of NAFLD. In some examples, the FXR agonist reduces NAFLD in the subject by at least 5%, at least 10%, at least 15%, at least 20%, at least 30%, at least 40%, at least 50%, or more. In some cases, NAFLD is reduced by about 5% to about 50%, by about 5% to about 25%, by about 10% to about 20%, or by about 10% to about 30%. In some instances, the level of NAFLD is relative to the level of NAFLD in a subject not treated with the FXR agonist.

Steatosis

In some embodiments, an FXR agonist disclosed herein reduces fatty liver (steatosis) in a subject. In some examples, the FXR agonist reduces steatosis in the subject by at least 5%, at least 10%, at least 15%, at least 20%, at least 30%, at least 40%, at least 50%, or more. In some instances, steatosis is reduced by about 5% to about 50%, by about 5% to about 25%, by about 10% to about 20%, or by about 10% to about 30%. In some instances, the level of steatosis is relative to the level of steatosis in a subject not treated with the FXR agonist.

Ballooning

Hepatocyte ballooning, a feature denoting cellular injury, is a feature of NASH. Ballooning is a feature that denotes progressive NAFL (types 3 and 4). The term applies to enlarged, swollen-appearing hepatocytes; the affected cells are often intermixed in areas of steatosis and, in classic steatohepatitis, in the perivenular regions. Hepatocellular ballooning is most commonly noted in regions of H & E-detectable perisinusoidal fibrosis. Ballooned hepatocytes are most easily noted when they contain MH (either typical or poorly formed). Hepatocyte ballooning is a structural manifestation of microtubular disruption and severe cell injury.

In some embodiments, an FXR agonist disclosed herein reduces liver ballooning in a subject. In some examples, the FXR agonist reduces liver ballooning in the subject by at least 5%, at least 10%, at least 15%, at least 20%, at least 30%, at least 40%, at least 50%, or more. In some instances, liver ballooning is reduced by about 5% to about 50%, by about 5% to about 25%, by about 10% to about 20%, or by about 10% to about 30%. In some instances, the liver ballooning is relative to the level of liver ballooning in a subject not treated with the FXR agonist.

Alcoholic Hepatitis

In some embodiments, an FXR agonist disclosed herein reduces alcoholic hepatitis in a subject. In some examples, the FXR agonist reduces alcoholic hepatitis in the subject by at least 5%, at least 10%, at least 15%, at least 20%, at least 30%, at least 40%, at least 50%, or more. In some instances, the level of alcoholic hepatitis is reduced by about 5% to about 50%, by about 5% to about 25%, by about 10% to about 20%, or by about 10% to about 30%. In some instances, the level of alcoholic hepatitis is relative to the level of alcoholic hepatitis in a subject not treated with the FXR agonist.

Primary Sclerosing Cholangitis

In some embodiments, an FXR agonist disclosed herein is used in the treatment of primary sclerosing cholangitis (PSC). PSC is a chronic and progressive cholestatic liver disease. PSC is characterized by progressive inflammation, fibrosis, and stricture formation in liver ducts. Common symptoms include pruritus and jaundice. The disease is strongly associated with inflammatory bowel disease (IBD)—about 5% of patients with ulcerative colitis will have PSC. Up to 70% of patients with PSC also have IBD, most commonly ulcerative colitis.

Additional Alcoholic and Non-Alcoholic Liver Diseases or Conditions

In some embodiments, an FXR agonist disclosed herein reduces liver enzymes in a subject. In some examples, the FXR agonist reduce liver enzymes (e.g., serum ALT and/or AST levels) in the subject by at least 5%, at least 10%, at least 15%, at least 20%, at least 30%, at least 40%, at least 50%, or more. In some instances, the level of liver enzymes is reduced by about 5% to about 50%, by about 5% to about 25%, by about 10% to about 20%, or by about 10% to about 30%. In some instances, the level of liver enzymes is relative to the level of liver enzymes in a subject not treated with the FXR agonist.

In some embodiments, an FXR agonist disclosed herein reduces liver triglycerides in a subject. In some examples, the FXR agonist reduces liver triglycerides in the subject by at least 5%, at least 10%, at least 15%, at least 20%, at least 30%, at least 40%, at least 50%, or more. In some instances, the level of liver triglycerides is reduced by about 5% to about 50%, by about 5% to about 25%, by about 10% to about 20%, or by about 10% to about 30%. In some instances, the level of liver triglycerides is relative to the level of liver triglycerides in a subject not treated with the FXR agonist.

Inflammatory Intestinal Condition

Disclosed herein are methods of treating or preventing an inflammatory intestinal condition. Exemplary inflammatory conditions include necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, an FXR agonist disclosed herein is administered to a subject having an inflammatory intestinal condition. In some embodiments, an FXR agonist disclosed herein is administered to a subject having necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection.

In some embodiments, an FXR agonist disclosed herein reduces inflammation of the intestines in a subject (such as a human). In some examples, the FXR agonist reduces intestinal inflammation in the subject by at least 5%, at least 10%, at least 15%, at least 20%, at least 30%, at least 40%, at least 50%, or more. In some instances, intestinal inflammation is reduced by about 5% to about 50%, by about 5% to about 25%, by about 10% to about 20%, or by about 10% to about 30%. In some instances, the level of intestinal inflammation is relative to the level of intestinal inflammation in a subject not treated with the FXR agonist.

Gastrointestinal Diseases

Disclosed herein, in certain embodiments, are methods of treating or preventing a gastrointestinal disease in a subject in need thereof, comprising administering to the subject a farnesoid X receptor (FXR) agonist as described herein. In some embodiments, the gastrointestinal disease is irritable bowel syndrome (IBS), irritable bowel syndrome with diarrhea (IBS-D), irritable bowel syndrome with constipation (IBS-C), mixed IBS (IBS-M), unsubtyped IBS (IBS-U), or bile acid diarrhea (BAD).

Irritable Bowel Syndrome

Irritable bowel syndrome (IBS) is a combination of symptoms including abdominal pain and changes in bowel movement patterns that persists over an extended period of time, often years. The causes of IBS remain unclear; however, gut motility problems, food sensitivity, genetic factors, small intestinal bacterial overgrowth, and gut-brain axis problems are thought to have a potential role. In some instances, IBS is accompanied with diarrhea and is categorized as IBS with diarrhea (IBS-D). In some instances, IBS is accompanied with constipation and is categorized as IBS with constipation (IBS-C). In some instances, IBS is accompanied with an alternating pattern of diarrhea and constipation and is categorized as mixed IBS (IBS-M). In some instances, IBS is not accompanied with either diarrhea or constipation and is categorized as unsubtyped IBS (IBS-U). In some instances, IBS has four different variations: IBS-D, IBS-C, IBS-M, and IBS-U.

In some embodiments, the symptoms of IBS are mimicked by a different condition. In some embodiments, sugar maldigestion, celiac disease, gluten intolerance without celiac disease, pancreatic exocrine insufficiency, small bowel bacterial overgrowth, microscopic colitis, or bile acid malabsorption (BAM) mimic IBS-D. In some embodiments, anismus, pelvic floor dyssynergia or puborectalis spasm, or descending perineum syndrome mimic IBS-C.

In some embodiments, an FXR agonist disclosed herein is used in the treatment of IBS or any of its variations in a mammal. In some examples, an FXR agonist therapeutic agent reduce IBS symptoms in the mammal by at least 5%, at least 10%, at least 15%, at least 20%, at least 30%, at least 40%, at least 50%, or more.

Bile Acid Malabsorption

Bile acid malabsorption (BAM), also known as bile acid diarrhea (BAD), bile acid-induced diarrhea, cholerheic or choleretic enteropathy, or bile salt malabsorption, is a condition in which the presence of bile acids in the colon causes diarrhea. BAM is caused by a number of conditions such as Crohn's disease, cholecystectomy, coeliac disease, radiotherapy, and pancreatic diseases. In some instances, BAM is caused by medications such as metformin. In some embodiments, BAM is caused by an overproduction of bile acids. Bile acid synthesis is negatively regulated by the ileal hormone fibroblast growth factor 19 (FGF-19); low levels of FGF-19 lead to an increase in bile acids. FXR activation promotes the synthesis of FGF-19, consequently lowering the levels of bile acids.

In some embodiments, an FXR agonist disclosed herein is used in the treatment of BAM in a mammal. In some embodiments, an FXR agonist disclosed herein decreases bile acid synthesis. In some embodiments, an FXR agonist disclosed herein decreases bile acid levels. In some embodiments, an FXR agonist and an additional therapeutic agent disclosed herein prevent BAD. In some examples, an FXR agonist reduces BAM symptoms in the mammal by at least 5%, at least 10%, at least 15%, at least 20%, at least 30%, at least 40%, at least 50%, or more.

Graft vs. Host Disease (GvHD)

Graft vs. host disease (GvHD) is a medical complication that arises after a transplant of tissue or cells from a histo-incompatible donor (i.e. a genetically or immunologically different donor). Immune cells in the donated tissue or cells (graft) recognize the recipient (the host) as foreign and initiate and attack. Non-limiting examples of transplanted tissue or cells that give rise to GvHD are blood products, stem cells such as bone marrow cells, and organs. There are different types of GvHD depending on where the symptoms manifest or develop: skin GvHD, liver GvHD, eye GvHD, neuromuscular GvHD, genitourinary tract GvHD, and gastrointestinal (GI) tract GvHD. Symptoms of GI tract GvHD include difficulty swallowing, pain with swallowing, weight loss, nausea, vomiting, diarrhea, and/or abdominal cramping. GI tract GvHD results in sloughing of the mucosal membrane and severe intestinal inflammation. Inflammation of the biliary epithelium is amenable to be controlled by nuclear receptors such as the glucocorticoid receptor (GR), FXR, or the peroxisome proliferator-activated receptors (PPARs).

In some embodiments, an FXR agonist disclosed herein is used in the treatment of GvHD or a complication of GvHD in a mammal. In some embodiments, an FXR agonist disclosed herein is used in the treatment of GI tract GvHD or a complication of GI tract GvHD in a mammal. In some examples, an FXR agonist reduces GI tract GvHD or a complication of GI tract GvHD in the mammal by at least 5%, at least 10%, at least 15%, at least 20%, at least 30%, at least 40%, at least 50%, or more. In some cases, GI tract GvHD or a complication of GI tract GvHD is reduced by about 5% to about 50%, by about 5% to about 25%, by about 10% to about 20%, or by about 10% to about 30%. In some embodiments, an FXR agonist disclosed herein decreases intestinal inflammation caused by GI tract GvHD. In some embodiments, an FXR agonist disclosed herein reduces intestinal inflammation caused by GI tract GvHD reduced by about 5% to about 50%, by about 5% to about 25%, by about 10% to about 20%, or by about 10% to about 30%.

Kidney Diseases

Disclosed herein, in certain embodiments, are methods of treating or preventing a kidney disease in a subject in need thereof, comprising administering to the subject a farnesoid X receptor (FXR) agonist described herein. In some embodiments, the kidney disease is associated with a liver disease. In some embodiments, the kidney disease is associated with a fibrotic liver disease. In some embodiments, the kidney disease is associated with a metabolic liver disease. In some embodiments, the kidney disease is associated with a metabolic condition such as but not limited to diabetes, metabolic syndrome, NAFLD, insulin resistance, fatty acid metabolism disorder, and cholestasis. In some embodiments, the kidney disease is diabetic nephropathy, kidney disease associated with fibrosis, kidney disease not associated with fibrosis, renal fibrosis, or any combination thereof.

Diabetic Nephropathy

Diabetic nephropathy is a kidney disease characterized by damage to the kidney's glomeruli. Diabetes contributes to an excessive production of reactive oxygen species, which leads to nephrotic syndrome and scarring of the glomeruli. As diabetic nephropathy progresses, the glomerular filtration barrier (GFB) is increasingly damaged and consequently, proteins in the blood leak through the barrier and accumulate in the Bowman's space.

In some embodiments, an FXR agonist disclosed herein is used in the treatment of diabetic nephropathy in a mammal.

Renal Fibrosis

Renal fibrosis is characterized by activation of fibroblasts and excessive deposition of extracellular matrix or connective tissue in the kidney, which is a hallmark of chronic kidney disease. FXR plays an important role in protecting against renal fibrosis. Activation of FXR suppresses renal fibrosis and decreases accumulation of extracellular matrix proteins in the kidney.

In some embodiments, an FXR agonist disclosed herein is used in the treatment of renal fibrosis in a mammal.

In one aspect, described herein is a method of treating or preventing a kidney disease or condition in a mammal, comprising administering to the mammal an FXR agonist disclosed herein, or a pharmaceutically acceptable salt or solvate thereof. In some embodiments, the kidney disease or condition is diabetic nephropathy, kidney disease associated with fibrosis, kidney disease not associated with fibrosis, renal fibrosis, kidney disease associated with a metabolic disease, chronic kidney disease, polycystic kidney disease, acute kidney disease, or any combination thereof.

Cell Proliferation Disease

Further disclosed herein are methods of preventing or treating cell proliferation diseases, for example, in certain types of cancer. In some embodiments, the FXR agonists disclosed herein are used in the prevention or treatment of adenocarcinomas, or a carcinoma derived from glandular tissue or in which the tumor cells form recognizable glandular structures. In some embodiments, adenocarcinomas are classified according to the predominant pattern of cell arrangement, as papillary, alveolar, or according to a particular product of the cells, as mucinous adenocarcinoma. In some instances, adenocarcinomas are observed for example, in colon, kidney, breast, cervix, esophagus, gastric, pancreas, prostate, or lung.

In some embodiments, the compounds disclosed herein are used in the prevention or treatment of a cancer of the intestine, such as colon cancer, e.g., cancer that forms in the tissues of the colon (the longest part of the large intestine), or a cancer of another part of the intestine, such as the jejunum, and/or ileum. In some instances, colon cancer is also referred to as "colorectal cancer." In some instances, the most common type of colon cancer is colon adenocarcinoma.

In some cases, cancer progression is characterized by stages, or the extent of cancer in the body. Staging is usually based on the size of the tumor, the presence of cancer in the lymph nodes, and the presence of the cancer in a site other than the primary cancer site. Stages of colon cancer include stage I, stage II, stage III, and stage IV. In some embodiments, colon adenocarcinoma is from any stage. In other embodiments, colon adenocarcinoma is a stage I cancer, a stage II cancer, or a stage III cancer.

In some embodiments, an FXR agonist described herein is administered to a subject having a stage I, stage II, stage III, or stage IV cancer. In some instances, an FXR agonist described herein is administered to a subject having a stage I, stage II, or stage III colon adenocarcinoma.

In some embodiments, an FXR agonist disclosed herein further reduces the tumor burden in a subject. In some examples, the FXR agonist reduces tumor burden (such as colon tumor burden) in the subject by at least 5%, at least 10%, at least 15%, at least 20%, at least 30%, at least 40%, at least 50%, or more. In some instances, tumor burden is reduced by about 5% to about 50%, by about 5% to about 25%, by about 10% to about 20%, or by about 10% to about 30%. In some instances, the level of tumor burden is relative to the level of tumor burden in a subject not treated with the FXR agonist.

In some instances, an FXR agonist disclosed herein further reduces tumor size and/or volume in a subject. In some cases, the FXR agonist reduces tumor size and/or volume (such as a colon tumor) in the subject by at least 5%, at least 10%, at least 15%, at least 20%, at least 30%, at least 40%, at least 50%, or more. In some instances, tumor size is reduced by about 5% to about 50%, by about 5% to about 25%, by about 10% to about 20%, or by about 10% to about 30%. In some instances, the tumor size is relative to the tumor size in a subject not treated with the FXR agonist.

In additional embodiments, an FXR agonist disclosed herein reduces effects of cachexia due to a tumor in a subject. In some examples, the FXR agonist reduces the effect of cachexia (such as due to a colon tumor) in the subject by at least 5%, at least 10%, at least 15%, at least 20%, at least 30%, at least 40%, at least 50%, or more. In some instances, the effect of cachexia is reduced by about 5% to about 50%, by about 5% to about 25%, by about 10% to about 20%, or by about 10% to about 30%. In some instances, the effect of cachexia is relative to the effect of cachexia in a subject not treated with the FXR agonist.

In other embodiments, an FXR agonist disclosed herein increases survival rates of a subject with a tumor. In some cases, the FXR agonist increases the survival rate of a subject with a tumor (such as a colon cancer) in the subject by at least 5%, at least 10%, at least 15%, at least 20%, at least 30%, at least 40%, at least 50%, or more. In some instances, survival rate is increased by about 5% to about 50%, by about 5% to about 25%, by about 10% to about 20%, or by about 10% to about 30%. In some instances, the survival rate is relative to the survival rate in a subject not treated with the FXR agonist.

Compounds

Compounds described herein, including pharmaceutically acceptable salts, prodrugs, active metabolites and pharmaceutically acceptable solvates thereof, are farnesoid X receptor agonists.

In some embodiments is a compound of Formula (I'), or a pharmaceutically acceptable salt or solvate thereof:

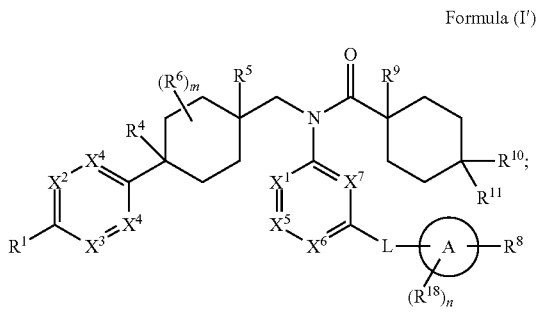

Formula (I')

wherein:

ring A is a 5-membered heteroaryl that is oxazolyl, thiazolyl, pyrazolyl, furanyl, thienyl, pyrrolyl, imidazolyl, triazolyl, tetrazolyl, isoxazolyl, isothiazolyl, oxadiazolyl, or thiadiazolyl;

or ring A is a 6-membered heteroaryl that is pyridinyl, pyrimidinyl, pyrazinyl, pyridazinyl, or triazinyl;

$X^1$, $X^5$, $X^6$, and $X^7$ are each independently $CR^7$ or N; wherein at least one of $X^1$, $X^5$, $X^6$, and $X^7$ are $CR^7$;

$R^1$ is selected from Fl, halogen, —CN, —OH, —N($R^{17}$)$_2$, —NR$^{17}$S(=O)$_2$(C$_1$-C$_4$alkyl), —S(=O)$_2$N(R$^{17}$)$_2$, —OC(=O)(C$_1$-C$_4$alkyl), —CO$_2$H, —CO$_2$(C$_1$-C$_4$alkyl), —C(=O)N(R$^{17}$)$_2$, —NR$^{17}$C(=O)(C$_1$-C$_4$alkyl), —NR$^{17}$C(=O)O(C$_1$-C$_4$alkyl), —OC(=O)N(R$^{17}$)$_2$, —NR$^{15}$C(=O)N(R$^{17}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, and monocyclic C$_2$-C$_5$heterocycloalkyl;

$X^2$ is $CR^2$ or N;

$R^2$ is H, halogen, —CN, —OH, —N(R$^{17}$)$_2$, —NR$^{17}$S(=O)$_2$(C$_1$-C$_4$alkyl), —S(=O)$_2$N(R$^{17}$)$_2$, —OC(=O)(C$_1$-C$_4$alkyl), —CO$_2$H, —CO$_2$(C$_1$-C$_4$alkyl), —C(=O)N(R$^{17}$)$_2$, —NR$^{17}$C(=O)(C$_1$-C$_4$alkyl), —NR$^{17}$C(=O)O(C$_1$-C$_4$alkyl), —OC(=O)N(R$^{17}$)$_2$, —NR$^{17}$C(=O)N(R$^{17}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, or monocyclic C$_2$-C$_5$heterocycloalkyl;

or $R^1$ and $R^2$ are taken together with the intervening atoms to form a fused 5- or 6-membered ring with 0-3 N atoms and 0-2 O or S atoms in the ring, wherein the fused 5- or 6-membered ring is optionally substituted with halogen or C$_1$-C$_4$alkyl;

$X^3$ is $CR^3$ or N;

$R^3$ is H, halogen, —CN, —OH, —N(R$^{17}$)$_2$, —NR$^{17}$S(=O)$_2$(C$_1$-C$_4$alkyl), —OC(=O)(C$_1$-C$_4$alkyl), —CO$_2$H, —CO$_2$(C$_1$-C$_4$alkyl), —C(=O)N(R$^{17}$)$_2$, —NR$^{17}$C(=O)(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, or C$_1$-C$_4$heteroalkyl;

each $X^4$ is independently CH, CF, or N;

$R^4$ is H, F, or —CH$_3$;

$R^5$ is H, F, or —CH$_3$;

or $R^4$ and $R^5$ are taken together to form a bridge that is —CH$_2$— or —CH$_2$CH$_2$—;

each $R^6$ is independently H, F, —OH, or —CH$_3$;

L is absent, —Y$^2$-L$^1$-, -L$^1$-Y$^2$—, cyclopropylene, cyclobutylene, or bicyclo[1.1.1]pentylene;

$Y^2$ is absent, —O—, —S—, —S(=O)—, —S(=O)$_2$—, —S(=O)$_2$NR$^{17}$—, —CH$_2$—, —CH=CH—, —C≡C—, —C(=O)—, —C(=O)O—, —OC(=O)—, —OC(=O)O—, —C(=O)NR$^{17}$—, —NR$^{17}$C(=O)—, —OC(=O)NR$^{17}$—, —NR$^{17}$C(=O)O—, —NR$^{17}$C(=O)NR$^{17}$—, —NR$^{17}$S(=O)$_2$—, or —NR$^{17}$—;

$L^1$ is absent or C$_1$-C$_4$alkylene;

each $R^7$ is independently selected from H, halogen, —CN, —OH, C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_3$-C$_6$cycloalkyl, and C$_1$-C$_4$heteroalkyl;

$R^8$ is C$_4$-C$_8$alkyl or C$_4$-C$_8$haloalkyl;

$R^9$ is H, F, or —CH$_3$;

$R^{10}$ is —OC(=O)N(R$^{12}$)(R$^{13}$), —N(R$^{16}$)C(=O)R$^{14}$, or —N(R$^{16}$)C(=O)OR$^{15}$;

$R^{11}$ is H, F, or —CH$_3$;

$R^{12}$ is —C$_1$-C$_6$alkyl-OR$^{17}$ or monocyclic C$_2$-C$_5$heterocycloalkyl optionally substituted with one or two oxo groups;

$R^{13}$ is H or C$_1$-C$_4$alkyl; or $R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N(C$_1$-C$_4$alkyl)$_2$, C$_1$-C$_6$alkyl, C$_1$-C$_6$alkoxy, —S(C$_1$-C$_4$alkyl), —S(=O)(C$_1$-C$_4$alkyl), —S(=O)$_2$(C$_1$-C$_4$alkyl), —C$_1$-C$_4$alkyl-S(=O)$_2$(C$_1$-C$_4$alkyl), —C$_1$-C$_6$alkyl-OR$^{17}$, and —O—C$_1$-C$_6$alkyl-OR$^{17}$;

$R^{14}$ is C$_1$-C$_6$alkyl, C$_3$-C$_6$cycloalkyl, or —C$_1$-C$_6$alkyl-OR$^{17}$;

$R^{15}$ is C$_1$-C$_6$alkyl, —C$_1$-C$_6$alkyl-OR$^{17}$, C$_3$-C$_6$cycloalkyl, or C$_2$-C$_6$heterocycloalkyl;

$R^{16}$ is H or C$_1$-C$_6$alkyl;

each $R^{17}$ is independently H or C$_1$-C$_6$alkyl;

each $R^{18}$ is independently halogen, —CN, —OH, —N(R$^{17}$)$_2$, —NR$^{17}$S(=O)$_2$(C$_1$-C$_4$alkyl), —S(C$_1$-C$_4$alkyl), —S(=O)(C$_1$-C$_4$alkyl), —S(=O)$_2$(C$_1$-C$_4$alkyl), —S(=O)$_2$N(R$^{17}$)$_2$, —C(=O)(C$_1$-C$_4$alkyl), —OC(=O)(C$_1$-C$_4$alkyl), —CO$_2$H, —CO$_2$(C$_1$-C$_4$alkyl), —NR$^{17}$C(=O)(C$_1$-C$_4$alkyl), —C(=O)N(R$^{17}$)$_2$, —NR$^{17}$C(=O)O(C$_1$-C$_4$alkyl), —OC(=O)N(R$^{17}$)$_2$, C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, monocyclic C$_2$-C$_6$heterocycloalkyl, phenyl, or monocyclic heteroaryl;

m is 0, 1, or 2; and n is 0, 1, or 2.

In some embodiments is a compound of Formula (I') having the structure of Formula (Ia'), or a pharmaceutically acceptable salt or solvate thereof:

Formula (Ia')

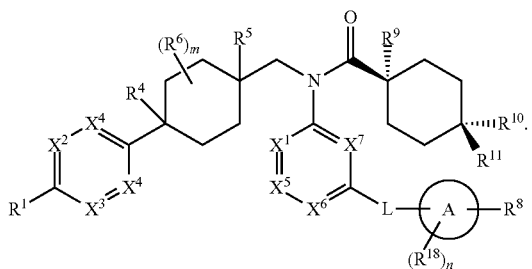

In some embodiments is a compound of Formula (I') or (Ia'), or a pharmaceutically acceptable salt or solvate thereof, wherein $X^1$ is N, and $X^5$, $X^6$, and $X^7$ are CH. In some embodiments is a compound of Formula (I') or (Ia'), or a pharmaceutically acceptable salt or solvate thereof, wherein $X^5$ is N, and $X^1$, $X^6$, and $X^7$ are CH. In some embodiments is a compound of Formula (I') or (Ia'), or a pharmaceutically acceptable salt or solvate thereof, wherein $X^6$ is N, and $X^1$, $X^5$, and $X^7$ are CH. In some embodiments is a compound of Formula (I') or (Ia'), or a pharmaceutically acceptable salt or solvate thereof, wherein $X^7$ is N, and $X^1$, $X^5$, and $X^6$ are CH. In some embodiments is a compound of Formula (I') or (Ia'), or a pharmaceutically acceptable salt or solvate thereof, wherein $X^1$ and $X^6$ are N, and $X^5$ and $X^7$ are CH. In some embodiments is a compound of Formula (I') or (Ia'), or a pharmaceutically acceptable salt or solvate thereof, wherein $X^1$ and $X^7$ are N, and $X^5$ and $X^6$ are CH. In some embodiments is a compound of Formula (I') or (Ia'), or a pharmaceutically acceptable salt or solvate thereof, wherein $X^1$, $X^5$, $X^6$, and $X^7$ are CH.

In some embodiments is a compound of Formula (I') or (Ia'), or a pharmaceutically acceptable salt or solvate thereof, wherein n is 0.

In some embodiments is a compound of Formula (I') or (Ia'), or a pharmaceutically acceptable salt or solvate thereof, wherein ring A is

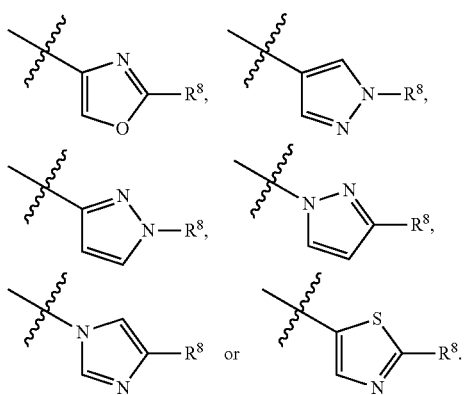

In some embodiments is a compound of Formula (I') or (Ia'), or a pharmaceutically acceptable salt or solvate thereof, wherein ring A is

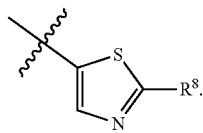

In some embodiments is a compound of Formula (I') or (Ia'), or a pharmaceutically acceptable salt or solvate thereof, wherein ring A is

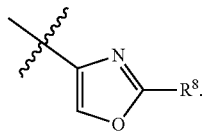

In some embodiments is a compound of Formula (I') or (Ia'), or a pharmaceutically acceptable salt or solvate thereof, wherein ring A is

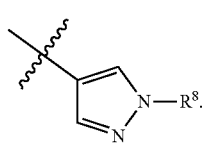

In some embodiments is a compound of Formula (I') or (Ia'), or a pharmaceutically acceptable salt or solvate thereof, wherein ring A is

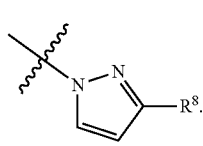

In some embodiments is a compound of Formula (I') or (Ia'), or a pharmaceutically acceptable salt or solvate thereof, wherein ring A is

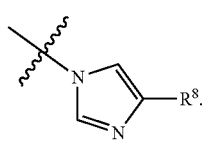

In some embodiments is a compound of Formula (I') or (Ia'), or a pharmaceutically acceptable salt or solvate thereof, wherein ring A is

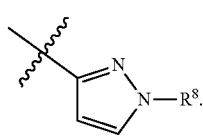

In some embodiments is a compound of Formula (I') or (Ia'), or a pharmaceutically acceptable salt or solvate thereof, wherein $R^8$ is $C_4$-$C_8$alkyl. In some embodiments is a compound of Formula (I') or (Ia'), or a pharmaceutically acceptable salt or solvate thereof, wherein $R^8$ is —C(CH$_3$)$_3$. In some embodiments is a compound of Formula (I') or (Ia'), or a pharmaceutically acceptable salt or solvate thereof, wherein $R^8$ is —C(CH$_2$CH$_3$)$_3$. In some embodiments is a compound of Formula (I') or (Ia'), or a pharmaceutically acceptable salt or solvate thereof, wherein $R^8$ is —C(CH$_2$CH$_3$)$_2$CH$_3$. In some embodiments is a compound of Formula (I') or (Ia'), or a pharmaceutically acceptable salt or solvate thereof, wherein $R^8$ is —C(CH$_3$)$_2$CH$_2$CH$_3$. In some embodiments is a compound of Formula (I') or (Ia'), or a pharmaceutically acceptable salt or solvate thereof, wherein $R^8$ is $C_1$-$C_8$haloalkyl. In some embodiments is a compound of Formula (I') or (Ia'), or a pharmaceutically acceptable salt or solvate thereof, wherein $R^8$ is —C(CH$_3$)$_2$CF$_3$.

In some embodiments is a compound of Formula (I') or (Ia'), or a pharmaceutically acceptable salt or solvate thereof, wherein $R^4$ is H and $R^5$ is H. In some embodiments is a compound of Formula (I') or (Ia'), or a pharmaceutically acceptable salt or solvate thereof, wherein $R^4$ and $R^5$ are taken together to form a bridge that is —CH$_2$CH$_2$—. In some embodiments is a compound of Formula (I') or (Ia'), or a pharmaceutically acceptable salt or solvate thereof, wherein $R^4$ and $R^5$ are taken together to form a bridge that is —CH$_2$—.

In some embodiments is a compound of Formula (I') or (Ia'), or a pharmaceutically acceptable salt or solvate thereof, wherein m is 0 or 1. In some embodiments is a compound of Formula (I') or (Ia'), or a pharmaceutically acceptable salt or solvate thereof, wherein m is 0. In some embodiment is a compound of Formula (I') or (Ia'), or a pharmaceutically acceptable salt or solvate thereof, wherein m is 1. In some embodiments is a compound of Formula (I') or (Ia'), or a pharmaceutically acceptable salt or solvate thereof, wherein m is 2.

In some embodiments is a compound of Formula (I') or (Ia'), or a pharmaceutically acceptable salt or solvate thereof, wherein $R^{10}$ is —OC(=O)N($R^{12}$)($R^{13}$). In some embodiments is a compound of Formula (I') or (Ia'), or a pharmaceutically acceptable salt or solvate thereof, wherein $R^{12}$ and $R^{13}$ are taken together to form a 4-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (I') or (Ia'), or a pharmaceutically acceptable salt or solvate thereof, wherein $R^{12}$ and $R^{13}$ are taken together to form a 4-membered heterocycloalkyl ring optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (I') or (Ia'), or a pharmaceutically acceptable salt or solvate thereof, wherein $R^{10}$ is

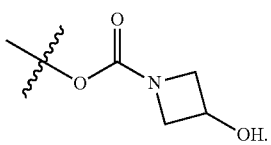 [SMILES: *OC(=O)N1CC(O)C1]

In some embodiments is a compound of Formula (I') or (Ia'), or a pharmaceutically acceptable salt or solvate thereof, wherein $R^{12}$ and $R^{13}$ are taken together to form a 5-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (I') or (Ia'), or a pharmaceutically acceptable salt or solvate thereof, wherein $R^{10}$ is

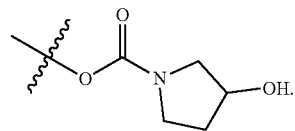 [SMILES: *OC(=O)N1CCC(O)C1]

In some embodiments is a compound of Formula (I') or (Ia'), or a pharmaceutically acceptable salt or solvate thereof, wherein $R^{12}$ and $R^{13}$ are taken together to form a 6-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (I') or (Ia'), or a pharmaceutically acceptable salt or solvate thereof, wherein $R^{10}$ is

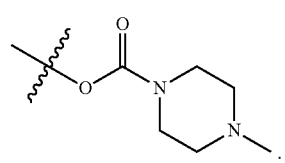 [SMILES: *OC(=O)N1CCN(C)CC1]

In some embodiments is a compound of Formula (I') or (Ia'), or a pharmaceutically acceptable salt or solvate thereof, wherein $R^{10}$ is —N($R^{16}$)C(=O)$R^{14}$. In some embodiments is a compound of Formula (I') or (Ia'), or a pharmaceutically acceptable salt or solvate thereof, wherein $R^{14}$ is C$_1$-C$_6$alkyl. In some embodiments is a compound of Formula (I') or (Ia'), or a pharmaceutically acceptable salt or solvate thereof, wherein $R^{14}$ is —C$_1$-C$_6$alkyl-O$R^{17}$. In some embodiments is a compound of Formula (I') or (Ia'), or a pharmaceutically acceptable salt or solvate thereof, wherein $R^{14}$ is —C$_1$-C$_6$alkyl-OH. In some embodiments is a compound of Formula (I') or (Ia'), or a pharmaceutically acceptable salt or solvate thereof, wherein $R^{14}$ is —C$_1$-C$_6$alkyl-OCH$_3$.

In some embodiments is a compound of Formula (I') or (Ia'), or a pharmaceutically acceptable salt or solvate thereof, wherein $R^{10}$ is —N($R^{16}$)C(=O)O$R^{15}$. In some embodiments is a compound of Formula (I') or (Ia'), or a pharmaceutically acceptable salt or solvate thereof, wherein $R^{15}$ is C$_1$-C$_6$alkyl. In some embodiments is a compound of Formula (I') or (Ia'), or a pharmaceutically acceptable salt or solvate thereof, wherein $R^{15}$ is —C$_1$-C$_6$alkyl-O$R^{17}$. In some embodiments is a compound of Formula (I') or (Ia'), or a pharmaceutically acceptable salt or solvate thereof, wherein $R^{15}$ is —C$_1$-C$_6$alkyl-OH. In some embodiments is a compound of Formula (I') or (Ia'), or a pharmaceutically acceptable salt or solvate thereof, wherein $R^{15}$ is —C$_1$-C$_6$alkyl-OCH$_3$. In some embodiments is a compound of Formula (I') or (Ia'), or a pharmaceutically acceptable salt or solvate thereof, wherein $R^{15}$ is C$_2$-C$_6$heterocycloalkyl. In some embodiments is a compound of Formula (I') or (Ia'), or a pharmaceutically acceptable salt or solvate thereof, wherein $R^{15}$ is In some embodiments is a compound of Formula (I') or (Ia'), or a pharmaceutically acceptable salt or solvate thereof, wherein $R^{16}$ is H.

In some embodiments is a compound of Formula (I') or (Ia'), or a pharmaceutically acceptable salt or solvate thereof, wherein $R^1$ is H, halogen, —CN, —OH, —N($R^{17}$)$_2$, —S(=O)$_2$($C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I') or (Ia'), or a pharmaceutically acceptable salt or solvate thereof, wherein $R^1$ is H, halogen, —CN, —OH, —N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (F) or (Ia'), or a pharmaceutically acceptable salt or solvate thereof, wherein $R^1$ is H, halogen, —CN, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl. In some embodiments is a compound of Formula (I') or (Ia'), or a pharmaceutically acceptable salt or solvate thereof, wherein $R^1$ is H, halogen, $C_1$-$C_4$alkyl, $C_1$-$C_4$alkoxy, or $C_1$-$C_4$fluoroalkyl. In some embodiments is a compound of Formula (I') or (Ia'), or a pharmaceutically acceptable salt or solvate thereof, wherein $R^1$ is $C_1$-$C_4$alkyl, $C_1$-$C_4$alkoxy, or $C_1$-$C_4$fluoroalkyl. In some embodiments is a compound of Formula (I') or (Ia'), or a pharmaceutically acceptable salt or solvate thereof, wherein $R^1$ is $C_1$-$C_4$alkyl or $C_1$-$C_4$alkoxy. In some embodiments is a compound of Formula (I') or (Ia'), or a pharmaceutically acceptable salt or solvate thereof, wherein $R^1$ is H. In some embodiments is a compound of Formula (I') or (Ia'), or a pharmaceutically acceptable salt or solvate thereof, wherein $R^1$ is halogen. In some embodiments is a compound of Formula (I') or (Ia'), or a pharmaceutically acceptable salt or solvate thereof, wherein $R^1$ is —F. In some embodiments is a compound of Formula (I') or (Ia'), or a pharmaceutically acceptable salt or solvate thereof, wherein $R^1$ is —Cl. In some embodiments is a compound of Formula (I') or (Ia'), or a pharmaceutically acceptable salt or solvate thereof, wherein $R^1$ is $C_1$-$C_4$alkyl. In some embodiments is a compound of Formula (I') or (Ia'), or a pharmaceutically acceptable salt or solvate thereof, wherein $R^1$ is —CH$_3$. In some embodiments is a compound of Formula (I') or (Ia'), or a pharmaceutically acceptable salt or solvate thereof, wherein $R^1$ is $C_1$-$C_4$alkoxy. In some embodiments is a compound of Formula (I') or (Ia'), or a pharmaceutically acceptable salt or solvate thereof, wherein $R^1$ is —OCH$_3$. In some embodiments is a compound of Formula (I') or (Ia'), or a pharmaceutically acceptable salt or solvate thereof, wherein $R^1$ is $C_1$-$C_4$fluoroalkyl. In some embodiments is a compound of Formula (I') or (Ia'), or a pharmaceutically acceptable salt or solvate thereof, wherein $R^1$ is —CF$_3$.

In some embodiments is a compound of Formula (I') or (Ia'), or a pharmaceutically acceptable salt or solvate thereof, wherein one $X^4$ is CH and one $X^4$ is N. In some embodiments is a compound of Formula (I') or (Ia'), or a pharmaceutically acceptable salt or solvate thereof, wherein each $X^4$ is CH. In some embodiments is a compound of Formula (F) or (Ia'), or a pharmaceutically acceptable salt or solvate thereof, wherein one $X^4$ is CF and one $X^4$ is N. In some embodiments is a compound of Formula (F) or (Ia'), or a pharmaceutically acceptable salt or solvate thereof, wherein one $X^4$ is CF and one $X^4$ is CH. In some embodiments is a compound of Formula (I') or (Ia'), or a pharmaceutically acceptable salt or solvate thereof, wherein each $X^4$ is CF.

In some embodiments is a compound of Formula (I') or (Ia'), or a pharmaceutically acceptable salt or solvate thereof, wherein $X^3$ is $CR^3$. In some embodiments is a compound of Formula (I') or (Ia'), or a pharmaceutically acceptable salt or solvate thereof, wherein $X^3$ is CH. In some embodiments is a compound of Formula (I') or (Ia'), or a pharmaceutically acceptable salt or solvate thereof, wherein $X^3$ is N.

In some embodiments is a compound of Formula (I') or (Ia'), or a pharmaceutically acceptable salt or solvate thereof, wherein $X^2$ is $CR^2$. In some embodiments is a compound of Formula (I') or (Ia'), or a pharmaceutically acceptable salt or solvate thereof, wherein $X^2$ is $CR^2$ and $R^2$ is halogen, —CN, —OH, —N($R^{17}$)$_2$, —S(=O)$_2$($C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I') or (Ia'), or a pharmaceutically acceptable salt or solvate thereof, wherein $X^2$ is $CR^2$ and $R^2$ is halogen, —CN, —OH, —N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I') or (Ia'), or a pharmaceutically acceptable salt or solvate thereof, wherein $X^2$ is $CR^2$ and $R^2$ is halogen, —CN, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl. In some embodiments is a compound of Formula (I') or (Ia'), or a pharmaceutically acceptable salt or solvate thereof, wherein $X^2$ is $CR^2$ and $R^2$ is halogen, $C_1$-$C_4$alkyl, $C_1$-$C_4$alkoxy, or $C_1$-$C_4$fluoroalkyl. In some embodiments is a compound of Formula (I') or (Ia'), or a pharmaceutically acceptable salt or solvate thereof, wherein $X^2$ is $CR^2$ and $R^2$ is halogen or $C_1$-$C_4$alkyl. In some embodiments is a compound of Formula (I') or (Ia'), or a pharmaceutically acceptable salt or solvate thereof, wherein $X^2$ is $CR^2$ and $R^2$ is halogen. In some embodiments is a compound of Formula (I') or (Ia'), or a pharmaceutically acceptable salt or solvate thereof, wherein $X^2$ is $CR^2$ and $R^2$ is —F. In some embodiments is a compound of Formula (I') or (Ia'), or a pharmaceutically acceptable salt or solvate thereof, wherein $X^2$ is $CR^2$ and $R^2$ is —Cl. In some embodiments is a compound of Formula (F) or (Ia'), or a pharmaceutically acceptable salt or solvate thereof, wherein $X^2$ is $CR^2$ and $R^2$ is $C_1$-$C_4$alkyl. In some embodiments is a compound of Formula (F) or (Ia'), or a pharmaceutically acceptable salt or solvate thereof, wherein $X^2$ is $CR^2$ and $R^2$ is —CH$_3$. In some embodiments is a compound of Formula (I') or (Ia'), or a pharmaceutically acceptable salt or solvate thereof, wherein $X^2$ is $CR^2$ and $R^2$ is $C_1$-$C_4$alkoxy. In some embodiments is a compound of Formula (I') or (Ia'), or a pharmaceutically acceptable salt or solvate thereof, wherein $X^2$ is $CR^2$ and $R^2$ is —OCH$_3$. In some embodiments is a compound of Formula (I') or (Ia'), or a pharmaceutically acceptable salt or solvate thereof, wherein $X^2$ is $CR^2$ and $R^2$ is $C_1$-$C_4$fluoroalkyl. In some embodiments is a compound of Formula (I') or (Ia'), or a pharmaceutically acceptable salt or solvate thereof, wherein $X^2$ is $CR^2$ and $R^2$ is —$CF_3$.

In some embodiments is a compound of Formula (I') or (Ia'), or a pharmaceutically acceptable salt or solvate thereof, wherein $X^2$ is N.

In some embodiments is a compound of Formula (I') or (Ia'), or a pharmaceutically acceptable salt or solvate thereof, wherein each $R^7$ is H.

In some embodiments is a compound of Formula (I') or (Ia'), or a pharmaceutically acceptable salt or solvate thereof, wherein L is absent.

In some embodiments is a compound of Formula (I') or (Ia'), or a pharmaceutically acceptable salt or solvate thereof, wherein $R^9$ is H.

In some embodiments is a compound of Formula (I') or (Ia'), or a pharmaceutically acceptable salt or solvate thereof, wherein $R^{11}$ is H.

In some embodiments is a compound of Formula (I), or a pharmaceutically acceptable salt or solvate thereof:

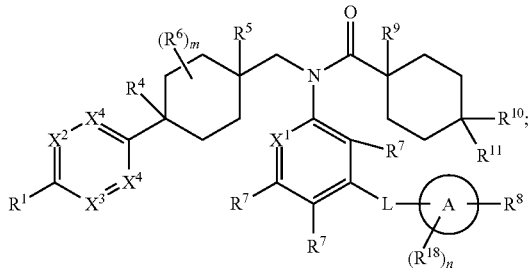

Formula (I)

wherein:
ring A is a 5-membered heteroaryl that is oxazolyl, thiazolyl, pyrazolyl, furanyl, thienyl, pyrrolyl, imidazolyl, triazolyl, tetrazolyl, isoxazolyl, isothiazolyl, oxadiazolyl, or thiadiazolyl;
or ring A is a 6-membered heteroaryl that is pyridinyl, pyrimidinyl, pyrazinyl, pyridazinyl, or triazinyl;
$X^1$ is C(H), C(F), or N;
$R^1$ is selected from H, halogen, —CN, —OH, —N($R^{17}$)$_2$, —$NR^{17}S(=O)_2(C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, —$NR^{15}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, and monocyclic $C_2$-$C_5$heterocycloalkyl;
$X^2$ is $CR^2$ or N;
$R^2$ is H, halogen, —CN, —OH, —N($R^{17}$)$_2$, —$NR^{17}S(=O)_2(C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, —$NR^{17}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl;
or $R^1$ and $R^2$ are taken together with the intervening atoms to form a fused 5- or 6-membered ring with 0-3 N atoms and 0-2 O or S atoms in the ring, wherein the fused 5- or 6-membered ring is optionally substituted with halogen or $C_1$-$C_4$alkyl;
$X^3$ is $CR^3$ or N;
$R^3$ is H, halogen, —CN, —OH, —N($R^{17}$)$_2$, —$NR^{17}S(=O)_2(C_1$-$C_4$alkyl), —OC(=O)($C_1$-$C_4$alkyl), —CO$_2$H, —CO$_2$($C_1$-$C_4$alkyl), —C(=O)N($R^{17}$)$_2$, —$NR^{17}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;
each $X^4$ is independently CH or N;
$R^4$ is H, F, or —CH$_3$;
$R^5$ is H, F, or —CH$_3$;
or $R^4$ and $R^5$ are taken together to form a bridge that is —CH$_2$— or —CH$_2$CH$_2$—;
each $R^6$ is independently H, F, —OH, or —CH$_3$;
L is absent, —$Y^2$-$L^1$-, -$L^1$-$Y^2$—, cyclopropylene, cyclobutylene, or bicyclo[1.1.1]pentylene;
$Y^2$ is absent, —O—, —S—, —S(=O)—, —S(=O)$_2$—, —S(=O)$_2$NR$^{17}$—, —CH$_2$—, —CH=CH—, —C≡C—, —C(=O)—, —C(=O)O—, —OC(=O)—, —OC(=O)O—, —C(=O)NR$^{17}$—, —NR$^{17}$C(=O)—, —OC(=O)NR$^{17}$—, —NR$^{17}$C(=O)O—, —NR$^{17}$C(=O)NR$^{17}$—, —NR$^{17}$S(=O)$_2$—, or —NR$^{17}$—;
$L^1$ is absent or $C_1$-$C_4$alkylene;
each $R^7$ is independently selected from H, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, and $C_1$-$C_4$heteroalkyl;
$R^8$ is $C_4$-$C_8$alkyl or $C_4$-$C_8$haloalkyl;
$R^9$ is H, F, or —CH$_3$;
$R^{10}$ is —OC(=O)N($R^{12}$)($R^{13}$), —N($R^{16}$)C(=O)$R^{14}$, or —N($R^{16}$)C(=O)O$R^{15}$;
$R^{11}$ is H, F, or —CH$_3$;
$R^{12}$ is —$C_1$-$C_6$alkyl-OR$^{17}$ or monocyclic $C_2$-$C_5$heterocycloalkyl optionally substituted with one or two oxo groups;
$R^{13}$ is H or $C_1$-$C_4$alkyl; or $R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N($C_1$-$C_4$alkyl)$_2$, $C_1$-$C_6$alkyl, $C_1$-$C_6$alkoxy, —S($C_1$-$C_4$alkyl), —S(=O)($C_1$-$C_4$alkyl), —S(=O)$_2$($C_1$-$C_4$alkyl), —$C_1$-$C_4$alkyl-S(=O)$_2$($C_1$-$C_4$alkyl), —$C_1$-$C_6$alkyl-OR$^{17}$, and —O—$C_1$-$C_6$alkyl-OR$^{17}$;
$R^{14}$ is $C_1$-$C_6$alkyl or —$C_1$-$C_6$alkyl-OR$^{17}$;
$R^{15}$ is $C_1$-$C_6$alkyl, —$C_1$-$C_6$alkyl-OR$^{17}$, or $C_2$-$C_6$heterocycloalkyl;
$R^{16}$ is H or $C_1$-$C_6$alkyl;
each $R^{17}$ is independently H or $C_1$-$C_6$alkyl;
each $R^{18}$ is independently halogen, —CN, —OH, —N($R^{17}$)$_2$, —$NR^{17}S(=O)_2(C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N($R^{17}$)$_2$, —C(=O)($C_1$-$C_4$alkyl), —OC(=O)($C_1$-$C_4$alkyl), —CO$_2$H, —CO$_2$($C_1$-$C_4$alkyl), —$NR^{17}$C(=O)($C_1$-$C_4$alkyl), —C(=O)N($R^{17}$)$_2$, —$NR^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, $C_3$-$C_6$cycloalkyl, monocyclic $C_2$-$C_6$heterocycloalkyl, phenyl, or monocyclic heteroaryl;

m is 0, 1, or 2; and
n is 0, 1, or 2.

In some embodiments is a compound of Formula (I) having the structure of Formula (Ia), or a pharmaceutically acceptable salt or solvate thereof:

Formula (Ia)

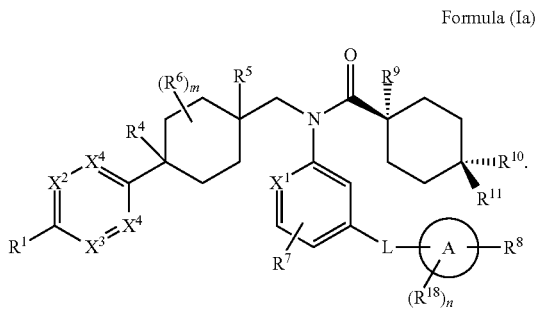

In some embodiments is a compound of Formula (I) or (Ia), or a pharmaceutically acceptable salt or solvate thereof, wherein n is 0.

In some embodiments is a compound of Formula (I) or (Ia), or a pharmaceutically acceptable salt or solvate thereof, wherein ring A is

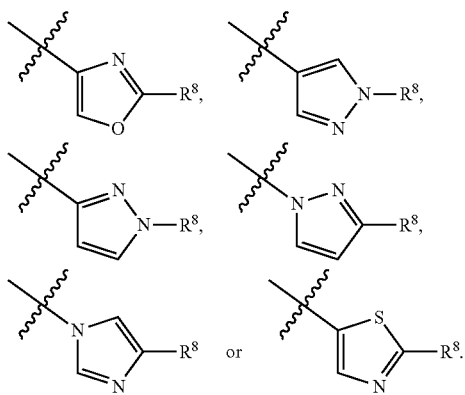

In some embodiments is a compound of Formula (I) or (Ia), or a pharmaceutically acceptable salt or solvate thereof, wherein ring A is

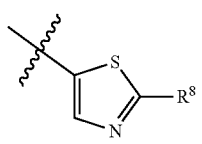

In some embodiments is a compound of Formula (I) or (Ia), or a pharmaceutically acceptable salt or solvate thereof, wherein ring A is

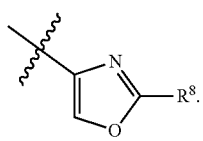

In some embodiments is a compound of Formula (I) or (Ia), or a pharmaceutically acceptable salt or solvate thereof, wherein ring A is

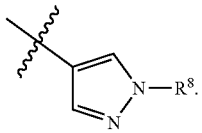

In some embodiments is a compound of Formula (I) or (Ia), or a pharmaceutically acceptable salt or solvate thereof, wherein ring A is

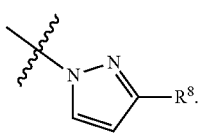

In some embodiments is a compound of Formula (I) or (Ia), or a pharmaceutically acceptable salt or solvate thereof, wherein ring A is

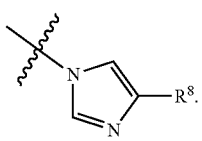

In some embodiments is a compound of Formula (I) or (Ia), or a pharmaceutically acceptable salt or solvate thereof, wherein ring A is

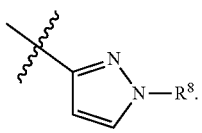

In some embodiments is a compound of Formula (I) or (Ia), or a pharmaceutically acceptable salt or solvate thereof, wherein $R^8$ is $C_4$-$C_8$alkyl. In some embodiments is a compound of Formula (I) or (Ia), or a pharmaceutically acceptable salt or solvate thereof, wherein $R^8$ is —C(CH$_3$)$_3$. In some embodiments is a compound of Formula (I) or (Ia), or a pharmaceutically acceptable salt or solvate thereof, wherein $R^8$ is —C(CH$_2$CH$_3$)$_3$. In some embodiments is a compound of Formula (I) or (Ia), or a pharmaceutically acceptable salt or solvate thereof, wherein $R^8$ is —C(CH$_2$CH$_3$)$_2$CH$_3$. In some embodiments is a compound of Formula (I) or (Ia), or a pharmaceutically acceptable salt or solvate thereof, wherein $R^8$ is —C(CH$_3$)$_2$CH$_2$CH$_3$. In some embodiments is a compound of Formula (I) or (Ia), or a pharmaceutically acceptable salt or solvate thereof, wherein $R^8$ is $C_1$-$C_8$haloalkyl. In some embodiments is a compound of Formula (I) or (Ia), or a pharmaceutically acceptable salt or solvate thereof, wherein $R^8$ is —C(CH$_3$)$_2$CF$_3$.

In some embodiments is a compound of Formula (I) or (Ia), or a pharmaceutically acceptable salt or solvate thereof, wherein R⁴ is H and R⁵ is H. In some embodiments is a compound of Formula (I) or (Ia), or a pharmaceutically acceptable salt or solvate thereof, wherein R⁴ and R⁵ are taken together to form a bridge that is —CH₂CH₂—. In some embodiments is a compound of Formula (I) or (Ia), or a pharmaceutically acceptable salt or solvate thereof, wherein R⁴ and R⁵ are taken together to form a bridge that is —CH₂—.

In some embodiments is a compound of Formula (I) or (Ia), or a pharmaceutically acceptable salt or solvate thereof, wherein m is 0 or 1. In some embodiments is a compound of Formula (I) or (Ia), or a pharmaceutically acceptable salt or solvate thereof, wherein m is 0. In some embodiment is a compound of Formula (I) or (Ia), or a pharmaceutically acceptable salt or solvate thereof, wherein m is 1. In some embodiments is a compound of Formula (I) or (Ia), or a pharmaceutically acceptable salt or solvate thereof, wherein m is 2.

In some embodiments is a compound of Formula (I) or (Ia), or a pharmaceutically acceptable salt or solvate thereof, wherein X¹ is C(H). In some embodiments is a compound of Formula (I) or (Ia), or a pharmaceutically acceptable salt or solvate thereof, wherein X¹ is C(F). In some embodiments is a compound of Formula (I) or (Ia), or a pharmaceutically acceptable salt or solvate thereof, wherein X¹ is N.

In some embodiments is a compound of Formula (I) or (Ia), or a pharmaceutically acceptable salt or solvate thereof, wherein R¹⁰ is —OC(=O)N(R¹²)(R¹³). In some embodiments is a compound of Formula (I) or (Ia), or a pharmaceutically acceptable salt or solvate thereof, wherein R¹² and R¹³ are taken together to form a 4-membered heterocycloalkyl ring optionally containing an additional heteroatom selected from O, S, and N and optionally substituted with 1 or 2 groups selected from —OH, —N(C₁-C₄alkyl)₂, C₁-C₆alkyl, and C₁-C₆alkoxy. In some embodiments is a compound of Formula (I) or (Ia), or a pharmaceutically acceptable salt or solvate thereof, wherein R¹² and R¹³ are taken together to form a 4-membered heterocycloalkyl ring optionally substituted with 1 or 2 groups selected from —OH, —N(C₁-C₄alkyl)₂, C₁-C₆alkyl, and C₁-C₆alkoxy. In some embodiments is a compound of Formula (I) or (Ia), or a pharmaceutically acceptable salt or solvate thereof, wherein R¹⁰ is

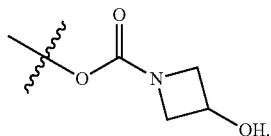 [SMILES: *OC(=O)N1CC(O)C1]

In some embodiments is a compound of Formula (I) or (Ia), or a pharmaceutically acceptable salt or solvate thereof, wherein R¹² and R¹³ are taken together to form a 5-membered heterocycloalkyl ring optionally containing an additional heteroatom selected from O, S, and N and optionally substituted with 1 or 2 groups selected from —OH, —N(C₁-C₄alkyl)₂, C₁-C₆alkyl, and C₁-C₆alkoxy. In some embodiments is a compound of Formula (I) or (Ia), or a pharmaceutically acceptable salt or solvate thereof, wherein R¹⁰ is

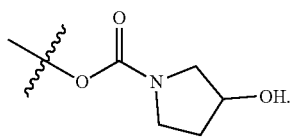 [SMILES: *OC(=O)N1CCC(O)C1]

In some embodiments is a compound of Formula (I) or (Ia), or a pharmaceutically acceptable salt or solvate thereof, wherein R¹² and R¹³ are taken together to form a 6-membered heterocycloalkyl ring optionally containing an additional heteroatom selected from O, S, and N and optionally substituted with 1 or 2 groups selected from —OH, —N(C₁-C₄alkyl)₂, C₁-C₆alkyl, and C₁-C₆alkoxy. In some embodiments is a compound of Formula (I) or (Ia), or a pharmaceutically acceptable salt or solvate thereof, wherein R¹⁰ is

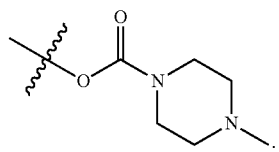 [SMILES: *OC(=O)N1CCN(C)CC1]

In some embodiments is a compound of Formula (I) or (Ia), or a pharmaceutically acceptable salt or solvate thereof, wherein R¹⁰ is —N(R¹⁶)C(=O)R¹⁴. In some embodiments is a compound of Formula (I) or (Ia), or a pharmaceutically acceptable salt or solvate thereof, wherein R¹⁴ is C₁-C₆alkyl. In some embodiments is a compound of Formula (I) or (Ia), or a pharmaceutically acceptable salt or solvate thereof, wherein R¹⁴ is —C₁-C₆alkyl-OR¹⁷. In some embodiments is a compound of Formula (I) or (Ia), or a pharmaceutically acceptable salt or solvate thereof, wherein R¹⁴ is —C₁-C₆alkyl-OH. In some embodiments is a compound of Formula (I) or (Ia), or a pharmaceutically acceptable salt or solvate thereof, wherein R¹⁴ is —C₁-C₆alkyl-OCH₃.

In some embodiments is a compound of Formula (I) or (Ia), or a pharmaceutically acceptable salt or solvate thereof, wherein R¹⁰ is —N(R¹⁶)C(=O)OR¹⁵. In some embodiments is a compound of Formula (I) or (Ia), or a pharmaceutically acceptable salt or solvate thereof, wherein R¹⁵ is C₁-C₆alkyl. In some embodiments is a compound of Formula (I) or (Ia), or a pharmaceutically acceptable salt or solvate thereof, wherein R¹⁵ is —C₁-C₆alkyl-OR¹⁷. In some embodiments is a compound of Formula (I) or (Ia), or a pharmaceutically acceptable salt or solvate thereof, wherein R¹⁵ is —C₁-C₆alkyl-OH. In some embodiments is a compound of Formula (I) or (Ia), or a pharmaceutically acceptable salt or solvate thereof, wherein R¹⁵ is —C₁-C₆alkyl-OCH₃. In some embodiments is a compound of Formula (I) or (Ia), or a pharmaceutically acceptable salt or solvate thereof, wherein R¹⁵ is C₂-C₆heterocycloalkyl. In some embodiments is a compound of Formula (I) or (Ia), or a pharmaceutically acceptable salt or solvate thereof, wherein R¹⁵ is

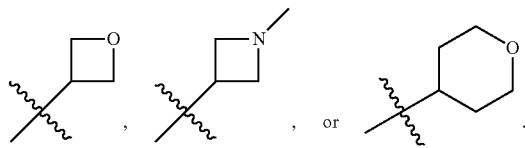

In some embodiments is a compound of Formula (I) or (Ia), or a pharmaceutically acceptable salt or solvate thereof, wherein R¹⁶ is H.

In some embodiments is a compound of Formula (I) or (Ia), or a pharmaceutically acceptable salt or solvate thereof, wherein R¹ is H, halogen, —CN, —OH, —N(R¹⁷)₂, —S(=O)₂(C₁-C₄alkyl), —S(=O)₂N(R¹⁷)₂, —OC(=O)

($C_1$-$C_4$alkyl), —$CO_2H$, —$CO_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I) or (Ia), or a pharmaceutically acceptable salt or solvate thereof, wherein $R^1$ is H, halogen, —CN, —OH, —N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I) or (Ia), or a pharmaceutically acceptable salt or solvate thereof, wherein $R^1$ is H, halogen, —CN, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl. In some embodiments is a compound of Formula (I) or (Ia), or a pharmaceutically acceptable salt or solvate thereof, wherein $R^1$ is H, halogen, $C_1$-$C_4$alkyl, $C_1$-$C_4$alkoxy, or $C_1$-$C_4$fluoroalkyl. In some embodiments is a compound of Formula (I) or (Ia), or a pharmaceutically acceptable salt or solvate thereof, wherein $R^1$ is $C_1$-$C_4$alkyl, $C_1$-$C_4$alkoxy, or $C_1$-$C_4$fluoroalkyl. In some embodiments is a compound of Formula (I) or (Ia), or a pharmaceutically acceptable salt or solvate thereof, wherein $R^1$ is $C_1$-$C_4$alkyl or $C_1$-$C_4$alkoxy. In some embodiments is a compound of Formula (I) or (Ia), or a pharmaceutically acceptable salt or solvate thereof, wherein $R^1$ is H. In some embodiments is a compound of Formula (I) or (Ia), or a pharmaceutically acceptable salt or solvate thereof, wherein $R^1$ is halogen. In some embodiments is a compound of Formula (I) or (Ia), or a pharmaceutically acceptable salt or solvate thereof, wherein $R^1$ is —F. In some embodiments is a compound of Formula (I) or (Ia), or a pharmaceutically acceptable salt or solvate thereof, wherein $R^1$ is —Cl. In some embodiments is a compound of Formula (I) or (Ia), or a pharmaceutically acceptable salt or solvate thereof, wherein $R^1$ is $C_1$-$C_4$alkyl. In some embodiments is a compound of Formula (I) or (Ia), or a pharmaceutically acceptable salt or solvate thereof, wherein $R^1$ is —$CH_3$. In some embodiments is a compound of Formula (I) or (Ia), or a pharmaceutically acceptable salt or solvate thereof, wherein $R^1$ is $C_1$-$C_4$alkoxy. In some embodiments is a compound of Formula (I) or (Ia), or a pharmaceutically acceptable salt or solvate thereof, wherein $R^1$ is —$OCH_3$. In some embodiments is a compound of Formula (I) or (Ia), or a pharmaceutically acceptable salt or solvate thereof, wherein $R^1$ is $C_1$-$C_4$fluoroalkyl. In some embodiments is a compound of Formula (I) or (Ia), or a pharmaceutically acceptable salt or solvate thereof, wherein $R^1$ is —$CF_3$.

In some embodiments is a compound of Formula (I) or (Ia), or a pharmaceutically acceptable salt or solvate thereof, wherein one $X^4$ is CH and one $X^4$ is N. In some embodiments is a compound of Formula (I) or (Ia), or a pharmaceutically acceptable salt or solvate thereof, wherein each $X^4$ is CH.

In some embodiments is a compound of Formula (I) or (Ia), or a pharmaceutically acceptable salt or solvate thereof, wherein $X^3$ is $CR^3$. In some embodiments is a compound of Formula (I) or (Ia), or a pharmaceutically acceptable salt or solvate thereof, wherein $X^3$ is CH. In some embodiments is a compound of Formula (I) or (Ia), or a pharmaceutically acceptable salt or solvate thereof, wherein $X^3$ is N.

In some embodiments is a compound of Formula (I) or (Ia), or a pharmaceutically acceptable salt or solvate thereof, wherein $X^2$ is $CR^2$. In some embodiments is a compound of Formula (I) or (Ia), or a pharmaceutically acceptable salt or solvate thereof, wherein $X^2$ is $CR^2$ and $R^2$ is halogen, —CN, —OH, —N($R^{17}$)$_2$, —S(=O)$_2$($C_1$-$C_4$alkyl), —S(=O)$_2$N($R^{17}$)$_2$, —OC(=O)($C_1$-$C_4$alkyl), —$CO_2H$, —$CO_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I) or (Ia), or a pharmaceutically acceptable salt or solvate thereof, wherein $X^2$ is $CR^2$ and $R^2$ is halogen, —CN, —OH, —N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (I) or (Ia), or a pharmaceutically acceptable salt or solvate thereof, wherein $X^2$ is $CR^2$ and $R^2$ is halogen, —CN, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl. In some embodiments is a compound of Formula (I) or (Ia), or a pharmaceutically acceptable salt or solvate thereof, wherein $X^2$ is $CR^2$ and $R^2$ is halogen, $C_1$-$C_4$alkyl, $C_1$-$C_4$alkoxy, or $C_1$-$C_4$fluoroalkyl. In some embodiments is a compound of Formula (I) or (Ia), or a pharmaceutically acceptable salt or solvate thereof, wherein $X^2$ is $CR^2$ and $R^2$ is halogen or $C_1$-$C_4$alkyl. In some embodiments is a compound of Formula (I) or (Ia), or a pharmaceutically acceptable salt or solvate thereof, wherein $X^2$ is $CR^2$ and $R^2$ is halogen. In some embodiments is a compound of Formula (I) or (Ia), or a pharmaceutically acceptable salt or solvate thereof, wherein $X^2$ is $CR^2$ and $R^2$ is —F. In some embodiments is a compound of Formula (I) or (Ia), or a pharmaceutically acceptable salt or solvate thereof, wherein $X^2$ is $CR^2$ and $R^2$ is —Cl. In some embodiments is a compound of Formula (I) or (Ia), or a pharmaceutically acceptable salt or solvate thereof, wherein $X^2$ is $CR^2$ and $R^2$ is $C_1$-$C_4$alkyl. In some embodiments is a compound of Formula (I) or (Ia), or a pharmaceutically acceptable salt or solvate thereof, wherein $X^2$ is $CR^2$ and $R^2$ is —$CH_3$. In some embodiments is a compound of Formula (I) or (Ia), or a pharmaceutically acceptable salt or solvate thereof, wherein $X^2$ is $CR^2$ and $R^2$ is $C_1$-$C_4$alkoxy. In some embodiments is a compound of Formula (I) or (Ia), or a pharmaceutically acceptable salt or solvate thereof, wherein $X^2$ is $CR^2$ and $R^2$ is —$OCH_3$. In some embodiments is a compound of Formula (I) or (Ia), or a pharmaceutically acceptable salt or solvate thereof, wherein $X^2$ is $CR^2$ and $R^2$ is $C_1$-$C_4$fluoroalkyl. In some embodiments is a compound of Formula (I) or (Ia), or a pharmaceutically acceptable salt or solvate thereof, wherein $X^2$ is $CR^2$ and $R^2$ is —$CF_3$.

In some embodiments is a compound of Formula (I) or (Ia), or a pharmaceutically acceptable salt or solvate thereof, wherein $X^2$ is N.

In some embodiments is a compound of Formula (I) or (Ia), or a pharmaceutically acceptable salt or solvate thereof, wherein each $R^7$ is H.

In some embodiments is a compound of Formula (I) or (Ia), or a pharmaceutically acceptable salt or solvate thereof, wherein L is absent.

In some embodiments is a compound of Formula (I) or (Ia), or a pharmaceutically acceptable salt or solvate thereof, wherein $R^9$ is H.

In some embodiments is a compound of Formula (I) or (Ia), or a pharmaceutically acceptable salt or solvate thereof, wherein $R^{11}$ is H.

In some embodiments, described herein is a compound of Formula (II), or a pharmaceutically acceptable salt or solvate thereof:

Formula (II)

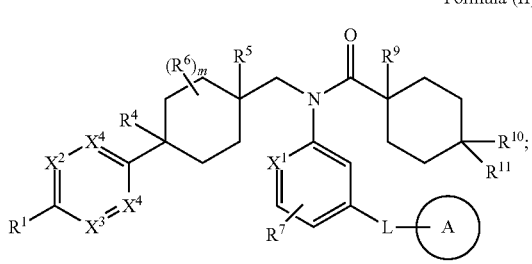

wherein:
ring A is

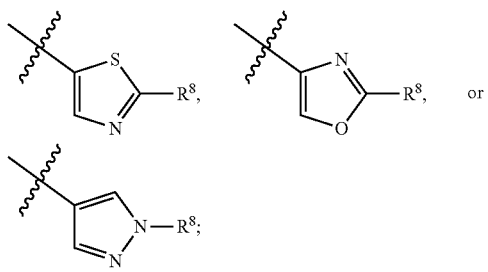

$X^1$ is CH or N;
$R^1$ is H, halogen, —CN, —OH, —N($R^{17}$)$_2$, —$NR^{17}$S(=O)$_2$($C_1$-$C_4$alkyl), —S(=O)$_2$N($R^{17}$)$_2$, —OC(=O)($C_1$-$C_4$alkyl), —$CO_2$H, —$CO_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, —$NR^{15}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl;
$X^2$ is $CR^2$ or N;
$R^2$ is H, halogen, —CN, —OH, —N($R^{17}$)$_2$, —$NR^{17}$S(=O)$_2$($C_1$-$C_4$alkyl), —S(=O)$_2$N($R^{17}$)$_2$, —OC(=O)($C_1$-$C_4$alkyl), —$CO_2$H, —$CO_2$($C_1$-$C_4$alkyl), —C(=O)N($R^{17}$)$_2$, —$NR^{17}$C(=O)($C_1$-$C_4$alkyl), —$NR^{17}$C(=O)O($C_1$-$C_4$alkyl), —OC(=O)N($R^{17}$)$_2$, —$NR^{17}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl;
or $R^1$ and $R^2$ are taken together with the intervening atoms to form a fused 5- or 6-membered ring with 0-3 N atoms and 0-2 O or S atoms in the ring, wherein the fused 5- or 6-membered ring is optionally substituted with halogen or $C_1$-$C_4$alkyl;
$X^3$ is $CR^3$ or N;
$R^3$ is H, halogen, —CN, —OH, —N($R^{17}$)$_2$, —$NR^{17}$S(=O)$_2$($C_1$-$C_4$alkyl), —OC(=O)($C_1$-$C_4$alkyl), —$CO_2$H, —$CO_2$($C_1$-$C_4$alkyl), —C(=O)N($R^{17}$)$_2$, —$NR^{17}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;
each $X^4$ is independently CH or N;

$R^4$ is H, F, or —$CH_3$;
$R^5$ is H, F, or —$CH_3$;
or $R^4$ and $R^5$ are taken together to form a bridge that is —$CH_2$— or —$CH_2CH_2$—;
each $R^6$ is independently H, F, —OH, or —$CH_3$;
$R^7$ is H, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;
L is absent, —$Y^2$-$L^1$-, -$L^1$-$Y^2$—, cyclopropylene, cyclobutylene, or bicyclo[1.1.1]pentylene;
$Y^2$ is absent, —O—, —S—, —S(=O)—, —S(=O)$_2$—, —S(=O)$_2NR^{17}$—, —$CH_2$—, —CH=CH—, —C≡C—, —C(=O)—, —C(=O)O—, —OC(=O)—, —OC(=O)O—, —C(=O)$NR^{17}$—, —$NR^{17}$C(=O)—, —OC(=O)$NR^{17}$—, —$NR^{17}$C(=O)O—, —$NR^{17}$C(=O)$NR^{17}$—, —$NR^{17}$S(=O)$_2$—, or —$NR^{17}$—;
$L^1$ is absent or $C_1$-$C_4$alkylene;
$R^8$ is $C_4$-$C_8$alkyl;
$R^9$ is H, F, or —$CH_3$;
$R^{10}$ is —OC(=O)N($R^{12}$)($R^{13}$), —N($R^{16}$)C(=O)$R^{14}$, or —N($R^{16}$)C(=O)O$R^{15}$;
$R^{11}$ is H, F, or —$CH_3$;
$R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N($C_1$-$C_4$alkyl)$_2$, $C_1$-$C_6$alkyl, and $C_1$-$C_6$alkoxy;
$R^{14}$ is $C_1$-$C_6$alkyl or —$C_1$-$C_6$alkyl-$OR^{17}$;
$R^{15}$ is $C_1$-$C_6$alkyl, —$C_1$-$C_6$alkyl-$OR^{17}$, or $C_2$-$C_6$heterocycloalkyl;
$R^{16}$ is H or $C_1$-$C_6$alkyl;
each $R^{17}$ is independently H or $C_1$-$C_6$alkyl; and
m is 0, 1, or 2.

In some embodiments is a compound of Formula (II) having the structure of Formula (IIa), or a pharmaceutically acceptable salt or solvate thereof:

Formula (IIa)

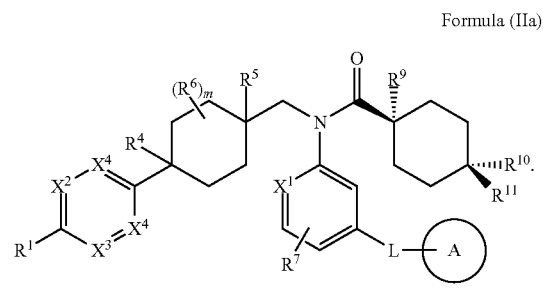

In some embodiments is a compound of Formula (II) or (IIa), or a pharmaceutically acceptable salt or solvate thereof, wherein ring A is

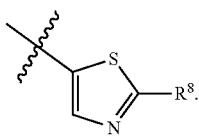

In some embodiments is a compound of Formula (II) or (IIa), or a pharmaceutically acceptable salt or solvate thereof, wherein ring A is

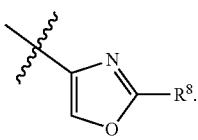

In some embodiments is a compound of Formula (II) or (IIa), or a pharmaceutically acceptable salt or solvate thereof, wherein ring A is

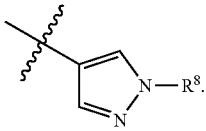

In some embodiments is a compound of Formula (II) or (IIa), or a pharmaceutically acceptable salt or solvate thereof, wherein $R^8$ is —C(CH$_3$)$_3$. In some embodiments is a compound of Formula (II) or (IIa), or a pharmaceutically acceptable salt or solvate thereof, wherein $R^8$ is —CH$_2$C(CH$_3$)$_3$. In some embodiments is a compound of Formula (II) or (IIa), or a pharmaceutically acceptable salt or solvate thereof, wherein $R^8$ is —C(CH$_2$CH$_3$)$_3$. In some embodiments is a compound of Formula (II) or (IIa), or a pharmaceutically acceptable salt or solvate thereof, wherein $R^8$ is —C(CH$_2$CH$_3$)$_2$CH$_3$. In some embodiments is a compound of Formula (II) or (IIa), or a pharmaceutically acceptable salt or solvate thereof, wherein $R^8$ is —C(CH$_3$)$_2$CH$_2$CH$_3$.

In some embodiments is a compound of Formula (II) or (IIa), or a pharmaceutically acceptable salt or solvate thereof, wherein $R^4$ is H and $R^5$ is H. In some embodiments is a compound of Formula (II) or (IIa), or a pharmaceutically acceptable salt or solvate thereof, wherein $R^4$ and $R^5$ are taken together to form a bridge that is —CH$_2$CH$_2$—. In some embodiments is a compound of Formula (II) or (IIa), or a pharmaceutically acceptable salt or solvate thereof, wherein $R^4$ and $R^5$ are taken together to form a bridge that is —CH$_2$—.

In some embodiments is a compound of Formula (II) or (IIa), or a pharmaceutically acceptable salt or solvate thereof, wherein m is 0 or 1. In some embodiments is a compound of Formula (II) or (IIa), or a pharmaceutically acceptable salt or solvate thereof, wherein m is 0. In some embodiment is a compound of Formula (II) or (IIa), or a pharmaceutically acceptable salt or solvate thereof, wherein m is 1. In some embodiments is a compound of Formula (II) or (IIa), or a pharmaceutically acceptable salt or solvate thereof, wherein m is 2.

In some embodiments is a compound of Formula (II) or (IIa), or a pharmaceutically acceptable salt or solvate thereof, wherein $X^1$ is CH. In some embodiments is a compound of Formula (II) or (IIa), or a pharmaceutically acceptable salt or solvate thereof, wherein each $X^1$ is N.

In some embodiments is a compound of Formula (II) or (IIa), or a pharmaceutically acceptable salt or solvate thereof, wherein $R^{10}$ is —OC(=O)N($R^{12}$)($R^{13}$). In some embodiments is a compound of Formula (II) or (IIa), or a pharmaceutically acceptable salt or solvate thereof, wherein $R^{12}$ and $R^{13}$ are taken together to form a 4-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (II) or (IIa), or a pharmaceutically acceptable salt or solvate thereof, wherein $R^{12}$ and $R^{13}$ are taken together to form a 4-membered heterocycloalkyl ring optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (II) or (IIa), or a pharmaceutically acceptable salt or solvate thereof, wherein $R^{10}$ is

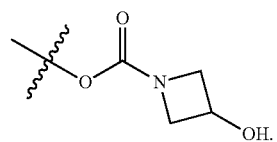 [SMILES: *OC(=O)N1CC(O)C1]

In some embodiments is a compound of Formula (II) or (IIa), or a pharmaceutically acceptable salt or solvate thereof, wherein $R^{12}$ and $R^{13}$ are taken together to form a 5-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (II) or (IIa), or a pharmaceutically acceptable salt or solvate thereof, wherein $R^{12}$ and $R^{13}$ are taken together to form a 6-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy. In some embodiments is a compound of Formula (II) or (IIa), or a pharmaceutically acceptable salt or solvate thereof, wherein $R^{10}$ is

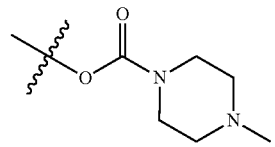

In some embodiments is a compound of Formula (II) or (IIa), or a pharmaceutically acceptable salt or solvate thereof, wherein $R^{10}$ is —N($R^{16}$)C(=O)$R^{14}$. In some embodiments is a compound of Formula (II) or (IIa), or a pharmaceutically acceptable salt or solvate thereof, wherein $R^{14}$ is C$_1$-C$_6$alkyl. In some embodiments is a compound of Formula (II) or (IIa), or a pharmaceutically acceptable salt or solvate thereof, wherein $R^{14}$ is —C$_1$-C$_6$alkyl-O$R^{17}$. In some embodiments is a compound of Formula (II) or (IIa), or a pharmaceutically acceptable salt or solvate thereof, wherein $R^{14}$ is —C$_1$-C$_6$alkyl-OH. In some embodiments is a compound of Formula (II) or (IIa), or a pharmaceutically acceptable salt or solvate thereof, wherein $R^{14}$ is —C$_1$-C$_6$alkyl-OCH$_3$.

In some embodiments is a compound of Formula (II) or (IIa), or a pharmaceutically acceptable salt or solvate thereof, wherein $R^{10}$ is —N($R^{16}$)C(=O)O$R^{15}$. In some embodiments is a compound of Formula (II) or (IIa), or a pharmaceutically acceptable salt or solvate thereof, wherein $R^{15}$ is C$_1$-C$_6$alkyl. In some embodiments is a compound of Formula (II) or (IIa), or a pharmaceutically acceptable salt or solvate thereof, wherein $R^{15}$ is —C$_1$-C$_6$alkyl-O$R^{17}$. In some embodiments is a compound of Formula (II) or (IIa), or a pharmaceutically acceptable salt or solvate thereof, wherein $R^{15}$ is —$C_1$-$C_6$alkyl-OH. In some embodiments is a compound of Formula (II) or (IIa), or a pharmaceutically acceptable salt or solvate thereof, wherein $R^{15}$ is —$C_1$-$C_6$alkyl-OCH$_3$. In some embodiments is a compound of Formula (II) or (IIa), or a pharmaceutically acceptable salt or solvate thereof, wherein $R^{15}$ is $C_2$-$C_6$heterocycloalkyl. In some embodiments is a compound of Formula (II) or (IIa), or a pharmaceutically acceptable salt or solvate thereof, wherein $R^{15}$ is

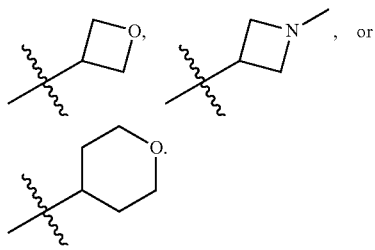

In some embodiments is a compound of Formula (II) or (IIa), or a pharmaceutically acceptable salt or solvate thereof, wherein $R^{16}$ is H.

In some embodiments is a compound of Formula (II) or (IIa), or a pharmaceutically acceptable salt or solvate thereof, wherein $R^1$ is H, halogen, —CN, —OH, —N($R^{17}$)$_2$, —S(=O)$_2$($C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —NR$^{17}$C(=O)($C_1$-$C_4$alkyl), —NR$^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (II) or (IIa), or a pharmaceutically acceptable salt or solvate thereof, wherein $R^1$ is H, halogen, —CN, —OH, —N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (II) or (IIa), or a pharmaceutically acceptable salt or solvate thereof, wherein $R^1$ is H, halogen, —CN, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl. In some embodiments is a compound of Formula (II) or (IIa), or a pharmaceutically acceptable salt or solvate thereof, wherein $R^1$ is H, halogen, $C_1$-$C_4$alkyl, $C_1$-$C_4$alkoxy, or $C_1$-$C_4$fluoroalkyl. In some embodiments is a compound of Formula (II) or (IIa), or a pharmaceutically acceptable salt or solvate thereof, wherein $R^1$ is $C_1$-$C_4$alkyl, $C_1$-$C_4$alkoxy, or $C_1$-$C_4$fluoroalkyl. In some embodiments is a compound of Formula (II) or (IIa), or a pharmaceutically acceptable salt or solvate thereof, wherein $R^1$ is $C_1$-$C_4$alkyl or $C_1$-$C_4$alkoxy. In some embodiments is a compound of Formula (II) or (IIa), or a pharmaceutically acceptable salt or solvate thereof, wherein $R^1$ is H. In some embodiments is a compound of Formula (II) or (IIa), or a pharmaceutically acceptable salt or solvate thereof, wherein $R^1$ is halogen. In some embodiments is a compound of Formula (II) or (IIa), or a pharmaceutically acceptable salt or solvate thereof, wherein $R^1$ is —F. In some embodiments is a compound of Formula (II) or (IIa), or a pharmaceutically acceptable salt or solvate thereof, wherein $R^1$ is —Cl. In some embodiments is a compound of Formula (II) or (IIa), or a pharmaceutically acceptable salt or solvate thereof, wherein $R^1$ is $C_1$-$C_4$alkyl. In some embodiments is a compound of Formula (II) or (IIa), or a pharmaceutically acceptable salt or solvate thereof, wherein $R^1$ is —CH$_3$. In some embodiments is a compound of Formula (II) or (IIa), or a pharmaceutically acceptable salt or solvate thereof, wherein $R^1$ is $C_1$-$C_4$alkoxy. In some embodiments is a compound of Formula (II) or (IIa), or a pharmaceutically acceptable salt or solvate thereof, wherein $R^1$ is —OCH$_3$. In some embodiments is a compound of Formula (II) or (IIa), or a pharmaceutically acceptable salt or solvate thereof, wherein $R^1$ is $C_1$-$C_4$fluoroalkyl. In some embodiments is a compound of Formula (II) or (IIa), or a pharmaceutically acceptable salt or solvate thereof, wherein $R^1$ is —CF$_3$.

In some embodiments is a compound of Formula (II) or (IIa), or a pharmaceutically acceptable salt or solvate thereof, wherein one $X^4$ is CH and one $X^4$ is N. In some embodiments is a compound of Formula (II) or (IIa), or a pharmaceutically acceptable salt or solvate thereof, wherein each $X^4$ is CH.

In some embodiments is a compound of Formula (II) or (IIa), or a pharmaceutically acceptable salt or solvate thereof, wherein $X^3$ is $CR^3$. In some embodiments is a compound of Formula (II) or (IIa), or a pharmaceutically acceptable salt or solvate thereof, wherein $X^3$ is CH. In some embodiments is a compound of Formula (II) or (IIa), or a pharmaceutically acceptable salt or solvate thereof, wherein $X^3$ is N.

In some embodiments is a compound of Formula (II) or (IIa), or a pharmaceutically acceptable salt or solvate thereof, wherein $X^2$ is $CR^2$. In some embodiments is a compound of Formula (II) or (IIa), or a pharmaceutically acceptable salt or solvate thereof, wherein $X^2$ is $CR^2$ and $R^2$ is halogen, —CN, —OH, —N($R^{17}$)$_2$, —S(=O)$_2$($C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —NR$^{17}$C(=O)($C_1$-$C_4$alkyl), —NR$^{17}$C(=O)O($C_1$-$C_4$alkyl), —OC(=O)N($R^{17}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (II) or (IIa), or a pharmaceutically acceptable salt or solvate thereof, wherein $X^2$ is $CR^2$ and $R^2$ is halogen, —CN, —OH, —N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, $C_1$-$C_4$heteroalkyl, or monocyclic $C_2$-$C_5$heterocycloalkyl. In some embodiments is a compound of Formula (II) or (IIa), or a pharmaceutically acceptable salt or solvate thereof, wherein $X^2$ is $CR^2$ and $R^2$ is halogen, —CN, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl. In some embodiments is a compound of Formula (II) or (IIa), or a pharmaceutically acceptable salt or solvate thereof, wherein $X^2$ is $CR^2$ and $R^2$ is halogen, $C_1$-$C_4$alkyl, $C_1$-$C_4$alkoxy, or $C_1$-$C_4$fluoroalkyl. In some embodiments is a compound of Formula (II) or (IIa), or a pharmaceutically acceptable salt or solvate thereof, wherein $X^2$ is $CR^2$ and $R^2$ is halogen or $C_1$-$C_4$alkyl. In some embodiments is a compound of Formula (II) or (IIa), or a pharmaceutically acceptable salt or solvate thereof, wherein $X^2$ is $CR^2$ and $R^2$ is halogen. In some embodiments is a compound of Formula (II) or (IIa), or a pharmaceutically acceptable salt or solvate thereof, wherein $X^2$ is $CR^2$ and $R^2$ is —F. In some embodiments is a compound of Formula (II) or (IIa), or a pharmaceutically acceptable salt or solvate thereof, wherein $X^2$ is $CR^2$ and $R^2$ is —Cl. In some embodiments is a compound of Formula (II) or (IIa), or a pharmaceutically acceptable salt or solvate thereof, wherein $X^2$ is $CR^2$ and $R^2$ is $C_1$-$C_4$alkyl. In some embodiments is a compound of Formula (II) or (IIa), or a pharmaceutically acceptable salt or solvate thereof, wherein $X^2$ is $CR^2$ and $R^2$ is —CH$_3$. In some embodiments is a compound of Formula (II) or (IIa), or a pharmaceutically acceptable salt or solvate thereof, wherein $X^2$ is $CR^2$ and $R^2$ is $C_1$-$C_4$alkoxy. In some embodiments is a compound of Formula (II) or (IIa), or a pharmaceutically acceptable salt or solvate thereof, wherein $X^2$ is $CR^2$ and $R^2$ is —$OCH_3$. In some embodiments is a compound of Formula (II) or (IIa), or a pharmaceutically acceptable salt or solvate thereof, wherein $X^2$ is $CR^2$ and $R^2$ is $C_1$-$C_4$fluoroalkyl. In some embodiments is a compound of Formula (II) or (IIa), or a pharmaceutically acceptable salt or solvate thereof, wherein $X^2$ is $CR^2$ and $R^2$ is —$CF_3$.

In some embodiments is a compound of Formula (II) or (IIa), or a pharmaceutically acceptable salt or solvate thereof, wherein $X^2$ is N.

In some embodiments is a compound of Formula (II) or (IIa), or a pharmaceutically acceptable salt or solvate thereof, wherein $R^7$ is H. In some embodiments is a compound of Formula (II) or (IIa), or a pharmaceutically acceptable salt or solvate thereof, wherein $R^7$ is halogen. In some embodiments is a compound of Formula (II) or (IIa), or a pharmaceutically acceptable salt or solvate thereof, wherein $R^7$ is $C_1$-$C_4$alkyl. In some embodiments is a compound of Formula (II) or (IIa), or a pharmaceutically acceptable salt or solvate thereof, wherein $R^7$ is $C_1$-$C_4$fluoroalkyl.

In some embodiments is a compound of Formula (II) or (IIa), or a pharmaceutically acceptable salt or solvate thereof, wherein L is absent.

In some embodiments is a compound of Formula (II) or (IIa), or a pharmaceutically acceptable salt or solvate thereof, wherein $R^9$ is H.

In some embodiments is a compound of Formula (II) or (IIa), or a pharmaceutically acceptable salt or solvate thereof, wherein $R^{11}$ is H.

In some embodiments is a compound of Formula (III), or a pharmaceutically acceptable salt or solvate thereof:

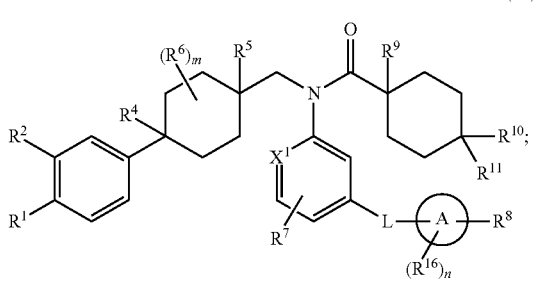

Formula (III)

wherein:
ring A is a 5-membered heteroaryl that is oxazolyl, thiazolyl, pyrazolyl, furanyl, thienyl, pyrrolyl, imidazolyl, triazolyl, tetrazolyl, isoxazolyl, isothiazolyl, oxadiazolyl, or thiadiazolyl;
or ring A is a 6-membered heteroaryl that is pyridinyl, pyrimidinyl, pyrazinyl, pyridazinyl, or triazinyl;
or ring A is phenyl;
$X^1$ is CH or N;
$R^1$ is $C_1$-$C_4$alkoxy;
$R^2$ is halogen;
$R^4$ is H, F, or —$CH_3$;
$R^5$ is H, F, or —$CH_3$;
or $R^4$ and $R^5$ are taken together to form a bridge that is —$CH_2$— or —$CH_2CH_2$—;
each $R^6$ is independently H, F, —OH, or —$CH_3$;
$R^7$ is H, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, or $C_1$-$C_4$heteroalkyl;
L is absent, —$Y^2$-$L^1$-, -$L^1$-$Y^2$—, cyclopropylene, cyclobutylene, or bicyclo[1.1.1]pentylene;
$Y^2$ is absent, —O—, —S—, —S(=O)—, —S(=O)$_2$—, —S(=O)$_2$$NR^{17}$—, —$CH_2$—, —CH=CH—, —C≡C—, —C(=O)—, —C(=O)O—, —OC(=O)—, —OC(=O)O—, —C(=O)$NR^{17}$—, —$NR^{17}$C(=O)—, —OC(=O)$NR^{17}$—, —$NR^{17}$C(=O)O—, —$NR^{17}$C(=O)$NR^{17}$—, —$NR^{17}$S(=O)$_2$—, or —$NR^{17}$—;
$L^1$ is absent or $C_1$-$C_4$alkylene;
$R^8$ is $C_4$-$C_8$alkyl or $C_4$-$C_8$haloalkyl;
$R^9$ is H, F, or —$CH_3$;
$R^{10}$ is —$CH_2OH$, —$CH_2CH_2OH$, $C_1$-$C_6$heteroalkyl, —C(=O)$R^{14}$, —C(=O)$OR^{14}$, —OC(=O)$R^{14}$, —OC(=O)$OR^{14}$, tetrazolyl, imidazole, 5-oxo-4,5-dihydro-1,2,4-oxadiazol-3-yl, —S(=O)$_2$N($R^{12}$)$_2$, —$NR^{15}$S(=O)$_2$$R^{14}$, —C(=O)$NR^{15}$S(=O)$_2$$R^{14}$, —S(=O)$_2$$NR^{15}$C(=O)$R^{14}$, —$CH_2$N($R^{12}$)$_2$, —$NR^{15}$C(=O)$R^{14}$, —C(=O)N($R^{12}$)$_2$, —$NR^{15}$C(=O)$OR^{14}$, —OC(=O)N($R^{12}$)$_2$, —$NR^{15}$C(=O)N($R^{12}$)$_2$, —C(=NH)$NH_2$, —NHC(=NH)$NH_2$, —C(=O)NHC(=NH)$NH_2$, —S(=O)$_2$OH or —OP(=O)($OR^{15}$)$_2$;
or $R^{10}$ is -$L^2$-$L^3$-$L^4$-$R^{13}$;
$L^2$ is absent, $C_1$-$C_6$alkylene, or $C_1$-$C_6$heteroalkylene;
$L^3$ is absent, —O—, —S—, —S(=O)—, —S(=O)$_2$—, —$NR^{15}$—, —C(=O)—, —C(=O)$NR^{15}$—, —$NR^{15}$C(=O)—, —C(=O)O—, —OC(=O)—, —OC(=O)$NR^{15}$—, —$NR^{15}$C(=O)$NR^{15}$—, —$NR^{15}$C(=O)O—, —OP(=O)($OR^{15}$)O—, or —($OCH_2CH_2$)$_r$—, r is 1 or 2;
$L^4$ is $C_1$-$C_6$alkylene or $C_1$-$C_6$heteroalkylene;
$R^{13}$ is H, —CN, —OH, —N($R^{12}$)$_2$, —$NR^{15}$S(=O)$_2$$R^{14}$, —S(=O)$_2$N($R^{12}$)$_2$, —$SR^{12}$, —S(=O)$R^{14}$, —S(=O)$_2$$R^{14}$, —$SO_3H$, —OP(=O)($OR^{15}$)$_2$, —C(=O)$R^{14}$, —OC(=O)$R^{14}$, —$CO_2H$, —$CO_2R^{14}$, —OC(=O)$OR^{14}$, —$NR^{15}$C(=O)$R^{14}$, —C(=O)N($R^{12}$)$_2$, —$NR^{15}$C(=O)$OR^{14}$, —OC(=O)N($R^{12}$)$_2$, $C_1$-$C_6$alkyl, $C_1$-$C_6$alkoxy, $C_1$-$C_6$heteroalkyl, $C_3$-$C_6$cycloalkyl, $C_2$-$C_6$heterocycloalkyl, phenyl, or heteroaryl;
$R^{11}$ is H, F, or —$CH_3$;
or $R^9$ and $R^{11}$ are taken together to form a bridge that is —$CH_2$— or —$CH_2CH_2$—;
each $R^{12}$ is independently H, $C_1$-$C_4$alkyl, —$C_1$-$C_4$alkyl-$OR^{15}$, $C_1$-$C_4$fluoroalkyl, $C_1$-$C_4$heteroalkyl, $C_3$-$C_6$cycloalkyl, $C_2$-$C_6$heterocycloalkyl, phenyl, benzyl, or monocyclic heteroaryl, wherein $C_3$-$C_6$cycloalkyl, $C_2$-$C_6$heterocycloalkyl, phenyl, benzyl, or monocyclic heteroaryl are optionally substituted with 1, 2, or 3 $R^{16}$ groups;
$R^{14}$ is $C_1$-$C_4$alkyl, —$C_1$-$C_4$alkyl-$OR^{15}$, $C_1$-$C_4$fluoroalkyl, $C_1$-$C_4$heteroalkyl, $C_3$-$C_6$cycloalkyl, $C_2$-$C_6$heterocycloalkyl, phenyl, benzyl, or monocyclic heteroaryl, wherein $C_3$-$C_6$cycloalkyl, $C_2$-$C_6$heterocycloalkyl, phenyl, benzyl, or monocyclic heteroaryl are optionally substituted with 1, 2, or 3 $R^{16}$ groups;
each $R^{15}$ is independently H or $C_1$-$C_6$alkyl;
each $R^{16}$ is independently halogen, —CN, —OH, —N($R^{15}$)$_2$, —$NR^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N($R^{15}$)$_2$, —C(=O)($C_1$-$C_4$alkyl), —OC(=O)($C_1$-$C_4$alkyl), —$CO_2H$, —$CO_2$($C_1$-

C₄alkyl), —NR¹⁵C(=O)(C₁-C₄alkyl), —C(=O)N(R¹⁵)₂, —NR¹⁵C(=O)O(C₁-C₄alkyl), —OC(=O)N(R¹⁵)₂, C₁-C₄alkyl, C₂-C₄alkenyl, C₂-C₄alkynyl, C₁-C₄alkoxy, C₁-C₄fluoroalkyl, C₁-C₄fluoroalkoxy, C₁-C₄heteroalkyl, C₃-C₆cycloalkyl, monocyclic C₂-C₆heterocycloalkyl, phenyl, or monocyclic heteroaryl;

m is 0, 1, or 2; and n is 0, 1, or 2.

In some embodiments is a compound of Formula (III), or a pharmaceutically acceptable salt or solvate thereof, wherein n is 0.

In some embodiments is a compound of Formula (III), or a pharmaceutically acceptable salt or solvate thereof, wherein n is 1 or 2. In some embodiments is a compound of Formula (III), or a pharmaceutically acceptable salt or solvate thereof, wherein n is 1. In some embodiments is a compound of Formula (III), or a pharmaceutically acceptable salt or solvate thereof, wherein n is 2.

In some embodiments is a compound of Formula (III) having the structure of Formula (IIIa), or a pharmaceutically acceptable salt or solvate thereof:

Formula (IIIA)

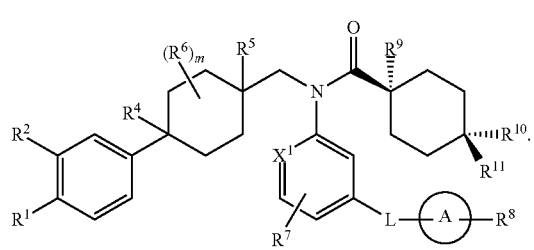

In some embodiments is a compound of Formula (III) or (IIIa), or a pharmaceutically acceptable salt or solvate thereof, wherein ring A is a 5-membered heteroaryl that is oxazolyl, thiazolyl, or pyrazolyl; or ring A is a 6-membered heteroaryl that is pyridinyl or pyrimidinyl. In some embodiments is a compound of Formula (III) or (IIIa), or a pharmaceutically acceptable salt or solvate thereof, wherein ring A is a 5-membered heteroaryl that is oxazolyl, thiazolyl, or pyrazolyl. In some embodiments is a compound of Formula (III) or (IIIa), or a pharmaceutically acceptable salt or solvate thereof, wherein ring A is a 6-membered heteroaryl that is pyridinyl or pyrimidinyl. In some embodiments is a compound of Formula (III) or (IIIa), or a pharmaceutically acceptable salt or solvate thereof, wherein ring A is phenyl.

In some embodiments is a compound of Formula (III) or (IIIa), or a pharmaceutically acceptable salt or solvate thereof, wherein

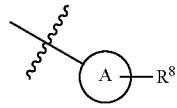

is

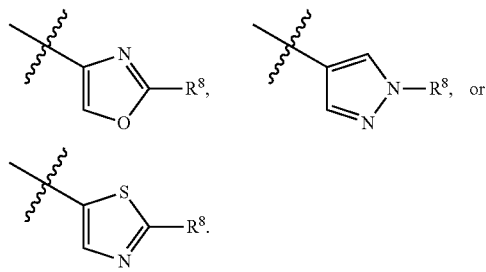

In some embodiments is a compound of Formula (III) or (IIIa), or a pharmaceutically acceptable salt or solvate thereof, wherein

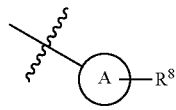

is

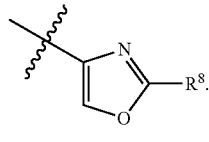

In some embodiments is a compound of Formula (III) or (IIIa), or a pharmaceutically acceptable salt or solvate thereof, wherein

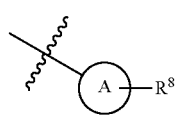

is

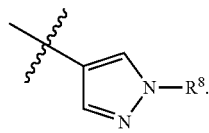

In some embodiments is a compound of Formula (III) or (IIIa), or a pharmaceutically acceptable salt or solvate thereof, wherein

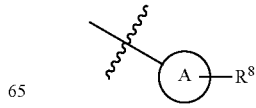

is

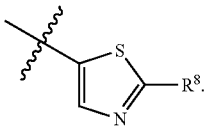

In some embodiments is a compound of Formula (III) or (IIIa), or a pharmaceutically acceptable salt or solvate thereof, wherein $R^8$ is $C_4$-$C_8$alkyl. In some embodiments is a compound of Formula (III) or (IIIa), or a pharmaceutically acceptable salt or solvate thereof, wherein $R^8$ is —C(CH$_3$)$_3$. In some embodiments is a compound of Formula (III) or (IIIa), or a pharmaceutically acceptable salt or solvate thereof, wherein $R^8$ is $C_4$-$C_8$haloalkyl.

In some embodiments is a compound of Formula (III) or (IIIa), or a pharmaceutically acceptable salt or solvate thereof, wherein $R^4$ is H and $R^5$ is H. In some embodiments is a compound of Formula (III) or (IIIa), or a pharmaceutically acceptable salt or solvate thereof, wherein $R^4$ and $R^5$ are taken together to form a bridge that is —CH$_2$CH$_2$—. In some embodiments is a compound of Formula (III) or (IIIa), or a pharmaceutically acceptable salt or solvate thereof, wherein $R^4$ and $R^5$ are taken together to form a bridge that is —CH$_2$—.

In some embodiments is a compound of Formula (III) or (IIIa), or a pharmaceutically acceptable salt or solvate thereof, wherein m is 0 or 1. In some embodiments is a compound of Formula (III) or (IIIa), or a pharmaceutically acceptable salt or solvate thereof, wherein m is 0. In some embodiment is a compound of Formula (III) or (IIIa), or a pharmaceutically acceptable salt or solvate thereof, wherein m is 1. In some embodiments is a compound of Formula (III) or (IIIa), or a pharmaceutically acceptable salt or solvate thereof, wherein m is 2.

In some embodiments is a compound of Formula (III) or (IIIa), or a pharmaceutically acceptable salt or solvate thereof, wherein $X^1$ is CH. In some embodiments is a compound of Formula (III) or (IIIa), or a pharmaceutically acceptable salt or solvate thereof, wherein each $X^1$ is N.

In some embodiments is a compound of Formula (III) or (IIIa), or a pharmaceutically acceptable salt or solvate thereof, wherein $R^{10}$ is —CH$_2$OH, $C_1$-$C_6$heteroalkyl, —OC(=O)R$^{14}$, —NR$^{15}$C(=O)R$^{14}$, —C(=O)N(R$^{12}$)$_2$, —NR$^{15}$C(=O)OR$^{14}$, or —OC(=O)N(R$^{12}$)$_2$. In some embodiments is a compound of Formula (III) or (IIIa), or a pharmaceutically acceptable salt or solvate thereof, wherein $R^{10}$ is —OC(=O)R$^{14}$. In some embodiments is a compound of Formula (III) or (IIIa), or a pharmaceutically acceptable salt or solvate thereof, wherein $R^{14}$ is $C_2$-$C_6$heterocycloalkyl optionally substituted with 1, 2, or 3 $R^{16}$ groups. In some embodiments is a compound of Formula (III) or (IIIa), or a pharmaceutically acceptable salt or solvate thereof, wherein $R^{14}$ is $C_2$-$C_6$heterocycloalkyl optionally substituted with 1 or 2 groups selected from —OH, —N(C$_1$-C$_4$alkyl)$_2$, C$_1$-C$_4$alkyl, and C$_1$-C$_4$alkoxy. In some embodiments is a compound of Formula (III) or (IIIa), or a pharmaceutically acceptable salt or solvate thereof, wherein $R^{14}$ is a 4-membered heterocycloalkyl ring optionally substituted with 1 or 2 groups selected from —OH, —N(C$_1$-C$_4$alkyl)$_2$, C$_1$-C$_4$alkyl, and C$_1$-C$_4$alkoxy. In some embodiments is a compound of Formula (III) or (IIIa), or a pharmaceutically acceptable salt or solvate thereof, wherein $R^{10}$ is

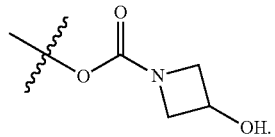 [SMILES: *OC(=O)N1CC(O)C1]

In some embodiments is a compound of Formula (III) or (IIIa), or a pharmaceutically acceptable salt or solvate thereof, wherein $R^{14}$ is a 5-membered heterocycloalkyl ring optionally substituted with 1 or 2 groups selected from —OH, —N(C$_1$-C$_4$alkyl)$_2$, C$_1$-C$_4$alkyl, and C$_1$-C$_4$alkoxy. In some embodiments is a compound of Formula (III) or (IIIa), or a pharmaceutically acceptable salt or solvate thereof, wherein $R^{14}$ is a 4-membered heterocycloalkyl ring optionally substituted with 1 or 2 groups selected from —OH, —N(C$_1$-C$_4$alkyl)$_2$, C$_1$-C$_4$alkyl, and C$_1$-C$_4$alkoxy. In some embodiments is a compound of Formula (III) or (IIIa), or a pharmaceutically acceptable salt or solvate thereof, wherein $R^{10}$ is

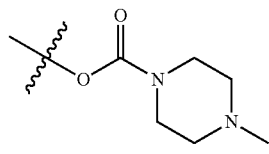

In some embodiments is a compound of Formula (III) or (IIIa), or a pharmaceutically acceptable salt or solvate thereof, wherein $R^{10}$ is —OC(=O)N(R$^{12}$)$_2$. In some embodiments is a compound of Formula (III) or (IIIa), or a pharmaceutically acceptable salt or solvate thereof, wherein each $R^{12}$ is independently H, C$_1$-C$_4$alkyl, or —C$_1$-C$_4$alkyl-OR$^{15}$. In some embodiments is a compound of Formula (III) or (IIIa), or a pharmaceutically acceptable salt or solvate thereof, wherein $R^{10}$ is —OC(=O)N(H)—C$_1$-C$_4$alkyl. In some embodiments is a compound of Formula (III) or (IIIa), or a pharmaceutically acceptable salt or solvate thereof, wherein $R^{10}$ is —OC(=O)N(H)—C$_1$-C$_4$alkyl-OR$^{15}$. In some embodiments is a compound of Formula (III) or (IIIa), or a pharmaceutically acceptable salt or solvate thereof, wherein $R^{10}$ is

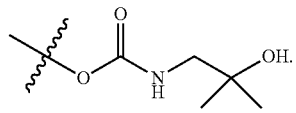 [SMILES: *OC(=O)NCC(C)(C)O]

In some embodiments is a compound of Formula (III) or (IIIa), or a pharmaceutically acceptable salt or solvate thereof, wherein $R^{10}$ is —N(R$^{15}$)C(=O)OR$^{14}$. In some embodiments is a compound of Formula (III) or (IIIa), or a pharmaceutically acceptable salt or solvate thereof, wherein $R^{14}$ is C$_1$-C$_4$alkyl. In some embodiments is a compound of Formula (III) or (IIIa), or a pharmaceutically acceptable salt or solvate thereof, wherein $R^{14}$ is —C$_1$-C$_6$alkyl-OH. In some embodiments is a compound of Formula (III) or (IIIa), or a pharmaceutically acceptable salt or solvate thereof, wherein $R^{14}$ is —C$_1$-C$_6$alkyl-OCH$_3$. In some embodiments is a compound of Formula (III) or (IIIa), or a pharmaceutically acceptable salt or solvate thereof, wherein $R^{14}$ is C$_2$-C$_6$heterocycloalkyl. In some embodiments is a compound of Formula (III) or (IIIa), or a pharmaceutically acceptable salt or solvate thereof, wherein $R^{14}$ is

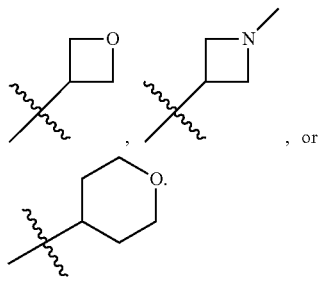

In some embodiments is a compound of Formula (III) or (IIIa), or a pharmaceutically acceptable salt or solvate thereof, wherein $R^{15}$ is H.

In some embodiments is a compound of Formula (III) or (IIIa), or a pharmaceutically acceptable salt or solvate thereof, wherein $R^1$ is —OCH$_3$.

In some embodiments is a compound of Formula (III) or (IIIa), or a pharmaceutically acceptable salt or solvate thereof, wherein $R^2$ is —F. In some embodiments is a compound of Formula (III) or (IIIa), or a pharmaceutically acceptable salt or solvate thereof, wherein $R^2$ is —Cl.

In some embodiments is a compound of Formula (III) or (IIIa), or a pharmaceutically acceptable salt or solvate thereof, wherein $R^7$ is H. In some embodiments is a compound of Formula (III) or (IIIa), or a pharmaceutically acceptable salt or solvate thereof, wherein $R^7$ is halogen. In some embodiments is a compound of Formula (III) or (IIIa), or a pharmaceutically acceptable salt or solvate thereof, wherein $R^7$ is $C_1$-$C_4$alkyl. In some embodiments is a compound of Formula (III) or (IIIa), or a pharmaceutically acceptable salt or solvate thereof, wherein $R^7$ is $C_1$-$C_4$fluoroalkyl.

In some embodiments is a compound of Formula (III) or (IIIa), or a pharmaceutically acceptable salt or solvate thereof, wherein L is absent.

In some embodiments is a compound of Formula (III) or (IIIa), or a pharmaceutically acceptable salt or solvate thereof, wherein $R^9$ is H.

In some embodiments is a compound of Formula (III) or (IIIa), or a pharmaceutically acceptable salt or solvate thereof, wherein $R^{11}$ is H.

Any combination of the groups described above for the various variables is contemplated herein. Throughout the specification, groups and substituents thereof are chosen by one skilled in the field to provide stable moieties and compounds.

In some embodiments, compounds described herein include, but are not limited to, those described in Table 1.

TABLE 1

| Compound | Structure | Chemical Name |
|---|---|---|
| 1 | 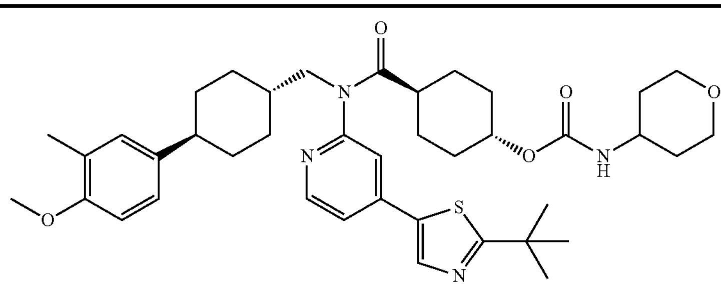 | trans-4-((4-(2-(tert-Butyl)thiazol-5-yl)pyridin-2-yl)((trans)-4-(4-methoxy-3-methylphenyl)cyclohexyl)methyl)carbamoyl)cyclohexyl (tetrahydro-2H-pyran-4-yl)carbamate |
| 1.01 | 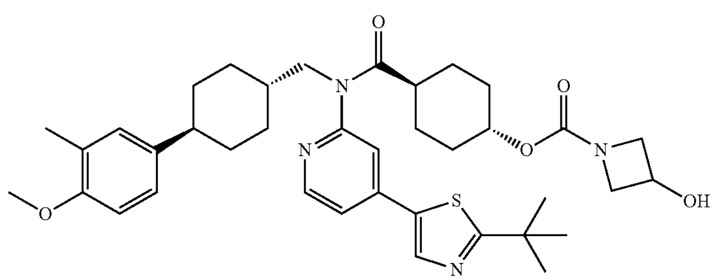 [SMILES: COc1ccc([C@H]2CC[C@H](CN(c3cc(-c4cnc(C(C)(C)C)s4)ccn3)C(=O)[C@H]3CC[C@H](OC(=O)N4CC(O)C4)CC3)CC2)cc1C] | trans-4-((4-(2-(tert-Butyl)thiazol-5-yl)pyridin-2-yl)(((trans)-4-(4-methoxy-3-methylphenyl)cyclohexyl)methyl)carbamoyl)cyclohexyl 3-hydroxyazetidine-1-carboxylate |
| 1.02 | 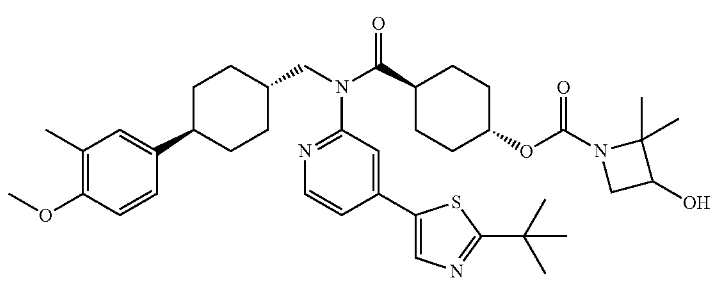 [SMILES: COc1ccc([C@H]2CC[C@H](CN(c3cc(-c4cnc(C(C)(C)C)s4)ccn3)C(=O)[C@H]3CC[C@H](OC(=O)N4CC(O)C4(C)C)CC3)CC2)cc1C] | trans-4-((4-(2-(tert-Butyl)thiazol-5-yl)pyridin-2-yl)(((trans)-4-(4-methoxy-3-methylphenyl)cyclohexyl)methyl)carbamoyl)cyclohexyl 3-hydroxy-2,2-dimethylazetidine-1-carboxylate |

TABLE 1-continued

| Compound | Structure | Chemical Name |
|---|---|---|
| 1.03 | 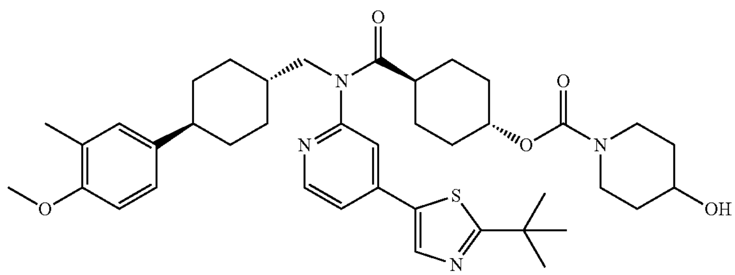 [SMILES: COc1ccc([C@H]2CC[C@H](CN(c3cc(-c4cnc(C(C)(C)C)s4)ccn3)C(=O)[C@H]3CC[C@H](OC(=O)N4CCC(O)CC4)CC3)CC2)cc1C] | trans-4-((4-(2-(tert-Butyl)thiazol-5-yl)pyridin-2-yl)(((trans)-4-(4-methoxy-3-methylphenyl)cyclohexyl)methyl)carbamoyl)cyclohexyl 4-hydroxypiperidine-1-carboxylate |
| 1.04 | 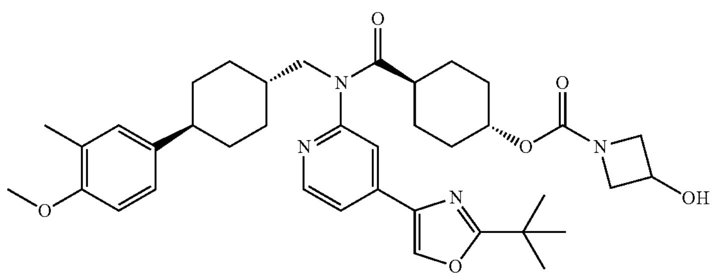 [SMILES: COc1ccc([C@H]2CC[C@H](CN(c3cc(-c4coc(C(C)(C)C)n4)ccn3)C(=O)[C@H]3CC[C@H](OC(=O)N4CC(O)C4)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl 3-hydroxyazetidine-1-carboxylate |
| 1.05 | 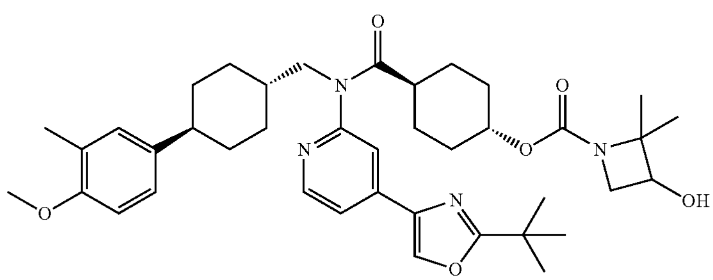 [SMILES: COc1ccc([C@H]2CC[C@H](CN(c3cc(-c4coc(C(C)(C)C)n4)ccn3)C(=O)[C@H]3CC[C@H](OC(=O)N4CC(O)C4(C)C)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl 3-hydroxy-2,2-dimethylazetidine-1-carboxylate |
| 1.06 | 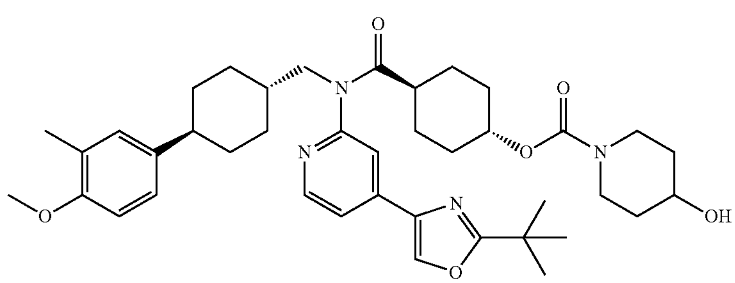 [SMILES: COc1ccc([C@H]2CC[C@H](CN(c3cc(-c4coc(C(C)(C)C)n4)ccn3)C(=O)[C@H]3CC[C@H](OC(=O)N4CCC(O)CC4)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl 4-hydroxypiperidine-1-carboxylate |
| 1.07 | 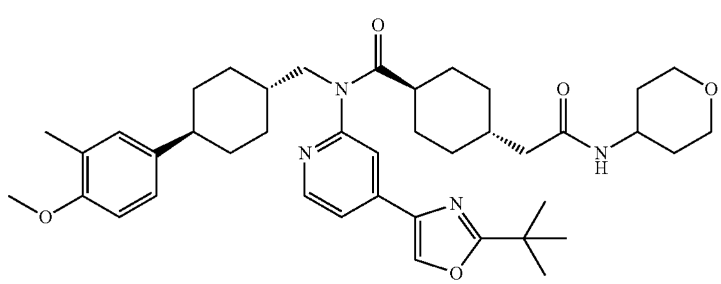 [SMILES: COc1ccc([C@H]2CC[C@H](CN(c3cc(-c4coc(C(C)(C)C)n4)ccn3)C(=O)[C@H]3CC[C@H](CC(=O)NC4CCOCC4)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl (tetrahydro-2H-pyran-4-yl)carbamate |

TABLE 1-continued

| Compound | Structure | Chemical Name |
|---|---|---|
| 1.08 | 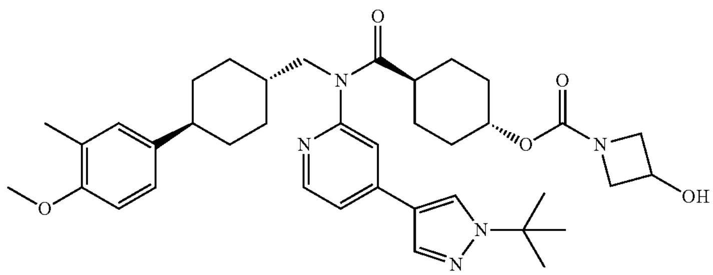 [SMILES: COc1ccc([C@H]2CC[C@H](CN(c3cc(-c4cnn(C(C)(C)C)c4)ccn3)C(=O)[C@H]3CC[C@H](OC(=O)N4CC(O)C4)CC3)CC2)cc1C] | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl 3-hydroxyazetidine-1-carboxylate |
| 1.09 | 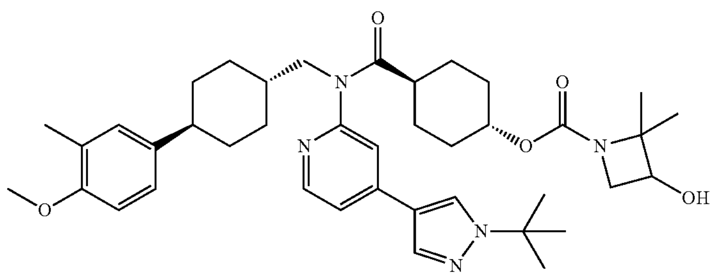 [SMILES: COc1ccc([C@H]2CC[C@H](CN(c3cc(-c4cnn(C(C)(C)C)c4)ccn3)C(=O)[C@H]3CC[C@H](OC(=O)N4CC(O)C4(C)C)CC3)CC2)cc1C] | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl 3-hydroxy-2,2-dimethylazetidine-1-carboxylate |
| 1.10 | 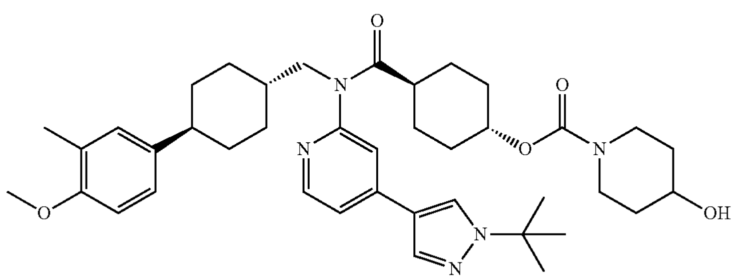 [SMILES: COc1ccc([C@H]2CC[C@H](CN(c3cc(-c4cnn(C(C)(C)C)c4)ccn3)C(=O)[C@H]3CC[C@H](OC(=O)N4CCC(O)CC4)CC3)CC2)cc1C] | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl 4-hydroxypiperidine-1-carboxylate |
| 1.11 | 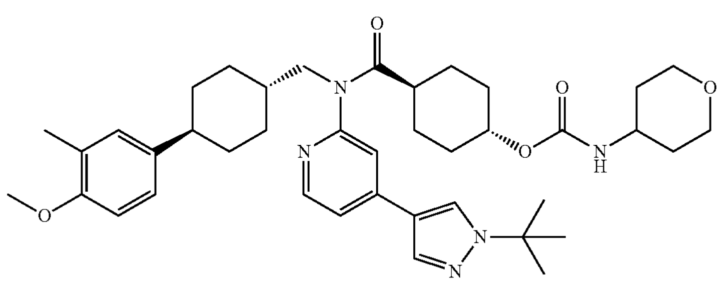 [SMILES: COc1ccc([C@H]2CC[C@H](CN(c3cc(-c4cnn(C(C)(C)C)c4)ccn3)C(=O)[C@H]3CC[C@H](OC(=O)NC4CCOCC4)CC3)CC2)cc1C] | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl (tetrahydro-2H-pyran-4-yl)carbamate |
| 1.12 | 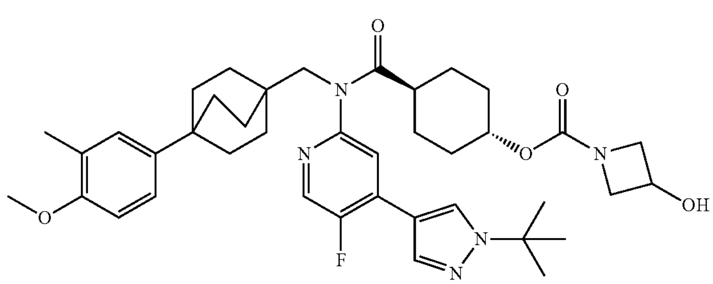 [SMILES: COc1ccc(C23CCC(CN(c4cc(-c5cnn(C(C)(C)C)c5)c(F)cn4)C(=O)[C@H]4CC[C@H](OC(=O)N5CC(O)C5)CC4)(CC2)CC3)cc1C] | 4-((4-(1-(tert-Butyl)-1H-pyrazol-4-yl)-5-fluoropyridin-2-yl)((4-(4-methoxy-3-methylphenyl)bicyclo[2.2.2]octan-1-yl)methyl)carbamoyl)(trans-cyclohexyl) 3-hydroxyazetidine-1-carboxylate |

TABLE 1-continued

| Compound | Structure | Chemical Name |
|---|---|---|
| 1.13 | 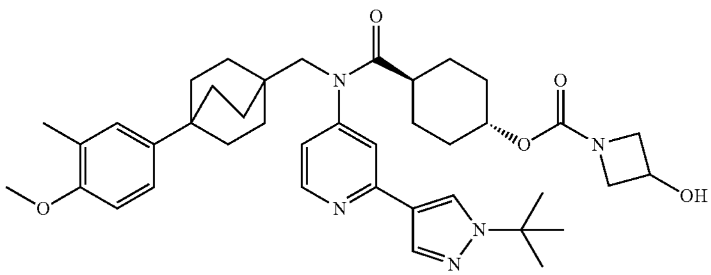 [SMILES: COc1ccc(C23CCC(CN(c4ccnc(-c5cnn(C(C)(C)C)c5)c4)C(=O)[C@H]4CC[C@H](OC(=O)N5CC(O)C5)CC4)(CC2)CC3)cc1C] | 4-((2-(1-(tert-Butyl)-1H-pyrazol-4-yl)pyridin-4-yl)((4-(4-methoxy-3-methylphenyl)bicyclo[2.2.2]octan-1-yl)methyl)carbamoyl)(trans-cyclohexyl) 3-hydroxyazetidine-1-carboxylate |
| 1.14 | 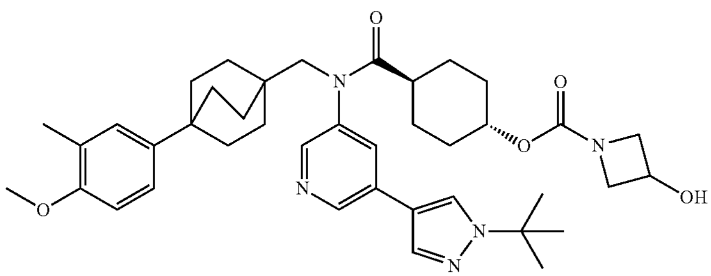 [SMILES: COc1ccc(C23CCC(CN(c4cncc(-c5cnn(C(C)(C)C)c5)c4)C(=O)[C@H]4CC[C@H](OC(=O)N5CC(O)C5)CC4)(CC2)CC3)cc1C] | 4-((5-(1-(tert-Butyl)-1H-pyrazol-4-yl)pyridin-3-yl)((4-(4-methoxy-3-methylphenyl)bicyclo[2.2.2]octan-1-yl)methyl)carbamoyl)(trans-cyclohexyl) 3-hydroxyazetidine-1-carboxylate |
| 1.15 | 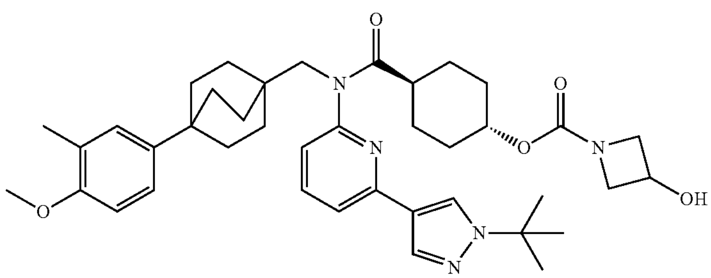 [SMILES: COc1ccc(C23CCC(CN(c4cccc(-c5cnn(C(C)(C)C)c5)n4)C(=O)[C@H]4CC[C@H](OC(=O)N5CC(O)C5)CC4)(CC2)CC3)cc1C] | 4-((6-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-hydroxyazetidine-1-carboxylate |
| 2 | 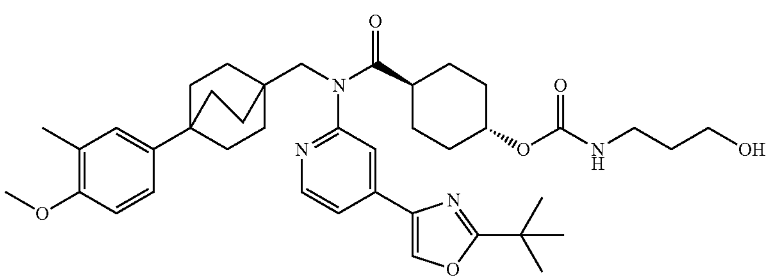 [SMILES: COc1ccc(C23CCC(CN(c4cc(-c5coc(C(C)(C)C)n5)ccn4)C(=O)[C@H]4CC[C@H](OC(=O)NCCCO)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate |
| 2.01 | 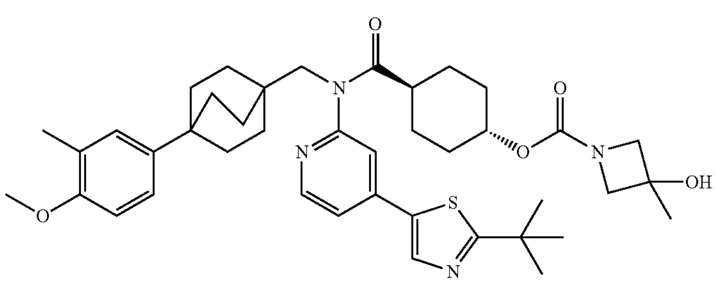 [SMILES: COc1ccc(C23CCC(CN(c4cc(-c5cnc(C(C)(C)C)s5)ccn4)C(=O)[C@H]4CC[C@H](OC(=O)N5CC(C)(O)C5)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) 3-hydroxy-3-methylazetidine-1-carboxylate |

TABLE 1-continued

| Compound | Structure | Chemical Name |
|---|---|---|
| 2.02 | 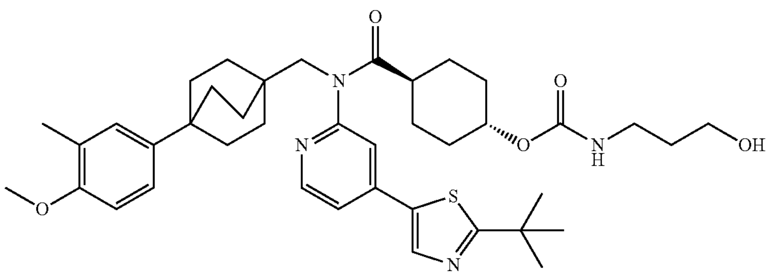 [SMILES: COc1ccc(C23CCC(CN(c4cc(-c5cnc(C(C)(C)C)s5)ccn4)C(=O)[C@H]4CC[C@H](OC(=O)NCCCO)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate |
| 2.03 | 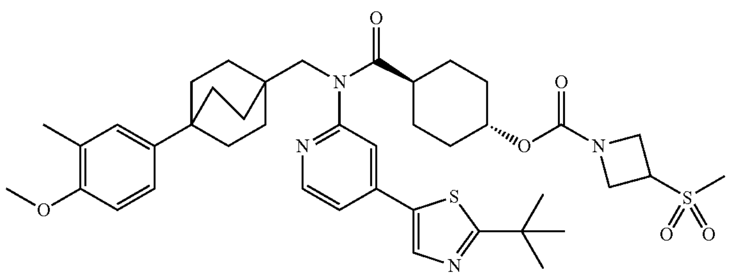 | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) 3-(methylsulfonyl)azetidine-1-carboxylate |
| 2.04 | 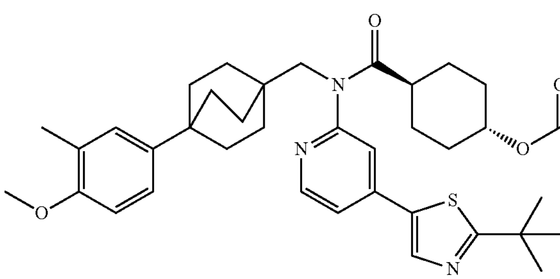 | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) oxetan-3-ylcarbamate |
| 2.05 | 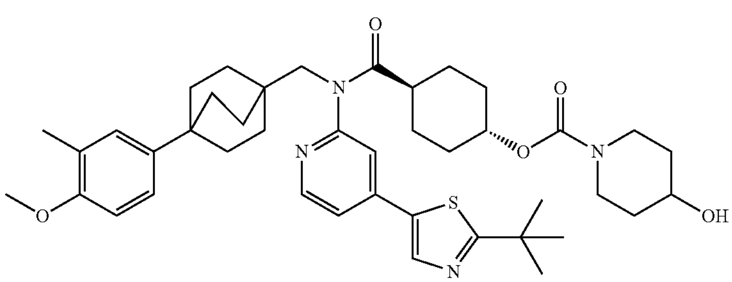 [SMILES: COc1ccc(C23CCC(CN(c4cc(-c5cnc(C(C)(C)C)s5)ccn4)C(=O)[C@H]4CC[C@H](OC(=O)N5CCC(O)CC5)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl 4-hydroxypiperidine-trans-1-carboxylate |
| 2.06 | 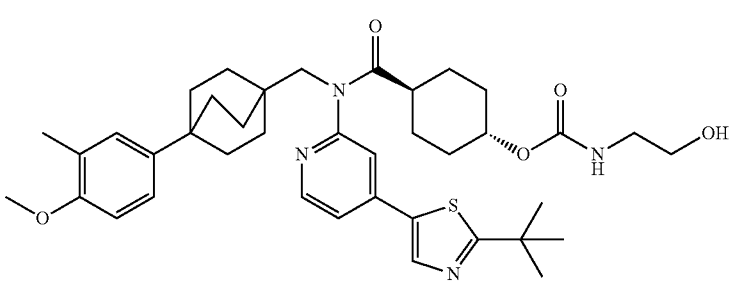 [SMILES: COc1ccc(C23CCC(CN(c4cc(-c5cnc(C(C)(C)C)s5)ccn4)C(=O)[C@H]4CC[C@H](OC(=O)NCCO)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl (2-hydroxyethyl)trans-carbamate |

TABLE 1-continued

| Compound | Structure | Chemical Name |
|---|---|---|
| 2.07 | 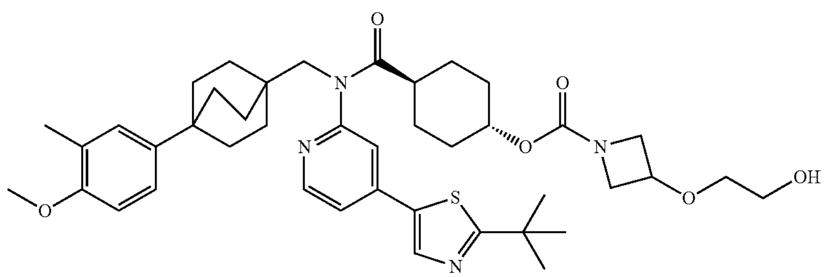 [SMILES: COc1ccc(C23CCC(CN(c4cc(-c5cnc(C(C)(C)C)s5)ccn4)C(=O)[C@H]4CC[C@H](OC(=O)N5CC(OCCO)C5)CC4)(CC2)CC3)cc1C] | 4-((4-(2-(tert-Butyl) thiazol-5-yl)pyridin-2-yl)((4-(4-methoxy-3-methylphenyl)bicyclo[2.2.2]octan-1-yl)methyl)carbamoyl) (trans-cyclohexyl) 3-(2-hydroxyethoxy)azetidine-1-carboxylate |
| 2.08 | 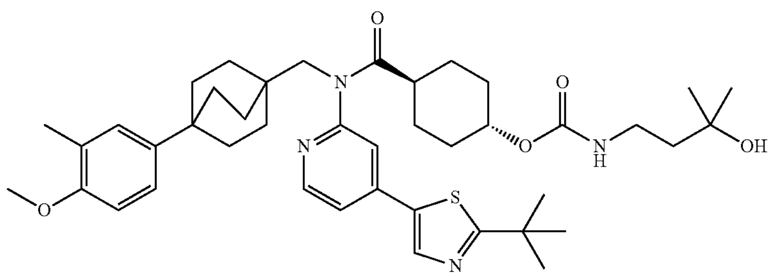 [SMILES: COc1ccc(C23CCC(CN(c4cc(-c5cnc(C(C)(C)C)s5)ccn4)C(=O)[C@H]4CC[C@H](OC(=O)NCCC(C)(C)O)CC4)(CC2)CC3)cc1C] | 4-((4-(2-(tert-Butyl) thiazol-5-yl)pyridin-2-yl)((4-(4-methoxy-3-methylphenyl)bicyclo[2.2.2]octan-1-yl)methyl)carbamoyl) (trans-cyclohexyl) (3-hydroxy-3-methylbutyl)carbamate |
| 2.09 | 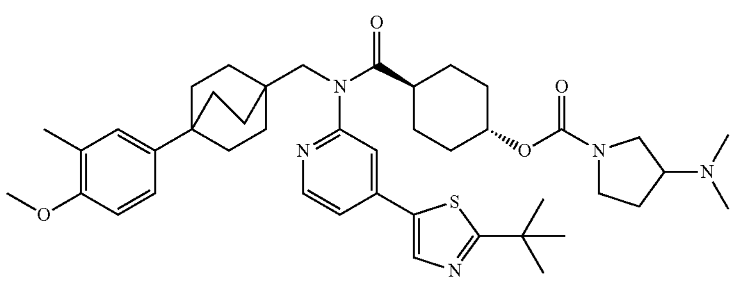 | 4-((4-(2-(tert-Butyl) thiazol-5-yl)pyridin-2-yl)((4-(4-methoxy-3-methylphenyl)bicyclo[2.2.2]octan-1-yl)methyl)carbamoyl)cyclohexyl 3-(dimethylamino)pyrrolidine-trans-1-carboxylate |
| 2.10 | 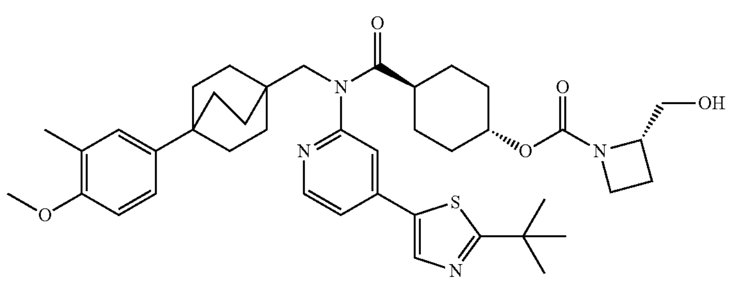 | (S)-4-((4-(2-(tert-Butyl) thiazol-5-yl)pyridin-2-yl)((4-(4-methoxy-3-methylphenyl)bicyclo[2.2.2]octan-1-yl)methyl)carbamoyl)cyclohexyl 2-(hydroxymethyl)azetidine-trans-1-carboxylate |
| 2.11 | 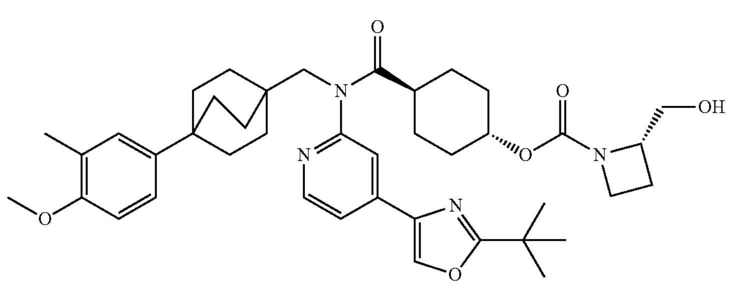 [SMILES: COc1ccc(C23CCC(CN(c4cc(-c5coc(C(C)(C)C)n5)ccn4)C(=O)[C@H]4CC[C@H](OC(=O)N5CC[C@H]5CO)CC4)(CC2)CC3)cc1C] | (S)-4-((4-(2-(tert-Butyl) oxazol-4-yl)pyridin-2-yl)((4-(4-methoxy-3-methylphenyl)bicyclo[2.2.2]octan-1-yl)methyl)carbamoyl)cyclohexyl 2-(hydroxymethyl)azetidine-trans-1-carboxylate |

TABLE 1-continued

| Compound | Structure | Chemical Name |
|---|---|---|
| 2.12 | 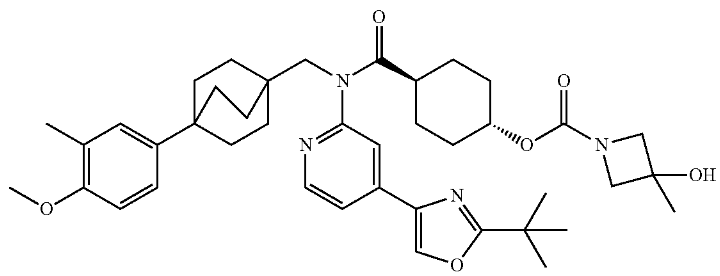 [SMILES: COc1ccc(C23CCC(CN(c4cc(-c5coc(C(C)(C)C)n5)ccn4)C(=O)[C@H]4CC[C@H](OC(=O)N5CC(C)(O)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-hydroxy-3-methylazetidine-1-carboxylate |
| 2.13 | 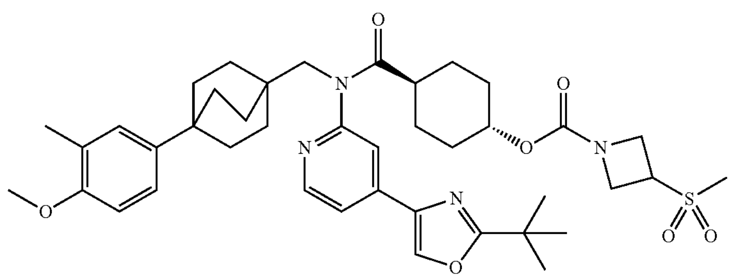 | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-(methylsulfonyl)azetidine-1-carboxylate |
| 2.14 | 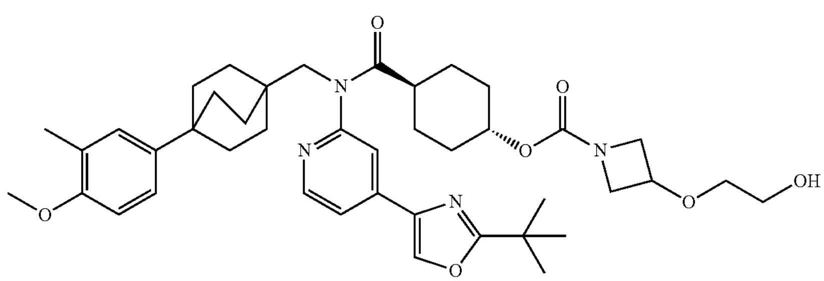 [SMILES: COc1ccc(C23CCC(CN(c4cc(-c5coc(C(C)(C)C)n5)ccn4)C(=O)[C@H]4CC[C@H](OC(=O)N5CC(OCCO)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-(2-hydroxyethoxy)azetidine-1-carboxylate |
| 2.15 | 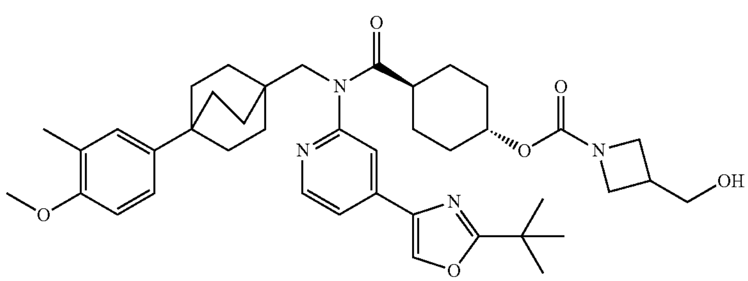 [SMILES: COc1ccc(C23CCC(CN(c4cc(-c5coc(C(C)(C)C)n5)ccn4)C(=O)[C@H]4CC[C@H](OC(=O)N5CC(CO)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-(hydroxymethyl)azetidine-1-carboxylate |
| 2.16 | 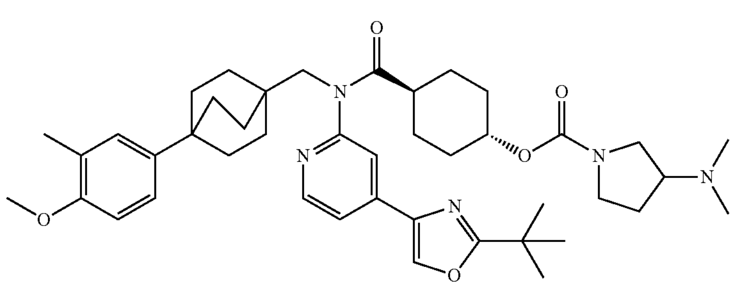 | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl 3-(dimethylamino)pyrrolidine-trans-1-carboxylate |

TABLE 1-continued

| Compound | Structure | Chemical Name |
|---|---|---|
| 2.17 | 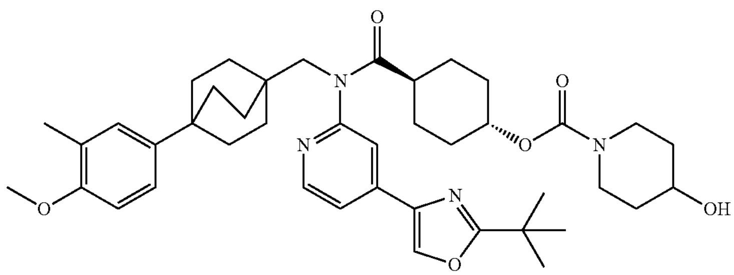 [SMILES: COc1ccc(C23CCC(CN(c4cc(-c5coc(C(C)(C)C)n5)ccn4)C(=O)[C@H]4CC[C@H](OC(=O)N5CCC(O)CC5)CC4)(CC2)CC3)cc1C] | 4-((4-(2-(tert-Butyl) oxazol-4-yl)pyridin-2-yl)((4-(4-methoxy-3-methylphenyl)bicyclo[2.2.2]octan-1-yl)methyl)carbamoyl)cyclohexyl 4-hydroxypiperidine-trans-1-carboxylate |
| 2.18 | 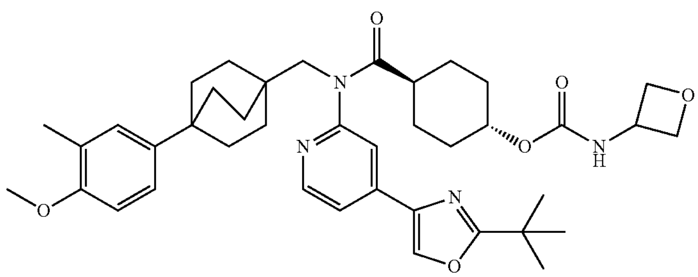 [SMILES: COc1ccc(C23CCC(CN(c4cc(-c5coc(C(C)(C)C)n5)ccn4)C(=O)[C@H]4CC[C@H](OC(=O)NC5COC5)CC4)(CC2)CC3)cc1C] | 4-((4-(2-(tert-Butyl) oxazol-4-yl)pyridin-2-yl)((4-(4-methoxy-3-methylphenyl)bicyclo[2.2.2]octan-1-yl)methyl)carbamoyl) (trans-cyclohexyl) oxetan-3-ylcarbamate |
| 2.19 | 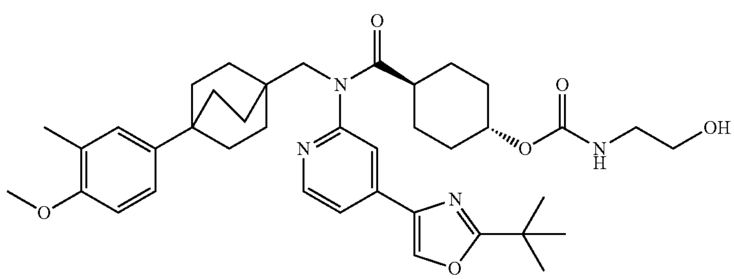 [SMILES: COc1ccc(C23CCC(CN(c4cc(-c5coc(C(C)(C)C)n5)ccn4)C(=O)[C@H]4CC[C@H](OC(=O)NCCO)CC4)(CC2)CC3)cc1C] | 4-((4-(2-(tert-Butyl) oxazol-4-yl)pyridin-2-yl)((4-(4-methoxy-3-methylphenyl)bicyclo[2.2.2]octan-1-yl)methyl)carbamoyl)cyclohexyl (2-hydroxyethyl)trans-carbamate |
| 2.20 | 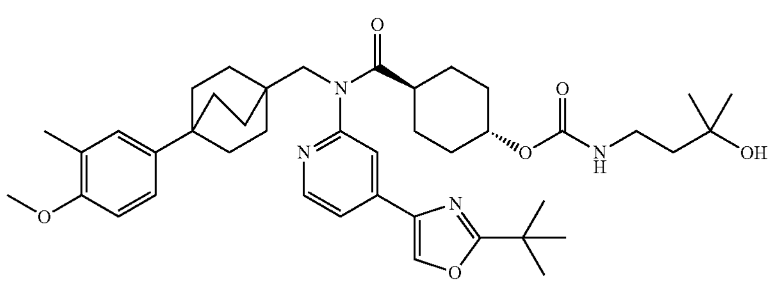 [SMILES: COc1ccc(C23CCC(CN(c4cc(-c5coc(C(C)(C)C)n5)ccn4)C(=O)[C@H]4CC[C@H](OC(=O)NCCC(C)(C)O)CC4)(CC2)CC3)cc1C] | 4-((4-(2-(tert-Butyl) oxazol-4-yl)pyridin-2-yl)((4-(4-methoxy-3-methylphenyl)bicyclo[2.2.2]octan-1-yl)methyl)carbamoyl) (trans-cyclohexyl) (3-hydroxy-3-methylbutyl)carbamate |
| 2.21 | 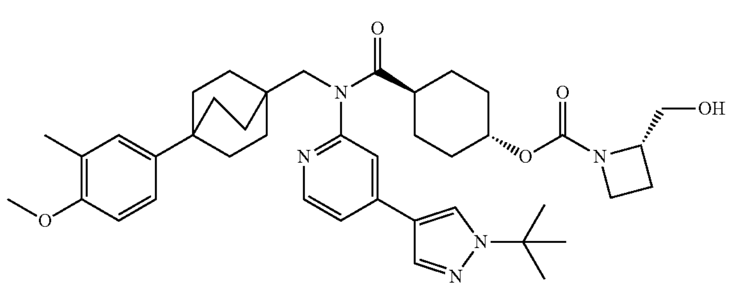 [SMILES: COc1ccc(C23CCC(CN(c4cc(-c5cnn(C(C)(C)C)c5)ccn4)C(=O)[C@H]4CC[C@H](OC(=O)N5CC[C@H]5CO)CC4)(CC2)CC3)cc1C] | (S)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 2-(hydroxymethyl)azetidine-trans-1-carboxylate |

TABLE 1-continued

| Compound | Structure | Chemical Name |
|---|---|---|
| 2.22 | 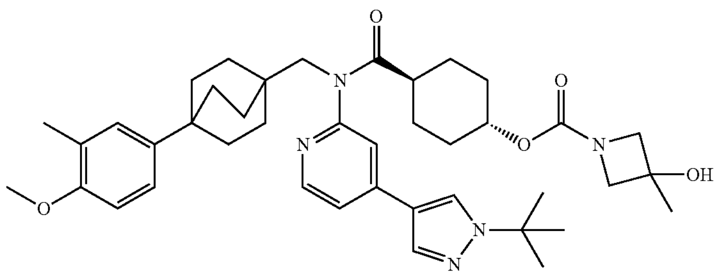 [SMILES: COc1ccc(C23CCC(CN(c4cc(-c5cnn(C(C)(C)C)c5)ccn4)C(=O)[C@H]4CC[C@H](OC(=O)N5CC(C)(O)C5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-hydroxy-3-methylazetidine-1-carboxylate |
| 2.23 | 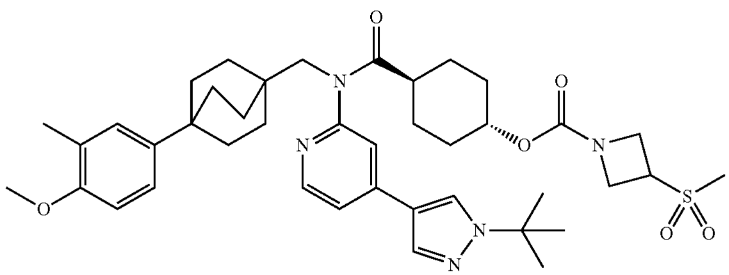 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-(methylsulfonyl)azetidine-1-carboxylate |
| 2.24 | 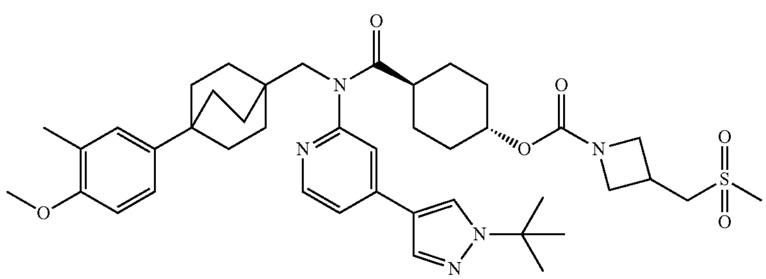 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-((methylsulfonyl)methyl)azetidine-1-carboxylate |
| 2.25 | 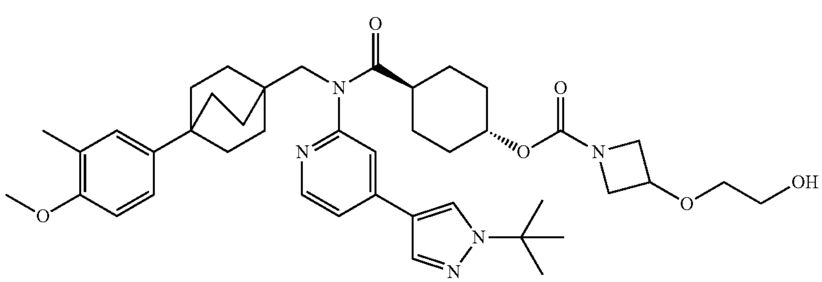 [SMILES: COc1ccc(C23CCC(CN(c4cc(-c5cnn(C(C)(C)C)c5)ccn4)C(=O)[C@H]4CC[C@H](OC(=O)N5CC(OCCO)C5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-(2-hydroxyethoxy)azetidine-1-carboxylate |
| 2.26 | 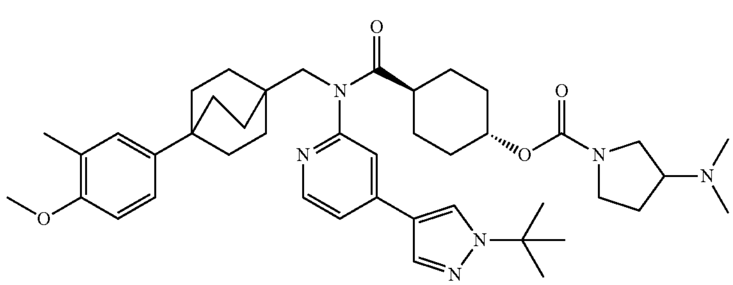 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 3-(dimethylamino)pyrrolidine-trans-1-carboxylate |

TABLE 1-continued

| Compound | Structure | Chemical Name |
|---|---|---|
| 2.27 | 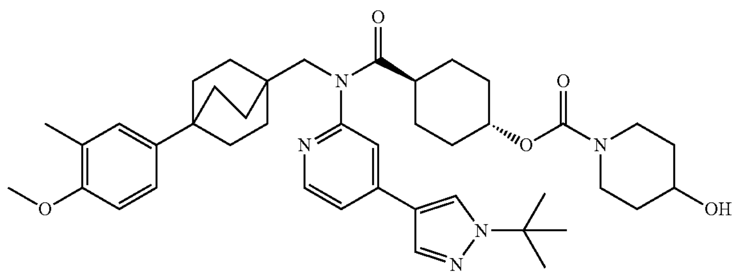 [SMILES: COc1ccc(C23CCC(CN(c4cc(-c5cnn(C(C)(C)C)c5)ccn4)C(=O)[C@H]4CC[C@H](OC(=O)N5CCC(O)CC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 4-hydroxypiperidine-trans-1-carboxylate |
| 2.28 | 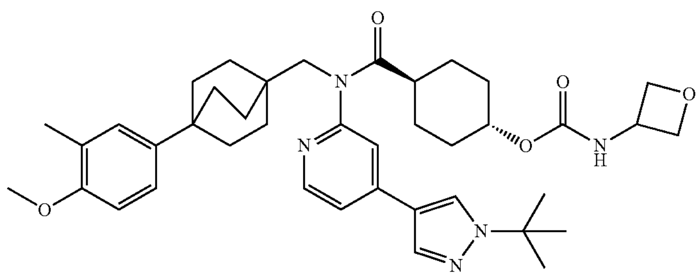 [SMILES: COc1ccc(C23CCC(CN(c4cc(-c5cnn(C(C)(C)C)c5)ccn4)C(=O)[C@H]4CC[C@H](OC(=O)NC5COC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) oxetan-3-ylcarbamate |
| 2.29 | 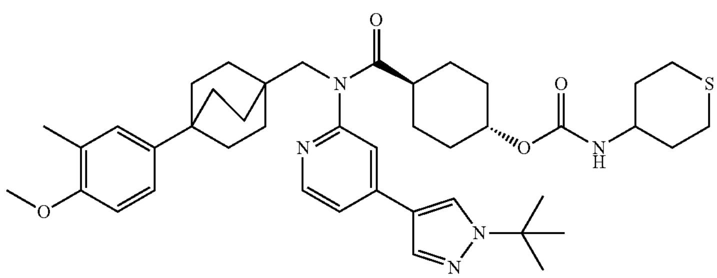 [SMILES: COc1ccc(C23CCC(CN(c4cc(-c5cnn(C(C)(C)C)c5)ccn4)C(=O)[C@H]4CC[C@H](OC(=O)NC5CCSCC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl trans-(tetrahydro-2H-thiopyran-4-yl)carbamate |
| 2.30 | 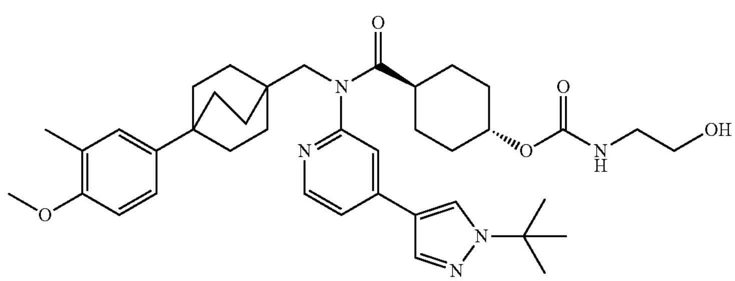 [SMILES: COc1ccc(C23CCC(CN(c4cc(-c5cnn(C(C)(C)C)c5)ccn4)C(=O)[C@H]4CC[C@H](OC(=O)NCCO)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl (2-hydroxyethyl)trans-carbamate |
| 2.31 | 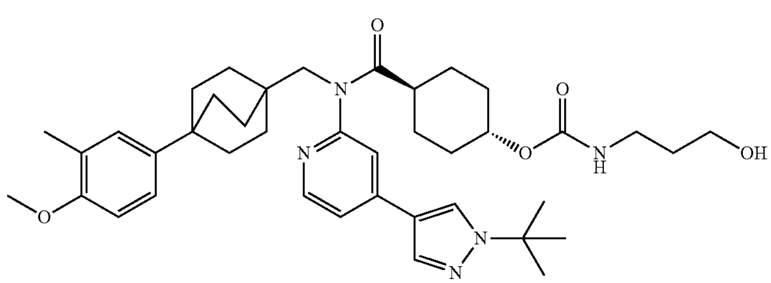 [SMILES: COc1ccc(C23CCC(CN(c4cc(-c5cnn(C(C)(C)C)c5)ccn4)C(=O)[C@H]4CC[C@H](OC(=O)NCCCO)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate |

TABLE 1-continued

| Compound | Structure | Chemical Name |
|---|---|---|
| 2.32 | 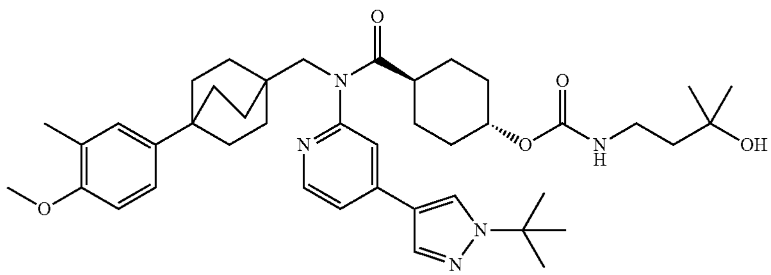 [SMILES: COc1ccc(C23CCC(CN(c4cc(-c5cnn(C(C)(C)C)c5)ccn4)C(=O)[C@H]4CC[C@H](OC(=O)NCCC(C)(C)O)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) (3-hydroxy-3-methylbutyl)carbamate |
| 2.33 | 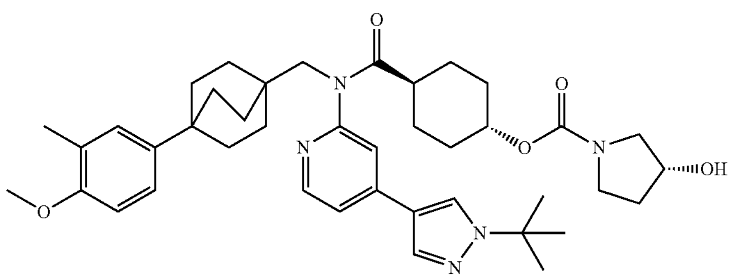 [SMILES: COc1ccc(C23CCC(CN(c4cc(-c5cnn(C(C)(C)C)c5)ccn4)C(=O)[C@H]4CC[C@H](OC(=O)N5CC[C@@H](O)C5)CC4)(CC2)CC3)cc1C] | (R)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl) cyclohexyl trans-3-hydroxypyrrolidine-1-carboxylate |
| 2.34 | 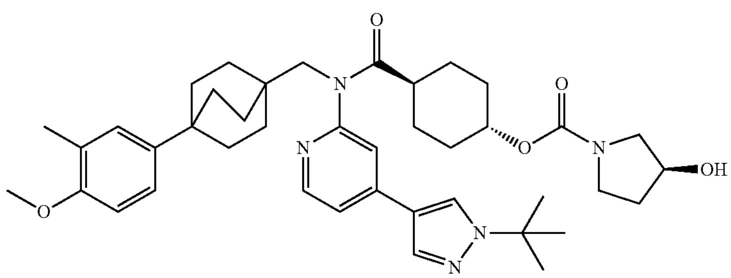 [SMILES: COc1ccc(C23CCC(CN(c4cc(-c5cnn(C(C)(C)C)c5)ccn4)C(=O)[C@H]4CC[C@H](OC(=O)N5CC[C@H](O)C5)CC4)(CC2)CC3)cc1C] | (S)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl) cyclohexyl trans-3-hydroxypyrrolidine-1-carboxylate |
| 2.35 | 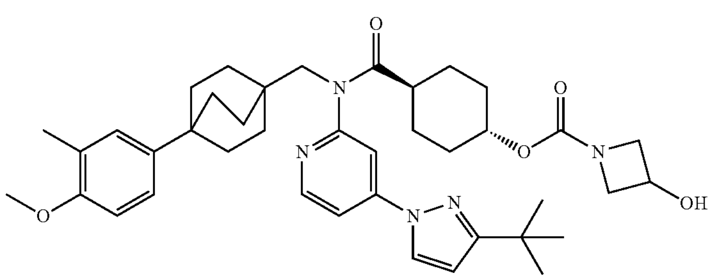 [SMILES: COc1ccc(C23CCC(CN(c4cc(-n5ccc(C(C)(C)C)n5)ccn4)C(=O)[C@H]4CC[C@H](OC(=O)N5CC(O)C5)CC4)(CC2)CC3)cc1C] | 4-((4-(3-(tert-Butyl)-1H-pyrazol-1-yl)pyridin-2-yl)((4-(4-methoxy-3-methylphenyl)bicyclo[2.2.2]octan-1-yl)methyl)carbamoyl) cyclohexyl trans-3-hydroxyazetidine-1-carboxylate |
| 2.36 | 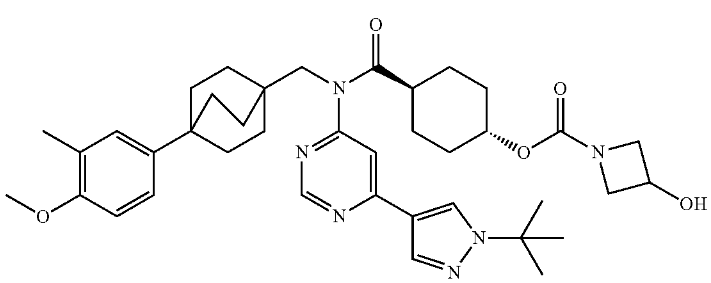 [SMILES: COc1ccc(C23CCC(CN(c4cc(-c5cnn(C(C)(C)C)c5)ncn4)C(=O)[C@H]4CC[C@H](OC(=O)N5CC(O)C5)CC4)(CC2)CC3)cc1C] | 4-((6-(1-(tert-Butyl)-1H-pyrazol-4-yl)pyrimidin-4-yl)((4-(4-methoxy-3-methylphenyl)bicyclo[2.2.2]octan-1-yl)methyl)carbamoyl)(trans-cyclohexyl) 3-hydroxyazetidine-1-carboxylate |

TABLE 1-continued

| Compound | Structure | Chemical Name |
|---|---|---|
| 2.37 | 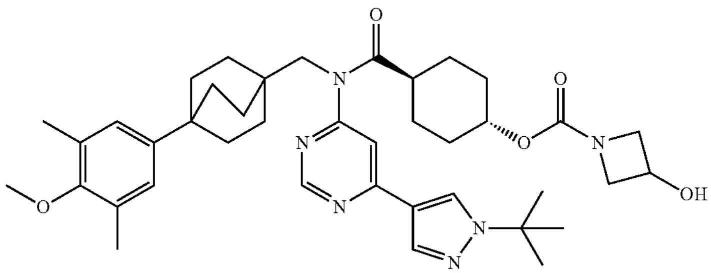 | 4-((6-(1-(tert-Butyl)-1H-pyrazol-4-yl)pyrimidin-4-yl)((4-(4-methoxy-3,5-dimethylphenyl)bicyclo[2.2.2]octan-1-yl)methyl)carbamoyl)(trans-cyclohexyl) 3-hydroxyazetidine-1-carboxylate |
| 2.38 | 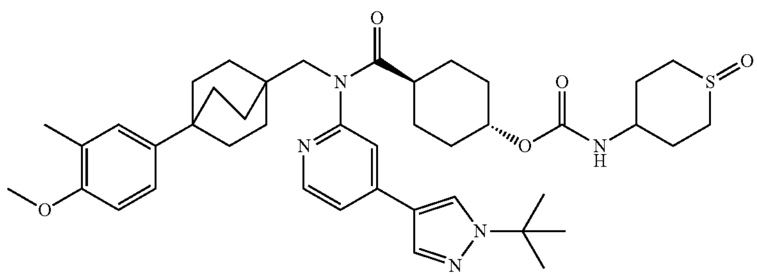 [SMILES: COc1ccc(C23CCC(CN(c4cc(-c5cnn(C(C)(C)C)c5)ccn4)C(=O)[C@H]4CC[C@H](OC(=O)NC5CCS(=O)CC5)CC4)(CC2)CC3)cc1C] | (1r,4r)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl (1-oxidotetrahydro-2H-thiopyran-4-yl)carbamate |
| 2.39 | 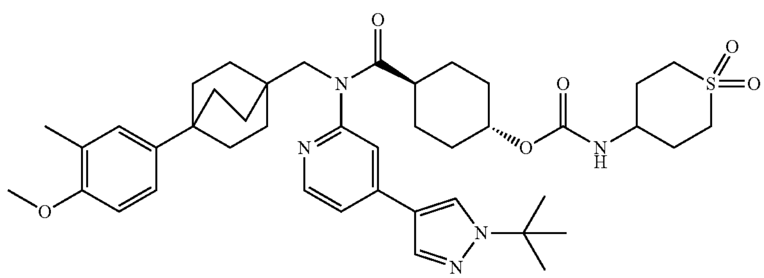 [SMILES: COc1ccc(C23CCC(CN(c4cc(-c5cnn(C(C)(C)C)c5)ccn4)C(=O)[C@H]4CC[C@H](OC(=O)NC5CCS(=O)(=O)CC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl trans-(1,1-dioxidotetrahydro-2H-thiopyran-4-yl)carbamate |
| 3 | 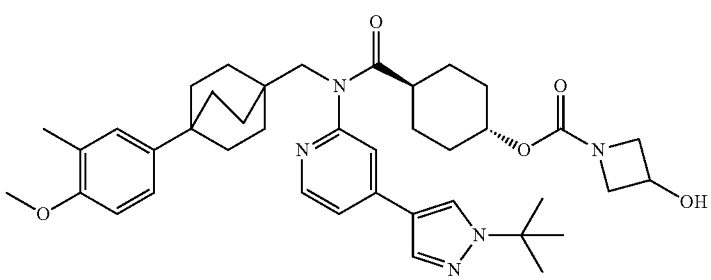 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 3-hydroxyazetidine-trans-1-carboxylate |
| 3.01 | 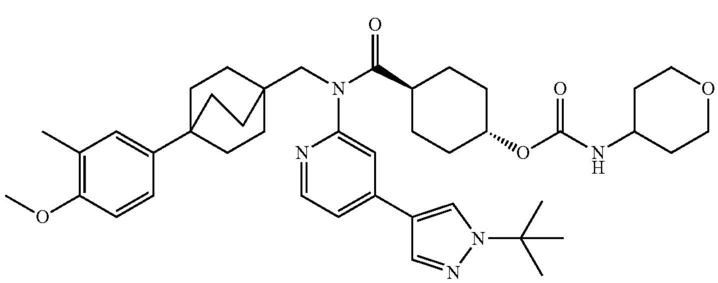 [SMILES: COc1ccc(C23CCC(CN(c4cc(-c5cnn(C(C)(C)C)c5)ccn4)C(=O)[C@H]4CC[C@H](OC(=O)NC5CCOCC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl (tetrahydro-2H-pyran-4-yl)trans-carbamate |

TABLE 1-continued

| Compound | Structure | Chemical Name |
|---|---|---|
| 3.02 | 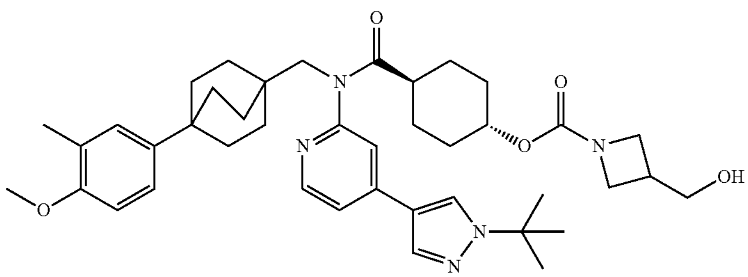 [SMILES: COc1ccc(C23CCC(CN(c4cc(-c5cnn(C(C)(C)C)c5)ccn4)C(=O)[C@H]4CC[C@H](OC(=O)N5CC(CO)C5)CC4)(CC2)CC3)cc1C] | 4-((4-(1-(tert-Butyl)-1H-pyrazol-4-yl)pyridin-2-yl)(trans(4-(4-methoxy-3-methylphenyl)bicyclo[2.2.2]octan-1-yl)methyl)carbamoyl)(trans-cyclohexyl) 3-(hydroxymethyl)azetidine-1-carboxylate |
| 3.03 | 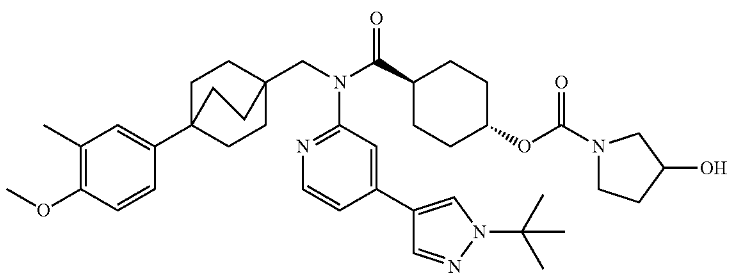 [SMILES: COc1ccc(C23CCC(CN(c4cc(-c5cnn(C(C)(C)C)c5)ccn4)C(=O)[C@H]4CC[C@H](OC(=O)N5CCC(O)C5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-hydroxypyrrolidine-1-carboxylate |
| 3.04 | 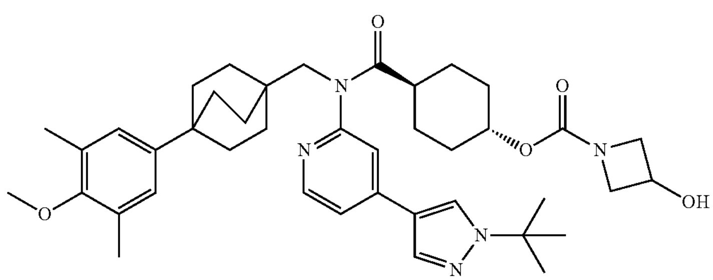 [SMILES: COc1c(C)cc(C23CCC(CN(c4cc(-c5cnn(C(C)(C)C)c5)ccn4)C(=O)[C@H]4CC[C@H](OC(=O)N5CC(O)C5)CC4)(CC2)CC3)cc1C] | 4-((4-(1-(tert-Butyl)-1H-pyrazol-4-yl)pyridin-2-yl)((4-(4-methoxy-3,5-dimethylphenyl)bicyclo[2.2.2]octan-1-yl)methyl)carbamoyl)(trans-cyclohexyl) 3-hydroxyazetidine-1-carboxylate |
| 3.05 | 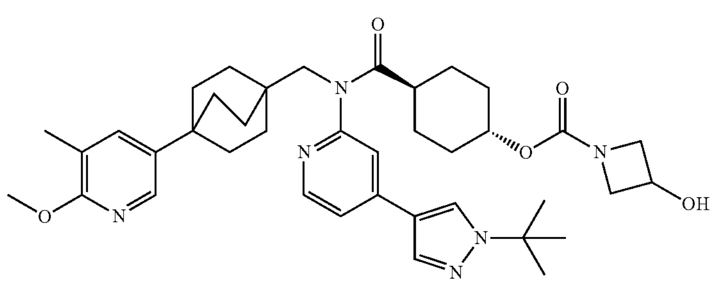 [SMILES: COc1ncc(C23CCC(CN(c4cc(-c5cnn(C(C)(C)C)c5)ccn4)C(=O)[C@H]4CC[C@H](OC(=O)N5CC(O)C5)CC4)(CC2)CC3)cc1C] | 4-((4-(1-(tert-Butyl)-1H-pyrazol-4-yl)pyridin-2-yl)((4-(6-methoxy-5-methylpyridin-3-yl)bicyclo[2.2.2]octan-1-yl)methyl)carbamoyl)(trans-cyclohexyl) 3-hydroxyazetidine-1-carboxylate |
| 3.06 | 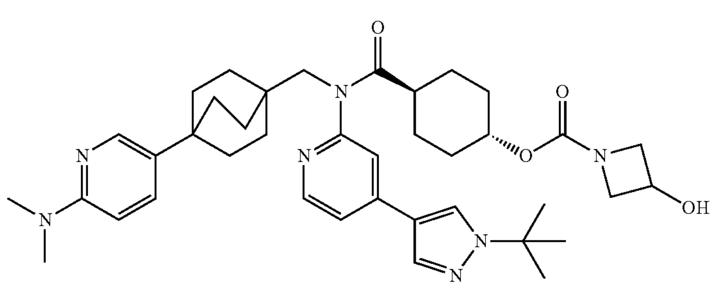 [SMILES: CN(C)c1ccc(C23CCC(CN(c4cc(-c5cnn(C(C)(C)C)c5)ccn4)C(=O)[C@H]4CC[C@H](OC(=O)N5CC(O)C5)CC4)(CC2)CC3)cn1] | 4-((4-(1-(tert-Butyl)-1H-pyrazol-4-yl)pyridin-2-yl)((4-(6-(dimethylamino)pyridin-3-yl)bicyclo[2.2.2]octan-1-yl)methyl)carbamoyl)(trans-cyclohexyl) 3-hydroxyazetidine-1-carboxylate |

TABLE 1-continued

| Compound | Structure | Chemical Name |
|---|---|---|
| 3.07 | 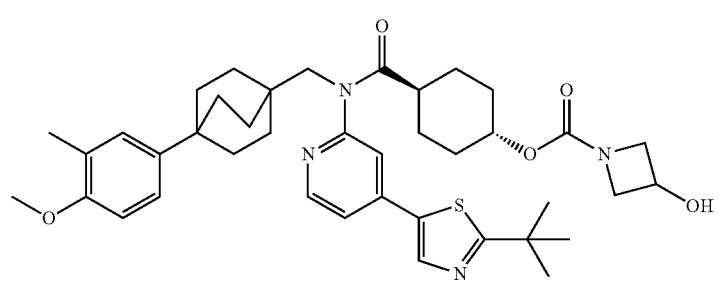 [SMILES: COc1ccc(C23CCC(CN(c4cc(-c5cnc(C(C)(C)C)s5)ccn4)C(=O)[C@H]4CC[C@H](OC(=O)N5CC(O)C5)CC4)(CC2)CC3)cc1C] | 4-((4-(2-(tert-Butyl) thiazol-5-yl)pyridin-2-yl)((4-(4-methoxy-3-methylphenyl)bicyclo[2.2.2]octan-1-yl)methyl)carbamoyl) cyclohexyl trans-3-hydroxyazetidine-1-carboxylate |
| 3.08 | 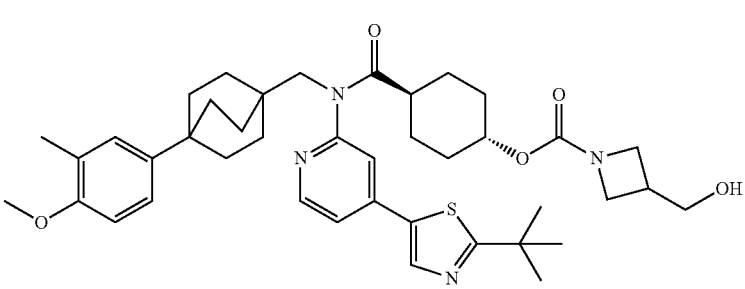 [SMILES: COc1ccc(C23CCC(CN(c4cc(-c5cnc(C(C)(C)C)s5)ccn4)C(=O)[C@H]4CC[C@H](OC(=O)N5CC(CO)C5)CC4)(CC2)CC3)cc1C] | 4-((4-(2-(tert-Butyl) thiazol-5-yl)pyridin-2-yl)((4-(4-methoxy-3-methylphenyl)bicyclo[2.2.2]octan-1-yl)methyl)carbamoyl) (trans-cyclohexyl) 3-(hydroxymethyl)azetidine-1-carboxylate |
| 3.09 | 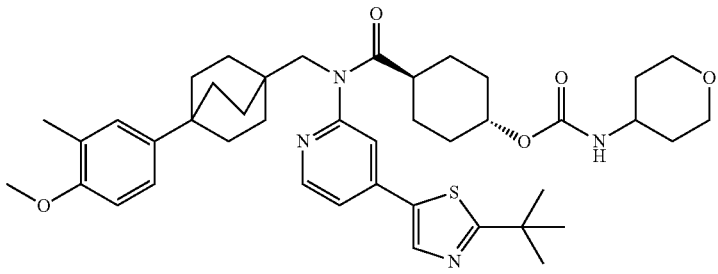 [SMILES: COc1ccc(C23CCC(CN(c4cc(-c5cnc(C(C)(C)C)s5)ccn4)C(=O)[C@H]4CC[C@H](OC(=O)NC5CCOCC5)CC4)(CC2)CC3)cc1C] | 4-((4-(2-(tert-Butyl) thiazol-5-yl)pyridin-2-yl)((4-(4-methoxy-3-methylphenyl)bicyclo[2.2.2]octan-1-yl)methyl)carbamoyl) cyclohexyl (tetrahydro-2H-pyran-4-yl)trans-carbamate |
| 3.10 | 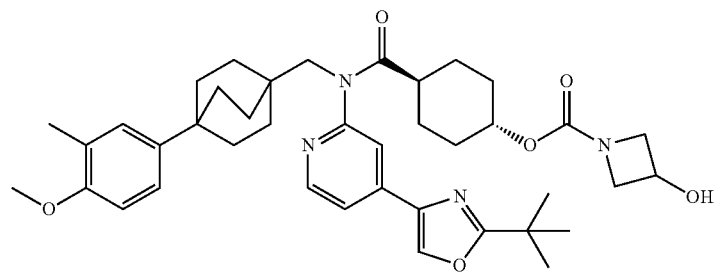 [SMILES: COc1ccc(C23CCC(CN(c4cc(-c5coc(C(C)(C)C)n5)ccn4)C(=O)[C@H]4CC[C@H](OC(=O)N5CC(O)C5)CC4)(CC2)CC3)cc1C] | 4-((4-(2-(tert-Butyl) oxazol-4-yl)pyridin-2-yl)((4-(4-methoxy-3-methylphenyl)bicyclo[2.2.2]octan-1-yl)methyl)carbamoyl)cyclohexyl 3-hydroxyazetidine-trans-1-carboxylate |
| 3.11 | 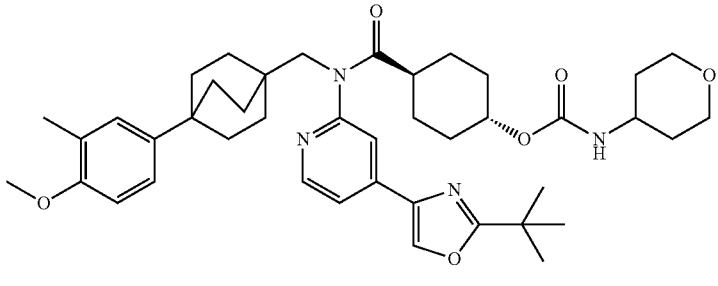 [SMILES: COc1ccc(C23CCC(CN(c4cc(-c5coc(C(C)(C)C)n5)ccn4)C(=O)[C@H]4CC[C@H](OC(=O)NC5CCOCC5)CC4)(CC2)CC3)cc1C] | 4-((4-(2-(tert-Butyl) oxazol-4-yl)pyridin-2-yl)((4-(4-methoxy-3-methylphenyl)bicyclo[2.2.2]octan-1-yl)methyl)carbamoyl) cyclohexyl (tetrahydro-2H-pyran-4-yl)trans-carbamate |

TABLE 1-continued

| Compound | Structure | Chemical Name |
|---|---|---|
| 3.12 | 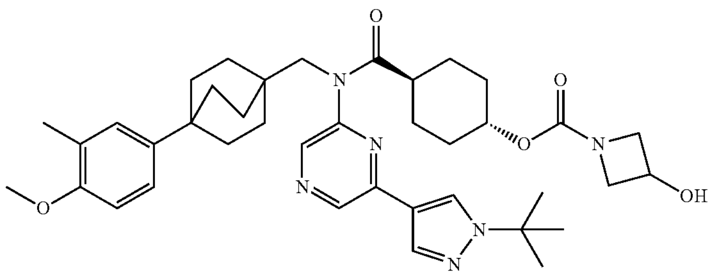 [SMILES: COc1ccc(C23CCC(CN(c4cncc(-c5cnn(C(C)(C)C)c5)n4)C(=O)[C@H]4CC[C@H](OC(=O)N5CC(O)C5)CC4)(CC2)CC3)cc1C] | 4-((6-(1-(tert-Butyl)-1H-pyrazol-4-yl)pyrazin-2-yl)((4-(4-methoxy-3-methylphenyl)bicyclo[2.2.2]octan-1-yl)methyl)carbamoyl) (trans-cyclohexyl) 3-hydroxyazetidine-1-carboxylate |
| 3.13 | 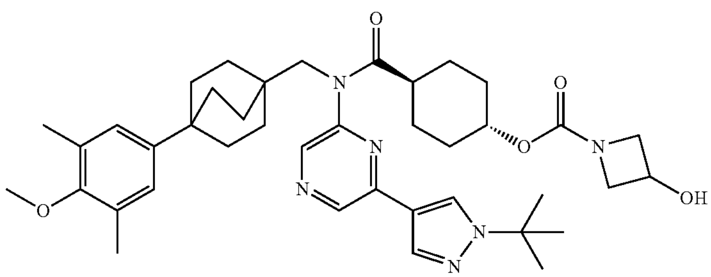 | 4-((6-(1-(tert-Butyl)-1H-pyrazol-4-yl)pyrazin-2-yl)((4-(4-methoxy-3,5-dimethylphenyl)bicyclo[2.2.2]octan-1-yl)methyl)carbamoyl) (trans-cyclohexyl) 3-hydroxyazetidine-1-carboxylate |
| 3.14 | 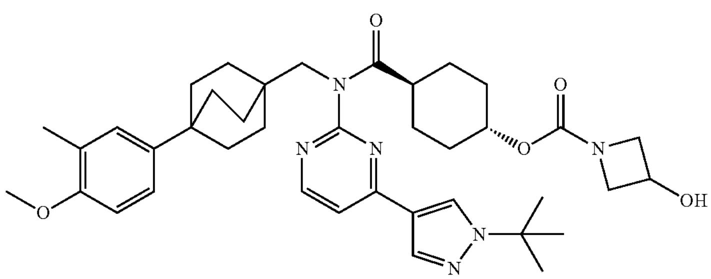 [SMILES: COc1ccc(C23CCC(CN(c4nccc(-c5cnn(C(C)(C)C)c5)n4)C(=O)[C@H]4CC[C@H](OC(=O)N5CC(O)C5)CC4)(CC2)CC3)cc1C] | 4-((4-(1-(tert-Butyl)-1H-pyrazol-4-yl)pyrimidin-2-yl)((4-(4-methoxy-3-methylphenyl)bicyclo[2.2.2]octan-1-yl)methyl)carbamoyl) (trans-cyclohexyl) 3-hydroxyazetidine-1-carboxylate |
| 3.15 | 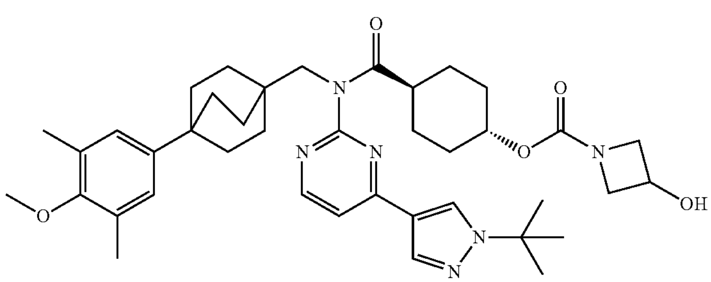 [SMILES: COc1c(C)cc(C23CCC(CN(c4nccc(-c5cnn(C(C)(C)C)c5)n4)C(=O)[C@H]4CC[C@H](OC(=O)N5CC(O)C5)CC4)(CC2)CC3)cc1C] | 4-((4-(1-(tert-Butyl)-1H-pyrazol-4-yl)pyrimidin-2-yl)((4-(4-methoxy-3,5-dimethylphenyl)bicyclo[2.2.2]octan-1-yl)methyl)carbamoyl) (trans-cyclohexyl) 3-hydroxyazetidine-1-carboxylate |
| 4 | 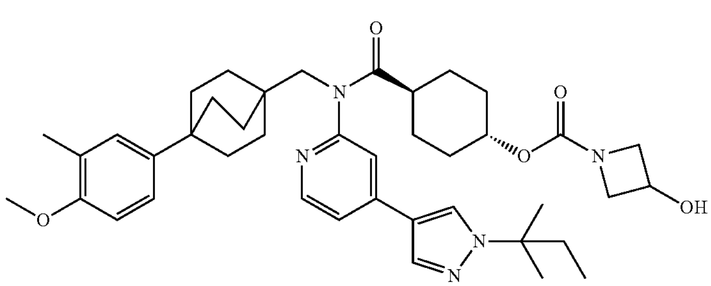 [SMILES: CCC(C)(C)n1cc(-c2ccnc(N(CC34CCC(c5ccc(OC)c(C)c5)(CC3)CC4)C(=O)[C@H]3CC[C@H](OC(=O)N4CC(O)C4)CC3)c2)cn1] | 4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl) cyclohexyl trans-3-hydroxyazetidine-1-carboxylate |

TABLE 1-continued

| Compound | Structure | Chemical Name |
|---|---|---|
| 4.01 | 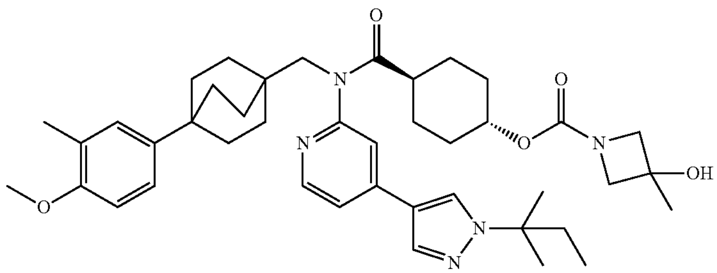 [SMILES: CCC(C)(C)n1cc(-c2ccnc(N(CC34CCC(c5ccc(OC)c(C)c5)(CC3)CC4)C(=O)[C@H]3CC[C@H](OC(=O)N4CC(C)(O)C4)CC3)c2)cn1] | 4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl trans-3-hydroxy-3-methylazetidine-1-carboxylate |
| 4.02 | 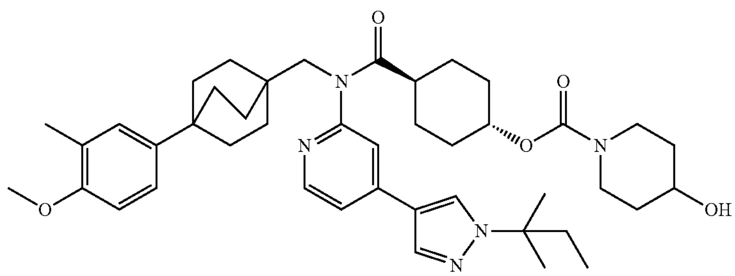 [SMILES: CCC(C)(C)n1cc(-c2ccnc(N(CC34CCC(c5ccc(OC)c(C)c5)(CC3)CC4)C(=O)[C@H]3CC[C@H](OC(=O)N4CCC(O)CC4)CC3)c2)cn1] | 4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl trans-4-hydroxypiperidine-1-carboxylate |
| 4.03 | 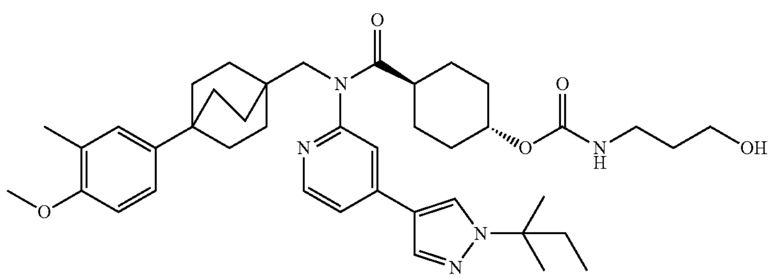 [SMILES: CCC(C)(C)n1cc(-c2ccnc(N(CC34CCC(c5ccc(OC)c(C)c5)(CC3)CC4)C(=O)[C@H]3CC[C@H](OC(=O)NCCCO)CC3)c2)cn1] | 4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl trans-(3-hydroxypropyl)carbamate |
| 4.04 | 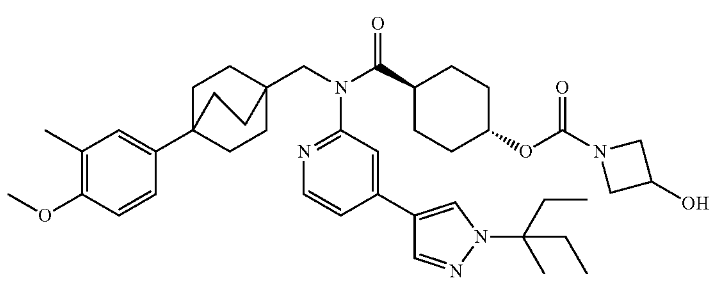 [SMILES: CCC(C)(CC)n1cc(-c2ccnc(N(CC34CCC(c5ccc(OC)c(C)c5)(CC3)CC4)C(=O)[C@H]3CC[C@H](OC(=O)N4CC(O)C4)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-3-hydroxyazetidine-1-carboxylate |
| 4.05 | 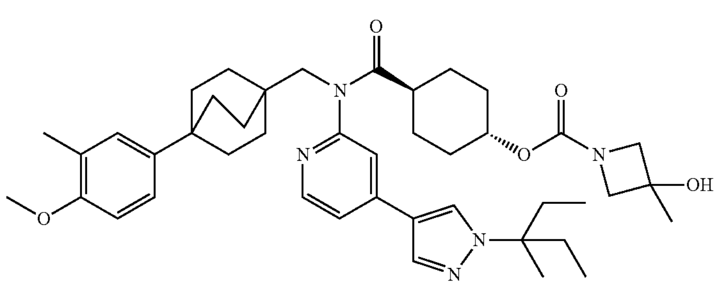 [SMILES: CCC(C)(CC)n1cc(-c2ccnc(N(CC34CCC(c5ccc(OC)c(C)c5)(CC3)CC4)C(=O)[C@H]3CC[C@H](OC(=O)N4CC(C)(O)C4)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-3-hydroxy-3-methylazetidine-1-carboxylate |

TABLE 1-continued

| Compound | Structure | Chemical Name |
|---|---|---|
| 4.06 | 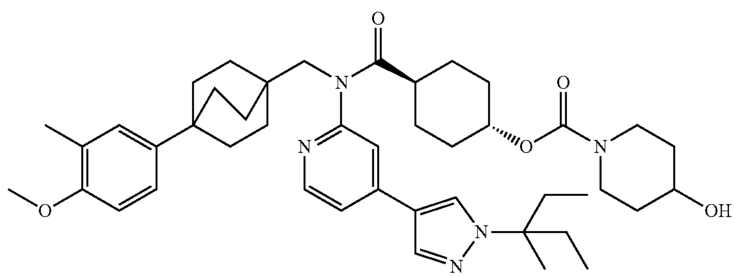 [SMILES: CCC(C)(CC)n1cc(-c2ccnc(N(CC34CCC(c5ccc(OC)c(C)c5)(CC3)CC4)C(=O)[C@H]3CC[C@H](OC(=O)N4CCC(O)CC4)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-4-hydroxypiperidine-1-carboxylate |
| 4.07 | 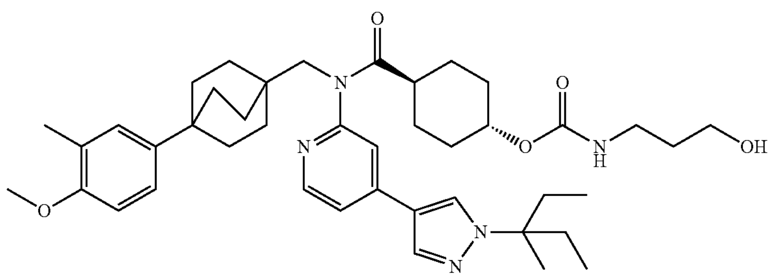 [SMILES: CCC(C)(CC)n1cc(-c2ccnc(N(CC34CCC(c5ccc(OC)c(C)c5)(CC3)CC4)C(=O)[C@H]3CC[C@H](OC(=O)NCCCO)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-(3-hydroxypropyl)carbamate |
| 4.08 | 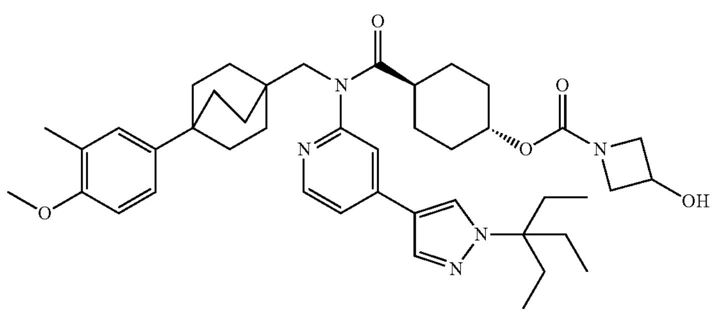 [SMILES: CCC(CC)(CC)n1cc(-c2ccnc(N(CC34CCC(c5ccc(OC)c(C)c5)(CC3)CC4)C(=O)[C@H]3CC[C@H](OC(=O)N4CC(O)C4)CC3)c2)cn1] | 4-((4-(1-(3-Ethylpentan-3-yl)-1H-pyrazol-4-yl)pyridin-2-yl)((4-(4-methoxy-3-methylphenyl)bicyclo[2.2.2]octan-1-yl)methyl)carbamoyl)cyclohexyl trans-3-hydroxyazetidine-1-carboxylate |
| 4.09 | 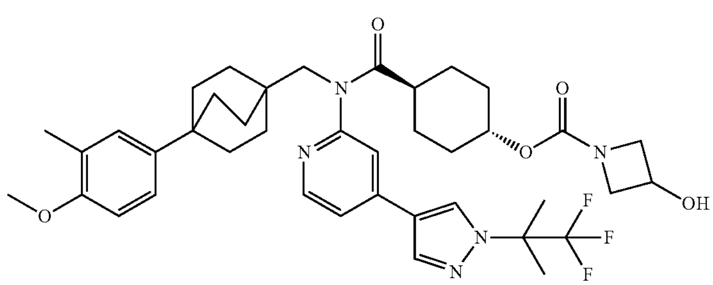 [SMILES: COc1ccc(C23CCC(CN(c4cc(-c5cnn(C(C)(C)C(F)(F)F)c5)ccn4)C(=O)[C@H]4CC[C@H](OC(=O)N5CC(O)C5)CC4)(CC2)CC3)cc1C] | 4-(((4-(4-Methoxy-3-methylphenyl)bicyclo[2.2.2]octan-1-yl)methyl)(4-(1-(1,1,1-trifluoro-2-methylpropan-2-yl)-1H-pyrazol-4-yl)pyridin-2-yl)carbamoyl)cyclohexyl trans-3-hydroxyazetidine-1-carboxylate |
| 4.10 | 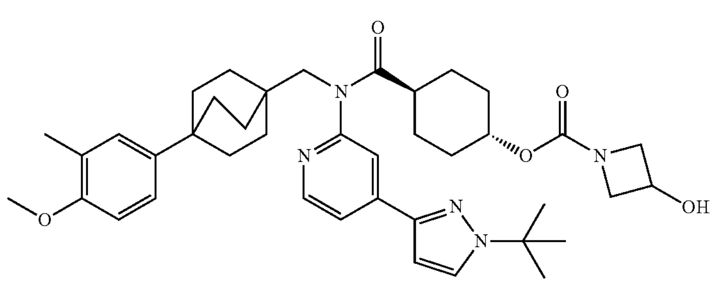 [SMILES: COc1ccc(C23CCC(CN(c4cc(-c5ccn(C(C)(C)C)n5)ccn4)C(=O)[C@H]4CC[C@H](OC(=O)N5CC(O)C5)CC4)(CC2)CC3)cc1C] | 4-((4-(1-(tert-Butyl)-1H-pyrazol-3-yl)pyridin-2-yl)((4-(4-methoxy-3-methylphenyl)bicyclo[2.2.2]octan-1-yl)methyl)carbamoyl)cyclohexyl trans-3-hydroxyazetidine-1-carboxylate |

TABLE 1-continued

| Compound | Structure | Chemical Name |
|---|---|---|
| 4.11 | 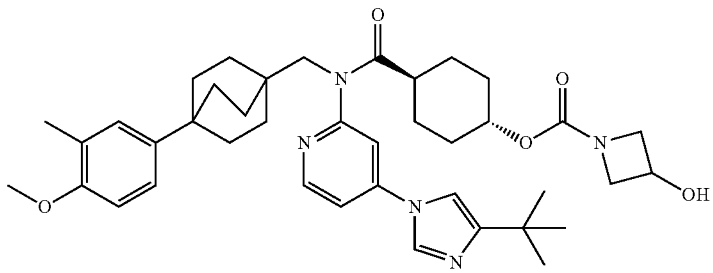 [SMILES: COc1ccc(C23CCC(CN(c4cc(-n5cnc(C(C)(C)C)c5)ccn4)C(=O)[C@H]4CC[C@H](OC(=O)N5CC(O)C5)CC4)(CC2)CC3)cc1C] | 4-((4-(4-(tert-Butyl)-1H-imidazol-1-yl)pyridin-2-yl)((4-(4-methoxy-3-methylphenyl)bicyclo[2.2.2]octan-1-yl)methyl)carbamoyl) cyclohexyl trans-3-hydroxyazetidine-1-carboxylate |

In some embodiments, provided herein is a pharmaceutically acceptable salt or solvate of a compound that is described in Table 1.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties*, Selection and Use, Weinheim/Zurich: Wiley-VCH/VHCA. 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt."

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic groups (e.g., alkyl groups, aromatic rings) of compounds described herein are susceptible to various metabolic reactions. Incorporation of appropriate substituents on the organic groups will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g., with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound. In some embodiments, a prodrug of the compound disclosed herein permits targeted delivery of the compound to a particular region of the gastrointestinal tract. Formation of a pharmacologically active metabolite by the colonic metabolism of drugs is a commonly used "prodrug" approach for the colon-specific drug delivery systems.

In some embodiments, a prodrug is formed by the formation of a covalent linkage between drug and a carrier in such a manner that upon oral administration the moiety remains intact in the stomach and small intestine. This approach involves the formation of a prodrug, which is a pharmacologically inactive derivative of a parent drug molecule that requires spontaneous or enzymatic transformation in the biological environment to release the active drug. Formation of prodrugs has improved delivery properties over the parent drug molecule. The problem of stability of certain drugs from the adverse environment of the upper gastrointestinal tract can be eliminated by prodrug formation, which is converted into the parent drug molecule once it reaches the colon. Site specific drug delivery through site specific prodrug activation may be accomplished by the utilization of some specific property at the target site, such as altered pH or high activity of certain enzymes relative to the non-target tissues for the prodrug-drug conversion.

In some embodiments, covalent linkage of the drug with a carrier forms a conjugate. Such conjugates include, but are not limited to, azo bond conjugates, glycoside conjugates, glucuronide conjugates, cyclodextrin conjugates, dextran conjugates or amino-acid conjugates.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, the compounds described herein are rapidly metabolized following absorption from the gastro-intestinal tract to metabolites that have greatly reduced FXR agonist activity.

In additional or further embodiments, the compounds are rapidly metabolized in plasma.

In additional or further embodiments, the compounds are rapidly metabolized by the intestines.

In additional or further embodiments, the compounds are rapidly metabolized by the liver.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

The compounds described herein are prepared by the general synthetic routes described below in Schemes 1 to 11.

In some embodiments, intermediates used in the preparation of compounds described herein are prepared as outlined in Scheme 1.

Scheme 1

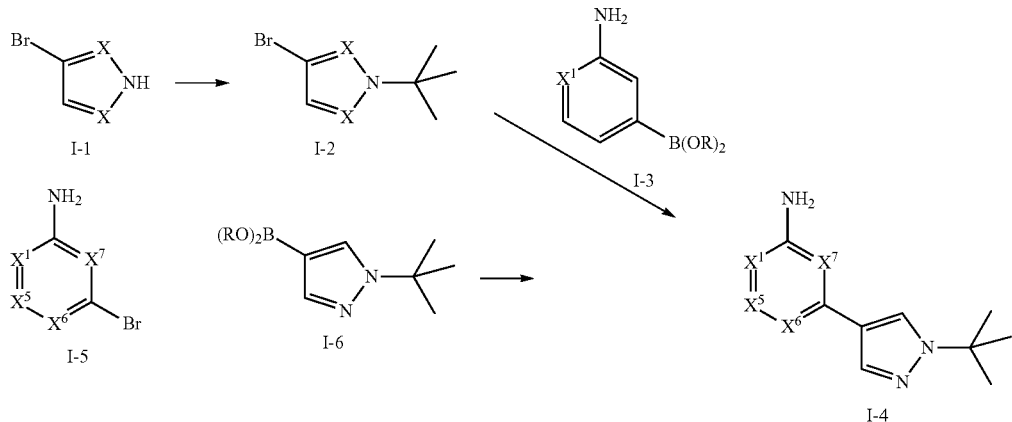

In Scheme 1, $X^1$, $X^5$, $X^6$, and $X^7$ are as described herein. In some embodiments, X is CH or N. In some embodiments, X is CH. In some embodiments, X is N. In some embodiments, R is an alkyl group. In some embodiments, R is hydrogen. In some embodiments, R is independently an alkyl group or hydrogen. In some embodiments, the alkyl groups bonded to the same boron atom, through the respective oxygen atoms on the same boron atom, are an alkylene group bridging the two oxygen atoms on the same boron atom. In some embodiments, the boron atom, the two oxygen atoms on the same boron atom, and the carbon atoms of the alkylene group that bridge the two oxygen atoms form a five- or six-member ring. In some embodiments, the bridging alkylene group is —C(CH$_3$)$_2$C(CH$_3$)$_2$— and is part of a five-member ring.

In some embodiments, heteroaryl I-1 is reacted under suitable SNI conditions to provide heteroaryl halide I-2. In some embodiments, suitable SNI conditions include reacting I-1 with tBuOH and an appropriate acid at the appropriate temperature for the appropriate time. In some embodiments, the appropriate acid is a strong acid. In some embodiments, the strong acid is sulfuric acid, hydrochloric acid, or hydrobromic acid. In some embodiments, the strong acid is sulfuric acid. In some embodiments, the strong acid is concentrated sulfuric acid. In some embodiments, the appropriate time is from about 1 hour to about 12-18 hours, where the range of time from about 12-18 hours is referred to, interchangeably herein, as "overnight". In some embodiments, the appropriate temperature is from about 60° C. to about 110° C. In some embodiments, the appropriate temperature is about 80° C. to about 90° C.

In some embodiments, boron reagent I-3 is reacted with a heteroaryl halide I-2 under suitable metal-catalyzed cross-coupling reaction conditions to provide I-4. In some embodiments, the boron reagent is an aryl boronic acid. In some embodiments, the boron reagent is an aryl boronic ester. In some embodiments, the boron reagent is a substituted pyridineboronic acid. In some embodiments, the heteroaryl halide is a pyrazolyl bromide. In some embodiments, the heteroaryl halide is a 3-bromopyrazole. In some embodiments, the heteroaryl halide is a 4-bromopyrazole. In some embodiments, suitable metal-catalyzed cross-coupling reaction conditions include palladium. In some embodiments, suitable metal-catalyzed cross-coupling reaction conditions include palladium, an appropriate base, and an appropriate solvent for an appropriate time and at an appropriate temperature. In some embodiments, the palladium is delivered in the form of Pd(dppf)Cl$_2$. In some embodiments, the appropriate base is an inorganic base. In some embodiments, the inorganic base is a carbonate, a phosphate, an oxide, or a hydroxide. In some embodiments, the inorganic base is an alkali metal inorganic base. In some embodiments, the alkali metal is sodium, potassium, cesium, or combinations thereof. In some embodiments, the inorganic base is Na$_2$CO$_3$, K$_2$CO$_3$, Cs$_2$CO$_3$, or combinations thereof. In some embodiments, the combination is a combination of Na$_2$CO$_3$ and K$_2$CO$_3$. In some embodiments, the inorganic base is K$_2$CO$_3$. In some embodiments, the inorganic base is Cs$_2$CO$_3$. In some embodiments, the appropriate solvent is an aqueous solvent. In some embodiments, the appropriate solvent is a mixture of water and an organic solvent. In some embodiments, the organic solvent in the mixture is a C$_{1-4}$-alcohol, THF, 2-MeTHF, DMF, dioxane, or a combination thereof. In some embodiments, the organic solvent in the mixture is dioxane. In some embodiments, the appropriate time is from about 1 hour to about 12-18 hours. In some embodiments, the appropriate temperature is from about 50° C. to about 115° C. In some embodiments, the appropriate temperature is about 80° C. In some embodiments, the reaction is performed in a microwave. In some embodiments, the appropriate time is from about 10 minutes to about 30 minutes. In some embodiments, the appropriate temperature is from about 130° C. to about 170° C. In some embodiments, the appropriate temperature is about 150° C. to about 160° C.

In some embodiments, aryl halide I-5 is reacted with boron reagent I-6 under suitable metal-catalyzed cross-coupling reaction conditions to provide I-4. In some embodiments, the aryl halide is an aryl bromide. In some embodiments, the aryl halide is a substituted pyridyl halide. In some embodiments, the aryl halide is a substituted pyridyl bromide. In some embodiments, the aryl halide is a substituted 4-bromopyridine. In some embodiments, the boron reagent is a heteroaryl boronic acid. In some embodiments, the boron reagent is a heteroaryl boronic ester. In some embodiments, the boron reagent is a heteroaryl pinacolyl boronic ester. In some embodiments, the heteroaryl boron reagent is a pyrazolyl boron reagent. In some embodiments, suitable metal-catalyzed cross-coupling reaction conditions include palladium. In some embodiments, suitable metal-catalyzed cross-coupling reaction conditions include palladium, an appropriate base, and an appropriate solvent for an appropriate time and at an appropriate temperature. In some embodiments, the palladium is delivered in the form of Pd(dppf)Cl$_2$. In some embodiments, the appropriate base is an inorganic base. In some embodiments, the inorganic base is a carbonate, a phosphate, an oxide, or a hydroxide. In some embodiments, the inorganic base is an alkali metal inorganic base. In some embodiments, the alkali metal is sodium, potassium, cesium, or combinations thereof. In some embodiments, the inorganic base is Na$_2$CO$_3$, K$_2$CO$_3$, Cs$_2$CO$_3$, or combinations thereof. In some embodiments, the combination is a combination of Na$_2$CO$_3$ and K$_2$CO$_3$. In some embodiments, the inorganic base is K$_2$CO$_3$. In some embodiments, the inorganic base is Cs$_2$CO$_3$. In some embodiments, the appropriate solvent is an aqueous solvent. In some embodiments, the appropriate solvent is a mixture of water and an organic solvent. In some embodiments, the organic solvent in the mixture is a C$_{1-4}$-alcohol, THF, 2-MeTHF, DME, DMF, dioxane, or a combination thereof. In some embodiments, the organic solvent in the mixture is dioxane. In some embodiments, the organic solvent in the mixture is 2-MeTHF. In some embodiments, the organic solvent in the mixture is DME. In some embodiments, the appropriate time and appropriate temperature are from about 2 hours to overnight and about 90° C. In some embodiments, the reaction is performed in a microwave. In some embodiments, the appropriate time is from about 10 minutes to about 30 minutes. In some embodiments, the appropriate temperature is from about 130° C. to about 170° C. In some embodiments, the appropriate temperature is about 150° C. to about 160° C.

In some embodiments, intermediates used in the preparation of compounds described herein are prepared as outlined in Scheme 2.

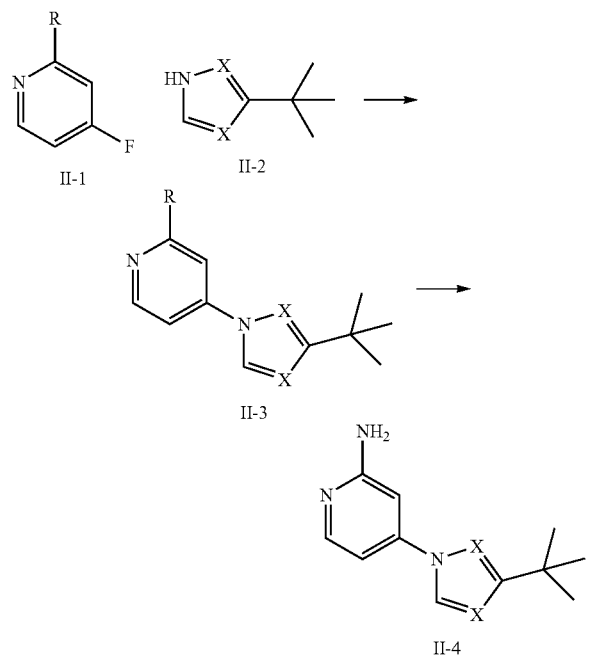

Scheme 2

II-1

II-2

II-3

II-4

In Scheme 2, X is C—H or N. In some embodiments, the 5-membered heterocycle of II-2 is pyrazolyl, pyrrolyl, imidazolyl, or triazolyl. In some embodiments, R is NHBoc, iodide, bromide, chloride, or trifluoromethanesulfonate (tri-flate, —OTf, CF$_3$SO$_3$—). In some embodiments, R is NHBoc. In some embodiments, R is bromide or chloride. In some embodiments, R is chloride.

In some embodiments, aryl fluoride II-1 is reacted with heteroaryl II-2 under suitable S$_N$Ar reaction conditions to provide II-3. In some embodiments, heteroaryl II-2 is reacted with aryl fluoride II-1 where R is chloro. In some embodiments, heteroaryl II-2 is reacted with aryl fluoride II-1 where R is NHBoc. In some embodiments, suitable S$_N$Ar reaction conditions include an appropriate base and an appropriate solvent, for an appropriate time at an appropriate temperature. In some embodiments, the appropriate base is an inorganic base. In some embodiments, the inorganic base is a carbonate base. In some embodiments, the carbonate base is an alkali metal carbonate. In some embodiments, the alkali metal carbonate is K$_2$CO$_3$. In some embodiments, the appropriate solvent is DMSO, NMP, toluene, or combinations thereof. In some embodiments, the appropriate solvent is a mixture of water and DMSO, NMP, toluene, or combinations thereof. In some embodiments, the appropriate solvent is NMP. In some embodiments, the appropriate time and appropriate temperature are overnight and about 100° C.

In some embodiments, II-3 is subjected to suitable palladium-catalyzed cross coupling reaction conditions in the presence of a suitable ammonia source to provide II-4. In some embodiments, II-3, wherein R is halo, is subjected to suitable palladium-catalyzed cross coupling reaction conditions in the presence of a suitable ammonia source to provide II-4. In some embodiments, II-3, wherein R is bromo or chloro, is subjected to suitable palladium-catalyzed cross coupling reaction conditions in the presence of a suitable ammonia source to provide II-4. In some embodiments, II-3, wherein R is chloro, is subjected to suitable palladium-catalyzed cross coupling reaction conditions in the presence of a suitable ammonia source to provide II-4. In some embodiments, the suitable ammonia source is LiHMDS. In some embodiments, suitable palladium-catalyzed cross-coupling reaction conditions include tris(dibenzylideneacetone)dipalladium(0), an appropriate ligand, and an appropriate solvent for an appropriate time at an appropriate temperature. In some embodiments, the appropriate ligand is 2-dicyclohexylphosphino-2',4',6'-triisopropylbiphenyl. In some embodiments, the appropriate solvent is dioxane or THF. In some embodiments, the appropriate time and appropriate temperature are from about 2 hours to overnight and about 100° C. In some embodiments, the appropriate time and appropriate temperature are overnight and about 60° C.

In some embodiments, the suitable hydrolysis reaction conditions are sufficient to deprotect the tert-butyloxycarbonyl-protected aniline II-3 and provide II-4. In some embodiments, the suitable hydrolysis reaction conditions are sufficient to deprotect the tert-butyloxycarbonyl-protected aniline II-3, wherein R is NHBoc, and provide II-4. In some embodiments, the suitable hydrolysis conditions include an appropriate acid and an appropriate solvent, for an appropriate time at an appropriate temperature. In some embodiments, the appropriate acid is aqueous HCl. In some embodiments, the appropriate solvent is methanol. In some embodiments, the appropriate solvent is EtOAc. In some embodiments, the appropriate acid is HCl in EtOAc. In some embodiments, the appropriate time and appropriate temperature are about overnight and 50° C.

In some embodiments, intermediates used in the preparation of compounds described herein are prepared as outlined in Scheme 3.

Scheme 3

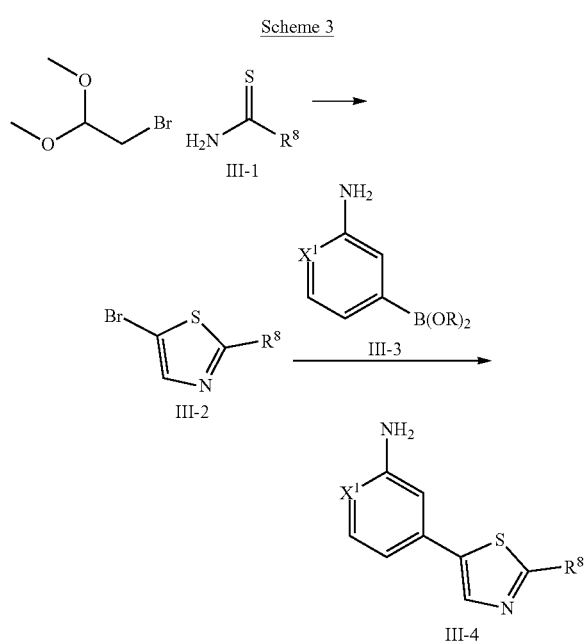

In Scheme 3, $X^1$ and $R^8$ are as described herein. In some embodiments, R is an alkyl group. In some embodiments, R is hydrogen. In some embodiments, R is independently an alkyl group or hydrogen. In some embodiments, the alkyl groups bonded to the same boron atom, through the respective oxygen atoms on the same boron atom, are an alkylene group bridging the two oxygen atoms on the same boron atom. In some embodiments, the boron atom, the two oxygen atoms on the same boron atom, and the carbon atoms of the alkylene group that bridge the two oxygen atoms form a five- or six-member ring. In some embodiments, the bridging alkylene group is —C(CH$_3$)$_2$C(CH$_3$)$_2$— and is part of a five-member ring.

In some embodiments, thioamide III-1 is reacted with bromoacetaldehyde dimethyl acetal (2-bromo-1,1-dimethoxyethane) under suitable condensation reaction conditions followed by suitable bromination reaction conditions to provide 2-substituted bromothiazole III-2. In some embodiments, the suitable condensation reaction conditions are sufficient to provide an intermediate 2-substituted thiazole that provides 2-substituted bromothiazole III-2 after bromination under suitable bromination reaction conditions. In some embodiments, suitable condensation reaction conditions include an appropriate acid catalyst and an appropriate solvent, for an appropriate time at an appropriate temperature. In some embodiments, the appropriate acid is para-toluenesulfonic acid. In some embodiments, the appropriate solvent is acetic acid. In some embodiments, the appropriate time and appropriate temperature are overnight and about 120° C. In some embodiments, the suitable bromination reaction conditions are sufficient to brominate the intermediate 2-substituted thiazole and provide III-2. In some embodiments, the suitable bromination conditions include an appropriate brominating agent and an appropriate solvent, for an appropriate time at an appropriate temperature. In some embodiments, the appropriate brominating agent is NBS. In some embodiments, the appropriate solvent is DMF. In some embodiments, the appropriate time and appropriate temperature are about 1 hour and room temperature.

In some embodiments, boron reagent III-3 is reacted with a 2-substituted bromothiazole III-2 under suitable metal-catalyzed cross-coupling reaction conditions to provide III-4. In some embodiments, the 2-substituted bromothiazole is a 5-bromo-2-substituted thiazole. In some embodiments, suitable metal-catalyzed cross-coupling reaction conditions include palladium. In some embodiments, suitable metal-catalyzed cross-coupling reaction conditions include palladium, an appropriate base, and an appropriate solvent for an appropriate time and at an appropriate temperature. In some embodiments, the palladium is delivered in the form of Pd(dppf)Cl$_2$. In some embodiments, the appropriate base is an inorganic base. In some embodiments, the inorganic base is carbonate, a phosphate, an oxide, or a hydroxide. In some embodiments, the inorganic base is an alkali metal inorganic base. In some embodiments, the alkali metal is sodium, potassium, cesium, or combinations thereof. In some embodiments, the inorganic base is Na$_2$CO$_3$, K$_2$CO$_3$, Cs$_2$CO$_3$, or combinations thereof. In some embodiments, the combination is a combination of Na$_2$CO$_3$ and K$_2$CO$_3$. In some embodiments, the inorganic base is K$_2$CO$_3$. In some embodiments, the inorganic base is Cs$_2$CO$_3$. In some embodiments, the appropriate solvent is an aqueous solvent. In some embodiments, the appropriate solvent is a mixture of water and an organic solvent. In some embodiments, the organic solvent in the mixture is a C$_{1-4}$-alcohol, THF, DMF, dioxane, or a combination thereof. In some embodiments, the organic solvent in the mixture is dioxane. In some embodiments, the appropriate time and appropriate temperature are overnight and about 80° C.

In some embodiments, intermediates used in the preparation of compounds described herein are prepared as outlined in Scheme 4.

Scheme 4

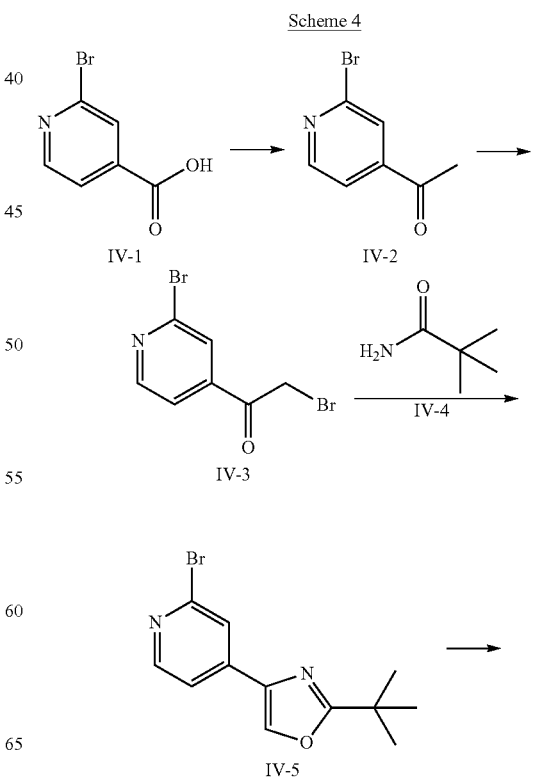

-continued

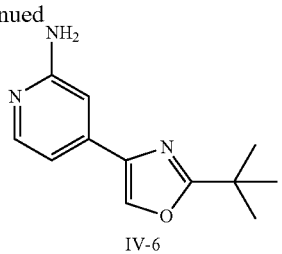

IV-6

In some embodiments, pyridine carboxylic acid IV-1 is converted to methyl ketone IV-2. In some embodiments, IV-1 is converted to IV-2 using a sequence of reactions referred to alternatively as the Weinreb ketone synthesis. In some embodiments, IV-1 is reacted under a series of suitable reaction conditions to provide IV-2. In some embodiments, the series includes suitable carboxylic acid activation reaction conditions, suitable Weinreb amide-forming reaction conditions, and suitable alkylation reaction conditions, applied in that sequence. In some embodiments, the carboxylic acid activation reaction conditions include an appropriate carboxylic acid activating agent and a solvent, for an appropriate time and at an appropriate temperature. In some embodiments, the carboxylic acid activating agent is carbonyldiimidazole. In some embodiments, the solvent is DCE or DCM. In some embodiments, the time and temperature are from 15 minutes to 60 minutes and room temperature. In some embodiments, the Weinreb amide-forming reaction conditions include an acid salt of N,O-dimethylhydroxylamine and an appropriate solvent, for an appropriate time at an appropriate temperature. In some embodiments, the acid salt of N,O-dimethylhyroxylamine is the hydrochloride salt. In some embodiments, the solvent is the same as included in the carboxylic acid activation reaction conditions. In some embodiments, the time and temperature are overnight and room temperature. In some embodiments, the alkylation reaction conditions include an appropriate alkyl organometallic reagent and a solvent, for an appropriate time and at an appropriate temperature. In some embodiments, the alkyl organometallic reagent is $CH_3MgBr$, $CH_3MgCl$, $CH_3MgI$, $(CH_3)_2Mg$, or $CH_3Li$. In some embodiments, the alkyl organometallic reagent is $CH_3MgBr$. In some embodiments, the solvent is THF, $Et_2O$, or combinations thereof. In some embodiments, the solvent is THF. In some embodiments, the time and temperature are overnight and from 0° C. to room temperature. In some embodiments, an initial temperature is maintained for a first time, after which the temperature is allowed to warm to a second temperature for second time. In some embodiments, the initial temperature is about 0° C., the first time is from 15 minutes to 60 minutes, the second temperature is room temperature, and the second time is overnight.

In some embodiments, α-bromoketone IV-3 is obtained by subjecting ketone IV-2 to suitable bromination conditions. In some embodiments, suitable bromination conditions include bromine, HBr, and acetic acid for a suitable time at a suitable temperature. In some embodiments, the suitable time is overnight. In some embodiments, the suitable temperature is about room temperature.

In some embodiments, α-haloketone IV-3 is treated with amide IV-4 and an appropriate silver salt, in an appropriate solvent for an appropriate time at an appropriate temperature to provide IV-5. In some embodiments, the silver salt is AgOTf, $AgBF_4$, $AgClO_4$, or $AgSbF_6$. In some embodiments, the silver salt is $AgSbF_6$. In some embodiments, the silver salt is AgOTf. In some embodiments, the solvent is EtOAc, dioxane, or DCE. In some embodiments, the time is overnight. In some embodiments, the temperature is from about 50° C. to about 100° C. In some embodiments, the temperature is about 70° C., or about 100° C.

In some embodiments, IV-5 is subjected to suitable palladium-catalyzed cross coupling reaction conditions in the presence of a suitable ammonia source to provide IV-6. In some embodiments, the suitable ammonia source is LiHMDS. In some embodiments, suitable palladium-catalyzed cross-coupling reaction conditions include tris(dibenzylideneacetone)dipalladium(0), an appropriate ligand, and an appropriate solvent for an appropriate time at an appropriate temperature. In some embodiments, the appropriate ligand is 2-dicyclohexylphosphino-2',4',6'-triisopropylbiphenyl. In some embodiments, the appropriate solvent is dioxane or THF. In some embodiments, the appropriate time and appropriate temperature are from about 2 hours to overnight and about 100° C. In some embodiments, the appropriate time and appropriate temperature are overnight and about 60° C.

In some embodiments, intermediates used in the preparation of compounds described herein are prepared as outlined in Scheme 5.

Scheme 5

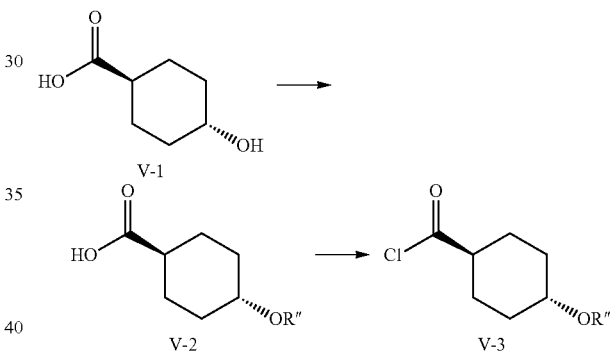

In some embodiments, R" is an alcohol protecting group. In some embodiments, the alcohol protecting group is methyl, a substituted methyl group, a substituted ethyl group, a substituted benzyl group, or a silyl group, as described in, for example, Wuts, P. G. M. "Greene's Protective Groups in Organic Synthesis" (2014) John Wiley & Sons ISBN: 978-1-118-05748-3. In some embodiments, the alcohol protecting group is a silyl group. In some embodiments, the silyl group is tert-butyldimethylsilyl.

In some embodiments, V-1 is subjected to suitable alcohol protection reaction conditions to form a bis-silyl intermediate, followed by suitable hydrolysis reaction conditions to form V-2, in the case where R" is a silyl group. In some embodiments, R" is tert-butyldimethylsilyl and the alcohol protection reaction conditions include a tert-butyldimethylsilyl halide and an appropriate base, in an appropriate solvent for an appropriate time at an appropriate temperature. In some embodiments, the tert-butyldimethylsilyl halide is tert-butyldimethylsilyl chloride. In some embodiments, the base is imidazole. In some embodiments, the solvent is DMF. In some embodiments, the time is about 2 hours and the temperature is about room temperature. In some embodiments, the bis-silyl intermediate (a silyl ester) is subjected to suitable hydrolysis reaction conditions to form V-2. In some embodiments, the suitable hydrolysis reaction conditions include a base, in an appropriate solvent, for an appropriate time, at an appropriate temperature. In some embodiments, the base is $K_2CO_3$. In some embodiments, the solvent is a mixture of water, ethanol, and THF. In some embodiments, the solvent is aqueous ethanol, aqueous THF, or combinations thereof. In some embodiments, the time is about 3 hours and the temperature is about room temperature.

In some embodiments, when R" is methyl, a substituted methyl group, a substituted ethyl group, or a substituted benzyl group, V-1 is subjected to suitable alcohol protection reaction conditions to form a bis-alkyl intermediate (where both the carboxylic acid and alcohol —OH are alkylated, to form an ester and ether, respectively, and, for the purposes of Scheme 5, and schemes referencing Scheme 5 or schemes referencing intermediates or products disclosed in Scheme 5, the alkyl groups on the bis-alkyl intermediate are methyl, a substituted methyl group, a substituted ethyl group, or a substituted benzyl group), followed by suitable hydrolysis reaction conditions to form V-2.

In some embodiments, protected alcohol V-2 is converted to acid chloride V-3, under suitable chlorination reaction conditions. In some embodiments, the chlorination reaction conditions include (chloromethylene)dimethyliminium chloride and an appropriate base, in an appropriate solvent for an appropriate time at an appropriate temperature. In some embodiments, the base is anhydrous $K_2CO_3$. In some embodiments, the solvent is toluene. In some embodiments, the time is from about 0.5 hr to about 2 hours. In some embodiments, the temperature is about 0° C. In some embodiments, the temperature is room temperature.

In some embodiments, intermediates used in the preparation of compounds described herein are prepared as outlined in Scheme 6.

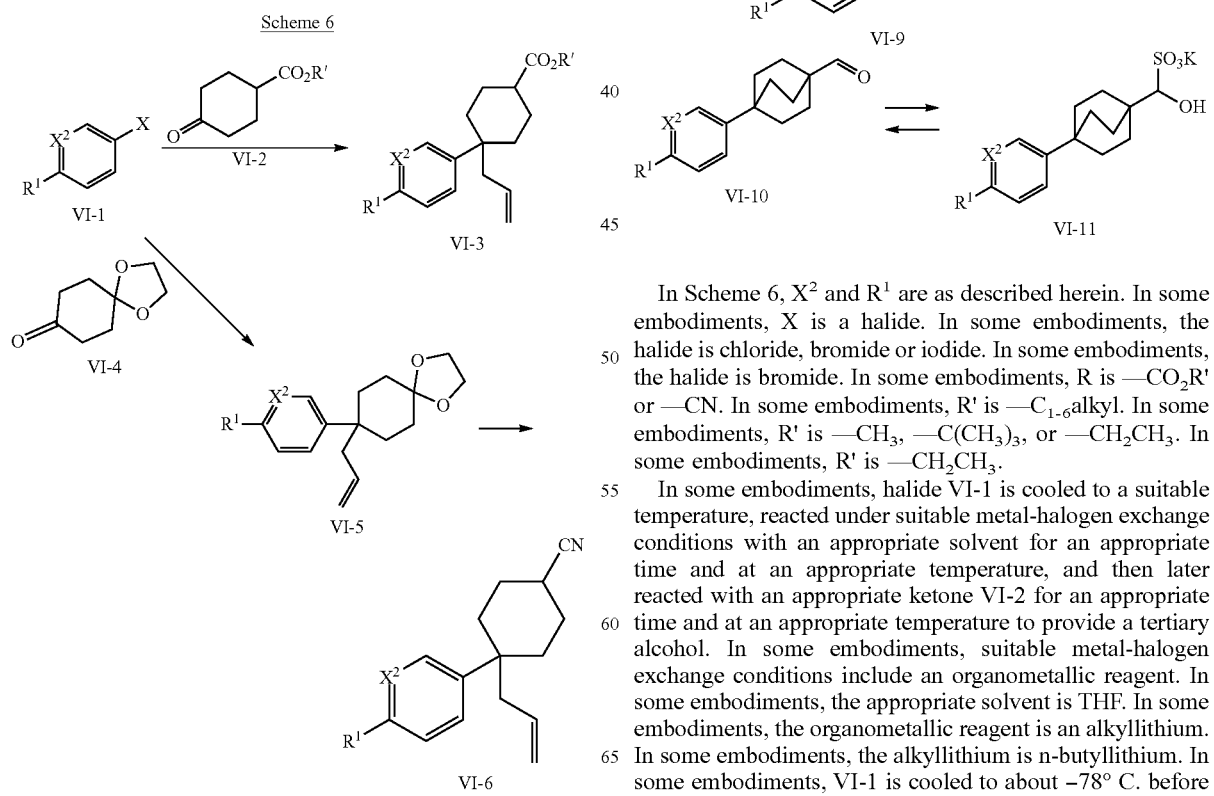

In Scheme 6, $X^2$ and $R^1$ are as described herein. In some embodiments, X is a halide. In some embodiments, the halide is chloride, bromide or iodide. In some embodiments, the halide is bromide. In some embodiments, R is —$CO_2R'$ or —CN. In some embodiments, R' is —$C_{1-6}$alkyl. In some embodiments, R' is —$CH_3$, —$C(CH_3)_3$, or —$CH_2CH_3$. In some embodiments, R' is —$CH_2CH_3$.

In some embodiments, halide VI-1 is cooled to a suitable temperature, reacted under suitable metal-halogen exchange conditions with an appropriate solvent for an appropriate time and at an appropriate temperature, and then later reacted with an appropriate ketone VI-2 for an appropriate time and at an appropriate temperature to provide a tertiary alcohol. In some embodiments, suitable metal-halogen exchange conditions include an organometallic reagent. In some embodiments, the appropriate solvent is THF. In some embodiments, the organometallic reagent is an alkyllithium. In some embodiments, the alkyllithium is n-butyllithium. In some embodiments, VI-1 is cooled to about −78° C. before addition of the organometallic reagent. In some embodiments, VI-1 is reacted for about one hour at about −78° C. before addition of ketone VI-2. In some embodiments, VI-1 is reacted for about 2 hours after the addition of ketone VI-2. In some embodiments, the appropriate temperature for reacting VI-1 and ketone VI-2 is about −78° C. In some embodiments, the tertiary alcohol is reacted under appropriate allylation conditions which include use of an allylating reagent and a Lewis acid, in an appropriate solvent for an appropriate time and at an appropriate temperature to form VI-3. In some embodiments, the appropriate allylating reagent is allyltrimethylsilane. In some embodiments, the appropriate Lewis acid is $BF_3$—$OEt_2$. In some embodiments, the appropriate solvent is DCM. In some embodiments, the appropriate temperature for the appropriate time is about −78° C. for about 1 hour. In some embodiments, the reaction is further warmed to about room temperature overnight. In some embodiments, the appropriate temperature for the appropriate time is about 0° C. for overnight.

In some embodiments, halide VI-1 is cooled to a suitable temperature, reacted under suitable metal-halogen exchange conditions with an appropriate solvent for an appropriate time and at an appropriate temperature, and then later reacted with an appropriate ketone VI-4 for an appropriate time and at an appropriate temperature to provide a tertiary alcohol. In some embodiments, suitable metal-halogen exchange conditions include an organometallic reagent. In some embodiments, the appropriate solvent is THF. In some embodiments, the organometallic reagent is an alkyllithium. In some embodiments, the alkyllithium is n-butyllithium. In some embodiments, VI-1 is cooled to about −60° C. before addition of the organometallic reagent. In some embodiments, VI-4 is added slowly for about 45 minutes at about −60° C. In some embodiments, VI-1 is reacted for about 1 hour at −60° C. after complete addition of ketone VI-4. In some embodiments, the appropriate temperature for reacting VI-1 and ketone VI-4 is about −60° C. In some embodiments, the tertiary alcohol is reacted under appropriate allylation conditions which include use of an allylating reagent and a Lewis acid, in an appropriate solvent for an appropriate time and at an appropriate temperature to form VI-5. In some embodiments, the appropriate allylating reagent is allyltrimethylsilane. In some embodiments, the appropriate Lewis acid is $BF_3$—$OEt_2$. In some embodiments, the appropriate solvent is DCM. In some embodiments, the appropriate temperature for the appropriate time is about −65° C. for about 1 hour.

In some embodiments, VI-5 is reach on under 1,3-dioxalane deprotection conditions for an appropriate time period, in an appropriate solvent, and at an appropriate temperature, followed by reductive cyanation of the resulting ketone-intermediate for an appropriate time period, in an appropriate solvent, and at an appropriate temperature to produce VI-6. In some embodiments, 1,3-dioxalane deprotection conditions include the use an appropriate acid. In some embodiments, the appropriate acid is formic acid. In some embodiments, the appropriate solvent is a THF/water mixture. In some embodiments, the appropriate temperature for the appropriate time is from about 40° C. to about 65° C. overnight. In some embodiments, the resulting ketone is reacted under the appropriate reductive cyanation conditions for an appropriate time period, in an appropriate solvent, and at an appropriate temperature to form VI-6. In some embodiments, the appropriate reductive cyanation conditions include the use of the appropriate cyanation reagent and an appropriate base. In some embodiments, the appropriate cyanation reagent is an appropriate isocyanide. In some embodiments, the appropriate isocyanide is toluenesulfonyl-methyl isocyanide (Tos-MIC). In some embodiments, the appropriate base is a strong, non-nucleophilic base. In some embodiments, the strong, non-nucleophilic base is t-BuOK. In some embodiments, the appropriate solvent is DME. In some embodiments, the ketone intermediate and the appropriate cyanation reagent is cooled to about 0 to 5° C. before addition of the appropriate base. In some embodiments, appropriate base is added slowly over about 1 hour at about 0 to 5° C. In some embodiments, the reductive cyanation reaction takes place for about 1 hour at 25° C. after complete addition of the base. In some embodiments, the reductive cyanation reaction takes place for about 2 hours at 25° C. after complete addition of the base. In some embodiments, the appropriate temperature for the reductive cyanation reaction is about 25° C.

In some embodiments, VI-3 or VI-6 are reacted under suitable oxidative cleavage conditions for an appropriate time period, in an appropriate solvent, and at an appropriate temperature to produce VI-7. In some embodiments, oxidative cleavage conditions include the use of an osmium reagent and V-methylmorpholine TV-oxide to form an intermediate diol. In some embodiments, the osmium reagent is $OsO_4$ or $K_2OsO_4 \cdot 2H_2O$. In some embodiments, the appropriate solvent is an ACN/water mixture. In some embodiments, the appropriate solvent is an acetone/water mixture. In some embodiments, the appropriate temperature for the appropriate time is from about 0° C. to about room temperature for overnight. In some embodiments, the appropriate temperature for the appropriate time is from about 0° C. to about room temperature for 2 hours. In some embodiments, the appropriate temperature for the appropriate time is about room temperature for 2 hours. In some embodiments, the diol is cleaved to form VI-7 under the appropriate oxidative cleavage conditions for an appropriate time period, in an appropriate solvent, and at an appropriate temperature. In some embodiments, appropriate oxidative cleavage conditions include the use of $NaIO_4$. In some embodiments, the appropriate solvent is a THF/water mixture. In some embodiments, the $NaIO_4$ is added to the diol intermediate over about 0.5 hours at about 0-5° C. In some embodiments, the appropriate temperature for the appropriate time after complete addition of $NaIO_4$ is from about 0° C. to about room temperature for 3 hours. In some embodiments, the appropriate temperature for the appropriate time after complete addition of $NaIO_4$ is about room temperature for 3 hours.

In some embodiments, VI-7 is reduced to a primary alcohol under suitable reducing conditions, and then halogenated under suitable halogenation conditions to produce VI-8. In some embodiments, suitable reducing conditions include the use of a borohydride reagent. In some embodiments, the reducing conditions include the use of $NaBH_4$ in an appropriate solvent, at an appropriate temperature for an appropriate amount of time. In some embodiments, the appropriate solvent is THF. In some embodiments, the appropriate temperature for the appropriate time is about 0° C. for about 1 hour. In some embodiments, the reaction is warmed to about room temperature for about 3 hours. In some embodiments, the primary alcohol is reacted under suitable halogenation conditions to produce an alkyl halide. In some embodiments, suitable halogenation conditions are bromination conditions that include use of $CBr_4$ in an appropriate solvent at an appropriate initial temperature followed by $PPh_3$ in the appropriate solvent, at an appropriate temperature for an appropriate time. In some embodiments, the appropriate solvent is a halogenated solvent, such as DCM. In some embodiments, the appropriate initial temperature is about 0° C. In some embodiments, the appropriate initial temperature is about 0° C. and PPh$_3$ is slowly added over about 1 hour. In some embodiments, the appropriate temperature and time after complete addition of PPh$_3$ is about 25° C. for about 1.5 hour. In some embodiments, an appropriate solvent for addition of PPh$_3$ is THF. In some embodiments, the reaction is further warmed to about room temperature for overnight.

In some embodiments, VI-8 is subjected to intramolecular alkylation conditions to form VI-9. In some embodiments, intramolecular alkylation conditions include a suitable base in an appropriate solvent at an appropriate temperature for an appropriate amount of time. In some embodiments, the suitable base is lithium diisopropylamide. In some embodiments, the appropriate solvent is a HMPA and THF mixture. In some embodiments, the suitable base is slowly added over 1 hour at about −65° C. In some embodiments, the appropriate temperature for the appropriate amount of time after complete addition of the appropriate base is about −65° C. for about 3 hours.

In some embodiments, when R is —CN, VI-9 is reduced to aldehyde VI-10 by suitable reduction conditions. In some embodiments, when R is —CO$_2$Et, VI-9 is reduced by suitable reduction conditions followed by oxidation to aldehyde VI-10 by suitable oxidation conditions. In some embodiments, suitable reduction conditions include the use of DIBALH in an appropriate solvent at an appropriate temperature for an appropriate time. In some embodiments, the appropriate solvent is toluene. In some embodiments, DIBALH is added at appropriate temperature for the appropriate time. In some embodiments, DIBALH is slowly added over 1 hour at about −65° C. In some embodiments, the appropriate temperature for the appropriate time after the complete addition of DIBALH is about −65° C. for about 1 hour. In some embodiments, suitable oxidation conditions are chromium-based oxidations. In some embodiments, suitable oxidation conditions include the use of PCC in an appropriate solvent at an appropriate temperature for an appropriate time. In some embodiments, silica gel is added. In some embodiments, the appropriate solvent is DCM. In some embodiments, the appropriate temperature is about room temperature for about 2 hours. Alternatively, in some embodiments, the oxidation conditions include the use of oxalyl chloride and DMSO with an amine base in an appropriate solvent at an appropriate temperature for an appropriate time. In some embodiments, the appropriate amine base is TEA. In some embodiments, the appropriate solvent is DCM. In some embodiments, the appropriate temperature for the appropriate amount of time is about −78° C. for about 1 hour.

In some embodiments, aldehyde VI-10 is transformed into bisulfite adduct VI-11 under suitable conditions. In some embodiments, suitable conditions include the use of the appropriate reagent in an appropriate solvent at an appropriate temperature for an appropriate time. In some embodiments, the appropriate reagent is aqueous potassium metabisulfite. In some embodiments, the appropriate solvent is THF. In some embodiments, the appropriate temperature and time is about 45° C. for about 3.5 hours. In some embodiments, the reaction is further cooled to about room temperature for overnight.

In some embodiments, bisulfite adduct VI-11 is converted back to aldehyde VI-10 by suitable conditions. In some embodiments, suitable conditions include the use of the appropriate base in an appropriate solvent at an appropriate temperature for an appropriate time. In some embodiments, the appropriate base is a carbonate salt. In some embodiments, the appropriate base is aqueous sodium carbonate. In some embodiments, the appropriate solvent is DCM. In some embodiments, the appropriate temperature and time is about 25° C. for about 1 hour.

In some embodiments, intermediates used in the preparation of compounds described herein are prepared as outlined in Scheme 7.

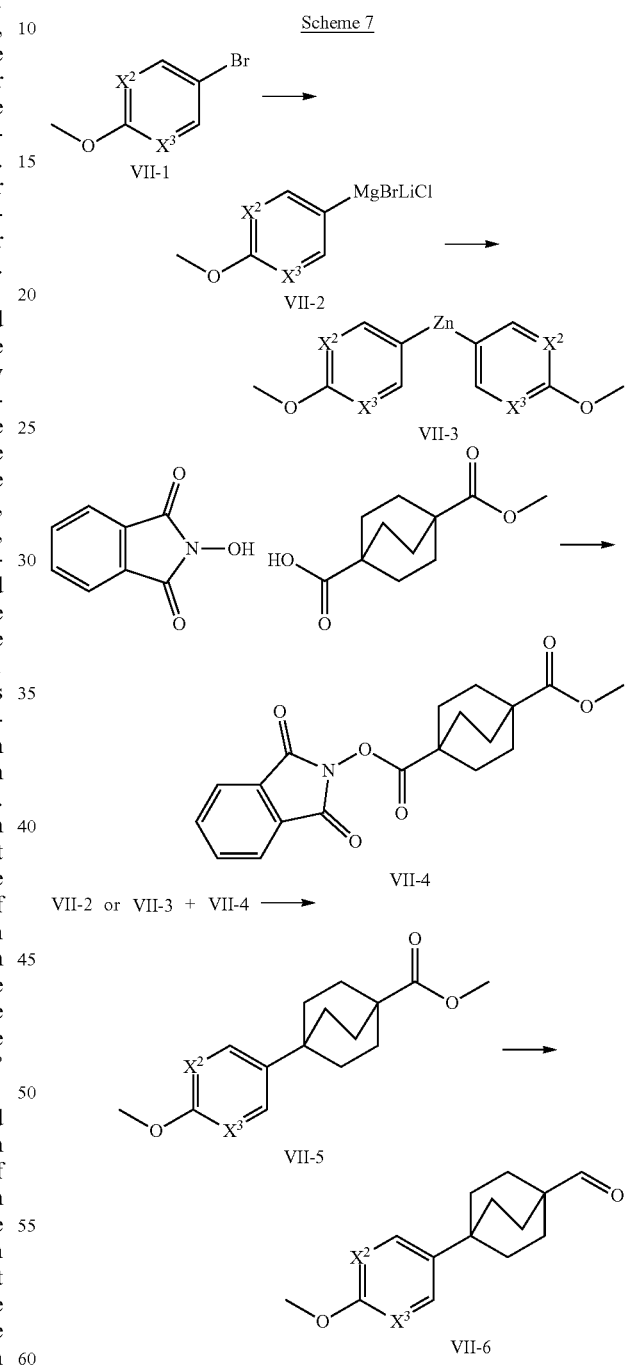

In Scheme 7, X$^2$, X$^3$, X$^4$, R$^1$, and R$^2$ are as described herein. In some embodiments, both X$^2$ and X$^3$ are N. In some embodiments, either X$^2$ or X$^3$ is N and the other is CR$^2$. In some embodiments, both X$^2$ and X$^3$ are CR$^2$.

In some embodiments, halide VII-1 is cooled to a suitable temperature and reacted under suitable metal-halogen exchange conditions with an appropriate solvent for an appropriate time and at an appropriate temperature to provide an aryl or heteroaryl magnesium bromide salt VII-2. In some embodiments, suitable metal-halogen exchange conditions include a metal reagent. In some embodiments, the appropriate solvent is THF. In some embodiments, the metal reagent is magnesium. In some embodiments, suitable metal-halogen exchange conditions include a salt. In some embodiments, a suitable salt includes lithium chloride. In some embodiments, suitable metal-halogen exchange conditions include a magnesium activating reagent. In some embodiments, a suitable magnesium activating reagent includes DIBAL-H. In some embodiments, the suitable metal, the suitable salt, and the suitable solvent are combined at 10° C., or room temperature. In some embodiments, magnesium, lithium chloride, and THF are combined at 10° C. In some embodiments, magnesium, lithium chloride, and THF are combined at room temperature. In some embodiments, DIBAL-H is added to the mixture of the suitable metal, the suitable salt, and the suitable solvent at 10° C., or room temperature, and the reaction is stirred for about 15 minutes. In some embodiments, the temperature is reduced or maintained. In some embodiments, the temperature is reduced to 0° C. In some embodiments, a solution of VII-1 in THF is added to the reaction. In some embodiments, VII-1 is reacted for about 1 hour to two hours after the addition of VII-1. In some embodiments, VII-1 is reacted for about 1 hour at about 10° C. In some embodiments, the appropriate temperature for reacting VII-1 is about 25° C.

In some embodiments, aryl or heteroaryl magnesium bromide salt VII-2 is reacted under suitable zinc displacement conditions with an appropriate solvent for an appropriate time and at an appropriate temperature to provide a zinc aryl or heteroaryl dimer VII-3. In some embodiments, suitable zinc displacement conditions include a zinc halide salt. In some embodiments, suitable zinc displacement conditions include a zinc chloride. In some embodiments, the appropriate solvent is THF. In some embodiments, VII-2 is reacted for about 1 hour after the addition of the zinc halide salt. In some embodiments, VII-2 is reacted for about 1 hour at about 25° C. after the addition of the zinc halide salt. In some embodiments, the appropriate temperature for reacting VII-2 is about 25° C.

In some embodiments, 1,4-endoethylenecyclohexyl carboxylic acid is reacted with N-hydroxyphthalimide under suitable coupling reaction conditions to provide VII-4. In some embodiments, suitable coupling reaction conditions include an appropriate coupling agent, an appropriate base, and an appropriate solvent for an appropriate time and at an appropriate temperature. In some embodiments, the coupling agent is N,N-diisopropylcarbodiimide. In some embodiments, the base is DMAP. In some embodiments, the solvent is DCM or DCE. In some embodiments, the time and the temperature are overnight and room temperature.

In some embodiments, VII-2 and VII-4 are reacted under suitable aryl-alkyl cross-coupling reaction conditions to provide aryl-alkyl VII-5. In some embodiments, VII-3 and VII-4 are reacted under suitable aryl-alkyl cross-coupling reaction conditions to provide aryl-alkyl VII-5. In some embodiments, VII-4 is reacted under suitable aryl-alkyl cross-coupling reaction conditions to provide aryl-alkyl VII-5. In some embodiments, the suitable aryl-alkyl cross-coupling reaction conditions include nickel. In some embodiments, the suitable aryl-alkyl cross-coupling reaction conditions include nickel when $X^2$ is —CMe and $X^3$ is —CMe or when $X^2$ is —CMe and $X^3$ is —CH. In some embodiments, the suitable aryl-alkyl cross-coupling reaction conditions include nickel when $X^2$ is —CMe and $X^3$ is —CMe. In some embodiments, the suitable aryl-alkyl cross-coupling reaction conditions include nickel when $X^2$ is —CMe and $X^3$ is —CH. In some embodiments, suitable aryl-alkyl cross-coupling reaction conditions include an appropriate source of Ni, an appropriate arylzinc or heteroarylzinc reagent, an appropriate auxiliary ligand, and a solvent, for an appropriate time at an appropriate temperature. In some embodiments, the source of Ni is nickel(II) acetylacetonate. In some embodiments, the source of Ni is a Ni(II) halide or a solvate thereof. In some embodiments, the Ni(II) halide is a Ni(II) chloride or Ni(II) bromide In some embodiments, the arylzinc reagent is a substituted phenylzinc reagent. In some embodiments, the substituted phenylzinc reagent is a methoxyphenylzinc reagent. In some embodiments, the methoxyphenylzinc reagent is bis(4-methoxy-3-methylphenyl)zinc or bis(4-methoxy-3,5-dimethylphenyl)zinc. In some embodiments, the heteroarylzinc reagent is a substituted pyridinylzinc reagent. In some embodiments, the substituted pyridinylzinc reagent is a methoxypyridinylzinc reagent. In some embodiments, the methoxypyridinylzinc reagent is bis(6-methoxy-5-methylpyridin-3-yl)zinc. In some embodiments, the auxiliary ligand is 2,2'-bipyridine. In some embodiments, when $X^2$ is —CMe and $X^3$ is —CMe, the auxiliary ligand is 2,2'-bipyridine. In some embodiments, the auxiliary ligand is an alkyl-substituted 2,2'-bipyridine. In some embodiments, the alkyl-substituted 2,2'-bipyridine is 6,6'-dimethyl-2,2'-bipyridine or 4,4'-di-tert-butyl-2,2'-bipyridine. In some embodiments, the alkyl-substituted 2,2'-bipyridine is 6,6'-dimethyl-2,2'-bipyridine. In some embodiments, when $X^2$ is —CMe and $X^3$ is —CH, the alkyl-substituted 2,2'-bipyridine is 6,6'-dimethyl-2,2'-bipyridine. In some embodiments, the suitable aryl-alkyl cross-coupling reaction conditions include iron. In some embodiments, the suitable aryl-alkyl cross-coupling reaction conditions include iron when $X^2$ is —CMe and $X^3$ is N. In some embodiments, the suitable aryl-alkyl cross-coupling reaction conditions include iron when VII-2 is $X^2$ is —CMe and $X^3$ is N, and reacted with VII-4. In some embodiments, the solvent is acetonitrile, N,N'-dimethylpropyleneurea (DMPU), DMF, THF or combinations thereof. In some embodiments, the solvent is DMPU. In some embodiments, the time and the temperature are overnight and 25° C.

In some embodiments, aryl-alkyl VII-5 is reduced to an alcohol by suitable reduction conditions followed by oxidation to aldehyde VII-6 by suitable oxidation conditions. In some embodiments, suitable reduction conditions include the use of DIBALH in an appropriate solvent at an appropriate temperature for an appropriate time. In some embodiments, the appropriate solvent is DCM. In some embodiments, the appropriate temperature for the appropriate time is about −78° C. for about 1 hour. In some embodiments, the reaction is further warmed to about room temperature for about two hours to produce an alcohol. In some embodiments, suitable oxidation conditions are chromium-based oxidations. In some embodiments, suitable oxidation conditions include the use of PCC in an appropriate solvent at an appropriate temperature for an appropriate time. In some embodiments, silica gel is added. In some embodiments, the appropriate solvent is DCM. In some embodiments, the appropriate temperature is about room temperature for about 2 hours. Alternatively, in some embodiments, the oxidation conditions include the use of oxalyl chloride and DMSO with an amine base in an appropriate solvent at an appropriate temperature for an appropriate time. In some embodiments, the appropriate amine base is TEA. In some embodiments, the appropriate solvent is DCM. In some embodiments, the appropriate temperature for the appropriate amount of time is about −78° C. for about 1 hour.

In some embodiments, intermediates used in the preparation of compounds described herein are prepared as outlined in Scheme 8.

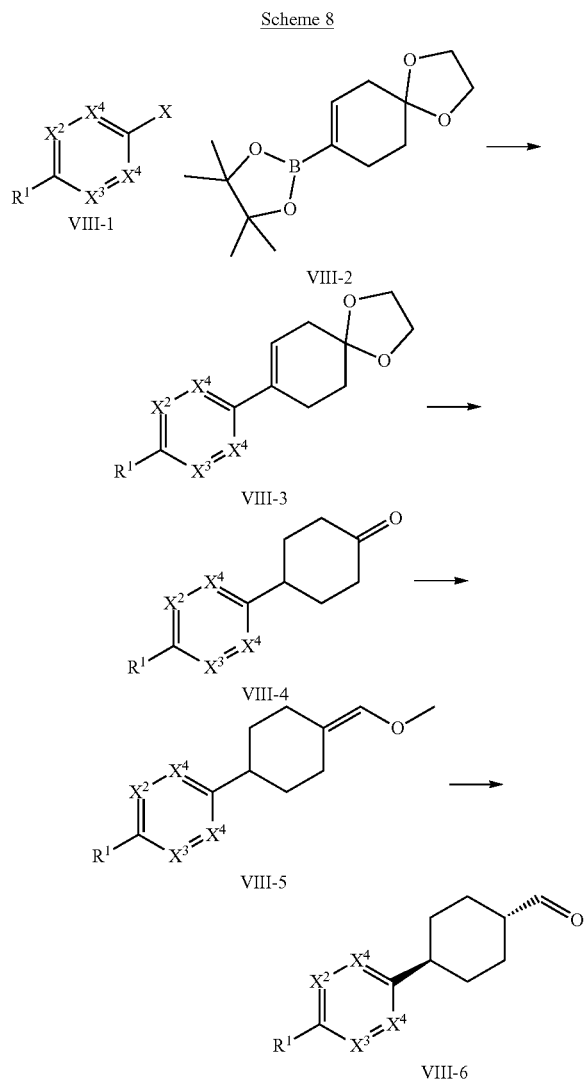

Scheme 8

In Scheme 8, substituents $X^2$, $X^3$, $X^4$, $R^1$, $R^2$, and $R^3$ are as described herein. In some embodiments, $X^2$ is C—$R^2$, $X^3$ is C—H, and each $X^4$ is C—H. In some embodiments, X is a halide. In some embodiments, the halide is chloride, bromide, or iodide.

In some embodiments, boronic ester VIII-2 is reacted with halide VIII-1 under suitable metal-catalyzed cross-coupling reaction conditions to provide VIII-3. In some embodiments, suitable metal-catalyzed cross-coupling conditions include palladium. In some embodiments, suitable metal-catalyzed cross-coupling reaction conditions include palladium, an appropriate base, and an appropriate solvent for an appropriate time and at an appropriate temperature. In some embodiments, the palladium is delivered in the form of Pd(dppf)Cl$_2$ or Pd(PPh$_3$)$_4$. In some embodiments, the appropriate base is an inorganic base. In some embodiments, the inorganic base is a carbonate, a phosphate, an oxide, or a hydroxide. In some embodiments, the inorganic base is an alkali metal inorganic base. In some embodiments, the alkali metal is sodium, potassium, cesium, or combinations thereof. In some embodiments, the inorganic base is Na$_2$CO$_3$, K$_2$CO$_3$, Cs$_2$CO$_3$, or combinations thereof. In some embodiments, the combination is a combination of Na$_2$CO$_3$ and K$_2$CO$_3$. In some embodiments, the inorganic base is K$_2$CO$_3$. In some embodiments, the inorganic base is Cs$_2$CO$_3$. In some embodiments, the appropriate solvent is an aqueous solvent. In some embodiments, the appropriate solvent is a mixture of water and an organic solvent. In some embodiments, the organic solvent in the mixture is a C$_{1-4}$-alcohol, THF, DMF, DME, dioxane, acetonitrile, or a combination thereof. In some embodiments, the organic solvent in the mixture is dioxane. In some embodiments, the appropriate time is from about 1 hour to overnight. In some embodiments, the appropriate temperature is from about 50° C. to about 115° C. In some embodiments, the appropriate temperature is about 50° C. In some embodiments, the appropriate temperature is about 100° C.

In some embodiments, VIII-3 is subjected to suitable hydrogenation conditions, followed by treatment under appropriate acidic conditions to provide cyclohexanone VIII-4. In some embodiments, suitable hydrogenation conditions include a palladium catalyst. In some embodiments, palladium-catalyzed hydrogenation conditions include 10% Pd/C under an atmosphere including hydrogen gas in an appropriate solvent for an appropriate time at an appropriate temperature. In some embodiments, the hydrogen gas is present in the atmosphere at a partial pressure of about 1 atm. In some embodiments, the solvent is EtOAc, ethanol, methanol, or a combination thereof. In some embodiments, the appropriate time is from about 4.5 hours to overnight and the appropriate temperature is about room temperature. In some embodiments, the acidic conditions include formic acid in a mixture of water and toluene for an appropriate time at an appropriate temperature. In some embodiments, the appropriate time is about 4 hours and the appropriate temperature is about 120° C. In some embodiments, the appropriate time is overnight and the appropriate temperature is the boiling point of the solvent. In some embodiments, the acidic conditions include PPTS in a mixture of acetone and water for an appropriate time at an appropriate temperature. In some embodiments, the appropriate time is about 10 hours and the appropriate temperature is about 60° C. In some embodiments, the acidic conditions include 3 M HCl and THF for an appropriate time at an appropriate temperature. In some embodiments, the appropriate time is from about 3 hours to overnight and the appropriate temperature is about 60° C.

In some embodiments, VIII-4 is reacted under suitable one carbon-homologation conditions to provide enol ether VIII-5. In some embodiments, suitable one carbon-homologation conditions include deprotonating a phosphonium salt with an appropriate base in an appropriate solvent for an appropriate first time at an appropriate first temperature, before adding the cyclohexanone VIII-4 for a second time at a second temperature. In some embodiments, the phosphonium salt is an alkyltriphenylphosphonium salt. In some embodiments, the alkyltriphenylphosphonium salt is an alkyltriphenylphosphonium chloride. In some embodiments, the alkyltriphenylphosphonium chloride is (methoxymethyl)triphenyl-phosphonium chloride [Ph$_3$P$^+$CH$_2$OCH$_3$ Cl$^-$]. In some embodiments, the appropriate base is LiHMDS, NaHMDS, or KHMDS. In some embodiments, the appropriate base is NaHMDS. In some embodiments, the appropriate solvent is THF. In some embodiments, the appropriate first time is from about 0.5 hour to about 2 hours and the appropriate first temperature is about 0° C. In some embodiments, the appropriate second time is from about 0.5 hour to about 3 hours and the appropriate second temperature is about 0° C. In some embodiments, the appropriate second time is overnight and the appropriate second temperature begins at 0° C. and is allowed to increase to about room temperature over the second time.

In some embodiments, enol ether VIII-5 is hydrolyzed under suitable acidic conditions to provide a mixture of cis- and trans-aldehydes, where the trans-aldehyde is VIII-6. In some embodiments, suitable acidic conditions include an appropriate acid in an appropriate solvent for an appropriate time at an appropriate temperature. In some embodiments, the acid is formic acid, the solvent is a mixture of water and toluene, the time is from about 2 hours to overnight, and the temperature is from about 120° C. to about 130° C. In some embodiments, the acid is HCl, the solvent is THF, the time is from about 1 hour to about 6 hours, and the temperature is about 60° C. In some embodiments, treatment of the mixture of cis- and trans-aldehydes under suitable basic conditions provides a mixture further enriched in trans-aldehyde VIII-6. In some embodiments, suitable basic conditions include an appropriate base in an appropriate solvent for an appropriate time at an appropriate temperature. In some embodiments, the base is NaOH. In some embodiments, the solvent is an aqueous solvent mixture including EtOH, toluene, THF, or combinations thereof. In some embodiments, the aqueous solvent mixture includes toluene. In some embodiments, the aqueous solvent mixture includes THF. In some embodiments, the appropriate time is from about 5 hours to overnight and the appropriate temperature is about room temperature. In some embodiments, the base is NaOMe. In some embodiments, the solvent is a $C_{1-4}$ alcohol, or mixtures thereof. In some embodiments, the solvent is methanol or ethanol. In some embodiments, the solvent is methanol. In some embodiments, the appropriate time is from 4 hours to overnight and the appropriate temperature is about room temperature. In some embodiments, further purification of the mixture of cis- and trans-aldehydes provides trans-aldehyde VIII-6. In some embodiments, the further purification includes the techniques of crystallization, chromatography, or combinations thereof. In some embodiments, the further purification includes crystallization.

In some embodiments, intermediates used in the preparation of compounds described herein are prepared as outlined in Scheme 9.

Scheme 9

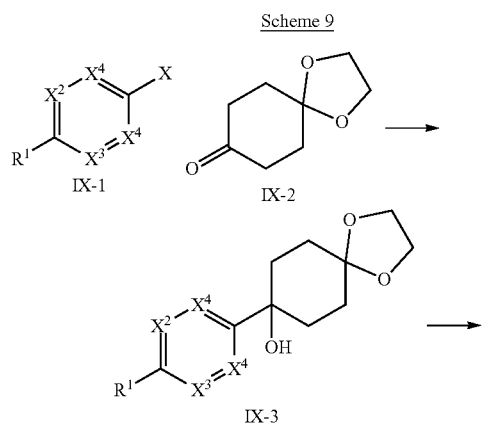

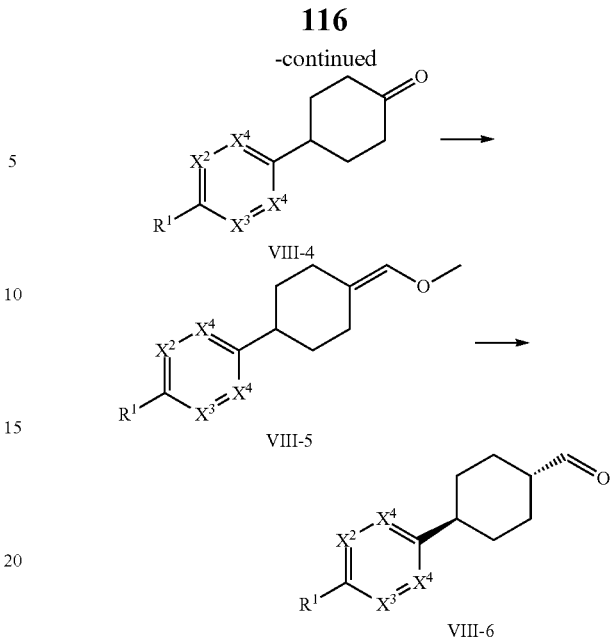

In Scheme 9, substituents $X^2$, $X^3$, $X^4$, $R^1$, $R^2$, $R^3$, and m are as described herein. In some embodiments, $X^2$ is C—$R^2$, $X^3$ is C—H, and each $X^4$ is C—H. In some embodiments, X is a halide. In some embodiments, the halide is chloride, bromide, or iodide.

In some embodiments, IX-1 is cooled to a suitable temperature, reacted under suitable metal-halogen exchange conditions in an appropriate solvent for an appropriate first time and at an appropriate first temperature, and then later reacted with an appropriate ketone IX-2 for an appropriate second time and at an appropriate second temperature to provide IX-3. In some embodiments, suitable metal-halogen exchange conditions include an organometallic reagent. In some embodiments, the organometallic reagent is an alkyl-lithium reagent. In some embodiments, the alkyllithium reagent is n-butyllithium. In some embodiments, the appropriate solvent is THF. In some embodiments, IX-1 is cooled to about −78° C. before addition of the organometallic reagent. In some embodiments, the first time is from about 1 hour to about 2 hours and the first temperature is about −78° C. In some embodiments, the second time is about 3 hours and the second temperature is about −78° C. In some embodiments, the second time is overnight and the second temperature is initially about −78° C. and is allowed to warm to room temperature over the course of the second time.

In some embodiments, alcohol IX-3 is reacted under suitable reduction conditions to form a mixture of saturated and unsaturated substituted cyclohexyl ketals derived from IX-3. In some embodiments, the suitable reduction conditions include an appropriate reducing agent and an appropriate acid in an appropriate solvent for an appropriate time and at an appropriate temperature. In some embodiments, the reducing agent is a silyl hydride and the acid is trifluoracetic acid. In some embodiments, the silyl hydride is triethylsilane. In some embodiments, the solvent is dichloromethane. In some embodiments, the time is from about 1 hour to overnight. In some embodiments, the temperature is from about 0° C. to about room temperature. In some embodiments, the temperature is about 0° C. In some embodiments, the mixture of saturated and unsaturated substituted cyclohexyl ketals derived from IX-3 is reacted under suitable hydrolysis reaction conditions to form a mixture of saturated and unsaturated substituted cyclohexyl ketones, including the saturated ketone VIII-4. In some embodiments, the suitable hydrolysis reaction conditions include an appropriate acid in an appropriate solvent for an appropriate time at an appropriate temperature. In some embodiments, the acid is formic acid, the solvent is a toluene/water mixture, the temperature is about 130° C., and the time is overnight. In some embodiments, the acid is formic acid, the solvent is a THF/water mixture, the temperature is about 80° C., and the time is overnight. In some embodiments, the mixture of saturated and unsaturated substituted cyclohexyl ketones, including the saturated ketone VIII-4, is reduced under suitable reduction reaction conditions to convert the unsaturated components to VIII-4. In some embodiments, the suitable reduction reaction conditions include an appropriate reducing agent and an appropriate solvent for an appropriate time at an appropriate temperature. In some embodiments, the reducing agent is hydrogen. In some embodiments, the hydrogen is delivered at a pressure of from about 15 psi to about 30 psi. In some embodiments, suitable reduction reaction conditions include a catalyst. In some embodiments, the catalyst includes palladium. In some embodiments, the catalyst including palladium is 10% palladium on carbon. In some embodiments, the solvent is ethyl acetate and concentrated HCl. In some embodiments, the solvent is ethyl acetate. In some embodiments, the time is from about 30 min to about overnight. In some embodiments, the temperature is about room temperature.

In some embodiments, ketone VIII-4 is transformed into trans-aldehyde VIII-6 under reaction conditions also suitable for conversion of ketone VIII-4 to trans-aldehyde VIII-6, as described in Scheme 8.

In some embodiments, intermediates used in the preparation of compounds described herein are prepared as outlined in Scheme 10.

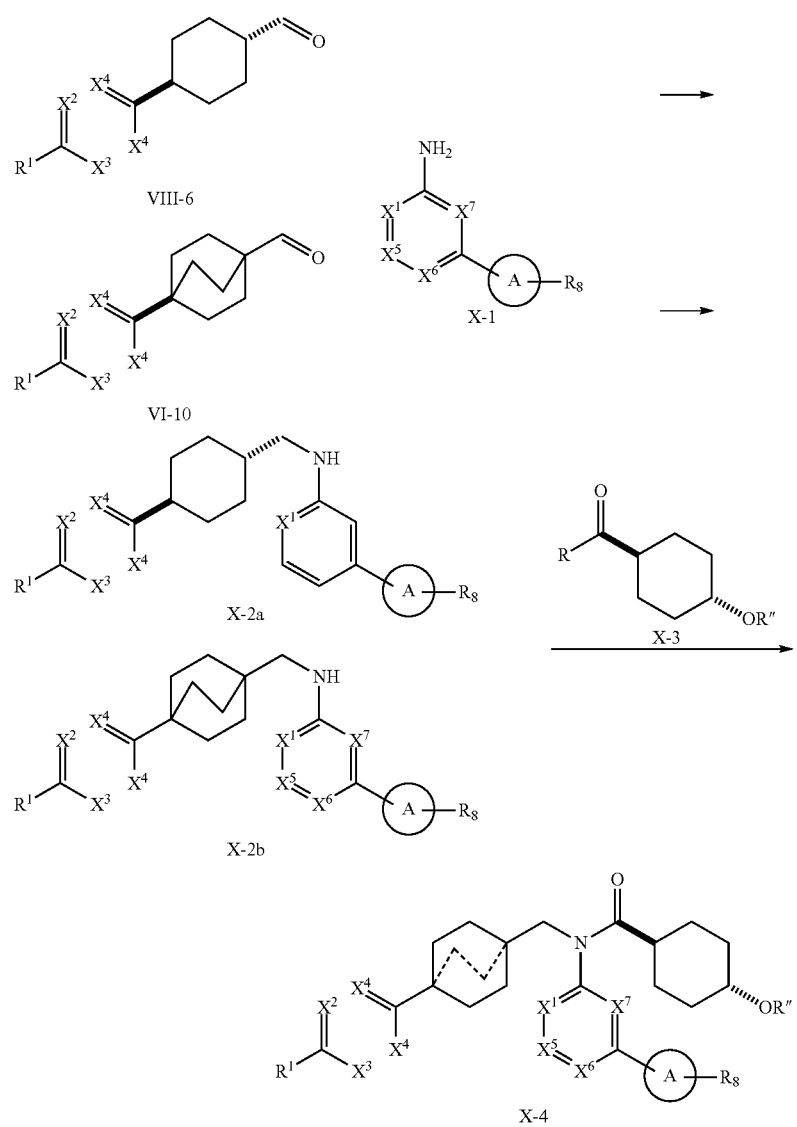

Scheme 10

In Scheme 10, Ring A, $X^1$, $X^2$, $X^3$, $X^4$, $X^5$, $X^6$, and $X^7$ and substituents $R^1$, $R^2$, and $R^8$ are as described herein. In some embodiments, the R is a halide or —OH. In some embodiments, the halide is iodo, bromo, or chloro. In some embodiments, the halide is chloro. In some embodiments, R is —OH. In some embodiments, R" is an alcohol protecting group. In some embodiments, the alcohol protecting group is methyl, a substituted methyl group, a substituted ethyl group, a substituted benzyl group, or a silyl group, as described in, for example, Wuts, P. G. M. "Greene's Protective Groups in Organic Synthesis" (2014) John Wiley & Sons ISBN: 978-1-118-05748-3. In some embodiments, the alcohol protecting group is a silyl group. In some embodiments, the silyl group is tert-butyldimethylsilyl.

In some embodiments, aldehyde VIII-6 (as in Scheme 8 where $X^3$ and each $X^4$ are CH, for example) is reacted with aniline X-1 under suitable reductive amination reaction conditions to provide X-2a. In some embodiments, suitable reductive amination reaction conditions include an appropriate reducing agent and an appropriate solvent, at an appropriate temperature for an appropriate time. In some embodiments, the reducing agent is picoline borane, sodium borohydride, or sodium triacetoxyborohydride. In some embodiments, the reducing agent is sodium triacetoxyborohydride. In some embodiments, the solvent is DCM, DCE, THF, acetonitrile, DMF, or N,N-dimethylacetamide. In some embodiments, the solvent is DCM, DCE, or combinations thereof. In some embodiments, the solvent is DCM. In some embodiments, the time is from about 30 minutes to overnight and the temperature is initially about 0° C. and increased to about room temperature over the time. In some embodiments, the temperature is about room temperature.

In some embodiments, aldehyde VI-10 (as in Scheme 6 where $X^3$ and each $X^4$ are CH, for example) is reacted with aniline X-1 under suitable reductive amination reaction conditions to provide X-2b. In some embodiments, suitable reductive amination reaction conditions include optionally an appropriate condensation catalyst, an appropriate reducing agent, and an appropriate solvent, at an appropriate temperature for an appropriate amount of time. In some embodiments, suitable reductive amination reaction conditions include holding VI-10, X-1, and the condensation catalyst in the appropriate solvent at a first temperature for a first amount of time, and subsequently adding the reducing agent and holding the resulting mixture at a second temperature for a second amount of time. In some embodiments, the solvent is an alcohol. In some embodiments, the solvent is methanol. In some embodiments, the condensation catalyst is acetic acid. In some embodiments, the first temperature is from about room temperature to about 60° C. and the first amount of time is about 3 hours to about 68 hours. In some embodiments, the first temperature is about room temperature and the first amount of time is overnight. In some embodiments, the first temperature is about 60° C. and the first amount of time is about 4 hours. In some embodiments, the reducing agent is picoline-$BH_3$. In some embodiments, the second temperature is room temperature. In some embodiments, the second temperature is about 40° C. In some embodiments, the second amount of time is from overnight to about 4 days.

In some embodiments, suitable reductive amination reaction conditions include the addition of a suitable reducing agent to a mixture of VI-10, X-1, and an appropriate solvent and holding the resulting mixture at an appropriate temperature for an appropriate amount of time. In some embodiments, the reducing agent is sodium triacetoxyborohydride. In some embodiments, 1 equivalent of AcOH is added prior to the reducing agent. In some embodiments, the solvent is DCM or DCE. In some embodiments, the time is about overnight and the temperature is about room temperature. In some embodiments, the temperature is about 45° C.

In some embodiments, amine X-2a or X-2b (referred to collectively and alternatively as "X-2" in the disclosure herein relating to Scheme 10) is reacted with cyclohexane X-3 (as in Scheme 10, for example) under suitable acylation reaction conditions followed by suitable hydrolysis reaction conditions to provide X-4, respectively. In some embodiments, the cyclohexane X-3 is an acid chloride or a carboxylic acid. In some embodiments, when X-3 is an acid chloride, the suitable acylation reaction conditions are sufficient to provide an intermediate protected cyclohexyl alcohol that provides X-4 after deprotection under suitable hydrolysis reaction conditions. In some embodiments, $X^1$ is N or CH, and the acylation reaction conditions include an appropriate base, an appropriate solvent, and optionally DMAP, at an appropriate temperature for an appropriate amount of time. In some embodiments, the base is TEA or pyridine. In some embodiments, the solvent is DCE, DCM, toluene, pyridine, or combinations thereof. In some embodiments, the solvent is DCM. In some embodiments, the solvent is toluene. In some embodiments the temperature is 80° C. and the time is from about 1 hour to overnight. In some embodiments the temperature is room temperature and the time is from 1 hour to overnight. In some embodiments the initial temperature is 0° C. and the reaction is warmed to room temperature, and the time is from about 15 minutes to about 5 hours. In some embodiments, the reaction conditions include DMAP. In some embodiments, $X^1$ is N, the reaction conditions include DMAP, the base is TEA, the solvent is toluene, the temperature is about 80° C., and the time is about 1 hour to about 2 hours. In some embodiments, $X^1$ is N, the reaction conditions include DMAP, the base is pyridine, the solvent is toluene, the temperature is about 80° C., and the time is from about 1 hour to overnight. In some embodiments, $X^1$ is CH, the base is TEA, the solvent is toluene, the temperature is about room temperature, and the time is from about 1 hour to about 2 hours. In some embodiments, $X^1$ is CH, the base is pyridine, the solvent is toluene, the temperature is about room temperature, and the time is from about 1 hour to overnight. In some embodiments, when X-3 is a carboxylic acid, a coupling reagent is used. In some embodiments, the coupling reagent is HATU, EDC, T3P, HBTU, BCTU, or pyBOP. In some embodiments, X-3 is a carboxylic acid, the base is triethylamine, the solvent is DCM, the coupling reagent is T3P, and optionally DMAP, at an appropriate temperature for an appropriate amount of time. In some embodiments, the base is TEA or pyridine. In some embodiments, the solvent is DCE, DCM, toluene, pyridine, or combinations thereof. In some embodiments, the solvent is DCM. In some embodiments the temperature is 40° C. and the time is from about 2 hour to about 63 hours. In some embodiments the temperature is room temperature and the time is from 1 hour to overnight. In some embodiments the initial temperature is 25° C. and the reaction is warmed to 40° C., and the time is from about 2 hours to about 63 hours. In some embodiments, the reaction conditions include DMAP.

In some embodiments, the suitable hydrolysis reaction conditions are sufficient to deprotect the intermediate protected cyclohexyl alcohol and provide X-4. In some embodiments, the hydrolysis reaction conditions include an appropriate acid, an appropriate solvent, at an appropriate temperature for an appropriate amount of time. In some embodiments, the acid is aqueous HCl. In some embodiments, the concentration of the aqueous HCl is about 1 M. In some embodiments, the solvent is THF, methanol, or combinations thereof. In some embodiments, the temperature is from about 0° C. to about room temperature and the time is from about 1 hour to about 4 hours. In some embodiments, R" is tert-butyldimethylsilyl, the acid is 1 M HCl, the solvent is a combination of THF and methanol, the temperature is from about 0° C. to about room temperature and the time is from about 1 hour to about 19 hours. In some embodiments, R" is other than tert-butyldimethylsilyl, and the protecting group, R", is removed to provide X-4 according to the corresponding methods, as disclosed, for example, in "Greene's Protective Groups in Organic Synthesis".

In some embodiments, intermediates used in the preparation of compounds described herein are prepared as outlined in Scheme 11.

Scheme 11

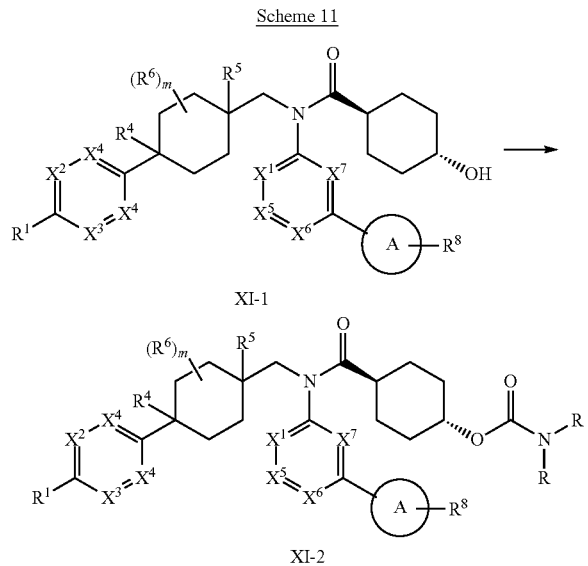

In Scheme 11, ring A and substituents $X^1$, $X^2$, $X^3$, $X^4$, $X^5$, $X^6$, $X^7$, $R^1$, $R^2$, $R^3$, $R^4$, $R^5$, $R^6$, $R^8$, and m are as described herein. In some embodiments, R is independently alkyl, heteroalkyl, hydroxyalkyl, or hydrogen, or both R are taken together to form a substituted or unsubstituted fused 4-, 5-, or 6-membered ring with 1-3 N atoms and 0-2 O or S atoms in the ring.

In some embodiments, XI-2 is prepared from XI-1 and an amine, $NHR_2$. In some embodiments, XI-1 is subjected to carbonyldiimidazole in an appropriate solvent, such as ACN, at an appropriate temperature, such as at about room temperature to about 80° C., for an appropriate amount of time to provide an intermediate carbamoyl imidazole. In some embodiments, the appropriate amount of time is from about 2 hours to about 6 hours or about overnight. In some embodiments, the intermediate carbamoyl imidazole is treated with $NHR_2$ in a suitable solvent, and the reaction is allowed to proceed for an appropriate amount of time at an appropriate temperature. In some embodiments, the suitable solvent is acetonitrile. In some embodiments, the suitable solvent is MeOH, THF, or DCM. In some embodiments, the $NHR_2$ is added as a solution in MeOH, THF, or DCM. In some embodiments, the $NHR_2$ is added neat. In some embodiments, the appropriate amount of time at the appropriate temperature is about 15 minutes to overnight at about room temperature. In some embodiments, the appropriate amount of time is about 1 day to about 7 days. In some embodiments, the appropriate temperature is from about room temperature to about 50° C., or from about room temperature to about 100° C. In some embodiments, the amine, $NHR_2$, is delivered as a salt. In some embodiments, the salt is a hydrochloride salt. In some embodiments, when the amine, $NHR_2$, is delivered as the hydrochloride salt, then a suitable base, such as $iPr_2NEt$, is combined with the intermediate carbonyl imidazole, prior to adding the hydrochloride salt.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, w-butyl, iso-butyl, sec-butyl, and 1-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl group. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon or nitrogen atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic group, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1]pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$fluoroalkyl.

The term "fluoroalkyl" refers to an alkyl in which one or more hydrogen atoms are replaced by a fluorine atom. In one aspect, a fluoroalkyl is a $C_1$-$C_6$ fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g., —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heteroalkylene" refers to a divalent heteroalkyl group.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or TV-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s). In some other embodiments, optional substituents are individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, —CH$_2$CO$_2$H, —CH$_2$CO$_2$alkyl, —CH$_2$C(=O)NH$_2$, —CH$_2$C(=O)NH(alkyl), —CH$_2$C(=O)N(alkyl)$_2$, —CH$_2$S(=O)$_2$NH$_2$, —CH$_2$S(=O)$_2$NH(alkyl), —CH$_2$S(=O)$_2$N(alkyl)$_2$, alkyl, alkenyl, alkynyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$alkyl, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH (C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O) C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound described herein, or a pharmaceutically acceptable salt thereof, and a co-agent, are both administered to a patient simultaneously in the form of a single entity or dosage. The term "non-fixed combination" means that the active ingredients, e.g., a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

In some embodiments, a compound disclosed herein is formulated in such a manner that delivery of the compound to a particular region of the gastrointestinal tract is achieved. For example, a compound disclosed herein is formulated for oral delivery with bioadhesive polymers, pH-sensitive coatings, time dependent, biodegradable polymers, microflora activated systems, and the like, in order to effect delivering of the compound to a particular region of the gastrointestinal tract.

In some embodiments, a compound disclosed herein is formulated to provide a controlled release of the compound. Controlled release refers to the release of the compound described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

Approaches to deliver the intact therapeutic compound to the particular regions of the gastrointestinal tract (e.g., such as the colon), include:

(i) Coating with polymers: The intact molecule can be delivered to the colon without absorbing at the upper part of the intestine by coating of the drug molecule with the suitable polymers, which degrade only in the colon.

(ii) Coating with pH-sensitive polymers: The majority of enteric and colon targeted delivery systems are based on the coating of tablets or pellets, which are filled into conventional hard gelatin capsules. Most commonly used pH-dependent coating polymers are methacrylic acid copolymers, commonly known as Eudragit® S, more specifically Eudragit® L and Eudragit® S. Eudragit® L100 and S 100 are copolymers of methacrylic acid and methyl methacrylate.

(iii) Coating with biodegradable polymers;
(iv) Embedding in matrices;
(v) Embedding in biodegradable matrices and hydrogels;
(vi) Embedding in pH-sensitive matrices;
(vii) Timed release systems;
(viii) Redox-sensitive polymers;
(ix) Bioadhesive systems;
(x) Coating with microparticles;
(xi) Osmotic controlled drug delivery.

Another approach towards colon-targeted drug delivery or controlled-release systems includes embedding the drug in polymer matrices to trap it and release it in the colon. These matrices can be pH-sensitive or biodegradable. Matrix-Based Systems, such as multi-matrix (MMX)-based delayed-release tablets, ensure the drug release in the colon.

Additional pharmaceutical approaches to targeted delivery of therapeutics to particular regions of the gastrointestinal tract are known. Chourasia M K, Jain S K, Pharmaceutical approaches to colon targeted drug delivery systems., J Pharm Sci. 2003 January-April; 6(1):33-66. Patel M, Shah T, Amin A. Therapeutic opportunities in colon-specific drug-delivery systems Crit Rev Ther Drug Carrier Syst. 2007; 24(2): 147-202. Kumar P, Mishra B. Colon targeted drug delivery systems—an overview. Curr Drug Deliv. 2008 July; 5(3): 186-98. Van den Mooter G. Colon drug delivery. Expert Opin Drug Deliv. 2006 January; 3(1): 111-25. Seth Amidon, Jack E. Brown, and Vivek S. Dave, Colon-Targeted Oral Drug Delivery Systems: Design Trends and Approaches, AAPS PharmSciTech. 2015 August; 16(4): 731-741.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of an FXR agonist. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

Disclosed herein, are methods of administering an FXR agonist in combination with an additional therapeutic agent. In some embodiments, the additional therapeutic agent comprises a therapeutic agent for treatment of diabetes or diabetes related disorder or conditions, alcoholic or non-alcoholic liver disease, inflammation related intestinal conditions, or cell proliferative disorders.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder, or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion, the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder, or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder, or condition being treated, thereby providing a greater overall benefit than administration of either therapeutic agent alone.

In any case, regardless of the disease, disorder, or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder, or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, an FXR agonist is administered in combination with an additional therapeutic agent for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anagliptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or a combination thereof. In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In some instances, nicotinamide ribonucleoside or its analogs thereof, which promote NAD$^+$ production, a substrate for many enzymatic reactions including p450s which is a target for FXR (e.g., see Yang et al., *J. Med, Chem.* 50:6458-61, 2007).

In some embodiments, an FXR agonist is administered in combination with an additional therapeutic agent such as a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anagliptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or combinations thereof, for the treatment of diabetes or diabetes related disorder or conditions. In some embodiments, an FXR agonist is administered in combination with an additional therapeutic agent such as fish oil, fibrate, vitamins such as niacin, retinoic acid (e.g., 9 cis-retinoic acid), nicotinamide ribonucleoside or its analogs thereof, or combinations thereof, for the treatment of diabetes or diabetes related disorder or conditions.

In some embodiments, an FXR agonist is administered in combination with a statin such as a HMG-CoA reductase inhibitor, fish oil, fibrate, niacin or a combination thereof, for the treatment of dyslipidemia.

In additional embodiments, an FXR agonist is administered in combination with a vitamin such as retinoic acid for the treatment of diabetes and diabetes related disorder or condition such as lowering elevated body weight and/or lowering elevated blood glucose from food intake.

In some embodiments, the farnesoid X receptor agonist is administered with at least one additional therapy. In some embodiments, the at least one additional therapy is a glucose-lowering agent. In some embodiments, the at least one additional therapy is an anti-obesity agent. In some embodiments, the at least one additional therapy is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the at least one additional therapy is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the at least one additional therapy is a lipid-lowering agent. In certain embodiments, the at least one additional therapy is administered at the same time as the farnesoid X receptor agonist. In certain embodiments, the at least one additional therapy is administered less frequently than the farnesoid X receptor agonist. In certain embodiments, the at least one additional therapy is administered more frequently than the farnesoid X receptor agonist. In certain embodiments, the at least one additional therapy is administered prior to administration of the farnesoid X receptor agonist. In certain embodiments, the at least one additional therapy is administered after administration of the farnesoid X receptor agonist.

In some embodiments, a compound described herein, or a pharmaceutically acceptable salt thereof, is administered in combination with chemotherapy, anti-inflammatory agents, radiation therapy, monoclonal antibodies, or combinations thereof.

In some embodiments, an FXR agonist is administered in combination with an additional therapeutic agent for the treatment of alcoholic or non-alcoholic liver disease. In some embodiments, the additional therapeutic agent includes antioxidant, corticosteroid, anti-tumor necrosis factor (TNF) or a combination thereof.

In some embodiments, an FXR agonist is administered in combination with an additional therapeutic agent such as antioxidant, corticosteroid, anti-tumor necrosis factor (TNF), or a combination thereof, for the treatment of alcoholic or non-alcoholic liver disease. In some embodiments, an FXR agonist is administered in combination with an antioxidant, a vitamin precursor, a corticosteroid, an anti-tumor necrosis factor (TNF), or a combination thereof, for the treatment of alcoholic or non-alcoholic liver disease.

In some embodiments, an FXR agonist is administered in combination with an additional therapeutic agent for the treatment of inflammation related intestinal conditions. In some instances, the additional therapeutic agent comprises an antibiotic (such as metronidazole, vancomycin, and/or fidaxomicin), a corticosteroid, or an additional anti-inflammatory or immuno-modulatory therapy.

In some instances, an FXR agonist is administered in combination with an additional therapeutic agent such as an antibiotic, a corticosteroid, or an additional anti-inflammatory or immuno-modulatory therapy, for the treatment of inflammation related intestinal conditions. In some cases, an FXR agonist is administered in combination with metronidazole, vancomycin, fidaxomicin, corticosteroid, or combinations thereof, for the treatment of inflammation related intestinal conditions.

As discussed above, inflammation is sometimes associated with pseudomembranous colitis. In some instances, pseudomembranous colitis is associated with bacterial overgrowth (such as *C. dificile* overgrowth). In some embodiments, an FXR agonist is administered in combination with an antibiotic such as metronidazole, vancomycin, fidaxomicin, or a combination thereof, for the treatment of inflammation associated with bacterial overgrowth (e.g., pseudomembranous colitis).

In some embodiments, the FXR agonist is administered in combination with an additional therapeutic agent for the treatment of cell proliferative disorders. In some embodiments, the additional therapeutic agent includes a chemotherapeutic, a biologic (e.g., antibody, for example bevacizumab, cetuximab, or panitumumab), a radiotherapeutic (e.g., FOLFOX, FOLFIRI, CapeOX, 5-FU, leucovorin, regorafenib, irinotecan, or oxaliplatin), or combinations thereof.

In some embodiments, the FXR agonist is administered in combination with an additional therapeutic agent for the treatment of primary biliary cirrhosis. In some embodiments, the additional therapeutic agent includes ursodeoxycholic acid (UDCA).

In some embodiments, an FXR agonist is administered in combination with an additional therapeutic agent such as a chemotherapeutic, a biologic, a radiotherapeutic, or combinations thereof, for the treatment of a cell proliferative disorder. In some instances, an FXR agonist is administered in combination with an antibody (e.g., bevacizumab, cetuximab, or panitumumab), chemotherapeutic, FOLFOX, FOLFIRI, CapeOX, 5-FU, leucovorin, regorafenib, irinotecan, oxaliplatin, or combinations thereof, for the treatment of a cell proliferative disorder.

EXAMPLES

The following examples are provided for illustrative purposes only and not to limit the scope of the claims provided herein.

As used above, and throughout the description of the invention, the following abbreviations, unless otherwise indicated, shall be understood to have the following meanings:

acac acetyl acetone
ACN or MeCN acetonitrile
AcOH acetic acid
Ac acetyl
BINAP 2,2'-bis(diphenylphosphino)-1,1'-binaphthalene
Bn benzyl
BOC or Boc tert-butyl carbamate
i-Bu iso-butyl
t-Bu tert-butyl
Cy cyclohexyl
CDI 1,1-carbonyldiimidazole
DBA or dba dibenzylideneacetone
DCE dichloroethane ($ClCH_2CH_2Cl$)
DCM dichloromethane ($CH_2Cl_2$)
DIBAL-H diisobutylaluminum hydride
DIPEA or DIEA diisopropylethylamine
DMAP 4-(N,N-dimethylamino)pyridine
DME 1,2-dimethoxy ethane
DMF N,N-dimethylformamide
DMA N,N-dimethylacetamide
DMPU N,N'-dimethylpropyleneurea
DMSO dimethylsulfoxide
Dppf or dppf 1,1'-bis(diphenylphosphino)ferrocene
EDC or EDCI N-(3-dimethylaminopropyl)-N'-ethylcarbodiimide hydrochloride
EEDQ 2-Ethoxy-1-ethoxy carbonyl-1,2-dihydroquinoline
eq equivalent(s)
Et ethyl
$Et_2O$ diethyl ether
EtOH ethanol
EtOAc ethyl acetate
HATU 1-[bis(dimethylamino)methylene]-1H-1,2,3-triazolo[4,5-b]pyridinium 3-oxid hexafluorophosphate
HMPA hexamethylphosphoramide
HOBt 1-hydroxybenzotriazole
HPLC high performance liquid chromatography
IBX 2-iodoxybenzoic acid
KHMDS potassium bis(trimethylsilyl)amide
NaHMDS sodium bis(trimethylsilyl)amide
LiHMDS lithium bis(trimethylsilyl)amide
LAH lithium aluminum anhydride
LCMS liquid chromatography mass spectrometry
2-MeTHF 2-methyltetrahydrofuran
Me methyl
MeOH methanol
MS mass spectroscopy
Ms mesyl
MTBE methyl tert-butyl ether
NBS A-bromosuccinimide
NMM A-methyl-morpholine
NMP A-methyl-pyrrolidin-2-one
NMR nuclear magnetic resonance
OTf trifluoromethanesulfonate
PCC pyridinium chlorochromate
PE petroleum ether
Ph phenyl
PPTS pyridium p-toluenesulfonate
iPr/i-Pr iso-propyl
RP-HPLC reverse-phase high-pressure liquid chromatography
rt room temperature
TBS tert-butyldimethylsilyl
TBAF tetra-n-butylammonium fluoride
TBAI tetra-n-butylammonium iodide
TEA triethylamine
TFA trifluoroacetic acid
THF tetrahydrofuran
TLC thin layer chromatography
TMEDA N,N,N',N'-tetramethylethylenediamine
TMS trimethylsilyl
TsOH/p-TsOH p-toluenesulfonic acid

Intermediate 1 trans-4-(4-Methoxy-3-methylphenyl)cyclohexanecarbaldehyde

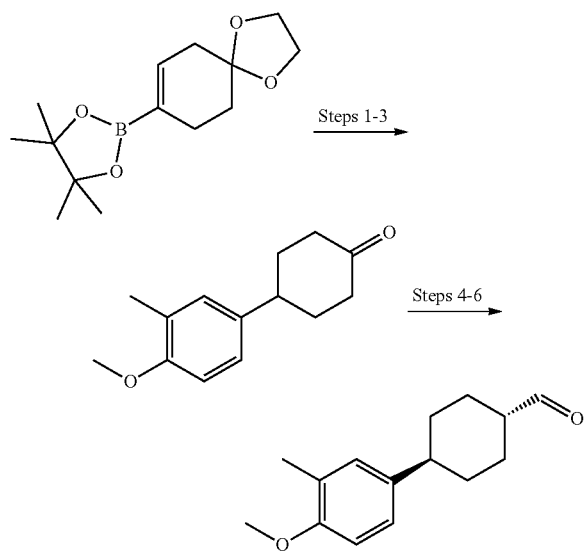

Step 1: 8-(4-Methoxy-3-methylphenyl)-1,4-dioxaspiro[4.5]dec-7-ene

A mixture of 1,4-dioxa-spiro[4,5]dec-7-en-8-boronic acid pinacol ester (25.0 g, 93.9 mmol), 4-iodo-2-methylanisole (28.0 g, 113 mmol), Pd(dppf)Cl$_2$ (1.38 g, 1.89 mmol), dioxane (470 mL) and 1 M Na$_2$CO$_3$ (282 mL, 282 mmol) was degassed with 3 vacuum/N$_2$ cycles, stirred at 50° C. for 2.5 h, and then allowed to cool to rt. The mixture was diluted with EtOAc (500 mL) and washed with saturated NaHCO$_3$ (2×500 mL). The aqueous layers were back extracted with EtOAc (200 mL). The combined EtOAc extracts were dried (Na$_2$SO$_4$), filtered, concentrated and purified by silica gel chromatography (0-5% EtOAc in hexanes) to give 8-(4-methoxy-3-methylphenyl)-1,4-dioxaspiro[4.5]dec-7-ene (19.9 g, 81%). $^1$H NMR (400 MHz, DMSO-d$_6$): δ 7.21-7.16 (m, 2H), 6.85 (d, 1H), 5.89-5.84 (m, 1H), 3.90 (s, 4H), 3.76 (s, 3H), 2.52-2.47 (m, 2H), 2.32 (br s, 2H), 2.13 (s, 3H), 1.77 (t, 2H); LCMS: 261.1 [M+H]$^+$.

Step 2: 8-(4-Methoxy-3-methylphenyl)-1,4-dioxaspiro[4.5]decane

Palladium on carbon (10 wt %, 8.08 g, 7.59 mmol) was added to a solution of 8-(4-methoxy-3-methylphenyl)-1,4-dioxaspiro[4.5]dec-7-ene (19.8 g, 76.1 mmol) in EtOAc (300 mL) at rt under N$_2$. The N$_2$ inlet was replaced with a balloon of H$_2$. The reaction was stirred for 4.5 h, filtered through Celite with EtOAc, and then concentrated to give 8-(4-methoxy-3-methylphenyl)-1,4-dioxaspiro[4.5]decane (18.2 g; contains 13% ketone) as a white solid. $^1$H NMR (400 MHz, DMSO-d$_6$): δ 7.00-6.95 (m, 2H), 6.81 (d, 1H), 3.91-3.84 (m, 4H), 3.73 (s, 3H), 2.49-2.42 (m, 1H), 2.11 (s, 3H), 1.76-1.68 (m, 4H), 1.67-1.55 (m, 4H); LCMS: 263.1 [M+H]$^+$.

Step 3: 4-(4-Methoxy-3-methylphenyl)cyclohexanone

Formic acid (96%, 14 mL, 356 mmol) and then H$_2$O (2.20 mL, 122 mmol) were added to a solution of 8-(4-methoxy-3-methylphenyl)-1,4-dioxaspiro[4.5]decane (18.2 g) in toluene (60 mL) at rt under N$_2$. The reaction was heated at 120° C. for 4 hours, allowed to cool to rt, and then poured into H$_2$O (200 mL) and toluene (200 mL). The toluene layer was washed (200 mL H$_2$O and then 200 mL saturated NaHCO$_3$). The aqueous layers were back extracted with toluene (100 mL). The combined toluene extracts were dried (Na$_2$SO$_4$), filtered and concentrated to give 4-(4-methoxy-3-methylphenyl)cyclohexanone (15.5 g, 88% over 2 steps) as a white solid. $^1$H NMR (400 MHz, DMSO-d$_6$): δ 7.08-7.03 (m, 2H), 6.84 (d, 1H), 3.74 (s, 3H), 3.00-2.91 (m, 1H), 2.61-2.51 (m, 2H), 2.28-2.20 (m, 2H), 2.12 (s, 3H), 2.06-1.98 (m, 2H), 1.88-1.76 (m, 2H); LCMS: 219.0 [M+H]$^+$.

Step 4: 1-Methoxy-4-(4-(methoxymethylene)cyclohexyl)-2-methylbenzene

A mixture of (methoxymethyl)triphenyl phosphonium chloride (35.74 g, 104.3 mmol) and THF (260 mL) under N$_2$ was cooled to −2.2° C. in an ice/brine bath. Sodium bis(trimethylsilyl)amide solution (2 M in THF, 50 mL, 100 mmol) was added dropwise via addition funnel over 12 min (internal temp ≤0.6° C.) with THF rinsing (5 mL). The reaction was stirred for 30 min, and then 4-(4-methoxy-3-methylphenyl)cyclohexanone (14.5 g, 66.6 mmol) was added portionwise over 5 min (exotherm to 7.3° C.). Residual cyclohexanone was rinsed into the reaction with THF (20 mL). The reaction was stirred at 0° C. for 25 min, and then poured into H$_2$O (400 mL) and toluene (400 mL). The toluene layer was washed (400 mL H$_2$O), dried (Na$_2$SO$_4$), filtered, concentrated and purified by silica gel chromatography (0-5% EtOAc in hexanes) to give 1-methoxy-4-(4-(methoxymethylene)cylcohexyl)-2-methylbenzene (15.6 g, 95%) as a pale gold oil. $^1$H NMR (400 MHz, DMSO-d$_6$): δ 6.99-6.94 (m, 2H), 6.80 (d, 1H), 5.87 (s, 1H), 3.73 (s, 3H), 3.48 (s, 3H), 2.78-2.71 (m, 1H), 2.56-2.44 (m, 1H), 2.10 (s, 3H), 2.17-2.09 (m, 1H), 2.01-1.91 (m, 1H), 1.83-1.73 (m, 2H), 1.72-1.63 (m, 1H), 1.38-1.23 (m, 2H); LCMS: 247.1 [M+H]$^+$.

Step 5: 4-(4-Methoxy-3-methylphenyl)cyclohexanecarbaldehyde

Formic acid (96%, 12.5 mL, 331 mmol) and then water (2.5 mL, 139 mmol) were added to a solution of 1-methoxy-4-(4-(methoxymethylene)cylcohexyl)-2-methylbenzene (16.05 g, 65.15 mmol) in toluene (130 mL) under N$_2$. The reaction was heated at 120° C. for 2 h, allowed to cool to rt, and then poured into 350 mL EtOAc and 350 mL H$_2$O. The organic layer was washed with 350 mL H$_2$O, dried (Na$_2$SO$_4$), filtered and concentrated to give 4-(4-methoxy-3-methylphenyl)cyclohexanecarbaldehyde (15.05 g) as a 1:1 mixture of stereoisomers.

Step 6: trans-4-(4-Methoxy-3-methylphenyl)cyclohexanecarbaldehyde

Aqueous sodium hydroxide (3.2 M, 31 mL, 99 mmol) was added to the crude mixture from Step 5 (14.68 g, 63.19 mmoL), toluene (60 mL) and ethanol (250 mL) at rt. The reaction was stirred for 5.5 hours (equilibration monitored by NMR) and then poured into 350 mL H$_2$O and 350 mL EtOAc. The organic layer was washed with 350 mL H₂O, and the aqueous layers were back extracted with 150 mL EtOAc. The combined extracts were dried (Na₂SO₄), filtered, concentrated and purified by silica gel chromatography (0-5% EtOAc in hexanes) to give trans-4-(4-methoxy-3-methylphenyl)cyclohexanecarbaldehyde (10.17 g, 69%) as a white solid. ¹H NMR (400 MHz, DMSO-d₆): δ 9.60 (s, 1H), 7.01-6.97 (m, 2H), 6.82 (d, 1H), 3.74 (s, 3H), 2.41-2.27 (m, 2H), 2.12 (s, 3H), 2.03-1.96 (m, 2H), 1.87-1.80 (m, 2H), 1.51-1.39 (m, 2H), 1.35-1.23 (m, 2H); LCMS: 233.0 [M+H]⁺.

Intermediate 2

4-(4-Methoxy-3-methylphenyl)bicyclo[2.2.2]octane-1-carbaldehyde

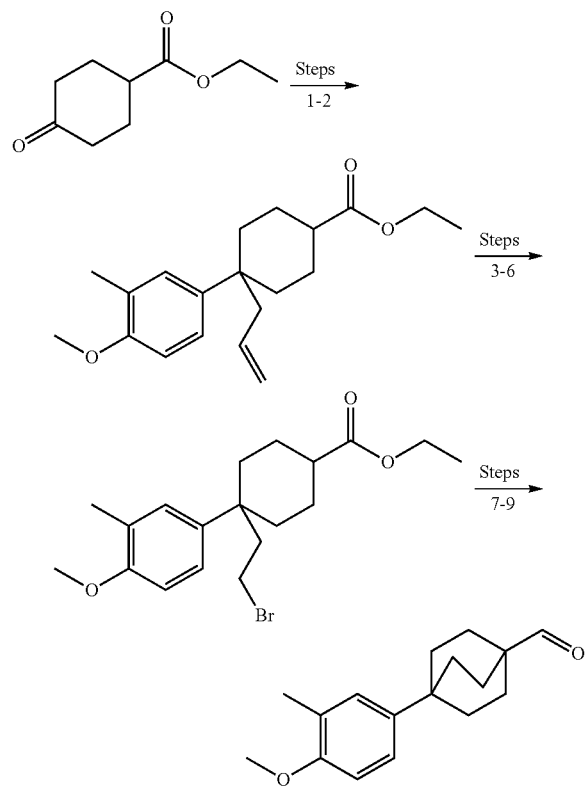

Step 1: Ethyl 4-hydroxy-4-(4-methoxy-3-methylphenyl)cyclohexanecarboxylate n-Butyllithium (2.5 M in hexanes, 60 mL, 150.0 mmol) was added dropwise to a solution of 4-bromo-1-methoxy-2-methylbenzene (27.78 g, 138.2 mmol) in THF (300 mL) at –78° C. The mixture was stirred at –78° C. for 1 h and then added dropwise to a solution of ethyl 4-oxocyclohexanecarboxylate (22.34 g, 131.3 mmol) and THF (300 mL) at –78° C. The reaction mixture was stirred at –78° C. for 2 h, added to saturated NH₄Cl (600 mL) and then extracted with EtOAc (2×600 mL). The combined organic extracts were washed (400 mL water and then 400 mL brine), dried (Na₂SO₄), filtered, and concentrated. The crude was purified by silica gel chromatography (petroleum ether/EtOAc=10/1) to give ethyl 4-hydroxy-4-(4-methoxy-3-methylphenyl)cyclohexanecarboxylate (18.9 g, 45%) as a yellow oil. ¹H NMR (400 MHz, DMSO-d₆): δ 7.11-7.26 (m, 2H), 6.75-6.84 (m, 1H), 4.59-4.64 (m, 1H), 3.98-4.11 (m, 2H), 3.72 (s, 3H), 2.25-2.39 (m, 1H), 2.07-2.13 (s, 3H), 1.77-1.93 (m, 3H), 1.42-1.75 (m, 5H), 1.11-1.23 (m, 3H); LCMS: 275.2 [M-OH]⁺.

Step 2: Ethyl 4-allyl-4-(4-methoxy-3-methylphenyl)cyclohexanecarboxylate

Boron trifluoride diethyl etherate (24.85 g, 84.03 mmol) was added to a solution of ethyl 4-hydroxy-4-(4-methoxy-3-methylphenyl)cyclohexanecarboxylate (18.90 g, 64.64 mmol), allyltrimethylsilane (11.82 g, 103.42 mmol), and CH₂Cl₂ (400 mL) at –78° C. The mixture was stirred at –78° C. for 1 h, stirred at rt overnight, and then added to brine (200 mL) and CH₂Cl₂ (200 mL). The organic layer was separated, washed (2×200 mL saturated NaHCO₃ and then 200 mL brine), dried (Na₂SO₄), filtered, and then concentrated. The crude was purified by silica gel chromatography (petroleum ether/EtOAc=20/1) to give ethyl 4-allyl-4-(4-methoxy-3-methylphenyl)cyclohexanecarboxylate (15 g, 71%) as a yellow oil. ¹H NMR (400 MHz, CDCl₃): δ 7.00-7.10 (m, 2H), 6.76 (d, 1H), 5.26-5.50 (m, 1H), 4.81-4.98 (m, 2H), 4.15 (q, 0.5H), 4.03 (q, 1.5H), 3.81 (s, 3H), 2.26-2.42 (m, 3H), 2.21 (s, 3H), 2.15 (d, 1.5H), 1.98 (d, 0.5H), 1.75-1.88 (m, 2.5H), 1.60-1.72 (m, 0.5H), 1.33-1.55 (m, 3H), 1.27 (t, 0.8H), 1.18 (t, 2.2H); LCMS: 339.3 [M+Na]⁺.

Step 3: Ethyl 4-(2,3-dihydroxypropyl)-4-(4-methoxy-3-methylphenyl)cyclohexane carboxylate Osmium tetroxide (0.1 M in tert-butanol, 7.6 mL, 0.76 mmol) was added to a solution of ethyl 4-allyl-4-(4-methoxy-3-methylphenyl)cyclohexanecarboxylate (4.81 g, 15.2 mmol), 4-methylmorpholine N-oxide (2.67 g, 22.8 mmol), CH₃CN (100 mL), and H₂O (25 mL) at 0° C. The reaction was stirred at rt overnight, and then saturated Na₂SO₃ (50 mL) was added. The mixture was stirred at rt for 30 min, concentrated, dissolved in water (80 mL), and then extracted with EtOAc (2×100 mL). The organic layers were dried (Na₂SO₄), filtered, and concentrated. The reside was purified by silica gel chromatography (petroleum ether/EtOAc=1/1) to give ethyl 4-(2,3-dihydroxypropyl)-4-(4-methoxy-3-methylphenyl)cyclohexanecarboxylate (5.23 g, 94%) as a yellow oil. ¹H NMR (400 MHz, CDCl₃): δ 7.05-7.16 (m, 2H), 6.78 (d, 1H), 4.06-4.17 (m, 0.5H), 3.95-4.05 (m, 1.5H), 3.80 (s, 3H), 3.48-3.66 (m, 1H), 3.18-3.32 (m, 2H), 2.40-2.53 (m, 2H), 2.27-2.37 (m, 1H), 2.19 (s, 3H), 1.80 (t, 3H), 1.32-1.68 (m, 7H), 1.24 (td, 0.8H), 1.17 (t, 2.2H); LCMS: 373.3 [M+Na]⁺.

Step 4: Ethyl 4-(4-methoxy-3-methylphenyl)-4-(2-oxoethyl)cyclohexanecarboxylate

Sodium periodate (3.83 g, 17.90 mmol) was added to a solution of ethyl 4-(2,3-dihydroxypropyl)-4-(4-methoxy-3-methylphenyl)cyclohexanecarboxylate (5.23 g, 14.9 mmol), THF (70 mL), and H₂O (35 mL) at 0° C. The mixture was stirred at rt overnight, added to water (50 mL), and extracted with EtOAc (2×100 mL). The organic layers were combined, washed (80 mL water and then 80 mL brine), dried (Na₂SO₄), filtered, and concentrated. The residue was purified by silica gel chromatography (petroleum ether/EtOAc=5/1) to give ethyl 4-(4-methoxy-3-methylphenyl)-4-(2-oxoethyl)cyclohexanecarboxylate (3.95 g, 82%) as a yellow oil. ¹H NMR (400 MHz, CDCl₃): δ 9.28-9.42 (m, 1H), 7.07-7.19 (m, 2H), 6.79 (d, 1H), 4.15 (q, 0.5H), 4.04 (q, 1.5H), 3.82 (s, 3H), 2.41-2.52 (m, 3H), 2.33 (s, 1H), 2.21 (s, 3H), 1.75-1.92 (m, 3H), 1.46-1.63 (m, 4H), 1.23-1.31 (t, 0.5H), 1.19 (t, 2.5H); LCMS: 341.3 [M+Na]⁺.

Step 5: Ethyl 4-(2-hydroxyethyl)-4-(4-methoxy-3-methylphenyl)cyclohexanecarboxylate Sodium borohydride (704 mg, 18.6 mmol) was added to a solution of ethyl 4-(4-methoxy-3-methylphenyl)-4-(2-oxoethyl)cyclohexanecarboxylate (3.95 g, 12.41 mmol) and THF (100 mL) at 0° C. The mixture was stirred at 0° C. for 1 h, stirred at rt overnight, and then diluted with water (100 mL). The organic solvent was removed under reduced pressure, and the aqueous layer was extracted with CH₂Cl₂ (2×300 mL). The organic extracts were dried (Na₂SO₄), filtered, and concentrated. The residue was purified by silica gel chromatography (petroleum ether/EtOAc=3/1) to give ethyl 4-(2-hydroxyethyl)-4-(4-methoxy-3-methylphenyl)cyclohexanecarboxylate (3.11 g, 67%) as a yellow oil. ¹H NMR (400 MHz, CDCl₃): δ 6.96-7.04 (m, 2H), 6.71 (d, 1H), 4.03-4.12 (q, 0.4H), 3.97 (q, 1.6H), 3.74 (s, 3H), 3.28-3.38 (m, 2H), 2.19-2.39 (m, 3H), 2.14 (s, 3H), 1.71-1.80 (m, 2H), 1.60-1.70 (m, 2H), 1.28-1.50 (m, 4H), 1.17-1.24 (t, 1H), 1.12 (t, 2H); LCMS: 343.2 [M+Na]⁺.

Step 6: Ethyl 4-(2-bromoethyl)-4-(4-methoxy-3-methylphenyl)cyclohexanecarboxylate A solution of triphenylphosphine (4.60 g, 17.54 mmol) and CH₂Cl₂ (20 mL) was added dropwise to a solution of ethyl 4-(2-hydroxyethyl)-4-(4-methoxy-3-methylphenyl)cyclohexanecarboxylate (2.81 g, 8.77 mmol), CBr₄ (4.36 g, 13.16 mmol), and CH₂Cl₂ (40 mL) at 0° C. The mixture was stirred at 0° C. for 1 h, stirred at rt overnight, and then concentrated. The residue was purified by silica gel chromatography (petroleum ether/EtOAc=20/1) to give ethyl 4-(2-bromoethyl)-4-(4-methoxy-3-methylphenyl)cyclohexanecarboxylate (2.62 g, 77%) as a yellow oil. ¹H NMR (400 MHz, CDCl₃): δ 6.96-7.08 (m, 2H), 6.77 (d, 1H), 4.15 (q, 0.3H), 4.03 (q, 1.7H), 3.81 (s, 3H), 2.91-3.06 (m, 2H), 2.24-2.41 (m, 3H), 2.15-2.24 (s, 3H), 1.95-2.06 (m, 2H), 1.77-1.87 (m, 2H), 1.34-1.53 (m, 4H), 1.27 (t, 1H), 1.18 (t, 2H); LCMS: 405.1 [M+Na]⁺.

Step 7: Ethyl 4-(4-methoxy-3-methylphenyl)bicyclo[2.2.2]octane-1-carboxylate

Lithium diisopropylamide (2 M in THF, 4.8 mL, 9.60 mmol) was added dropwise to a solution of ethyl 4-(2-bromoethyl)-4-(4-methoxy-3-methylphenyl)cyclohexanecarboxylate (1.81 g, 4.72 mmol), HMPA (4.23 g, 23.61 mmol), and THF (90 mL) at −78° C. The mixture was stirred at −78° C. for 3 h, added to saturated NH₄Cl (90 mL), and then extracted with EtOAc (2×150 mL). The combined organic layers were washed (100 mL H₂O and then 100 mL brine), dried (Na₂SO₄), filtered, and concentrated. The residue was purified by silica gel chromatography (petroleum ether/EtOAc=30/1) to give ethyl 4-(4-methoxy-3-methylphenyl)bicyclo[2.2.2]octane-1-carboxylate (1.17 g, 82%) as a yellow solid. ¹H NMR (400 MHz, CDCl₃): δ 6.98-7.05 (m, 2H), 6.69 (d, 1H), 4.05 (q, 2H), 3.73 (s, 3H), 2.14 (s, 3H), 1.70-1.87 (m, 12H), 1.18 (t, 3H); LCMS: 303.3 [M+H]⁺.

Step 8: (4-(4-Methoxy-3-methylphenyl)bicyclo[2.2.2]octan-1-yl)methanol

Diisobutylaluminum hydride (1 M in toluene, 14 mL, 14.0 mmol) was added to a solution of ethyl 4-(4-methoxy-3-methylphenyl)bicyclo[2.2.2]octane-1-carboxylate (1.64 g, 5.42 mmol) and CH₂Cl₂ (100 mL) at −78° C. The mixture was stirred at −78° C. for 1 h, stirred at rt for 2 h, and then added to ice H₂O (80 mL). The pH was adjusted (pH=6) with 1 N HCl, and the mixture was filtered. The layers were separated, and the aqueous layer was extracted with CH₂Cl₂ (2×200 mL). The combined organic layers were washed (100 mL water and then 100 mL brine), dried (Na₂SO₄), filtered, and concentrated. The residue was purified by silica gel chromatography (petroleum ether/EtOAc=10/1) to give (4-(4-methoxy-3-methylphenyl)bicyclo[2.2.2]octan-1-yl)methanol (1.22 g, 82%) as a yellow solid. ¹H NMR (400 MHz, CDCl₃): δ 6.99-7.07 (m, 2H), 6.64-6.72 (m, 1H), 3.73 (s, 3H), 3.25 (s, 2H), 2.14 (s, 3H), 1.69-1.81 (m, 6H), 1.40-1.50 (m, 6H); LCMS: 261.2 [M+H]⁺.

Step 9: 4-(4-Methoxy-3-methylphenyl)bicyclo[2.2.2]octane-1-carbaldehyde

Pyridinium chlorochromate (1.03 g, 4.78 mmol) was added to a mixture of (4-(4-methoxy-3-methylphenyl)bicyclo[2.2.2]octan-1-yl)methanol (621 mg, 2.39 mmol), SiO₂ (1.93 g, 32.19 mmol) and CH₂Cl₂ (120 mL). The mixture was stirred at rt for 2 h, filtered through a neutral alumina plug and then concentrated to give 4-(4-methoxy-3-methylphenyl)bicyclo[2.2.2]octane-1-carbaldehyde (601 mg, 93%) as a white solid. ¹H NMR (400 MHz, CDCl₃): δ 9.48-9.56 (s, 1H), 7.06-7.11 (m, 2H), 6.72-6.78 (m, 1H), 3.81 (s, 3H), 2.22 (s, 3H), 1.83-1.91 (m, 6H), 1.71-1.80 (m, 6H); LCMS: 259.3 [M+H]⁺.

The Intermediate below was synthesized from 5-bromo-N,N-dimethylpyridine-2-amine following the procedures described for Intermediate 2.

| Int | Structure | Name | [M + H]⁺ |
|---|---|---|---|
| 2.01 | 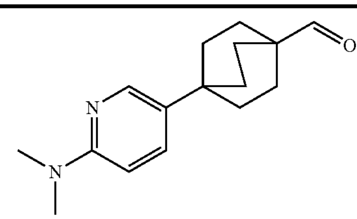 | trans-4-(6-(Dimethylamino)pyridine-3-yl)cyclohexanecarbaldehyde | 259.2 |

Alternate conditions: Step 2: 0° C., overnight; Step 3: K₂OsO₄·2H₂O; Step 7: −78° C., 1 h then rt, overnight; Step 9: oxalyl chloride, DMSO, Et₃N, −78° C.

Intermediate 3

4-(4-Methoxy-3,5-dimethylphenyl)bicyclo[2.2.2]octane-1-carbaldehyde

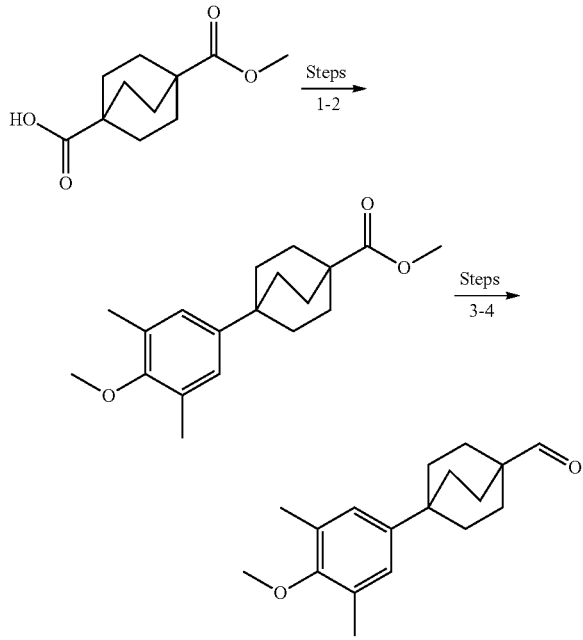

Step 1: 1-(1,3-Dioxoisoindolin-2-yl) 4-methyl bicyclo[2.2.2]octane-1,4-dicarboxylate N,N-Diisopropylcarbodiimide (17.98 g, 142.5 mmol) was added to a solution of 4-(methoxycarbonyl)bicyclo[2.2.2]octane-1-carboxylic acid (25 g, 117.8 mmol), 2-hydroxyisoindoline-1,3-dione (19.22 g, 117.8 mmol), DMAP (4.32 g, 35.3 mmol), and $CH_2Cl_2$ (500 mL) at rt under $N_2$. The mixture was stirred at rt overnight, washed with $H_2O$ (300 mL×2), dried ($Na_2SO_4$), filtered, concentrated, and then purified by silica gel chromatography (petroleum ether/EtOAc: 10/1-2/1) to give 1-(1,3-dioxoisoindolin-2-yl) 4-methyl bicyclo[2.2.2]octane-1,4-dicarboxylate (23 g) as a white solid. $^1$H NMR (400 MHz, $CDCl_3$): δ 7.88 (d, 2H), 7.78 (d, 2H), 3.68 (s, 3H), 2.10-2.04 (m, 6H), 1.93-1.87 (m, 6H); LCMS: 358.1 [M+H]+.

Step 2a: (4-Methoxy-3,5-dimethylphenyl)magnesium lithium bromide chloride

Magnesium (2.37 g, 97.6 mmol) and dry LiCl (4.14 g, 97.6 mmol) were weighed into an oven-dried 250 mL 2-necked flask connected to a double manifold. The flask was sealed, evacuated, and backfilled with $N_2$ (3 times). Tetrahydrofuran (70 mL) was added, the mixture was stirred for 15 min, and then DIBAL-H (1 M in toluene, 1.30 mL) was added dropwise at rt. The reaction was stirred for 15 min, cooled to 0° C., and then a solution of 5-bromo-2-methoxy-1,3-dimethylbenzene (14 g, 65.09 mmol) and THF (70 mL) was added dropwise. The mixture was allowed to warm to rt and stirred for 2 h to give (4-methoxy-3,5-dimethylphenyl)magnesium lithium bromide chloride as a gray solution in THF (~140 mL).

Step 2b: Bis(4-methoxy-3,5-dimethylphenyl)zinc

Zinc (II) chloride (1 M THF, 39 mL) was added dropwise to the (4-methoxy-3,5-dimethylphenyl)magnesium lithium bromide chloride THF solution (~140 mL) at rt. The mixture was stirred at rt for 1 h to give bis(4-methoxy-3,5-dimethylphenyl)zinc as a gray solution in THF (~180 mL).

Step 2c: Methyl 4-(4-methoxy-3,5-dimethylphenyl)bicyclo[2.2.2]octane-1-carboxylate The bis(4-methoxy-3,5-dimethylphenyl)zinc THF solution (~180 mL) was added to a solution of 1-(1,3-dioxoisoindolin-2-yl) 4-methyl bicyclo[2.2.2]octane-1,4-dicarboxylate (4.9 g, 13.71 mmol), 2-methyl-6-(6-methyl-2-pyridyl)pyridine (1.52 g, 8.23 mmol), Ni(acac)$_2$ (1.76 g, 6.86 mmol), and DMF (50 mL) at rt. The mixture was stirred at rt overnight, concentrated to remove the organic solvent, and then diluted with EtOAc (500 mL). The organic layer was washed with water (200 mL), dried ($Na_2SO_4$), filtered, concentrated, and then purified by silica gel chromatography (petroleum ether/EtOAc=50/1) to give methyl 4-(4-methoxy-3,5-dimethylphenyl)bicyclo[2.2.2]octane-1-carboxylate (2.3 g) as white solid. LCMS: 303.2 [M+H]+

Step 3: (4-(4-Methoxy-3,5-dimethylphenyl)bicyclo[2.2.2]octan-1-yl)methanol

DIBAL-H (1 M in toluene, 34 mL) was added to a solution of methyl 4-(4-methoxy-3,5-dimethylphenyl)bicyclo[2.2.2]octane-1-carboxylate (3.4 g, 11.24 mmol) and $CH_2Cl_2$ (30 mL) at −78° C. The mixture was allowed to warm to rt, stirred at rt overnight, poured into a saturated sodium potassium tartrate solution (100 mL), diluted with $CH_2Cl_2$ (100 mL), and then stirred at rt for 3 h. The aqueous phase was extracted with $CH_2Cl_2$ (50 mL×2). The combined organic layers were washed with brine (30 mL), dried over $Na_2SO_4$, filtered, concentrated, and then purified by silica gel chromatography (petroleum ether/EtOAc=2/1) to give (4-(4-methoxy-3,5-dimethylphenyl)bicyclo[2.2.2]octan-1-yl)methanol (2.3 g, 74%) as a black brown solid. $^1$H NMR (400 MHz, $CDCl_3$): δ 6.95 (s, 2H), 3.71 (s, 3H), 3.33 (s, 2H), 2.27 (s, 6H), 1.84-1.80 (m, 6H), 1.56-1.52 (m, 6H); LCMS: 275.2 [M+H]+.

Step 4: 4-(4-Methoxy-3,5-dimethylphenyl)bicyclo[2.2.2]octane-1-carbaldehyde

Pyridinium chlorochromate (3.61 g, 16.76 mmol) and $SiO_2$ (6.80 g, 113.16 mmol) were added to a solution of (4-(4-methoxy-3,5-dimethylphenyl)bicyclo[2.2.2]octan-1-yl)methanol (2.3 g, 8.38 mmol) and $CH_2Cl_2$ (20 mL) at rt. The mixture was stirred at rt for 2 h and then filtered through a neutral alumina plug. The filtrate was concentrated and purified by silica gel chromatography (petroleum ether/EtOAc=20/1) to give 4-(4-methoxy-3,5-dimethylphenyl)bicyclo[2.2.2]octane-1-carbaldehyde (1.9 g, 74% yield) as a white solid. $^1$H NMR (400 MHz, DMSO-d$_6$): δ 9.46 (s, 1H), 6.95 (s, 2H), 3.59 (s, 3H), 2.18 (s, 6H), 1.78-1.74 (m, 6H), 1.69-1.64 (m, 6H); LCMS: 273.1 [M+H]+.

The Intermediates below were synthesized from Intermediate 3 (Step 1) and the appropriate starting materials following the procedures described for Intermediate 3.

| Int | Structure | Name | [M + H]+ |
|---|---|---|---|
| 3.01[1,2] | 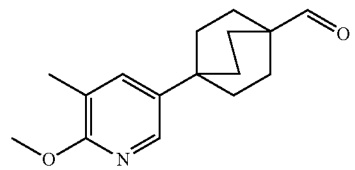 [SMILES: COc1ncc(C23CCC(C=O)(CC2)CC3)cc1C] | 4-(6-Methoxy-5-methylpyridin-3-yl)bicyclo[2.2.2]octane-1-carbaldehyde | 260.1 |
| 2[3] | 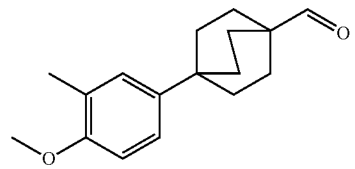 [SMILES: COc1ccc(C23CCC(C=O)(CC2)CC3)cc1C] | 4-(4-Methoxy-3-methylphenyl)bicyclo[2.2.2]octane-1-carbaldehyde | 259.3 |

Alternate conditions: [1]Grignard from Step 2a used directly in Step 2c (No Step 2b). Step 2c: [2]Fe(acac)₃ (1 equiv rel to carboxylate), no ligand, DMPU, THF, rt, overnight; [3]Ni(acac)₂ (1 equiv rel to carboxylate), 6,6'-dimethyl-2,2'-dipyridyl (1.3 equiv rel to carboxylate), DMF, 0-35° C., 16 h.

Intermediate 2

4-(4-Methoxy-3-methylphenyl)bicyclo[2.2.2]octane-1-carbaldehyde

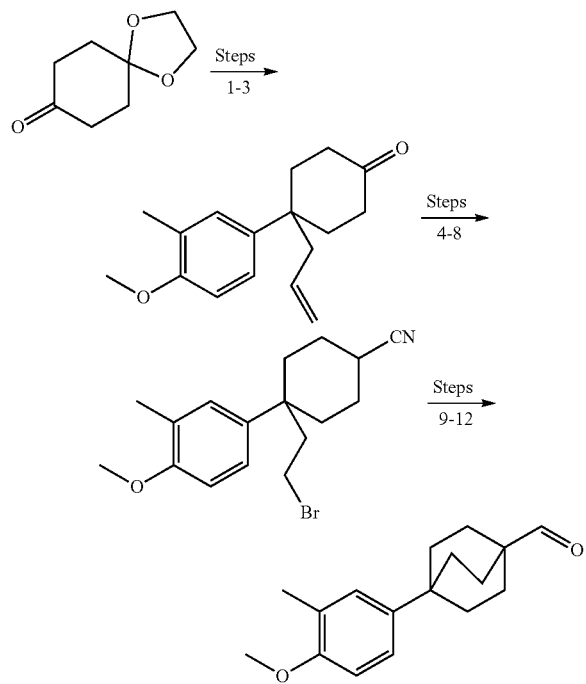

Step 1: 8-(4-Methoxy-3-methylphenyl)-1,4-dioxaspiro[4.5]decan-8-ol 3 batches were run in parallel: n-BuLi (762 mL, 1.90 mol, 2.5 M in n-hexane) was added dropwise over 1 h to a solution of 4-bromo-1-methoxy-2-methylbenzene (333 g, 1.66 mol) and dry THF (2 L) at −60° C. under N₂. The reaction was stirred at −60° C. for 1 h, and then a solution of 1,4-dioxaspiro[4.5]decan-8-one (284.53 g, 1.82 mol) and dry THF (1 L) was added dropwise over 45 min. The reaction was stirred at −60° C. for 1 h, and then the 3 batches were poured into sat. aq. NH₄Cl (3 L). This mixture was extracted with EtOAc (5 L×2). The combined organic layers were washed with brine (5 L), dried over Na₂SO₄, filtered, concentrated, and then triturated in n-hexane (1.2 L) at rt overnight. The mixture was filtered, and the filter cake was washed with cool n-hexane (200 mL×2) and then dried under vacuum to give 8-(4-methoxy-3-methylphenyl)-1,4-dioxaspiro[4.5]decan-8-ol (1100 g, 82%) as a white solid. ¹H NMR (400 MHz, CDCl₃): δ 7.30-7.20 (m, 2H), 6.74 (d, 1H), 4.02-3.87 (m, 4H), 3.78 (s, 3H), 2.18 (s, 3H), 2.15-2.00 (m, 4H), 1.82-1.73 (m, 2H), 1.68-1.60 (m, 2H), 1.48 (s, 1H).

Step 2: 8-Allyl-8-(4-methoxy-3-methylphenyl)-1,4-dioxaspiro[4.5]decane 4 batches were run in parallel: BF₃.Et₂O (376.95 g, 2.65 mol) was added to a solution of 8-(4-methoxy-3-methylphenyl)-1,4-dioxaspiro[4.5]decan-8-ol (275 g, 0.99 mol), allyltrimethylsilane (180.62 g, 1.58 mol), and dry DCM (3 L) at −65° C. under N₂. The reaction mixture was stirred at −65° C. for 1 h, and then the 4 batches were carefully poured into sat. aq. NaHCO₃ (10 L). This mixture was extracted with DCM (5 L×3). The combined organic layers were washed with brine (5 L), dried over Na₂SO₄, filtered, and concentrated to give 8-allyl-8-(4-methoxy-3-methylphenyl)-1,4-dioxaspiro[4.5]decane (1350 g) as a yellow oil. ¹H NMR (400 MHz, CDCl₃): δ 7.17-7.01 (m, 2H), 6.85-6.75 (m, 1H), 5.53-5.37 (m, 1H), 5.01-4.85 (m, 2H), 3.99-3.87 (m, 4H), 3.82 (s, 3H), 2.37-2.29 (m, 1H), 2.28-2.21 (m, 5H), 2.20-2.10 (m, 2H), 1.82-1.71 (m, 2H), 1.70-1.52 (m, 3H).

Step 3: 4-Allyl-4-(4-methoxy-3-methylphenyl)cyclohexanone 3 batches were run in parallel: Water (450 mL) and then formic acid (285.95 g, 5.95 mol) were added to a solution of 8-allyl-8-(4-methoxy-3-methylphenyl)-1,4-dioxaspiro[4.5]decane (450 g) and THF (1.8 L) at rt. The reaction mixture was refluxed overnight, allowed to cool to rt, and then the 3 batches were poured into sat. aq. NaHCO₃ (3 L). This mixture was extracted with EA (3 L×3). The combined organic layers were washed with brine (3 L), dried over Na₂SO₄, filtered, concentrated, and then purified by chromatography on silica gel (petroleum ether/EtOAc=1/0-50/1) to give 4-allyl-4-(4-methoxy-3-methylphenyl)cyclohexanone (800 g, 69.3% over 2 steps) as a yellow oil. ¹H NMR (400 MHz, CDCl₃): δ 7.16-7.06 (m, 2H), 6.80-6.73

(m, 1H), 5.48-5.30 (m, 1H), 4.96-4.79 (m, 2H), 3.77 (s, 3H), 2.48-2.35 (m, 2H), 2.32-2.05 (m, 9H), 1.89-1.77 (m, 2H).

Step 4: 4-Allyl-4-(4-methoxy-3-methylphenyl)cyclohexanecarbonitrile 3 batches were run in parallel: 1-BuOK (299.69 g, 2.67 mol) was added portionwise over 1 h (keeping internal temp. <5° C.) to a solution of 4-ally1-4-(4-methoxy-3-methylphenyl)cyclohexanone (230 g, 890.25 mmol), Tos-MIC (260.72 g, 1.34 mol), and DME (2 L) at 0° C. under $N_2$. The mixture was stirred at rt for 2 h, and then the 3 batches were poured into sat. aq. $NH_4Cl$ (5 L). The mixture was extracted with EtOAc (5 L×2). The combined organic layers were washed with brine (5 L), dried over $Na_2SO_4$, filtered, concentrated, and then purified by chromatography on silica gel (petroleum ether/EtOAc=1/0-50/1) to give 4-allyl-4-(4-methoxy-3-methylphenyl)cyclohexanecarbonitrile (508 g, 70.6%) as a yellow oil. $^1$H NMR (400 MHz, $CDCl_3$): δ 7.13-6.99 (m, 2H), 6.83-6.75 (m, 1H), 5.51-5.31 (m, 1H), 5.03-4.85 (m, 2H), 3.84 (s, 3H), 2.58-2.48 (m, 1H), 2.38-2.02 (m, 7H), 1.98-1.79 (m, 2H), 1.78-1.56 (m, 3H), 1.54-1.40 (m, 1H).

Step 5: 4-(2,3-Dihydroxypropyl)-4-(4-methoxy-3-methylphenyl)cyclohexanecarbonitrile 3 batches were run in parallel: NMO (242.66 g, 2.07 mol) and then $K_2OsO_4 \cdot 2H_2O$ (7.63 g, 20.71 mmol) were added to a solution of 4-allyl-4-(4-methoxy-3-methylphenyl)cyclohexanecarbonitrile (186 g, 690.47 mmol), acetone (2 L), and $H_2O$ (250 mL) at 0° C. The reaction was allowed to warm to rt and stirred for 2 h. The 3 batches were poured into sat. aq. $Na_2SO_3$ (4 L), and the mixture was extracted with EtOAc (3 L×2). The combined organic layers were washed with brine (3 L), dried over $Na_2SO_4$, filtered, and then purified by chromatography on silica gel (petroleum ether/EtOAc=5/1-1/2) to give 4-(2,3-dihydroxypropyl)-4-(4-methoxy-3-methylphenyl)cyclohexanecarbonitrile (600 g, 95.4%) as a yellow oil. $^1$H NMR (400 MHz, $CDCl_3$): δ 7.21-7.01 (m, 2H), 6.87-6.74 (m, 1H), 3.83 (s, 3H), 3.65-3.49 (m, 1H), 3.35-3.17 (m, 2H), 2.60-2.45 (m, 1H), 2.41-2.11 (m, 5H), 2.01-1.81 (m, 4H), 1.79-1.38 (m, 6H).

Step 6: 4-(4-Methoxy-3-methylphenyl)-4-(2-oxoethyl)cyclohexanecarbonitrile 3 batches were run in parallel: $NaIO_4$ (169.20 g, 791.05 mmol) was added portionwise over 30 min (keeping internal temp. <5° C.) to a solution of 4-(2,3-dihydroxypropyl)-4-(4-methoxy-3-methylphenyl)cyclohexanecarbonitrile (200 g, 659.21 mmol), THF (2 L), and $H_2O$ (1 L) at 0° C. The mixture was stirred at rt for 3 h, and then the 3 batches were poured into water (2 L). The mixture was extracted with EtOAc (2 L×2). The combined organic layers were washed with brine (2 L), dried over $Na_2SO_4$, filtered, and concentrated to give 4-(4-methoxy-3-methylphenyl)-4-(2-oxoethyl)cyclohexanecarbonitrile (510 g) as a colorless oil. $^1$H NMR (400 MHz, $CDCl_3$): δ 9.43-9.22 (m, 1H), 7.20-6.99 (m, 2H), 6.87-6.71 (m, 1H), 3.82 (s, 3H), 2.63-2.48 (m, 2H), 2.46-2.36 (m, 1H), 2.33-2.13 (m, 4H), 2.02-1.71 (m, 5H), 1.71-1.57 (m, 2H).

Step 7: 4-(2-Hydroxyethyl)-4-(4-methoxy-3-methylphenyl)cyclohexanecarbonitrile 3 batches were run in parallel: $NaBH_4$ (35.55 g, 939.73 mmol) was added to a solution of 4-(4-methoxy-3-methylphenyl)-4-(2-oxoethyl)cyclohexanecarbonitrile (170 g) and THF (1.7 L) at 0° C. under $N_2$. The mixture was stirred at rt for 3 h, and then the 3 batches were poured into ice-cold water (3 L). This mixture was extracted with EtOAc (1.5 L×2). The combined organic layers were washed with brine (2 L), dried over $Na_2SO_4$, filtered, concentrated to give 4-(2-hydroxyethyl)-4-(4-methoxy-3-methylphenyl)cyclohexanecarbonitrile (495 g) as a colorless oil. $^1$H NMR (400 MHz, $CDCl_3$): δ 7.18-6.97 (m, 2H), 6.88-6.71 (m, 1H), 3.85-3.78 (m, 3H), 3.76-3.70 (m, 1H), 3.44-3.33 (m, 2H), 2.71-2.69 (m, 0.5H), 2.60-2.48 (m, 0.5H), 2.37-2.35 (m, 0.5H), 2.27-2.19 (m, 3H), 2.14-2.12 (m, 0.5H), 1.96-1.79 (m, 5H), 1.78-1.61 (m, 3H), 1.58-1.45 (m, 1H).

Step 8: 4-(2-Bromoethyl)-4-(4-methoxy-3-methylphenyl)cyclohexanecarbonitrile 3 batches were run in parallel: A solution of $PPh_3$ (316.62 g, 1.21 mol) and DCM (1 L) was added dropwise over 1 h to a solution of 4-(2-hydroxyethyl)-4-(4-methoxy-3-methylphenyl)cyclohexanecarbonitrile (165 g), $CBr_4$ (300.24 g, 905.37 mmol), and DCM (1.5 L) at 0° C. under $N_2$. The mixture was stirred at rt for 1.5 h, combined with the other 2 batches, and concentrated. The crude product was triturated in MTBE (5 L) at rt overnight. The solid was removed by filtration, the cake was washed with MTBE (500 mL×2), and the filtrate was concentrated and then purified by chromatography on silica gel (petroleum ether/EtOAc=30/1) to give 4-(2-bromoethyl)-4-(4-methoxy-3-methylphenyl)cyclohexanecarbonitrile (530 g, 80%) as a white solid. $^1$H NMR (400 MHz, $CDCl_3$): δ 7.11-6.96 (m, 2H), 6.86-6.73 (m, 1H), 3.87-3.73 (m, 3H), 3.09-2.93 (m, 2H), 2.78-2.68 (m, 0.5H), 2.62-2.50 (m, 0.5H), 2.38-2.34 (m, 1H), 2.28-2.18 (m, 3H), 2.17-2.10 (m, 2H), 2.08-1.99 (m, 1H), 1.99-1.79 (m, 3H), 1.77-1.45 (m, 3H).

Step 9: 4-(4-Methoxy-3-methylphenyl)bicyclo[2.2.2]octane-1-carbonitrile 3 batches were run in parallel: LDA (420 mL, 840 mmol, 2 M in THF) was added drop wise over 1 h to a solution of 4-(2-bromoethyl)-4-(4-methoxy-3-methyl-phenyl)cyclohexanecarbonitrile (143 g, 425.26 mmol), HMPA (381.03 g, 2.13 mol), and THF (1430 mL) at −65° C. under $N_2$. The mixture was stirred at −65° C. for 3 h, and then the 3 batches were poured into sat. aq. $NH_4Cl$ (5 L). This mixture was extracted with EtOAc (3 L×2). The combined organic layers were washed with water (3 L), washed with brine (3 L), dried over $Na_2SO_4$, filtered, concentrated, and then triturated in EA:Hexane (1:30, 775 mL) at rt overnight. The mixture was filtered, and the filter cake was washed with EA:Hexane (1:30, 150 mL) and dried under vacuum to give 4-(4-methoxy-3-methylphenyl)bicyclo[2.2.2]octane-1-carbonitrile (240 g, 73%) as a yellow solid. $^1$H NMR (400 MHz, $CDCl_3$): δ 7.13-6.98 (m, 2H), 6.83-6.73 (m, 1H), 3.82 (s, 3H), 2.22 (s, 3H), 2.12-1.98 (m, 6H), 1.94-1.80 (m, 6H).

Step 10: 4-(4-Methoxy-3-methylphenyl)bicyclo[2.2.2]octane-1-carbaldehyde 3 batches were run in parallel: DIBAL-H (1 M PhMe, 830 mL, 830 mmol) was added to a solution of 4-(4-methoxy-3-methyl-phenyl)bicyclo[2.2.2]octane-1-carbonitrile (106 g, 415.11 mmol) in DCM (1 L) at −65° C. under $N_2$. The mixture was stirred at −65° C. for 1 h, and then the 3 batches were poured into sat. aq. NaK tartrate (3 L) and diluted by DCM (1.5 L). This mixture was stirred at rt for 3 h. The organic layer was separated, and the aqueous phase was extracted with DCM (2 L×2). The organic layers were combined, washed with brine (3 L), dried over Na₂SO₄, filtered, and concentrated to give 4-(4-methoxy-3-methylphenyl)bicyclo[2.2.2]octane-1-carbaldehyde (336 g) as a yellow solid. ¹H NMR (400 MHz, DMSO-d₆): δ 9.50-9.43 (m, 1H), 7.11-7.00 (m, 2H), 6.83-6.79 (m, 1H), 3.77-3.68 (m, 3H), 2.18-2.02 (m, 3H), 1.82-1.72 (m, 6H), 1.71-1.60 (m, 6H).

Step 11: Potassium-hydroxy(4-(4-methoxy-3-methylphenyl)bicyclo[2.2.2]octan-1-yl)methanesulfonate 6 batches were run in parallel: Aqueous potassium metabisulfite (2 M, 54 mL, 108 mmol) was added over 10 min to a solution of 4-(4-methoxy-3-methyl-phenyl)bicyclo[2.2.2]octane-1-carbaldehyde (56 g) in THF (300 mL) at 45° C. The mixture was stirred for 3.5 h at 45° C., allowed to cool to rt, and then stirred at rt overnight. The 6 batches were filtered, and the filter cake was washed with PE (400 mL) and dried under vacuum to give potassium-hydroxy(4-(4-methoxy-3-methylphenyl)bicyclo[2.2.2]octan-1-yl)methanesulfonate (381 g, 81% over 2 steps) as a white solid. ¹H NMR (400 MHz, DMSO-d₆) 7.12-6.97 (m, 2H), 6.88-6.71 (m, 1H), 4.51 (d, 1H), 3.73 (s, 3H), 3.56 (d, 1H), 2.11 (s, 3H), 1.88-1.56 (m, 12H).

Step 12: 4-(4-Methoxy-3-methylphenyl)bicyclo[2.2.2]octane-1-carbaldehyde 6 batches were run in parallel: Saturated aq. Na₂CO₃ (300 mL) was added to a mixture of potassium-hydroxy(4-(4-methoxy-3-methylphenyl)bicyclo[2.2.2]octan-1-yl)methanesulfonate (63.5 g, 167.76 mmol) and DCM (300 mL) at rt under N₂. The mixture was stirred for 1 h, and then the 6 batches were poured into a mixture of DCM (1500 mL) and H₂O (1500 mL). The organic layer was separated, and the aqueous phase was extracted with DCM (1500 mL×3). The combined organic layers were washed with brine (2 L), dried over Na₂SO₄, filtered, and concentrated to give 4-(4-methoxy-3-methylphenyl)bicyclo[2.2.2]octane-1-carbaldehyde (240.3 g, 92%) as a white solid, ¹H NMR (400 MHz, DMSO-d₆): δ 9.52-9.41 (m, 1H), 7.14-7.02 (m, 2H), 6.84-7.80 (m, 1H), 3.73 (s, 3H), 2.12 (s, 3H), 1.83-1.72 (m, 6H), 1.71-1.56 (m, 6H); LCMS: 259.1 [M+H]⁺

Intermediate 4

(2-Aminopyridin-4-yl)boronic acid

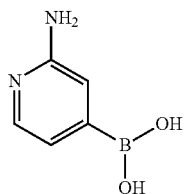

Potassium acetate (47.93 g, 488.4 mmol), Pd(OAc)₂ (1.04 g, 4.62 mmol), and 2-(dicyclohexylphosphino)biphenyl (3.34 g, 9.54 mmol) were added to a solution of 4-bromopyridin-2-amine (50 g, 289 mmol), bis(pinacolato)diboron (110.1 g, 433.5 mmol), and dioxane (1000 mL) at rt. The mixture was degassed with 3 vacuum/N₂ cycles, heated at 100° C. overnight, cooled to rt, and then poured into water (1000 mL) to give an aqueous suspension. This suspension was washed with EtOAc (500 mL×3) and filtered. The filter cake was washed with H₂O (100 mL) and dried under vacuum to give (2-aminopyridin-4-yl)boronic acid (25 g, 62%) as a white solid. ¹H NMR (400 MHz, CD₃OD): δ 7.57 (d, 1H), 7.09 (s, 1H), 7.01 (d, 1H); LCMS: 139.0 [M+H]⁺.

Intermediate 5

4-(1-(1,1,1-Trifluoro-2-methylpropan-2-yl)-1H-pyrazol-4-yl)pyridin-2-amine

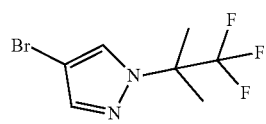

A mixture of (1,1,1-trifluoro-2-methylpropan-2-yl)hydrazine hydrochloride (27 g, 151.19 mmol), 2-bromomalonaldehyde (27.4 g, 181.43 mmol), and HOAc (400 mL) was stirred at rt overnight. The reaction mixture was adjusted to pH=7 with 1 M NaOH (~400 mL) and then extracted with EtOAc (300 mL×3). The combined organic layers were washed with brine (200 mL), dried over Na₂SO₄, filtered, concentrated, and then purified by silica gel chromatography (petroleum ether/ethyl acetate=50/1→20/1) to give 4-bromo-1-(1,1,1-trifluoro-2-methylpropan-2-yl)-1H-pyrazole (18 g, 46%) as a yellow oil. ¹H NMR (400 MHz, CDCl₃): δ 7.64 (s, 1H), 7.52 (s, 1H), 1.81 (s, 6H); LCMS: 257.0 [M+H]⁺.

Intermediate 6

4-(2-(tert-Butyl)thiazol-5-yl)pyridin-2-amine

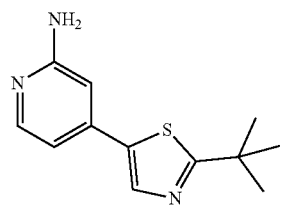 [SMILES: CC(C)(C)c1ncc(-c2ccnc(N)c2)s1]

Step 1: 2-(tert-Butyl)thiazole

2-Bromo-1,1-dimethoxyethane (45.06 g, 266.6 mmol) was added to a solution of 2,2-dimethylpropanethioamide (25.0 g, 213 mmol). pTsOH (4.59 g, 26.6 mmol), and AcOH (50 mL) at rt. The mixture was degassed with 3 vacuum/N₂ cycles, stirred at 120° C. overnight, cooled to rt, poured into water (100 mL), and then extracted with ethyl acetate (50 mL×3). The organic layers were combined, washed with brine (100 mL), dried over Na₂SO₄, filtered, and concentrated to give 2-(tert-butyl)thiazole (30 g) as a yellow oil. ¹H NMR (400 MHz, CDCl₃): δ 7.71 (d, 1H), 7.19 (d, 1H), 1.48 (s, 9H); LCMS: 142.0 [M+H]⁺.

Step 2: 5-Bromo-2-(tert-butyl)thiazole

A-Bromosuccinimide (75.61 g, 424.8 mmol) was added to a solution of 2-(tert-butyl)thiazole (30 g, 212.4 mmol) and CHCl₃ (300 mL) at 0° C. The mixture was degassed with 3 vacuum/N₂ cycles, stirred at rt overnight, diluted with EtOAc (100 mL), and then washed with sat'd NaHCO₃ (30 mL×3). The organic layer was dried over (Na₂SO₄), filtered, concentrated, and then purified by column chromatography (petroleum ether/ethyl acetate: 10/3→2/1) to give 5-bromo-2-(tert-butyl)thiazole (30 g, 64%) as a yellow oil. ¹H NMR (400 MHz, CDCl₃): δ 7.57 (s, 1H), 1.43 (s, 9H); LCMS: 220.2 [M+H]⁺.

Step 3: 4-(2-(tert-Butyl)thiazol-5-yl)pyridin-2-amine

Pd(dppf)Cl₂ (5.32 g, 7.27 mmol) was added to a mixture of 5-bromo-2-(tert-butyl)thiazole (16 g, 72.68 mmol), Cs₂CO₃ (71.05 g, 218.05 mmol), Intermediate 4 (15.04 g, 109.03 mmol), dioxane (40 mL), and H₂O (10 mL) at rt under N₂. The reaction mixture was degassed with 3 vacuum/N₂ cycles, stirred at 80° C. overnight, cooled to rt, poured into water (100 mL), and then extracted with ethyl acetate (3×50 mL). The combined organic layers were washed with brine (30 mL), dried over Na₂SO₄, filtered, concentrated, and then purified by silica gel chromatography (petroleum ether/ethyl acetate=10/3 to 1/1) to give 4-(2-(tert-butyl)thiazol-5-yl)pyridin-2-amine (8.1 g, 48%) as a white solid. ¹H NMR (400 MHz, DMSO-d₆): δ 8.11 (s, 1H), 7.91 (d, 1H), 6.78 (d, 1H), 6.60 (s, 1H), 6.03 (s, 2H), 1.40 (s, 9H); LCMS: 234.1 [M+H]⁺.

Intermediate 7

4-(2-(tert-Butyl)oxazol-4-yl)pyridin-2-amine

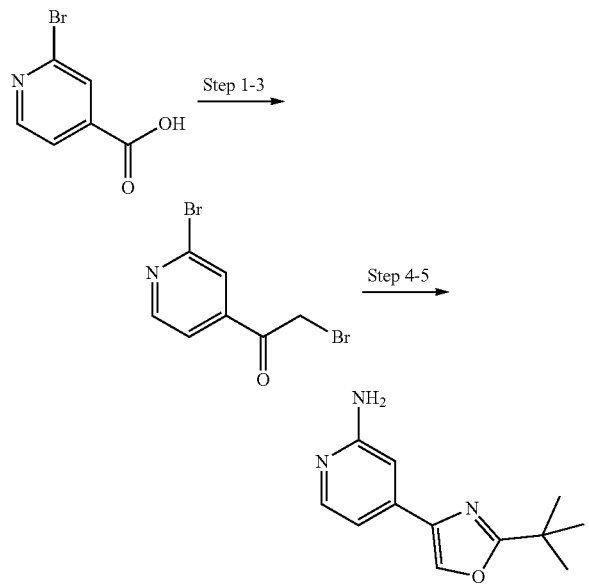

Step 1:
2-Bromo-N-methoxy-N-methylisonicotinamide

A mixture of 2-bromopyridine-4-carboxylic acid (50 g, 247.52 mmol) and CDI (42.14 g, 259.9 mmol) in CH₂Cl₂ (500 mL) was stirred at 25° C. for 0.5 h. N-methoxymethanamine hydrochloride (48.29 g, 495.4 mmol) was added, and the mixture was stirred at rt overnight. The mixture was poured into ice H₂O (1000 mL) and extracted with EtOAc (500 mL×2). The organic layer was washed with sat'd NaHCO₃ (200 mL) and brine (300 mL), and then concentrated to give 2-bromo-N-methoxy-N-methyl-pyridine-4-carboxamide (60 g, crude) as a brown oil.

Step 2: 1-(2-Bromopyridin-4-yl)ethanone

Methylmagnesium bromide solution (3 M in ether, 204 mL) was added dropwise at 40° C. to a solution of 2-bromo-N-methoxy-N-methyl-pyridine-4-carboxamide (60 g, crude) in THF (500 mL). The mixture was stirred at rt for 4 h, poured into aq. NH₄Cl (300 mL), and then extracted with EA (200 mL×3). The combined organic layers were washed with brine (100 mL), dried over Na₂SO₄, concentrated, and then triturated (PE, 200 mL) to give 1-(2-bromo-4-pyridyl)ethanone (40 g, 81% over two steps) as a white solid. ¹H NMR (400 MHz, CDCl₃): δ 8.56 (d, 1H), 7.91 (s, 1H), 7.63 (d, 1H), 2.62 (s, 3H).

Step 3: 2-Bromo-1-(2-bromopyridin-4-yl)ethanone

Bromine (12.4 mL, 240 mmol) was added dropwise to a solution of 1-(2-bromopyridin-4-yl)ethanone (30 g, 149.98 mmol) and HBr (400 mL, 30% in AcOH) at rt. The mixture was stirred at rt overnight, poured into MTBE (1000 mL), and then filtered. The filter cake was poured into water (300 mL) and EtOAc (300 mL). The mixture was adjusted to pH=8 with sat'd NaHCO₃ and extracted with EtOAc (500 mL×2). The combined organic layers were dried (Na₂SO₄), filtered, concentrated, and then purified by trituration (MTBE, 150 mL) to give 2-bromo-1-(2-bromopyridin-4-yl)ethanone (36 g, 86%) as a yellow solid. ¹H NMR (400 MHz, CDCl₃): δ 8.60 (d, 1H), 7.95 (s, 1H), 7.72 (d, 1H), 4.38 (s, 2H); LCMS: 278.0 [M+H]⁺.

Step 4: 4-(2-Bromopyridin-4-yl)-2-(tert-butyl)oxazole

Silver trifluoromethanesulfonate (27.63 g, 107.6 mmol) was added to a mixture of 2-bromo-1-(2-bromopyridin-4-yl)ethanone (15 g, 53.8 mmol), pivalamide (7.07 g, 69.9 mmol), and EtOAc (400 mL) at rt. The reaction was heated at 80° C. for 22 h, cooled to rt, and then poured into H₂O (100 mL). The organic layer was separated, and the aqueous layer was extracted with EtOAc (100 mL×2). The combined organic layers were dried over Na₂SO₄, filtered, concentrated, and then purified by silica gel chromatography (petroleum ether/ethyl acetate=50/1→20/1) to give 4-(2-bromopyridin-4-yl)-2-(tert-butyl)oxazole (12.5 g, 85%) as a brown oil. ¹H NMR (400 MHz, CDCl₃): δ 8.35 (d, 1H), 7.99 (s, 1H), 7.85 (s, 1H), 7.56 (d, 1H), 1.44 (s, 9H); LCMS: 281.1 [M+H]⁺.

Step 5: 4-(2-(tert-Butyl)oxazol-4-yl)pyridin-2-amine

Lithium bis(trimethylsilyl)amide (1 M in THF, 56.8 mL, 56.8 mmol) was added dropwise to a solution of 4-(2-bromopyridin-4-yl)-2-(tert-butyl)oxazole (14.5 g, 51.6 mmol), XPhos (2.46 g, 5.2 mmol), Pd₂(dba)₃ (2.36 g, 2.58 mmol), and dioxane (400 mL) at rt under N₂. The mixture was degassed with 3 vacuum/N₂ cycles, heated at 100° C. overnight, cooled to rt, poured into H₂O (500 mL), and then extracted with EtOAc (200 mL×3). The organic layers were dried over Na₂SO₄, filtered, and then concentrated. The crude material was purified by silica gel chromatography (petroleum ether/ethyl acetate=10/1→0/1) to give impure material, which was triturated by PE/EA=5:1 (30 mL), filtered, and then dried to give 4-(2-(tert-butyl)oxazol-4-yl)pyridin-2-amine (7.15 g, 63%) as a yellow solid. ¹H NMR (400 MHz, DMSO-d₆): δ 8.53 (s, 1H), 7.89 (d, 1H), 6.82 (s, 1H), 6.78 (d, 1H), 5.99 (s, 2H), 1.35 (s, 9H); LCMS: 218.1 [M+H]⁺.

Intermediate 8

4-(1-(tert-Butyl)-1H-pyrazol-4-yl)pyridin-2-amine

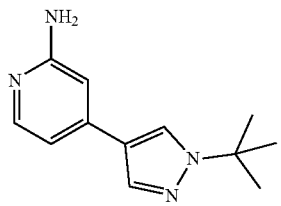

2-Methyltetrahydrofuran (10 mL), Pd(dppf)Cl₂, and then aq. K₂CO₃ (3 M, 10 mL, 30 mmol) were added to 4-bromopyridin-2-amine (1.87 g, 10.8 mmol) and 1-(tert-butyl)-4-(4,4,5,5-tetramethyl-1,3,2-dioxaborolan-2-yl)-1H-pyrazole (2.50 g, 10.0 mmol) in a 40 mL vial. The reaction was degassed with 3 vacuum/N₂ cycles, heated at 50° C. for 21 h, and then allowed to cool to rt. The layers were separated, and the organic layer was washed with sat'd aq. NaK tartrate (25 mL) and then washed with brine (25 mL). The aqueous layers were back extracted with 2-methyltetrahydrofuran (25 mL). The combined organics were dried (MgSO₄), filtered, concentrated, and then dried under vacuum for 1 h. A suspension of the crude material and MTBE (25 mL) was refluxed for 2 h, allowed to cool to rt overnight, and then filtered. The filter cake was washed with MTBE (2×3 mL) and then dried under vacuum to give 4-(1-(tert-butyl)-1H-pyrazol-4-yl)pyridin-2-amine (1.15 g, 53%). ¹H NMR (400 MHz, DMSO-d₆): δ 8.27 (s, 1H), 7.86-7.82 (m, 2H), 6.74 (d, 1H), 6.61 (s, 1H), 5.77 (s, 2H), 1.54 (s, 9H); LCMS: 217.1 [M+H]⁺.

Intermediate 9

4-(1-(tert-Pentyl)-1H-pyrazol-4-yl)pyridin-2-amine

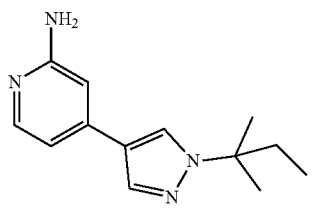 [SMILES: CCC(C)(C)n1cc(-c2ccnc(N)c2)cn1]

Step 1: 4-Bromo-1-(tert-pentyl)-1H-pyrazole

Concentrated sulfuric acid (3.9 mL, 74.8 mmol) was added to a solution of 4-bromo-1H-pyrazole (10 g, 68.04 mmol) and 2-methylbutan-2-ol (74 mL) at rt. The mixture was heated at 100° C. for 48 h, concentrated, diluted with H₂O (20 mL), and then extracted with ethyl acetate (20 mL). The organic layer was washed with brine (20 mL), dried over Na₂SO₄, filtered, concentrated, and then purified by silica gel chromatography (petroleum ether/ethyl acetate=1/0→200/1) to give 4-bromo-1-(tert-pentyl)-1H-pyrazole (5.3 g, 35%) as a colorless oil. ¹H NMR (400 MHz, CDCl₃): δ 7.49 (s, 1H), 7.48 (s, 1H), 1.90-1.84 (m, 2H), 1.54 (s, 6H), 0.70 (t, 3H).

Step 2: 4-(1-(tert-Pentyl)-1H-pyrazol-4-yl) pyridin-2-amine

Pd(dppf)C₁₋₂ (1.45 g, 1.98 mmol) was added to a mixture of 4-bromo-1-(tert-pentyl)-1H-pyrazole (8.6 g, 39.61 mmol), Intermediate 4 (6.56 g, 47.53 mmol), K₂CO₃ (10.95 g, 79.22 mmol), dioxane (90 mL), and H₂O (45 mL) at rt under N₂. The mixture was degassed with 3 vacuum/N₂ cycles, heated at 80° C. for 4 h, cooled to rt, and then poured into H₂O (100 mL). The precipitate was filtered off. The filtrate was diluted with ethyl acetate (200 mL) and H₂O (100 mL). The layers were separated, and the aqueous layer was extracted with ethyl acetate (3×200 mL). The combined organic layers were washed with brine (100 mL), dried over Na₂SO₄, filtered, concentrated, and then purified by silica gel chromatography (CH₂Cl₂/CH₃OH=100/1→30/1) to give 2.7 g of an impure red solid. HCl in CH₃OH (4M, 30 mL) was added. The solution was stirred at rt for 2 h, concentrated, diluted with ethyl acetate (15 mL), and then stirred overnight. The solids were filtered, washed with ethyl acetate (10 mL), and dried to give 4-(1-(tert-pentyl)-1H-pyrazol-4-yl) pyridin-2-amine hydrochloride (3.1 g). This material was dissolved in H₂O (5 mL). Aqueous potassium carbonate (2 M, ~8 mL) was added slowly until pH=9-10. The mixture was extracted with ethyl acetate (20 mL×6). The combined organics were washed with brine (10 mL), dried over Na₂SO₄, filtered, and concentrated to give 4-(1-(tert-pentyl)-1H-pyrazol-4-yl) pyridin-2-amine (2.35 g, 90%) as an off white solid. ¹H NMR (400 MHz, DMSO-d₆): δ 8.24 (s, 1H), 7.84-7.83 (m, 2H), 6.75-6.73 (m, 1H), 6.60 (s, 1H), 5.74 (s, 2H), 1.87-1.81 (m, 2H), 1.52 (s, 6H), 0.62 (t, 3H); LCMS: 231.2 [M+H]⁺.

The Intermediates below were synthesized using the appropriate alcohol or the appropriate Intermediate following the procedures described for Intermediate 9.

| Int | Structure | Name | [M + H]⁺ |
|---|---|---|---|
| 9.01 | ![structure] | 4-(1-(tert-Butyl)-1H-pyrazol-3-yl)pyridin-2-amine | 217.1 |

| Int | Structure | Name | [M + H]+ |
|---|---|---|---|
| 9.02[1,2] | 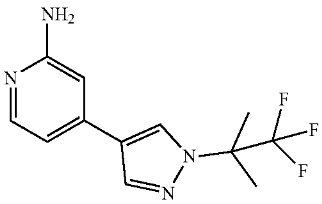 [SMILES: CC(C)(n1cc(-c2ccnc(N)c2)cn1)C(F)(F)F] | 4-(1-(1,1,1-Trifluoro-2-methylpropan-2-yl)-1H-pyrazol-4-yl)pyridin-2-amine | 271.1 |
| 9.03[a] | 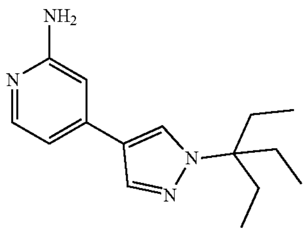 [SMILES: CCC(CC)(CC)n1cc(-c2ccnc(N)c2)cn1] | 4-(1-(3-Ethylpentan-3-yl)-1H-pyrazol-4-yl)pyridin-2-amine | 259.1 |
| 9.04[3] | 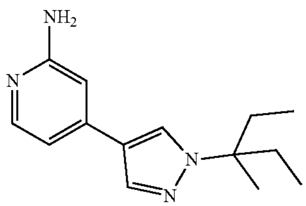 [SMILES: CCC(C)(CC)n1cc(-c2ccnc(N)c2)cn1] | 4-(1-(3-Methylpentan-3-yl)-1H-pyrazol-4-yl)pyridin-2-amine | 245.1 |
| 8[2] | 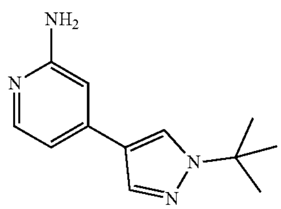 [SMILES: CC(C)(C)n1cc(-c2ccnc(N)c2)cn1] | 4-(1-(tert-Butyl)-1H-pyrazol-4-yl)pyridin-2-amine | 217.1 |

Alternate conditions: Step 1; 30-90° C., 6-18 h. Step 2: 90° C., overnight; [1]Step 2 only; [2]Isolated via trituration with MTBE following sgc purification; [3]Isolated via prep-TLC (100% EtOAc) following sgc purification.

Intermediate 10 trans-4-((tert-Butyldimethylsilyl)oxy)cyclohexan-ecarboxylic Acid

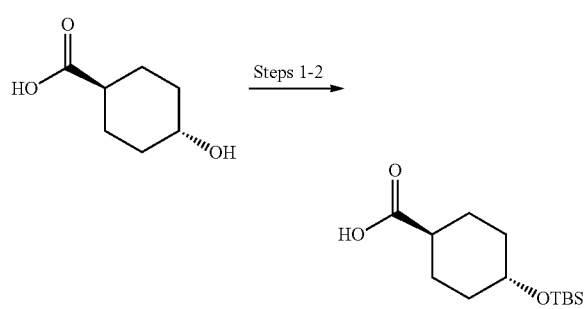

Step 1: trans-tert-Butyldimethylsilyl 4-((tert-butyldimethylsilyl)oxy)cyclohexanecarboxylate tert-Butyldimethylsilyl chloride (31.47 g, 208.8 mmol) was added to a mixture of trans-4-hydroxy-cyclohexanecarboxylic acid (10.03 g, 69.57 mmol), imidazole (18.96 g, 278.5 mmol), and DMF (140 mL) at rt under N$_2$ (reaction exothermed to 32° C.). The reaction was stirred at rt for 2 h and then diluted with diethyl ether (300 mL). The organic layer was washed (2×300 mL 1 N HCl and then 300 mL brine), dried (Na$_2$SO$_4$), filtered, and concentrated to give trans-tert-butyldimethylsilyl 4-((tert-butyldimethylsilyl)oxy)cyclohexanecarboxylate (31.5 g) as a clear oil. $^1$H NMR (400 MHz, DMSO-d$_6$): δ 3.61-3.53 (m, 1H), 2.26-2.18 (m, 1H), 2.04-1.96 (m, 2H), 1.92-1.85 (m, 2H), 1.51-1.39 (m, 2H), 1.39-1.27 (m, 2H), 0.94 (s, 9H), 0.89 (s, 9H), 0.26 (s, 6H), 0.06 (s, 6H).

Step 2: trans-4-((tert-Butyldimethylsilyl)oxy)cyclohexanecarboxylic Acid

Potassium carbonate (58.01 g, 419.7 mmol) in H$_2$O (300 mL) was added to a mixture of trans-tert-butyldimethylsilyl 4-((tert-butyldimethylsilyl)oxy)cyclohexanecarboxylate (31.5 g crude, 69.6 mmol), ethanol (1000 mL) and THF (300 mL) at rt under N$_2$. The reaction was stirred at rt for 3 h, concentrated until 300 mL remained, diluted with brine (600 mL), and then acidified to pH 2-3 with 20% NaHSO$_4$ (550 mL). The aqueous layer was extracted with diethyl ether (800 mL). The organic layer was washed (800 mL brine), dried (Na$_2$SO$_4$), filtered, concentrated, and dried under high vacuum (to remove silanol byproducts) to give trans-4-

((tert-butyldimethylsilyl)oxy)cyclohexanecarboxylic acid (17.3 g, 96% over 2 steps) as a white solid. ¹H NMR (400 MHz, DMSO-d₆): δ 12.30 (br s, 1H), 3.59-3.51 (m, 1H), 2.15-2.05 (m, 1H), 1.88-1.74 (m, 4H), 1.41-1.29 (m, 2H), 1.28-1.16 (m, 2H), 0.84 (s, 9H), 0.02 (s, 6H).

Intermediate 11 trans-4-((tert-Butyldimethylsilyl)oxy)cyclohexanecarbonyl chloride

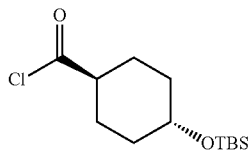 [SMILES: CC(C)(C)[Si](C)(C)O[C@H]1CC[C@H](C(=O)Cl)CC1]

trans-4-((tert-Butyldimethylsilyl)oxy)cyclohexanecarbonyl chloride (Chloromethylene)dimethyl iminium chloride (34.02 g, 265.78 mmol) was weighed into a 1000 mL round bottom flask (3 neck) and degassed with vacuum/N₂ cycles (3×). Toluene (240 mL) was added to the flask, and the mixture was cooled (1.3° C.) in an ice bath. Anhydrous potassium carbonate* (68.71 g, 497.14 mmol) and Intermediate 10 (34.29 g, 132.69 mmol) were sequentially added to the reaction. The ice bath was removed, and the mixture was stirred for 35 min. Celite (7 g) was added to the reaction, and then the reaction was filtered through Celite (70 g, Chemglass 465 mL fritted funnel) with toluene washes (3×100 mL). This solution (451 g, 8.5% acid chloride, 100% yield, 72 mg/mL) was used immediately in the acylation reaction. ¹H NMR (400 MHz, CDCl₃): δ 3.77-3.68 (m, 1H), 2.83-2.74 (m, 1H), 2.31-2.22 (m, 2H), 2.09-1.99 (m, 2H), 1.76-1.63 (m, 2H), 1.54-1.42 (m, 2H), 1.02 (s, 9H), 0.20 (s, 6H). *Potassium carbonate was dried under vacuum by heating with a heat gun for ~5 min and then allowing to cool overnight.

Intermediate 12

2,2-Dimethylazetidin-3-ol hydrochloride

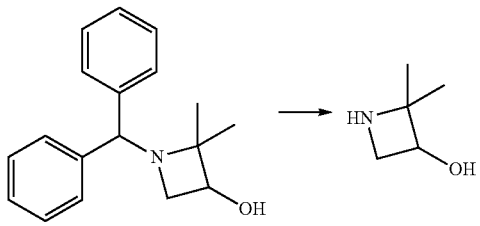

Step 1: 2-Cyclopropyl-4-(3-nitrophenyl)oxazole

A solution of 1-benzhydryl-2,2-dimethylazetidin-3-ol (6.03 g, 22.6 mmol) in CH₃OH (90 mL) was degassed with 2 vacuum/N₂ cycles. Aqueous hydrochloric acid (1.0 N, 22 mL, 22 mmol) and then Pd/C (10 wt %, 2.40 g, 2.25 mmol) were added to the reaction. The reaction was stirred under a balloon of H₂ at rt for 15 h, filtered through Celite, and the filter cake was rinsed with CH₃OH (5×20 mL). The filtrate was concentrated, lyophilized, and then dried under vacuum to give 2,2-dimethylazetidin-3-ol hydrochloride (1.99 g, 64%) as a pale yellow solid. ¹H NMR (400 MHz, DMSO-d₆): δ 8.94 (s, 2H), 6.12 (s, 1H), 4.17 (t, 1H), 3.88 (dd, 1H), 3.54 (dd, 1H), 1.41 (d, 6H).

Intermediate 13

3-((Methylsulfonyl)methyl)azetidine hydrochloride

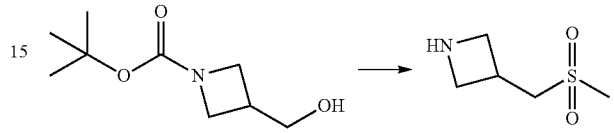

Step 1: tert-Butyl 3-(((methylsulfonyl)oxy)methyl)azetidine-1-carboxylate

Methanesulfonyl chloride (9.8 g, 85.55 mmol) was added to a solution of tert-butyl 3-(hydroxymethyl)azetidine-1-carboxylate (10 g, 53.41 mmol) and Et₃N (10.81 g, 106.8 mmol) in CH₂Cl₂ (100 mL) at 0° C. under N₂. The reaction was warmed to rt, stirred for 2 h, poured into water (200 mL), and then extracted with CH₂Cl₂ (100 mL×3). The combined organic layers were washed with sat'd NaHCO₃ (100 mL), washed with brine (100 mL), dried over Na₂SO₄, filtered, concentrated and then purified by silica gel chromatography (PE/EA=4/1 to 3/1) to give tert-butyl 3-(((methylsulfonyl)oxy)methyl)azetidine-1-carboxylate (13 g, 83% yield) as a yellow oil. ¹H NMR (400 MHz, CDCl₃): δ 4.36 (d, 2H), 4.06 (t, 2H), 3.78-3.67 (m, 2H), 3.06 (s, 3H), 2.99-2.87 (m, 1H), 1.44 (s, 9H).

Step 2: tert-Butyl 3-((methylthio)methyl)azetidine-1-carboxylate

Sodium thiomethoxide (36.5 g, 104.2 mmol, 20% purity) was added to a solution of tert-butyl 3-(((methylsulfonyl)oxy)methyl)azetidine-1-carboxylate (13 g, 44.1 mmol) in DMF (150 mL) at rt under N₂. The reaction was stirred overnight, poured into water (300 mL), and then extracted with EtOAc (200 mL×3). The combined organic layers were washed with brine (200 mL), dried over Na₂SO₄, filtered, concentrated, and then purified by silica gel chromatography (PE/EA=20/1 to 10/1) to give tert-butyl 3-((methylthio)methyl)azetidine-1-carboxylate (9.86 g, 93%) as a colorless oil. ¹H NMR (400 MHz, CDCl₃): δ 4.08-3.97 (m, 2H), 3.62 (d, 2H), 2.82-2.67 (m, 3H), 2.11 (s, 3H), 1.44 (s, 9H); LCMS: 218.1 [M+H]⁺.

Step 3: tert-Butyl 3-((methylsulfonyl)methyl)azetidine-1-carboxylate

3-Chloroperbenzoic acid (14.90 g, 73.38 mmol, 85% purity) was added in portions to a solution of tert-butyl 3-((methylthio)methyl)azetidine-1-carboxylate (8.86 g, 36.69 mmol) in CH₂Cl₂ (90 mL) at 0° C. The reaction mixture was warmed to rt, stirred at rt for 2 h, and then filtered. The filtrate was diluted with CH₂Cl₂ (100 mL), washed with sat'd K₂CO₃ (100 mL×2), washed with brine (100 mL), dried over Na₂SO₄, filtered, concentrated, and then purified by silica gel chromatography (PE/EA=60/40) to give tert-butyl 3-((methylsulfonyl)methyl)azetidine-1-carboxylate (6.5 g, 71%) as a white solid, ¹H NMR (400 MHz, DMSO-d₆): δ 4.08-3.90 (m, 2H), 3.80-3.62 (m, 2H), 3.48 (d, 2H), 3.08-2.88 (m, 4H), 1.37 (s, 9H); LCMS: 272.0 [M+Na]⁺

Step 4: 3-((Methylsulfonyl)methyl)azetidine hydrochloride

A mixture of tert-butyl 3-((methylsulfonyl)methyl)azetidine-1-carboxylate (1 g, 4.01 mmol) and HCl (4 M in EtOAc, 20 mL) was stirred at rt for 1 h, and then concentrated to give 3-((methylsulfonyl)methyl)azetidine hydrochloride (650 mg) as a white solid. $^1$H NMR (400 MHz, DMSO-$d_6$): δ 9.25 (s, 1H), 9.07 (s, 1H), 4.10-3.98 (m, 2H), 3.91-3.80 (m, 2H), 3.55 (d, 2H), 3.33-3.20 (m, 1H), 2.99 (s, 3H); LCMS: 150.1[M+H]$^+$.

Intermediate 14

6-(1-(tert-Butyl)-1H-pyrazol-4-yl)pyrimidin-4-amine

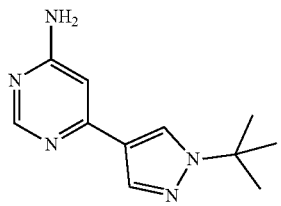

4-Amino-6-bromo pyrimidine (500 mg, 2.87 mmol), 1-(tert-butyl)-4-(4,4,5,5-tetramethyl-1,3,2-dioxaborolan-2-yl)-1H-pyrazole (898 mg, 3.59 mmol), and 1-1'-bis(diphenylphosphinoferrocene dichloropalladium (II) (105 mg, 0.144 mmol) were weighed into a 20 mL microwave vial. 1,4-Dioxane (3.92 mL) and aqueous potassium carbonate solution (2.2 M, 3.92 mL, 8.62 mmol) were added to the vial. The reaction mixture was heated in microwave at 150° C. for 15 min. The aqueous layer was pipetted off, and EtOAc (20 mL) followed by Celite and Na$_2$SO$_4$ were added to the organic layer. The organic layer was filtered and concentrated. The residue was purified by silica gel chromatography (0-100% EtOAc in CH$_2$Cl$_2$ then 0-12% CH$_3$OH in CH$_2$Cl$_2$) to give 6-(1-(tert-butyl)-1H-pyrazol-4-yl)pyrimidin-4-amine (484 mg, 77%) as a purple solid, $^1$H NMR (400 MHz, DMSO-$d_6$): δ 8.33 (s, 2H), 7.93 (s, 1H), 6.71 (br, 2H), 6.59 (d, 1H), 1.55 (s, 9H); LCMS: 217.9 [M+H]$^+$.

The Intermediates below were synthesized from the appropriate amino/halo-(hetero)aromatic starting material and 1-(tert-butyl)-4-(4,4,5,5-tetramethyl-1,3,2-dioxaborolan-2-yl)-1H-pyrazole following the procedure described for Intermediate 14.

| Int | Structure | Name | [M + H]$^+$ |
| --- | --- | --- | --- |
| 14.01 | 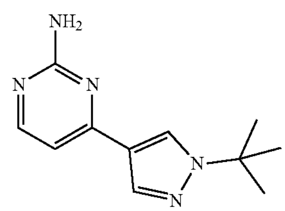 [SMILES: CC(C)(C)n1cc(-c2ccnc(N)n2)cn1] | 4-(1-(tert-Butyl)-1H-pyrazol-4-yl)pyrimidin-2-amine | 217.9 |
| 14.02 | 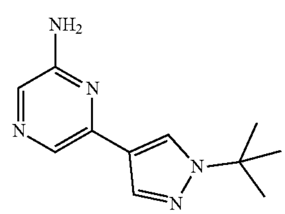 [SMILES: CC(C)(C)n1cc(-c2cncc(N)n2)cn1] | 6-(1-(tert-Butyl)-1H-pyrazol-4-yl)pyrazin-2-amine | 218.0 |
| 14.03 | 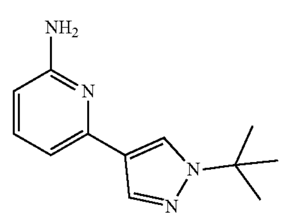 [SMILES: CC(C)(C)n1cc(-c2cccc(N)n2)cn1] | 6-(1-(tert-Butyl)-1H-pyrazol-4-yl)pyridin-2-amine | 217.0 |
| 14.04 | 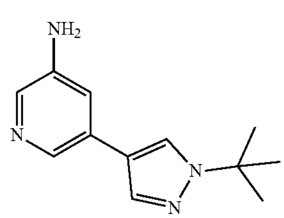 [SMILES: CC(C)(C)n1cc(-c2cncc(N)c2)cn1] | 5-(1-(tert-Butyl)-1H-pyrazol-4-yl)pyridin-3-amine | 217.0 |

| Int | Structure | Name | [M + H]+ |
|---|---|---|---|
| 14.05 | ![structure] | 2-(1-(tert-Butyl)-1H-pyrazol-4-yl)pyridin-4-amine | 217.0 |
| 14.06 | ![structure] | 4-(1-(tert-Butyl)-1H-pyrazol-4-yl)-5-fluoropyridin-2-amine | 235.1 |

Alternate conditions: 160° C., 20 min; DME/2.2 K₂CO₃ (1:1 or 1.5:1); Dioxane/2.2M K₂CO₃ (2:1).

Intermediate 15

4-(4-(tert-Butyl)-1H-imidazol-1-yl)pyridin-2-amine

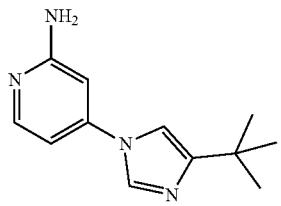 [SMILES: CC(C)(C)c1cn(-c2ccnc(N)c2)cn1]

Step 1: 4-(tert-Butyl)-1H-imidazole

A mixture of 1-bromo-3,3-dimethyl-butan-2-one (15 g, 83.77 mmol) and formamide (84.75 g, 1.88 mol) was stirred at 170° C. for 5 h, allowed to cool to rt, poured into water (200 mL), and then extracted with EtOAc (3×200 mL). The combined organic layers were washed with brine (200 mL), dried over Na₂SO₄, filtered, and then concentrated to give 4-(tert-butyl)-1H-imidazole (8 g) as a yellow oil, which was used directly in the next step. LCMS: 125.2 [M+H]⁺.

Step 2: 4-(4-(tert-Butyl)-1H-imidazol-1-yl)-2-chloropyridine

Potassium carbonate (18.92 g, 136.89 mmol) was added to a solution of 4-tert-butyl-1H-imidazole (8 g, 54.76 mmol), 2-chloro-4-fluoro-pyridine (14.41 g, 109.52 mmol), and NMP (80 mL) at rt. The mixture was stirred at 100° C. overnight, allowed to cool to rt, poured into water (200 mL), and then extracted with EtOAc (3×200 mL). The combined organic layers were washed with brine (300 mL), dried over Na₂SO₄, filtered, concentrated, and then purified by silica gel chromatography (petroleum ether/EtOAc=70/30) to give 4-(4-(tert-butyl)-1H-imidazol-1-yl)-2-chloropyridine (4 g, 31%) as a white solid. ¹H NMR (400 MHz, DMSO-d₆) δ 8.50 (d, 1H), 8.44 (d, 1H), 7.97 (d, 1H), 7.80 (dd, 1H), 7.72 (d, 1H), 1.25 (s, 9H); LCMS: 236.1 [M+H]⁺.

Step 3: 4-(4-(tert-Butyl)-1H-imidazol-1-yl)pyridin-2-amine

Lithium bis(trimethylsilyl)amide (1 M in THF, 31.2 mL) was added to a solution of 4-(4-(tert-butyl)-1H-imidazol-1-yl)-2-chloropyridine (3.5 g, 14.85 mmol), Pd₂(dba)₃ (543.9 mg, 0.59 mmol), XPhos (566.2 mg, 1.19 mmol), and dioxane (100 mL) at rt under N₂. The mixture was degassed with 3 vacuum/N₂ cycles, stirred at 100° C. overnight, allowed to cool to rt, poured into water (100 mL), and then extracted with EtOAc (3×200 mL). The combined organic layers were washed with brine (50 mL), dried over Na₂SO₄, filtered, concentrated, and then purified by silica gel chromatography (petroleum ether/EtOAc=30/70) to give impure material (2.1 g), which was further purified by reverse-phase HPLC (water (10 mM NH₄HCO₃)/CH₃CN) to give 4-(4-(tert-butyl)-1H-imidazol-1-yl)pyridin-2-amine (1.36 g, 71%) as a brown solid. ¹H NMR (400 MHz, DMSO-d₆) δ 8.16 (s, 1H), 7.95 (d, 1H), 7.35 (s, 1H), 6.80 (dd, 1H), 6.60 (s, 1H), 6.10 (s, 2H), 1.24 (s, 9H); LCMS: 217.1 [M+H]⁺.

The Intermediate below was synthesized from 2-chloro-4-fluoropyridine and 3-(tert-butyl)-1H-pyrazole following the procedures described for Intermediate 15, Steps 2-3.

| Int | Structure | Name | [M + H]+ |
|---|---|---|---|
| 15.01 | ![structure] | 4-(3-(tert-Butyl)-1H-pyrazol-1-yl)pyridin-2-amine | 217.1 |

Compound 1 trans-4-((4-(2-(tert-Butyl)thiazol-5-yl)pyridin-2-yl)
(((trans)-4-(4-methoxy-3-methylphenyl)cyclohexyl)
methyl)carbamoyl)cyclohexyl (tetrahydro-2H-pyran-
4-yl)carbamate

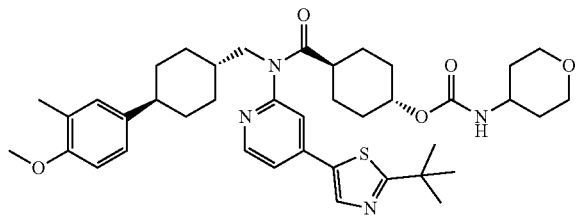 [SMILES: COc1ccc([C@H]2CC[C@H](CN(c3cc(-c4cnc(C(C)(C)C)s4)ccn3)C(=O)[C@H]3CC[C@H](OC(=O)NC4CCOCC4)CC3)CC2)cc1C]

Step 1: 4-(2-(tert-Butyl)thiazol-5-yl)-N-((trans-4-(4-
methoxy-3-methylphenyl)cyclohexyl)methyl)pyri-
din-2-amine Intermediate 1 (1.0 g, 4.30 mmol) and then sodium triacetoxyborohydride (1.33 g, 6.26 mmol) were added to a solution Intermediate 6 (913 mg, 3.91 mmol) in $CH_2Cl_2$ (12 mL) at 0° C. The ice/water bath was removed. The reaction was stirred at rt overnight and then diluted with EtOAc (15 mL). The organic layer was washed with 3.0 M $K_2CO_3$ (20 mL), washed with brine (20 mL), dried ($Na_2SO_4$), filtered, concentrated, and then purified by silica gel chromatography (0-50% EtOAc in $CH_2Cl_2$). Residual AcOH was noted, so the product fractions were concentrated, diluted with EtOAc (20 mL), washed with 3.0 M $K_2CO_3$ (20 mL), washed with brine (20 mL), dried ($Na_2SO_4$), filtered, and then concentrated to give 4-(2-(tert-butyl)thiazol-5-yl)-N-((trans-4-(4-methoxy-3-methylphenyl)cyclohexyl)methyl)pyridin-2-amine (1.34 g, 76%) as a beige solid. $^1$H NMR (400 MHz, DMSO-$d_6$): δ 8.11 (s, 1H), 7.95 (d, 1H), 7.02-6.96 (m, 2H), 6.83-6.69 (m, 1H), 6.75-6.69 (m, 2H), 6.65 (s, 1H), 3.76 (s, 3H), 3.15 (t, 2H), 2.42-2.32 (m, 1H), 2.11 (s, 3H), 1.93-1.75 (m, 4H), 1.65-1.52 (m, 1H), 1.46-1.32 (m, 11H), 1.15-1.02 (m, 2H); LCMS: 450.3 [M+H]$^+$.

Step 2: trans-N-(4-(2-(tert-Butyl)thiazol-5-yl)pyri-
din-2-yl)-4-((tert-butyldimethylsilyl)oxy)-N-((trans-
4-(4-methoxy-3-methylphenyl)cyclohexyl)methyl)
cyclohexanecarboxamide Intermediate 11 (10.4 mL, 70.6 mg/mL, 2.66 mmol) was added to a mixture of 4-(2-(tert-butyl)thiazol-5-yl)-N-((trans-4-(4-methoxy-3-methylphenyl)cyclohexyl)methyl) pyridin-2-amine (600 mg, 1.33 mmol), DMAP (165 mg, 1.33 mmol), triethylamine (744 μL, 5.33 mmol), and toluene (2.5 mL) at rt. The reaction was heated at 80° C. overnight. Additional Intermediate 11 (10.4 mL, 70.6 mg/mL, 2.66 mmol) was added. The reaction was heated at 80° C. for 2 h, allowed cooled to rt, diluted with EtOAc (30 mL), washed with 1.0 M $KH_2PO_4$ (15 mL), washed with brine (30 mL), dried ($Na_2SO_4$), filtered, concentrated, and then purified by silica gel chromatography (0-20% EtOAc in hexanes) to give trans-N-(4-(2-(tert-butyl)thiazol-5-yl)pyridin-2-yl)-4-((tert-butyldimethylsilyl)oxy)-N-((trans-4-(4-methoxy-3-methylphenyl)cyclohexyl)methyl)cyclohexanecarboxamide (566 mg, 61%) as a white foam. $^1$H NMR (400 MHz, DMSO-$d_6$): δ 8.53 (d, 1H), 8.46 (s, 1H), 7.73 (s, 1H), 7.62 (dd, 1H), 6.97-6.91 (m, 2H), 6.81-6.76 (m, 1H), 3.74-3.68 (m, 5H), 3.58-3.47 (m, 1H), 2.48-2.15 (m, 2H), 2.08 (s, 3H), 1.83-1.68 (m, 8H), 1.52-1.39 (m, 12H), 1.35-1.20 (m, 2H), 1.19-0.92 (m, 4H), 0.81 (s, 9H), 0.00 (s, 6H); LCMS: 690.6 [M+H]$^+$.

Step 3: trans-N-(4-(2-(tert-Butyl)thiazol-5-yl)pyri-
din-2-yl)-4-hydroxy-N-((trans-4-(4-methoxy-3-
methylphenyl)cyclohexyl)methyl)cyclohexanecar-
boxamide Aqueous hydrochloric acid (1 N, 1.27 mL, 1.27 mmol) was added to a solution of trans-N-(4-(2-(tert-butyl)thiazol-5-yl)pyridin-2-yl)-4-((tert-butyldimethylsilyl)oxy)-N-((trans-4-(4-methoxy-3-methylphenyl)cyclohexyl)methyl) cyclohexanecarboxamide (562 mg, 0.82 mmol), THF (3 mL), and $CH_3OH$ (3 mL) at 0° C. The reaction stirred at rt for 1 h, diluted with EtOAc (15 mL), washed with sat'd $NaHCO_3$ (10 mL), washed with brine (10 mL), dried ($Na_2SO_4$), filtered, concentrated, and then purified by silica gel chromatography (0-100% EtOAc in $CH_2Cl_2$) to give trans-N-(4-(2-(tert-butyl)thiazol-5-yl)pyridin-2-yl)-4-hydroxy-N-((trans-4-(4-methoxy-3-methylphenyl)cyclohexyl) methyl)cyclohexanecarboxamide (406 mg, 86%) as a white foam. $^1$H NMR (400 MHz, DMSO-$d_6$): δ 8.53 (d, 1H), 8.46 (s, 1H), 7.73 (s, 1H), 7.61 (dd, 1H), 6.97-6.91 (m, 2H), 6.80-6.75 (m, 1H), 4.45 (d, 1H), 3.74-3.68 (m, 5H), 3.33-3.25 (m, 1H), 2.38-2.25 (m, 1H), 2.22-2.12 (m, 1H), 2.08 (s, 3H), 1.82-1.68 (m, 8H), 1.50-1.38 (m, 12H), 1.32-1.20 (m, 2H), 1.09-0.95 (m, 2H), 0.95-0.80 (m, 2H); LCMS: 576.4 [M+H]$^+$.

Step 4: trans-4-((4-(2-(tert-Butyl)thiazol-5-yl)pyri-
din-2-yl)((trans-4-(4-methoxy-3-methylphenyl)cy-
clohexyl)methyl)carbamoyl)cyclohexyl (tetrahydro-
2H-pyran-4-yl)carbamate A solution of trans-N-(4-(2-(tert-butyl)thiazol-5-yl)pyridin-2-yl)-4-hydroxy-N-((trans-4-(4-methoxy-3-methylphenyl)cyclohexyl)methyl)cyclohexanecarboxamide (220 mg, 0.38 mmol), CDI (97 mg, 0.60 mmol), and $CH_3CN$ (8 mL) was heated at 80° C. overnight and then cooled to rt. Aminotetrahydropyran (34 μL, 0.34 mmol) was added to a portion of the $CH_3CN$ solution (0.45 mL, 0.085 mmol), and the mixture was stirred at rt overnight. Additional 4-amino-tetrahydropyran (34 μL, 0.34 mmol) was added, and the mixture was stirred at rt for 1 day. Additional 4-aminotetrahydropyran (9 μL, 0.09 mmol) was added, and the mixture was stirred at rt for another day. The reaction was diluted with EtOAc (10 mL), washed with sat'd $NaHCO_3$ (10 mL), washed with brine (10 mL), dried ($Na_2SO_4$), filtered, concentrated, and then purified by silica gel chromatography (0-10% $CH_3OH$ in $CH_2Cl_2$) to give trans-4-((4-(2-(tert-butyl)thiazol-5-yl)pyridin-2-yl)((trans-4-(4-methoxy-3-methylphenyl)cyclohexyl)methyl)carbamoyl)cyclohexyl (tetrahydro-2H-pyran-4-yl)carbamate (51 mg, 86%) as a white foam. $^1$H NMR (400 MHz, DMSO-$d_6$): δ 8.53 (d, 1H), 8.46 (s, 1H), 7.74 (s, 1H), 7.61 (dd, 1H), 7.08-7.02 (d, 1H), 6.96-6.91 (m, 2H), 6.80-6.75 (m, 1H), 4.45 (d, 1H), 3.81-3.68 (m, 7H), 3.49-3.38 (m, 1H), 3.33-3.25 (t, 2H), 2.38-2.25 (m, 2H), 2.08 (s, 3H), 1.93-1.60 (m, 10H), 1.57-1.40 (m, 12H), 1.39-1.20 (m, 4H), 1.09-0.95 (m, 4H); LCMS: 703.5 [M+H]$^+$.

The Compounds below were synthesized from the appropriate Intermediates and the appropriate amines following the procedures described for Compound 1.

| Cmpd | Structure | Name | [M + H]+ |
|---|---|---|---|
| 1.01 | 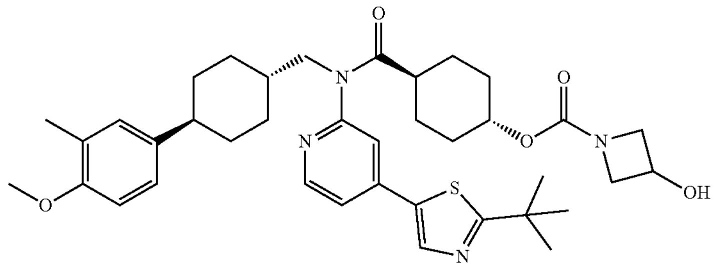 [SMILES: COc1ccc([C@H]2CC[C@H](CN(c3cc(-c4cnc(C(C)(C)C)s4)ccn3)C(=O)[C@H]3CC[C@H](OC(=O)N4CC(O)C4)CC3)CC2)cc1C] | trans-4-((4-(2-(tert-Butyl)thiazol-5-yl)pyridin-2-yl)(((trans)-4-(4-methoxy-3-methylphenyl)cyclohexyl)methyl)carbamoyl)cyclohexyl 3-hydroxyazetidine-1-carboxylate | 675.2 |
| 1.02 | 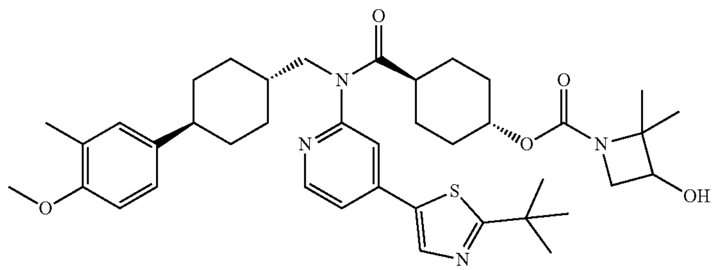 [SMILES: COc1ccc([C@H]2CC[C@H](CN(c3cc(-c4cnc(C(C)(C)C)s4)ccn3)C(=O)[C@H]3CC[C@H](OC(=O)N4CC(O)C4(C)C)CC3)CC2)cc1C] | trans-4-((4-(2-(tert-Butyl)thiazol-5-yl)pyridin-2-yl)(((trans)-4-(4-methoxy-3-methylphenyl)cyclohexyl)methyl)carbamoyl)cyclohexyl 3-hydroxy-2,2-dimethylazetidine-1-carboxylate | 703.5 |
| 1.03 | 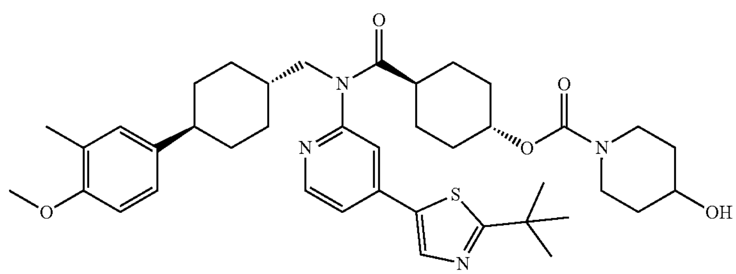 | trans-4-((4-(2-(tert-Butyl)thiazol-5-yl)pyridin-2-yl)(((trans)-4-(4-methoxy-3-methylphenyl)cyclohexyl)methyl)carbamoyl)cyclohexyl 4-hydroxypiperidine-1-carboxylate | 703.5 |
| 1.04 | 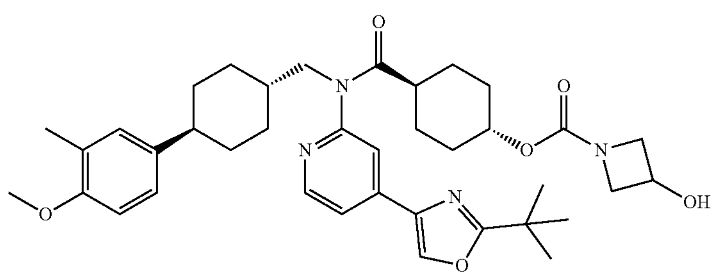 [SMILES: COc1ccc([C@H]2CC[C@H](CN(c3cc(-c4coc(C(C)(C)C)n4)ccn3)C(=O)[C@H]3CC[C@H](OC(=O)N4CC(O)C4)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl 3-hydroxyazetidine-1-carboxylate | 659.5 |
| 1.05 | 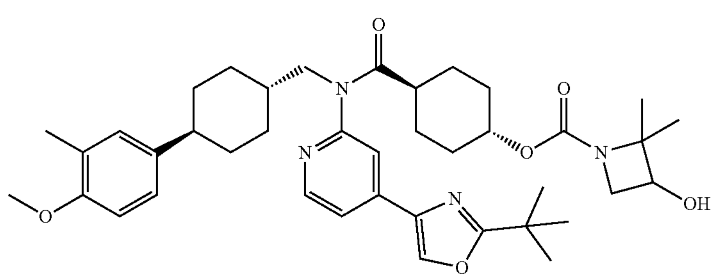 [SMILES: COc1ccc([C@H]2CC[C@H](CN(c3cc(-c4coc(C(C)(C)C)n4)ccn3)C(=O)[C@H]3CC[C@H](OC(=O)N4CC(O)C4(C)C)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl 3-hydroxy-2,2-dimethylazetidine-1-carboxylate | 687.5 |

| Cmpd | Structure | Name | [M + H]+ |
|---|---|---|---|
| 1.06 | 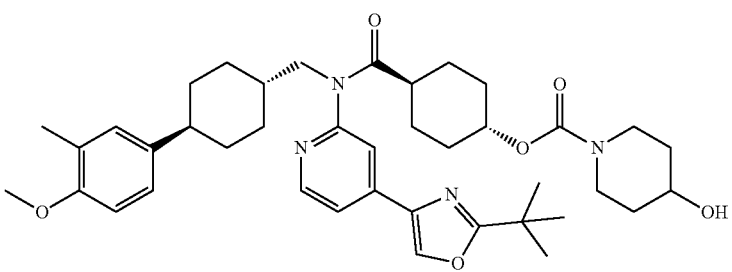 [SMILES: COc1ccc([C@H]2CC[C@H](CN(c3cc(-c4coc(C(C)(C)C)n4)ccn3)C(=O)[C@H]3CC[C@H](OC(=O)N4CCC(O)CC4)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl 4-hydroxypiperidine-1-carboxylate | 687.5 |
| 1.07 | 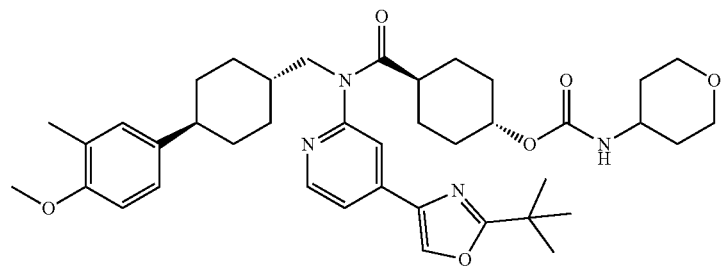 [SMILES: COc1ccc([C@H]2CC[C@H](CN(c3cc(-c4coc(C(C)(C)C)n4)ccn3)C(=O)[C@H]3CC[C@H](OC(=O)NC4CCOCC4)CC3)CC2)cc1C] | trans-4-((4-(2-(tert-Butyl)oxazol-4-yl)pyridin-2-yl)(((trans)-4-(4-methoxy-3-methylphenyl)cyclohexyl)methyl)carbamoyl)cyclohexyl (tetrahydro-2H-pyran-4-yl)carbamate | 687.6 |
| 1.08 | 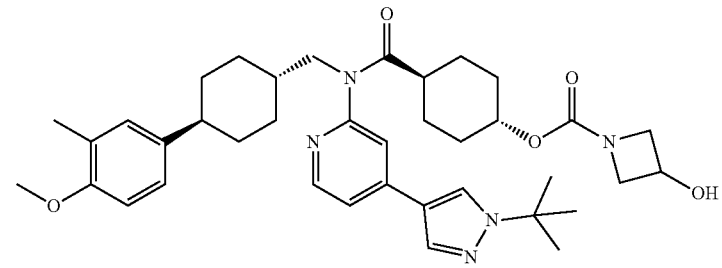 [SMILES: COc1ccc([C@H]2CC[C@H](CN(c3cc(-c4cnn(C(C)(C)C)c4)ccn3)C(=O)[C@H]3CC[C@H](OC(=O)N4CC(O)C4)CC3)CC2)cc1C] | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl 3-hydroxyazetidine-1-carboxylate | 658.5 |
| 1.09 | 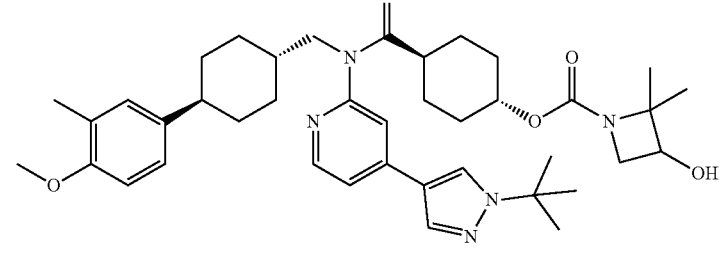 | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl 3-hydroxy-2,2-dimethylazetidine-1-carboxylate | 686.5 |
| 1.10 | 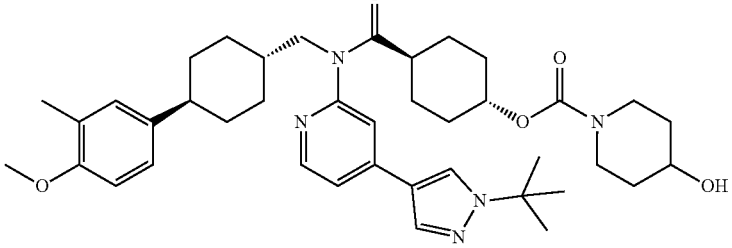 | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl 4-hydroxypiperidine-1-carboxylate | 686.6 |

-continued

| Cmpd | Structure | Name | [M + H]+ |
|---|---|---|---|
| 1.11 | 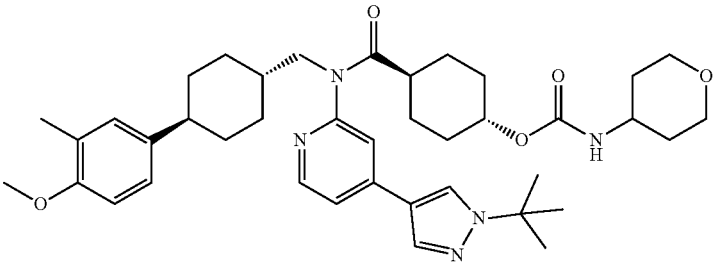 [SMILES: COc1ccc([C@H]2CC[C@H](CN(c3cc(-c4cnn(C(C)(C)C)c4)ccn3)C(=O)[C@H]3CC[C@H](OC(=O)NC4CCOCC4)CC3)CC2)cc1C] | trans-4-((4-(1-(tert-Butyl)-1H-pyrazol-4-yl)pyridin-2-yl)((trans-4-(4-methoxy-3-methylphenyl)cyclohexyl)methyl)carbamoyl)cyclohexyl (tetrahydro-2H-pyran-4-yl)carbamate | 686.6 |
| 1.12 | 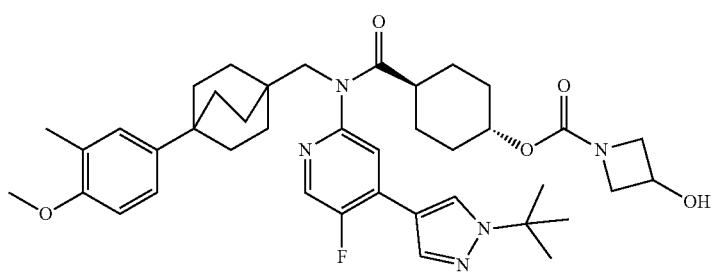 [SMILES: COc1ccc(C23CCC(CN(c4cc(-c5cnn(C(C)(C)C)c5)c(F)cn4)C(=O)[C@H]4CC[C@H](OC(=O)N5CC(O)C5)CC4)(CC2)CC3)cc1C] | 4-((4-(1-(tert-Butyl)-1H-pyrazol-4-yl)-5-fluoropyridin-2-yl)((4-(4-methoxy-3-methylphenyl)bicyclo[2.2.2]octan-1-yl)methyl)carbamoyl)(trans-cyclohexyl 3-hydroxyazetidine-1-carboxylate | 702.4 |
| 1.13 | 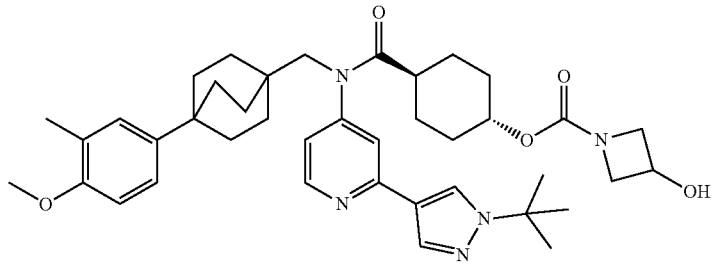 [SMILES: COc1ccc(C23CCC(CN(c4ccnc(-c5cnn(C(C)(C)C)c5)c4)C(=O)[C@H]4CC[C@H](OC(=O)N5CC(O)C5)CC4)(CC2)CC3)cc1C] | 4-((2-(1-(tert-Butyl)-1H-pyrazol-4-yl)pyridin-4-yl)((4-(4-methoxy-3-methylphenyl)bicyclo[2.2.2]octan-1-yl)methyl)carbamoyl)(trans-cyclohexyl 3-hydroxyazetidine-1-carboxylate | 684.5 |
| 1.14 | 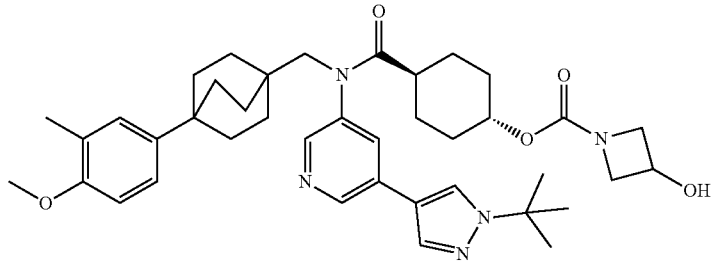 [SMILES: COc1ccc(C23CCC(CN(c4cncc(-c5cnn(C(C)(C)C)c5)c4)C(=O)[C@H]4CC[C@H](OC(=O)N5CC(O)C5)CC4)(CC2)CC3)cc1C] | 4-((5-(1-(tert-Butyl)-1H-pyrazol-4-yl)pyridin-3-yl)((4-(4-methoxy-3-methylphenyl)bicyclo[2.2.2]octan-1-yl)methyl)carbamoyl)(trans-cyclohexyl 3-hydroxyazetidine-1-carboxylate | 684.5 |
| 1.15 | 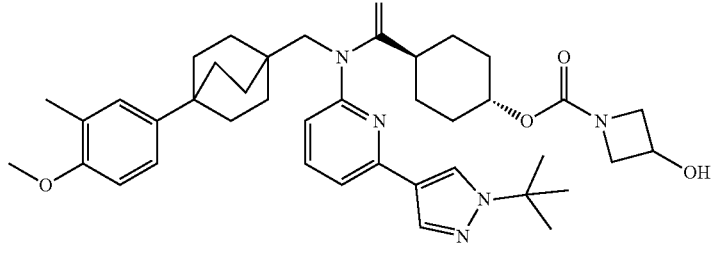 | 4-((6-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl 3-hydroxyazetidine-1-carboxylate | 684.5 |

Alternate conditions: Step 1: 0-45° C.; 15-21 h; In some instances, 1 equiv AcOH was added. Step 2: rt-80° C.; 1-20 h; CH$_2$Cl$_2$ as solvent; In some instances, no DMAP was used; 2 equiv Intermediate 11 was usually sufficient. Step 3: THF/CH$_3$OH (1:1 or 2:1); 1-2.5 h; In some instances, additional purification by HPLC needed. Step 4a: rt-80° C.; 2-16 h; In some instances, more than 1.5 equiv CDI needed for full conversion to acyl imidazole. Step 4b: 2 h-5 days; iPr$_2$NEt (2 equiv relative to amine) added when amine was and HCl salt.

Compound 2

4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate

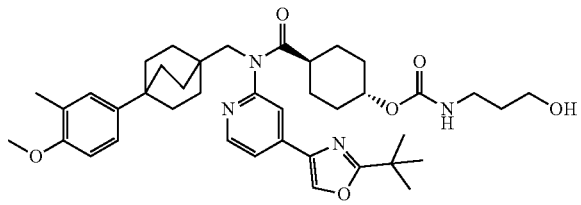 [SMILES: COc1ccc(C23CCC(CN(c4cc(-c5coc(C(C)(C)C)n5)ccn4)C(=O)[C@H]4CC[C@H](OC(=O)NCCCO)CC4)(CC2)CC3)cc1C]

Step 1: 4-(2-(tert-Butyl)oxazol-4-yl)-N-((4-(4-methoxy-3-methylphenyl)bicyclo[2.2.2]octan-1-yl)methyl)pyridin-2-amine Methanol (4.0 mL) and acetic acid (38 µL, 0.61 mmol) were added to Intermediate 2 (523 mg, 2.02 mmol) and Intermediate 7 (398 mg, 1.83 mmol) in a 40 mL vial. The mixture stirred at 60° C. for 3 h and cooled to rt. 2-Methylpyridine borane complex (196 mg, 1.83 mmol) was added. The reaction was stirred at rt for 63 h, diluted with EtOAc (10 mL), washed with sat'd NH$_4$Cl (10 mL), washed with sat'd NaHCO$_3$ (10 mL), washed with brine (10 mL), dried (Na$_2$SO$_4$), filtered, concentrated, and then purified by silica gel chromatography (0-40% EtOAc in hexanes) to give 4-(2-(tert-butyl)oxazol-4-yl)-A-((4-(4-methoxy-3-methylphenyl)bicyclo[2.2.2]octan-1-yl)methyl)pyridin-2-amine (685 mg, 81%) as a white foam. $^1$H NMR (400 MHz, DMSO-d$_6$): δ 8.55 (s, 1H), 7.91 (d, 1H), 7.26-7.07 (m, 2H), 6.97 (s, 1H), 6.82 (d, 1H), 6.72 (dd, 1H), 6.53 (t, 1H), 3.73 (s, 3H), 3.13 (d, 2H), 2.11 (s, 3H), 1.75-1.69 (m, 6H), 1.57-1.50 (m, 6H), 1.37 (s, 9H); LCMS: 460.4 [M+H]$^+$.

Step 2: trans-N-(4-(2-(tert-Butyl)oxazol-4-yl)pyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide Dichloromethane (7.0 mL) and triethylamine (831 µL, 5.96 mmol) were added to 4-(2-(tert-butyl)oxazol-4-yl)-A-((4-(4-methoxy-3-methylphenyl)bicyclo[2.2.2]octan-1-yl)methyl)pyridin-2-amine (685 mg, 1.49 mmol) and Intermediate 10 (462 mg, 1.79 mmol) in a 40 mL vial. 1-Propylphosphonic acid cyclic anhydride (T3P 50+% w/w soln. in CH$_2$Cl$_2$, 1.90 g, 2.98 mmol) was weighed into a separate vial and then added to the reaction. Dichloromethane (2 mL) was added to the T3P vial, and this solution was added to the reaction. The reaction was stirred at rt for 15 h, washed with water (10 mL), dried (Na$_2$SO$_4$), filtered, concentrated, and then purified by silica gel chromatography (0-15% EtOAc in hexanes) to give trans-N-(4-(2-(tert-butyl)oxazol-4-yl)pyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide (995 mg, 95%) as a white foam. $^1$H NMR (400 MHz, DMSO-d$_6$): δ 8.85 (s, 1H), 8.53 (d, 1H), 7.77 (s, 1H), 7.67 (d, 1H), 7.02-6.97 (m, 2H), 6.76 (d, 1H), 3.75 (s, 2H), 3.71 (s, 3H), 3.59-3.47 (m, 1H), 2.36-2.20 (m, 1H), 2.08 (s, 3H), 1.80-1.70 (m, 4H), 1.65-1.57 (m, 6H), 1.52-1.42 (2H), 1.41-1.17 (m, 15H), 1.04-0.90 (m, 2H), 0.81 (s, 9H), 0.14 (s, 6H); LCMS: 700.1 [M+H]$^+$.

Step 3: trans-N-(4-(2-(tert-butyl)oxazol-4-yl)pyridin-2-yl)-4-hydroxy-N-((4-(4-methoxy-3-methylphenyl)bicyclo[2.2.2]octan-1-yl)methyl)cyclohexanecarboxamide Aqueous hydrochloric acid (1 N, 2.12 mL, 2.12 mmol) was added to a solution of trans-N-(4-(2-(tert-butyl)oxazol-4-yl)pyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide (990 mg, 1.41 mmol), CH$_3$OH (5.0 mL), and THF (5.0 mL) at 0° C. The ice/water bath was removed. The reaction was stirred at rt for 1 h, cooled in ice/water bath, diluted with sat'd NaHCO$_3$ (7 mL), and then extracted with EtOAc (10 mL). The organic layer was washed with brine (10 mL), dried (Na$_2$SO$_4$), filtered, concentrated, and then purified by silica gel chromatography (0-50% EtOAc in CH$_2$Cl$_2$) then (0-5% CH$_3$OH in CH$_2$Cl$_2$) to give trans-N-(4-(2-(tert-butyl)oxazol-4-yl)pyridin-2-yl)-4-hydroxy-N-((4-(4-methoxy-3-methylphenyl)bicyclo[2.2.2]octan-1-yl)methyl)cyclohexanecarboxamide (727 mg, 87%) as a white foam. $^1$H NMR (400 MHz, DMSO-d$_6$): δ 8.85 (s, 1H), 8.53 (d, 1H), 7.78 (s, 1H), 7.67 (d, 1H), 7.02-6.97 (m, 2H), 6.76 (d, 1H), 4.44 (d, 1H), 3.73 (s, 2H), 3.70 (s, 3H), 3.33-3.26 (m, 1H), 2.33-2.15 (m, 1H), 2.08 (s, 3H), 1.80-1.67 (m, 4H), 1.65-1.54 (m, 6H), 1.49-1.32 (m, 17H), 0.94-0.78 (m, 2H); LCMS: 586.4 [M+H]$^+$.

Step 4: 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate A solution of trans-N-(4-(2-(tert-butyl)oxazol-4-yl)pyridin-2-yl)-4-hydroxy-N-((4-(4-methoxy-3-methylphenyl)bicyclo[2.2.2]octan-1-yl)methyl)cyclohexanecarboxamide (100 mg, 0.17 mmol), CDI (42 mg, 0.26 mmol), and CH$_3$CN (1 mL) was heated at 80° C. overnight and then cooled to rt. 3-Amino-1-propanol (26 µL, 0.34 mmol) was added to a portion of the CH$_3$CN solution (0.5 mL, 0.085 mmol). The mixture was stirred at rt for 4 h, diluted with EtOAc (10 mL), washed with sat'd NaHCO$_3$ (10 mL), washed with brine (10 mL), dried (Na$_2$SO$_4$), filtered, concentrated, and then purified by silica gel chromatography (0-5.5% CH$_3$OH in CH$_2$Cl$_2$) to give 4-((4-(2-(tert-butyl)oxazol-4-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate (53 mg, 91%) as a white foam. $^1$H NMR (400 MHz, DMSO-d$_6$): δ 8.85 (s, 1H), 8.54 (d, 1H), 7.79 (s, 1H), 7.68 (d, 1H), 7.02-6.97 (m, 2H), 6.91 (t, 0.90H), 6.77 (d, 1H), 6.67-6.59 (m, 0.10H), 4.40-4.32 (m, 2H), 3.75 (s, 2H), 3.70 (s, 3H), 3.39-3.31 (m, 2H), 3.01-2.95 (m, 2H), 2.36-2.25 (m, 1H), 2.08 (s, 3H), 1.92-1.75 (m, 4H), 1.65-1.57 (m, 6H), 1.55-1.42 (m, 4H), 1.41-1.31 (m, 15H), 1.08-0.93 (m, 2H); LCMS: 687.5 [M+H]$^+$.

The Compounds below were synthesized from the appropriate Intermediates and the appropriate amines following the procedures described for Compound 2.

| Cmpd | Structure | Name | [M + H]+ |
|---|---|---|---|
| 2.01 | 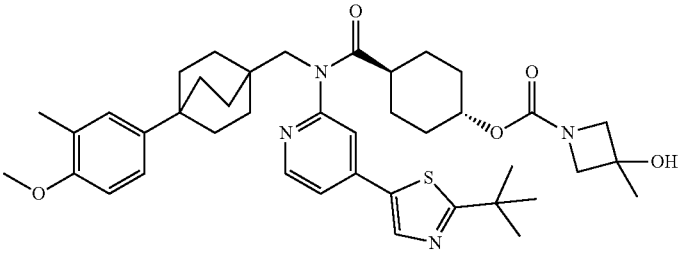 [SMILES: COc1ccc(C23CCC(CN(c4cc(-c5cnc(C(C)(C)C)s5)ccn4)C(=O)[C@H]4CC[C@H](OC(=O)N5CC(C)(O)C5)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) 3-hydroxy-3-methylazetidine-1-carboxylate | 715.2 |
| 2.02 | 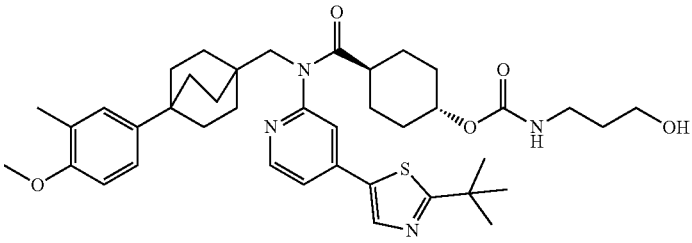 [SMILES: COc1ccc(C23CCC(CN(c4cc(-c5cnc(C(C)(C)C)s5)ccn4)C(=O)[C@H]4CC[C@H](OC(=O)NCCCO)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate | 703.0 |
| 2.03 | 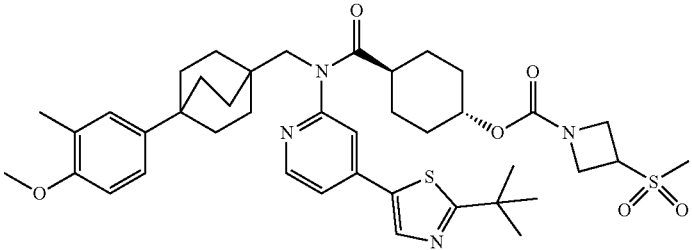 | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) 3-(methylsulfonyl)azetidine-1-carboxylate | 763.2 |
| 2.04 | 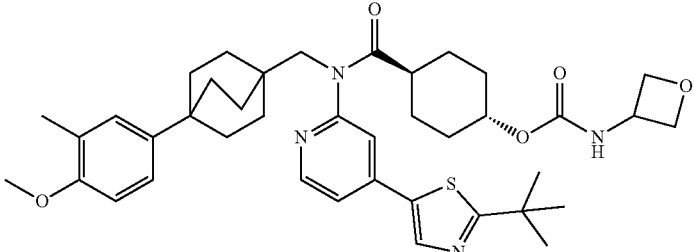 | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) oxetan-3-ylcarbamate | 701.4 |
| 2.05 | 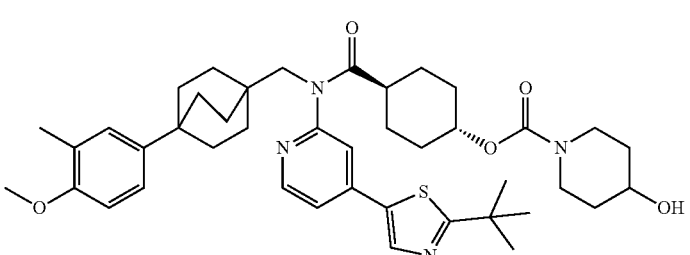 | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl 4-hydroxypiperidine-trans-1-carboxylate | 729.4 |
| 2.06 | 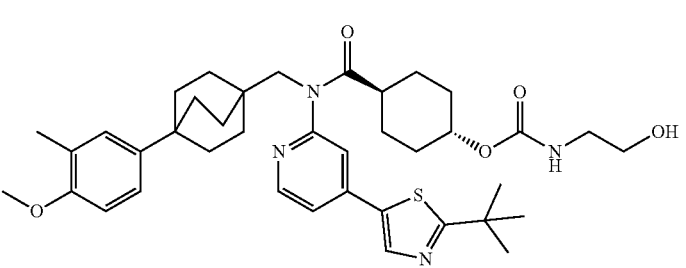 [SMILES: COc1ccc(C23CCC(CN(c4cc(-c5cnc(C(C)(C)C)s5)ccn4)C(=O)[C@H]4CC[C@H](OC(=O)NCCO)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl (2-hydroxyethyl)trans-carbamate | 689.2 |

-continued

| Cmpd | Structure | Name | [M + H]⁺ |
|---|---|---|---|
| 2.07 | 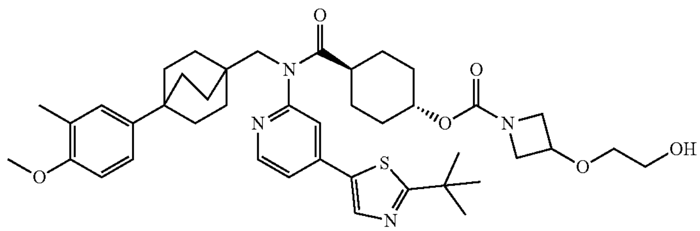 [SMILES: COc1ccc(C23CCC(CN(c4cc(-c5cnc(C(C)(C)C)s5)ccn4)C(=O)[C@H]4CC[C@H](OC(=O)N5CC(OCCO)C5)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) 3-(2-hydroxyethoxy)azetidine-1-carboxylate | 745.2 |
| 2.08 | 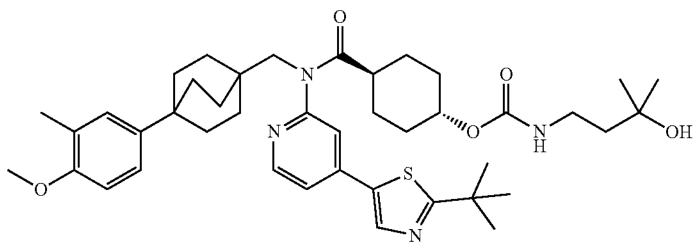 [SMILES: COc1ccc(C23CCC(CN(c4cc(-c5cnc(C(C)(C)C)s5)ccn4)C(=O)[C@H]4CC[C@H](OC(=O)NCCC(C)(C)O)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) (3-hydroxy-3-methylbutyl)carbamate | 731.4 |
| 2.09 | 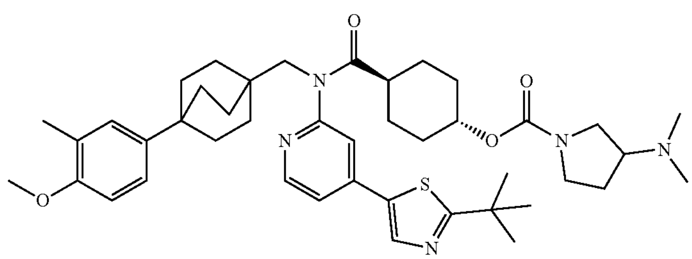 | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl 3-(dimethylamino)pyrrolidine-trans-1-carboxylate | 742.6 |
| 2.10 | 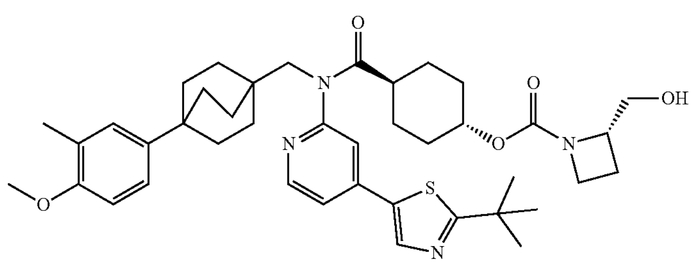 [SMILES: COc1ccc(C23CCC(CN(c4cc(-c5cnc(C(C)(C)C)s5)ccn4)C(=O)[C@H]4CC[C@H](OC(=O)N5CC[C@H]5CO)CC4)(CC2)CC3)cc1C] | (S)-4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl 2-(hydroxymethyl)azetidine-trans-1-carboxylate | 715.5 |
| 2.11 | 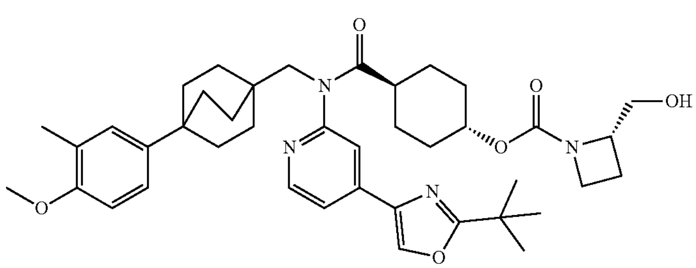 [SMILES: COc1ccc(C23CCC(CN(c4cc(-c5coc(C(C)(C)C)n5)ccn4)C(=O)[C@H]4CC[C@H](OC(=O)N5CC[C@H]5CO)CC4)(CC2)CC3)cc1C] | (S)-4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl 2-(hydroxymethyl)azetidine-trans-1-carboxylate | 699.5 |
| 2.12 | 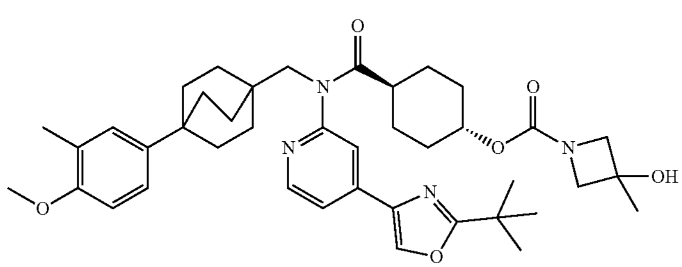 [SMILES: COc1ccc(C23CCC(CN(c4cc(-c5coc(C(C)(C)C)n5)ccn4)C(=O)[C@H]4CC[C@H](OC(=O)N5CC(C)(O)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-hydroxy-3-methylazetidine-1-carboxylate | 699.3 |

-continued

| Cmpd | Structure | Name | [M + H]⁺ |
|---|---|---|---|
| 2.13 | 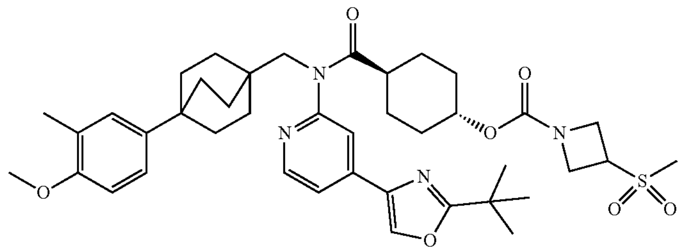 | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-(methylsulfonyl)azetidine-1-carboxylate | 747.3 |
| 2.14 | 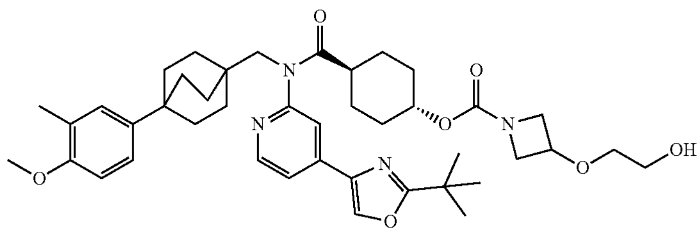 [SMILES: COc1ccc(C23CCC(CN(c4cc(-c5coc(C(C)(C)C)n5)ccn4)C(=O)[C@H]4CC[C@H](OC(=O)N5CC(OCCO)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-(2-hydroxyethoxy)azetidine-1-carboxylate | 729.1 |
| 2.15 | 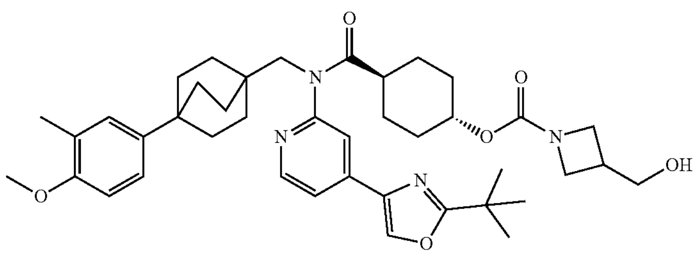 [SMILES: COc1ccc(C23CCC(CN(c4cc(-c5coc(C(C)(C)C)n5)ccn4)C(=O)[C@H]4CC[C@H](OC(=O)N5CC(CO)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) 3-(hydroxymethyl)azetidine-1-carboxylate | 699.6 |
| 2.16 | 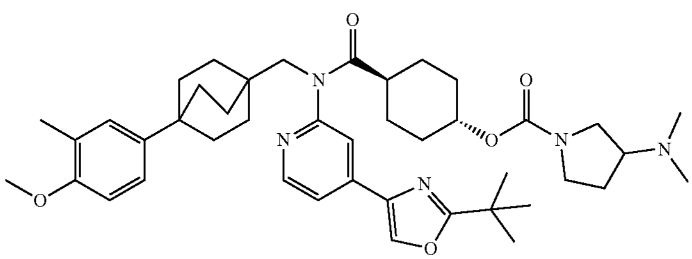 | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl 3-(dimethylamino)pyrrolidine-trans-1-carboxylate | 726.6 |
| 2.17 | 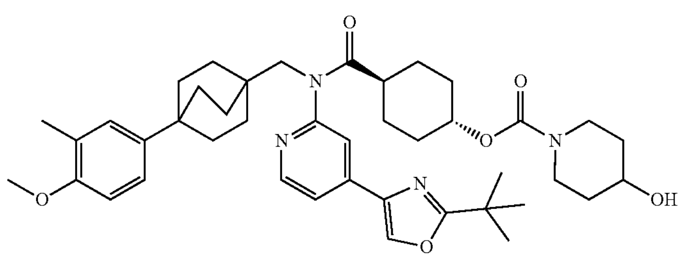 [SMILES: COc1ccc(C23CCC(CN(c4cc(-c5coc(C(C)(C)C)n5)ccn4)C(=O)[C@H]4CC[C@H](OC(=O)N5CCC(O)CC5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl 4-hydroxypiperidine-trans-1-carboxylate | 713.4 |
| 2.18 | 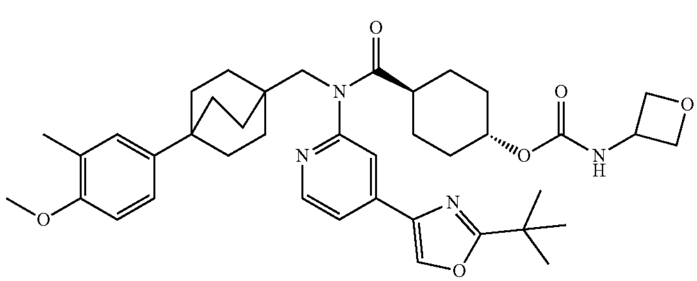 [SMILES: COc1ccc(C23CCC(CN(c4cc(-c5coc(C(C)(C)C)n5)ccn4)C(=O)[C@H]4CC[C@H](OC(=O)NC5COC5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) oxetan-3-ylcarbamate | 685.4 |

-continued

| Cmpd | Structure | Name | [M + H]+ |
|---|---|---|---|
| 2.19 | 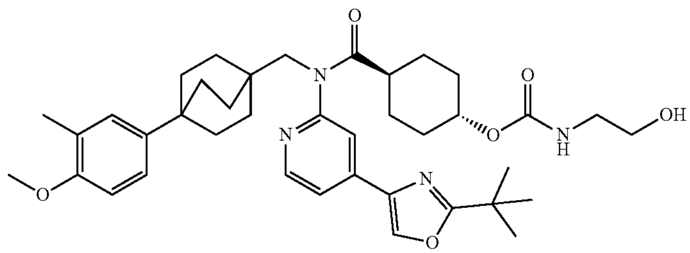 [SMILES: COc1ccc(C23CCC(CN(c4cc(-c5coc(C(C)(C)C)n5)ccn4)C(=O)[C@H]4CC[C@H](OC(=O)NCCO)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl (2-hydroxyethyl)trans-carbamate | 673.2 |
| 2.20 | 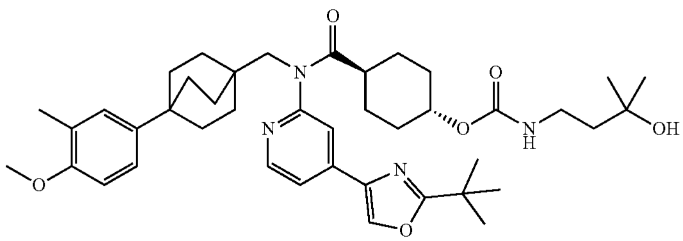 [SMILES: COc1ccc(C23CCC(CN(c4cc(-c5coc(C(C)(C)C)n5)ccn4)C(=O)[C@H]4CC[C@H](OC(=O)NCCC(C)(C)O)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)(trans-cyclohexyl) (3-hydroxy-3-methylbutyl)carbamate | 715.3 |
| 2.21 | 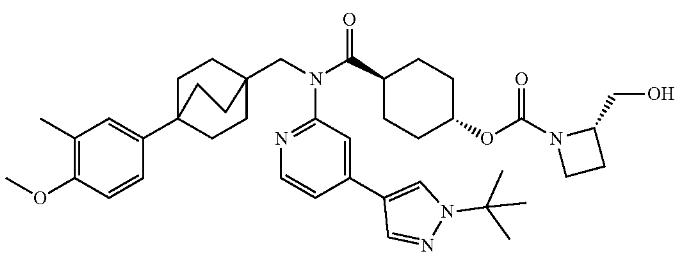 [SMILES: COc1ccc(C23CCC(CN(c4cc(-c5cnn(C(C)(C)C)c5)ccn4)C(=O)[C@H]4CC[C@H](OC(=O)N5CC[C@H]5CO)CC4)(CC2)CC3)cc1C] | (S)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 2-(hydroxymethyl)azetidine-trans-1-carboxylate | 698.5 |
| 2.22 | 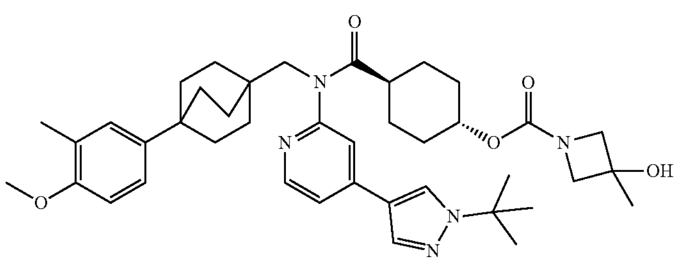 [SMILES: COc1ccc(C23CCC(CN(c4cc(-c5cnn(C(C)(C)C)c5)ccn4)C(=O)[C@H]4CC[C@H](OC(=O)N5CC(C)(O)C5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-hydroxy-3-methylazetidine-1-carboxylate | 698.5 |
| 2.23 | 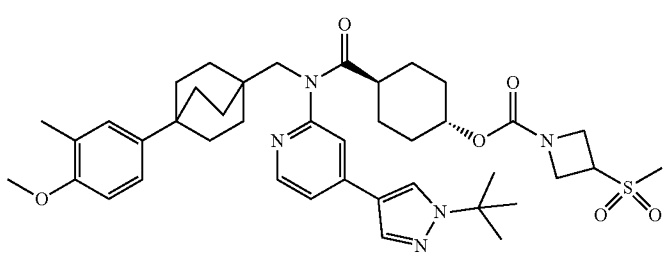 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-(methylsulfonyl)azetidine-1-carboxylate | 746.6 |
| 2.24 | 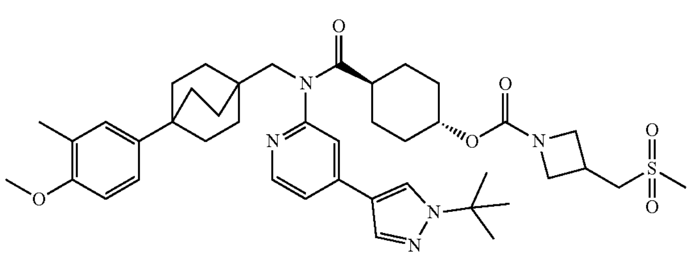 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-((methylsulfonyl)methyl)azetidine-1-carboxylate | 760.6 |

| Cmpd | Structure | Name | [M + H]+ |
|---|---|---|---|
| 2.25 | 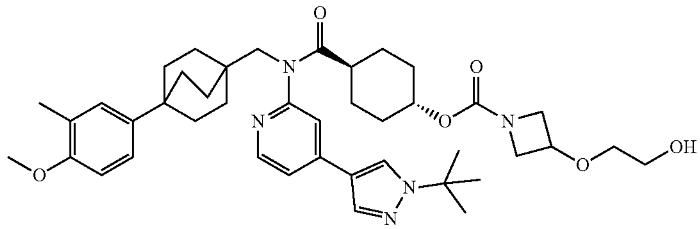 [SMILES: COc1ccc(C23CCC(CN(c4cc(-c5cnn(C(C)(C)C)c5)ccn4)C(=O)[C@H]4CC[C@H](OC(=O)N5CC(OCCO)C5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-(2-hydroxyethoxy)azetidine-1-carboxylate | 728.5 |
| 2.26 | 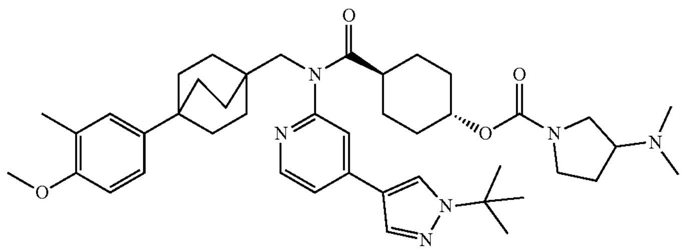 | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 3-(dimethylamino)pyrrolidine-trans-1-carboxylate | 725.6 |
| 2.27 | 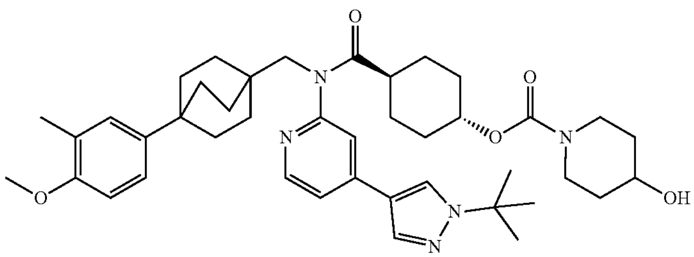 [SMILES: COc1ccc(C23CCC(CN(c4cc(-c5cnn(C(C)(C)C)c5)ccn4)C(=O)[C@H]4CC[C@H](OC(=O)N5CCC(O)CC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 4-hydroxypiperidine-trans-1-carboxylate | 712.6 |
| 2.28 | 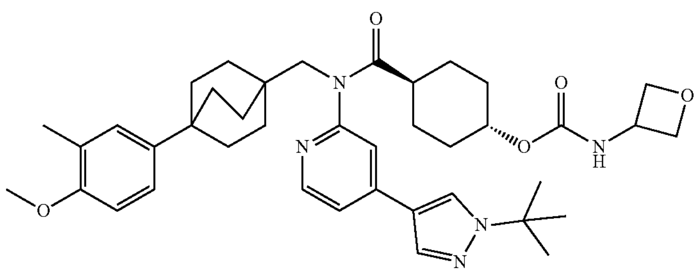 [SMILES: COc1ccc(C23CCC(CN(c4cc(-c5cnn(C(C)(C)C)c5)ccn4)C(=O)[C@H]4CC[C@H](OC(=O)NC5COC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) oxetan-3-ylcarbamate | 684.6 |
| 2.29 | 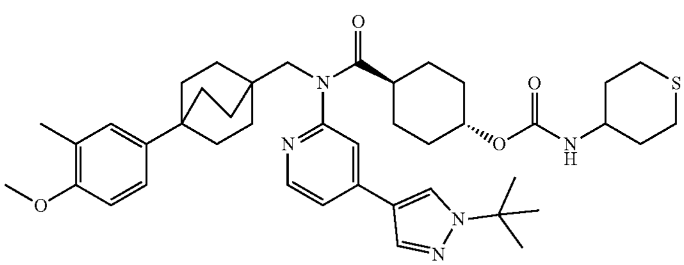 [SMILES: COc1ccc(C23CCC(CN(c4cc(-c5cnn(C(C)(C)C)c5)ccn4)C(=O)[C@H]4CC[C@H](OC(=O)NC5CCSCC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl trans(tetrahydro-2H-thiopyran-4-yl)carbamate | 728.2 |
| 2.30 | 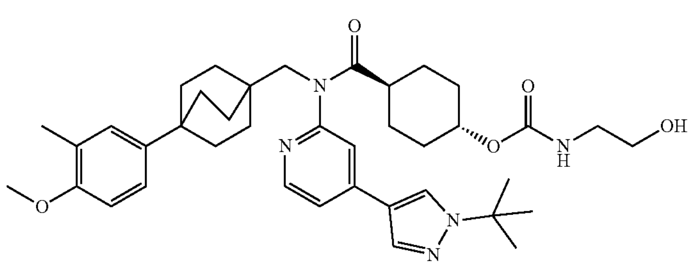 [SMILES: COc1ccc(C23CCC(CN(c4cc(-c5cnn(C(C)(C)C)c5)ccn4)C(=O)[C@H]4CC[C@H](OC(=O)NCCO)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl (2-hydroxyethyl)trans-carbamate | 672.6 |

-continued

| Cmpd | Structure | Name | [M + H]⁺ |
|---|---|---|---|
| 2.31 | 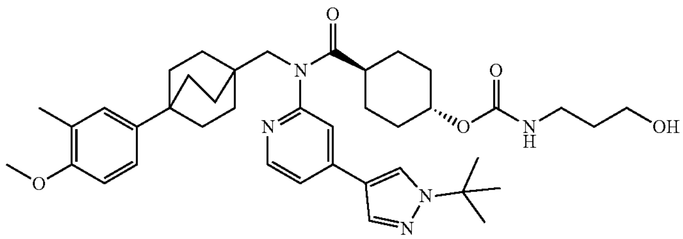 [SMILES: COc1ccc(C23CCC(CN(c4cc(-c5cnn(C(C)(C)C)c5)ccn4)C(=O)[C@H]4CC[C@H](OC(=O)NCCCO)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) (3-hydroxypropyl)carbamate | 686.5 |
| 2.32 | 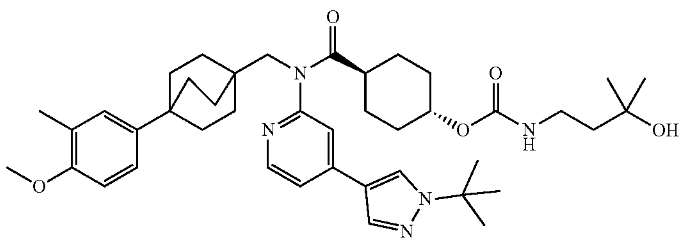 [SMILES: COc1ccc(C23CCC(CN(c4cc(-c5cnn(C(C)(C)C)c5)ccn4)C(=O)[C@H]4CC[C@H](OC(=O)NCCC(C)(C)O)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) (3-hydroxy-3-methylbutyl)carbamate | 714.6 |
| 2.33 | 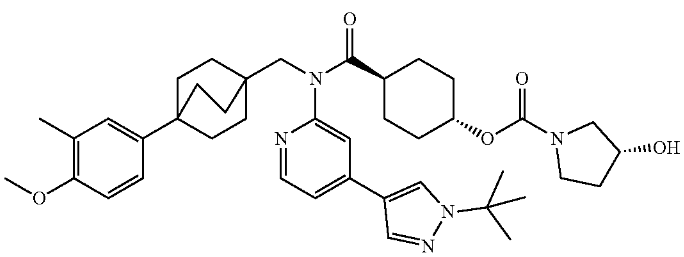 [SMILES: COc1ccc(C23CCC(CN(c4cc(-c5cnn(C(C)(C)C)c5)ccn4)C(=O)[C@H]4CC[C@H](OC(=O)N5CC[C@@H](O)C5)CC4)(CC2)CC3)cc1C] | (R)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl trans-3-hydroxypyrrolidine-1-carboxylate | 698.6 |
| 2.34 | 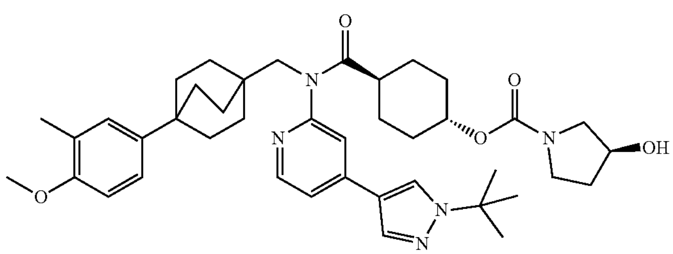 [SMILES: COc1ccc(C23CCC(CN(c4cc(-c5cnn(C(C)(C)C)c5)ccn4)C(=O)[C@H]4CC[C@H](OC(=O)N5CC[C@H](O)C5)CC4)(CC2)CC3)cc1C] | (S)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl trans-3-hydroxypyrrolidine-1-carboxylate | 698.6 |
| 2.35 | 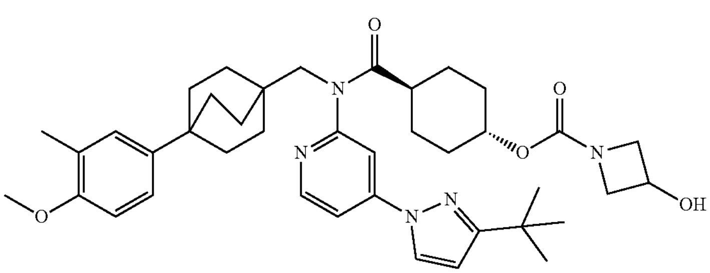 [SMILES: COc1ccc(C23CCC(CN(c4cc(-n5ccc(C(C)(C)C)n5)ccn4)C(=O)[C@H]4CC[C@H](OC(=O)N5CC(O)C5)CC4)(CC2)CC3)cc1C] | 4-((4-(3-(tert-Butyl)-1H-pyrazol-1-yl)pyridin-2-yl)((4-(4-methoxy-3-methylphenyl)bicyclo[2.2.2]octan-1-yl)methyl)carbamoyl)cyclohexyl trans-3-hydroxyazetidine-1-carboxylate | 684.2 |
| 2.36 | 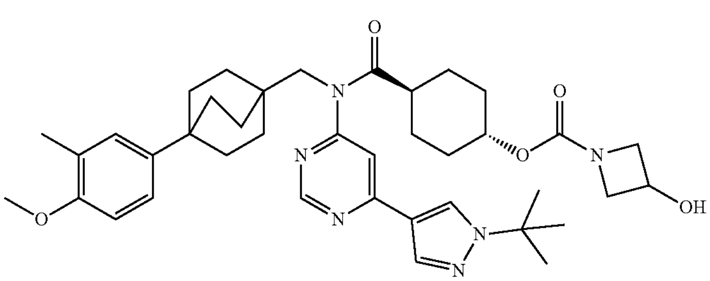 | 4-((6-(1-(tert-Butyl)-1H-pyrazol-4-yl)pyrimidin-4-yl)((4-(4-methoxy-3-methylphenyl)bicyclo[2.2.2]octan-1-yl)methyl)carbamoyl)(trans-cyclohexyl) 3-hydroxyazetidine-1-carboxylate | 685.6 |

| Cmpd | Structure | Name | [M + H]⁺ |
|---|---|---|---|
| 2.37 | 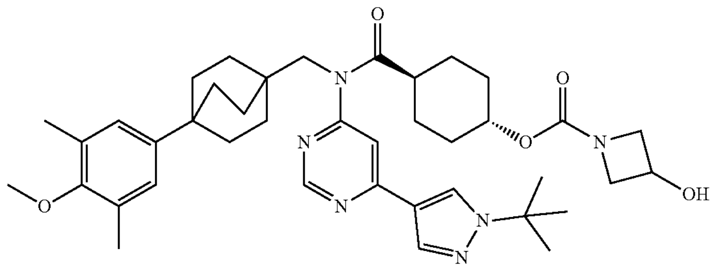 [SMILES: COc1c(C)cc(C23CCC(CN(c4cc(-c5cnn(C(C)(C)C)c5)ncn4)C(=O)[C@H]4CC[C@H](OC(=O)N5CC(O)C5)CC4)(CC2)CC3)cc1C] | 4-((6-(1-(tert-Butyl)-1H-pyrazol-4-yl)pyrimidin-4-yl)((4-(4-methoxy-3,5-dimethylphenyl)bicyclo[2.2.2]octan-1-yl)methyl)carbamoyl)(trans-cyclohexyl) 3-hydroxyazetidine-1-carboxylate | 699.5 |

Alternative conditions: Step 1a: 60-65° C.; 3-69 h; In some instances, 1 equiv AcOH was used. Step 1b: 0-40° C., 15-24 h. Step 2: rt-40° C.; 15-63 h; In some instances, more equiv of T3P, Intermediate 10, and Et₃N were needed for full conversion; In some instances, DMAP was used. Step 3: 1-19 h. Step 4a: rt-80° C., 3.5-19 h; In some instances, more than 1.5 equiv CDI needed for full conversion to acyl imidazole. Step 4b: rt-50° C.; 2-96 h; iPr₂NEt (2 equiv relative to amine) added when amine was an HCl salt.

The Compound below was synthesized from Compound 2.29 using NaIO₄, THF, H₂O, 0-50° C., 1-37 h.

| Cmpd | Structure | Name | [M + H]⁺ |
|---|---|---|---|
| 2.38 | 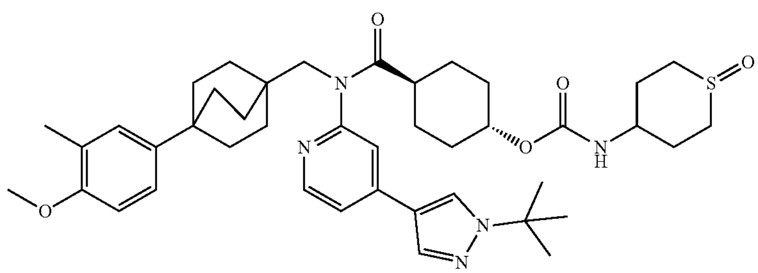 [SMILES: COc1ccc(C23CCC(CN(c4cc(-c5cnn(C(C)(C)C)c5)ccn4)C(=O)[C@H]4CC[C@H](OC(=O)NC5CCS(=O)CC5)CC4)(CC2)CC3)cc1C] | (1r,4r)-4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl (1-oxidotetrahydro-2H-thiopyran-4-yl)carbamate | 744.6 |

The Compound below was synthesized from Compound 2.29 using m-CPBA, CH₂Cl₂. 0° C.-rt. 4 h.

| Cmpd | Structure | Name | [M + H]⁺ |
|---|---|---|---|
| 2.39 | 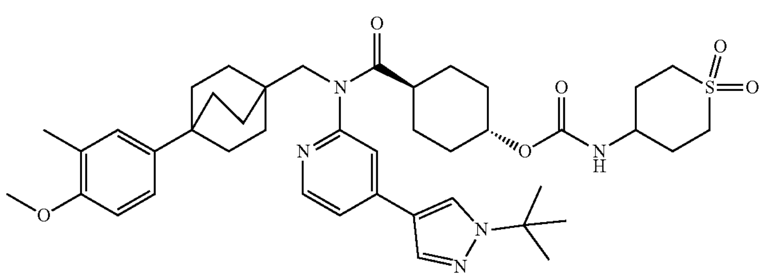 [SMILES: COc1ccc(C23CCC(CN(c4cc(-c5cnn(C(C)(C)C)c5)ccn4)C(=O)[C@H]4CC[C@H](OC(=O)NC5CCS(=O)(=O)CC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl trans-(1,1-dioxidotetrahydro-2H-thiopyran-4-yl)carbamate | 760.5 |

Compound 3

4-((4-(1-(tert-Butyl)-1H-pyrazol-4-yl)pyridin-2-yl)
((4-(4-methoxy-3-methylphenyl)bicyclo[2.2.2]octan-
1-yl)methyl)carbamoyl)cyclohexyl 3-hydroxyazeti-
dine-trans-1-carboxylate

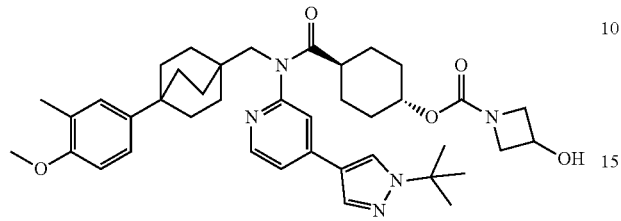

Step 1: 4-(1-(tert-Butyl)-1H-pyrazol-4-yl)-N-((4-(4-methoxy-3-methylphenyl)bicyclo[2.2.2]octan-1-yl)methyl)pyridin-2-amine Intermediate 2 (199 mg, 0.77 mmol) and Intermediate 8 (200 mg, 0.925 mmol) were suspended in $CH_3OH$ (4 mL). Acetic acid (13.2 µL, 0.23 mmol) was added. The reaction mixture was heated in a 60° C. oil bath for 4 h and allowed to cool to rt. 2-Methylpyridine borane complex (82 mg, 0.77 mmol) was added. The reaction was stirred at rt for 16 h, diluted with 20 mL sat'd $NH_4Cl$, and then extracted with 20 mL EtOAc. The organic layer was washed with 20 mL brine, dried ($Na_2SO_4$), filtered, concentrated, and then purified by silica gel chromatography (20-80% EtOAc in hexanes) to give 4-(1-(tert-butyl)-1H-pyrazol-4-yl)-N-((4-(4-methoxy-3-methyl phenyl)bicyclo[2.2.2]octan-1-yl)methyl)pyridin-2-amine (255 mg, 72%) as an off-white foam. $^1H$ NMR (400 MHz, DMSO-$d_6$): δ 8.26 (s, 1H), 7.86 (d, 1H), 7.84 (s, 1H), 7.09-7.04 (m, 2H), 6.80 (d, 1H), 6.70 (s, 1H), 6.68 (d, 1H), 6.16 (t, 1H), 3.72 (s, 3H), 3.11 (d, 2H), 2.12 (s, 3H), 1.77-1.67 (m, 6H), 1.59-1.47 (m, 15H); LCMS: 459.6 [M+H]$^+$.

Step 2: trans-N-(4-(1-(tert-Butyl)-1H-pyrazol-4-yl)pyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide 4-(1-(tert-Butyl)-1H-pyrazol-4-yl)-A-((4-(4-methoxy-3-methylphenyl)bicyclo[2.2.2]octan-1-yl)methyl)pyridin-2-amine (250 mg, 0.545 mmol) and DMAP (69 mg, 0.57 mmol) were combined in toluene (1 mL). Triethylamine (0.3 mL, 2.15 mmol) and then Intermediate 11 (4.4 mL, 71 mg/mL, 1.12 mmol) were added at rt. The reaction was heated at 80° C. for 2 h, allowed to cool to rt, diluted with 5 mL 1 M $K_2HPO_4$, and then extracted with 20 mL EtOAc. The organic layer was washed with 20 mL brine, dried ($Na_2SO_4$), filtered, and then purified by silica gel chromatography (10-25% EtoAc in hexanes) to give trans-N-(4-(1-(tert-butyl)-1H-pyrazol-4-yl)pyridin-2-yl)-4-((tert-butyldimethylsilyl)oxy)-N-(4-(4-methoxy-3-methylphenyl)bicyclo[2.2.2]octan-1-yl)methyl)cyclohexanecarboxamide (308 mg, 81%) as a white foam. $^1H$ NMR (400 MHz, DMSO-$d_6$): δ 8.61 (s, 1H), 8.40 (d, 1H), 8.15 (s, 1H), 7.73 (s, 1H), 7.58 (d, 1H), 7.02-6.96 (m, 2H), 6.76 (d, 1H), 3.75-3.68 (m, 5H), 3.56-3.45 (m, 1H), 2.31-2.20 (m, 1H), 2.08 (s, 3H), 1.80-1.68 (m, 4H), 1.66-1.52 (m, 15H), 1.50- 1.29 (m, 8H), 0.98-0.84 (m, 2H), 0.79 (s, 9H), -0.02 (s, 6H); LCMS: 699.6 [M+H]$^+$. Note: Compound 3, Step 2 can also be synthesized following the procedure for Compound 2, Step 2.

Step 3: trans-N-(4-(1-(tert-Butyl)-1H-pyrazol-4-yl)pyridin-2-yl)-4-hydroxy-N-((4-(4-methoxy-3-methylphenyl)bicyclo[2.2.2]octan-1-yl)methyl)cyclohexanecarboxamide Aqueous hydrochloric acid (1 N, 0.65 mL, 0.65 mmol) was added to a solution of trans-N-(4-(1-(tert-butyl)-1H-pyrazol-4-yl)pyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide (303 mg, 0.433 mmol) in THF (1.3 mL) and $CH_3OH$ (1.3 mL) at 0° C. The reaction was stirred at rt for 2.5 h, cooled to 0° C. in an ice/water bath, diluted with 20 mL sat'd $NaHCO_3$, and then extracted with 20 mL EtOAc. The organic layer was washed with 20 mL sat'd $NaHCO_3$, washed with 20 mL brine, dried ($Na_2SO_4$), filtered, concentrated, and then purified by silica gel chromatography (0-5% $CH_3OH$ in $CH_2Cl_2$) to give trans-N-(4-(1-(tert-butyl)-1H-pyrazol-4-yl)pyridin-2-yl)-4-hydroxy-N-((4-(4-methoxy-3-methylphenyl)bicyclo[2.2.2]octan-1-yl)methyl)cyclohexanecarboxamide (214 mg, 85%) as a white solid. $^1H$ NMR (400 MHz, DMSO-$d_6$): δ 8.61 (s, 1H), 8.41 (d, 1H), 8.15 (s, 1H), 7.74 (s, 1H), 7.58 (d, 1H), 7.03-6.96 (m, 2H), 6.76 (d, 1H), 3.75-3.67 (m, 5H), 3.32-3.23 (m, 1H), 2.28-2.17 (m, 1H), 2.08 (s, 3H), 1.80-1.67 (m, 4H), 1.64-1.52 (m, 16H), 1.46-1.31 (m, 8H), 0.89-0.74 (m, 2H); LCMS: 585.7 [M+H]$^+$.

Step 4: 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl 3-hydroxyazetidine-trans-1-carboxylate A mixture of trans-N-(4-(1-(tert-butyl)-1H-pyrazol-4-yl)pyridin-2-yl)-4-hydroxy-N-((4-(4-methoxy-3-methylphenyl)bicyclo[2.2.2]octan-1-yl)methyl)cyclohexanecarboxamide (100 mg, 0.171 mmol), CDI (42 mg, 0.26 mmol), and $CH_3CN$ (1 mL) was heated at 80° C. for 2 h and then allowed to cool to rt. 3-Hydroxy azetidine hydrochloride (37 mg, 0.34 mmol) and then $iPr_2NEt$ (0.12 mL, 0.68 mmol) were added to a portion of this solution (0.5 mL, 0.09 mmol) at rt. The reaction was stirred at rt for 20 h, diluted with 10 mL EtoAc, washed with 10 mL sat'd $NaHCO_3$, washed with 10 mL brine, dried ($Na_2SO_4$), filtered, concentrated, and then purified by silica gel chromatography (0-50% EtOAc in $CH_2Cl_2$ and then 0-10% $CH_3OH$ in $CH_2Cl_2$) to give 4-((4-(1-(tert-butyl)-1H-pyrazol-4-yl)pyridin-2-yl)((4-(4-methoxy-3-methylphenyl)bicyclo[2.2.2]octan-1-yl)methyl)carbamoyl)cyclohexyl 3-hydroxy azetidine-trans-1-carboxylate (51 mg, 87%) as a white foam. $^1H$ NMR (400 MHz, DMSO-$d_6$): δ 8.62 (s, 1H), 8.41 (d, 1H), 8.16 (s, 1H), 7.75 (s, 1H), 7.58 (d, 1H), 7.03-6.95 (m, 2H), 6.76 (d, 1H), 5.63 (d, 1H), 4.40-4.29 (m, 2H), 4.01-3.94 (m, 2H), 3.76-3.67 (m, 5H), 3.59-3.52 (m, 2H), 2.36-2.25 (m, 1H), 2.08 (s, 3H), 1.89-1.74 (m, 4H), 1.65-1.53 (m, 15H), 1.52-1.39 (m, 2H), 1.39-1.30 (m, 6H), 1.06-0.91 (m, 2H); LCMS 684.6 [M+H]$^+$.

The Compounds below were synthesized from the appropriate Intermediates following the procedures described for Compound 3.

| Cmpd | Structure | Name | [M + H]+ |
|---|---|---|---|
| 3.01 | 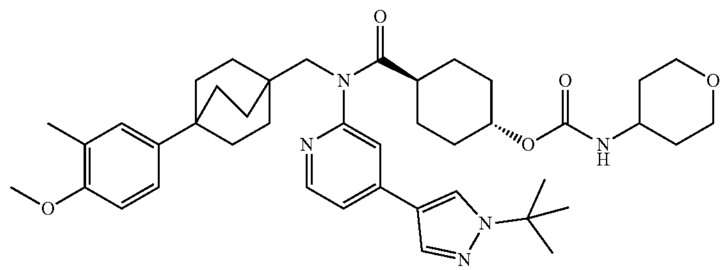 [SMILES: COc1ccc(C23CCC(CN(c4cc(-c5cnn(C(C)(C)C)c5)ccn4)C(=O)[C@H]4CC[C@H](OC(=O)NC5CCOCC5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)cyclohexyl (tetrahydro-2H-pyran-4-yl)trans-carbamate | 712.6 |
| 3.02 | 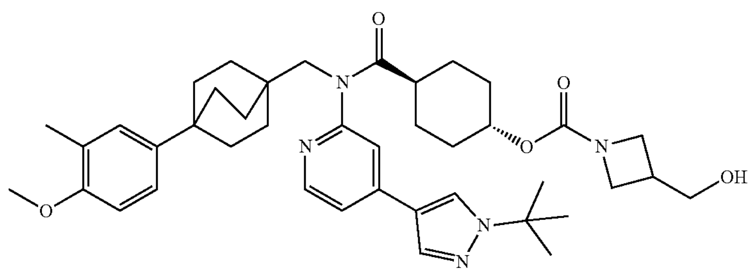 [SMILES: COc1ccc(C23CCC(CN(c4cc(-c5cnn(C(C)(C)C)c5)ccn4)C(=O)[C@H]4CC[C@H](OC(=O)N5CC(CO)C5)CC4)(CC2)CC3)cc1C] | 4-((4-(1-(tert-Butyl)-1H-pyrazol-4-yl)pyridin-2-yl)(trans(4-(4-methoxy-3-methylphenyl)bicyclo[2.2.2]octan-1-yl)methyl)carbamoyl)(trans-cyclohexyl) 3-(hydroxymethyl)azetidine-1-carboxylate | 698.5 |
| 3.03 | 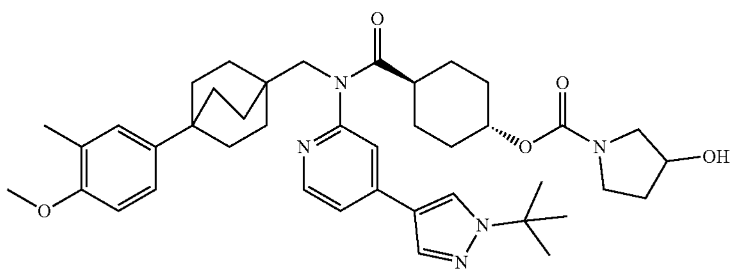 [SMILES: COc1ccc(C23CCC(CN(c4cc(-c5cnn(C(C)(C)C)c5)ccn4)C(=O)[C@H]4CC[C@H](OC(=O)N5CCC(O)C5)CC4)(CC2)CC3)cc1C] | 4-((4-(1-(tert-Butyl)-1H-pyrazol-4-yl)pyridin-2-yl)((4-(4-methoxy-3-methylphenyl)bicyclo[2.2.2]octan-1-yl)methyl)carbamoyl)(trans-cyclohexyl) 3-hydroxypyrrolidine-1-carboxylate | 698.5 |
| 3.04 | 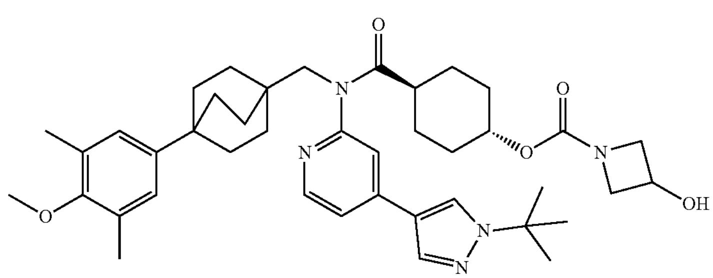 [SMILES: COc1c(C)cc(C23CCC(CN(c4cc(-c5cnn(C(C)(C)C)c5)ccn4)C(=O)[C@H]4CC[C@H](OC(=O)N5CC(O)C5)CC4)(CC2)CC3)cc1C] | 4-((4-(1-(tert-Butyl)-1H-pyrazol-4-yl)pyridin-2-yl)((4-(4-methoxy-3,5-dimethylphenyl)bicyclo[2.2.2]octan-1-yl)methyl)carbamoyl)(trans-cyclohexyl) 3-hydroxy-azetidine-1-carboxylate | 698.6 |
| 3.05 | 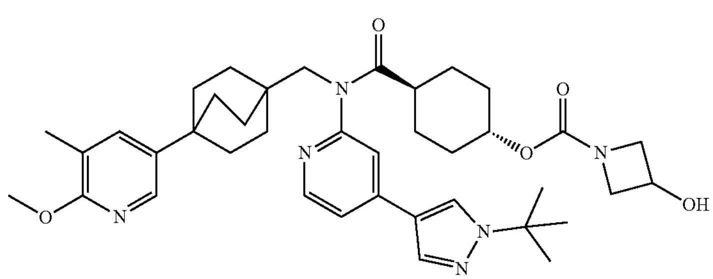 | 4-((4-(1-(tert-Butyl)-1H-pyrazol-4-yl)pyridin-2-yl)((4-(6-methoxy-5-methylpyridin-3-yl)bicyclo[2.2.2]octan-1-yl)methyl)carbamoyl)(trans-cyclohexyl) 3-hydroxyazetidine-1-carboxylate | 685.6 |

| Cmpd | Structure | Name | [M + H]+ |
|---|---|---|---|
| 3.06 | 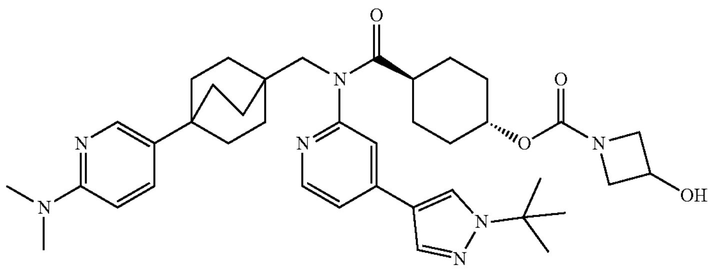 [SMILES: CN(C)c1ccc(C23CCC(CN(c4cc(-c5cnn(C(C)(C)C)c5)ccn4)C(=O)[C@H]4CC[C@H](OC(=O)N5CC(O)C5)CC4)(CC2)CC3)cn1] | 4-((4-(1-(tert-Butyl)-1H-pyrazol-4-yl)pyridin-2-yl)((4-(6-(dimethylamino)pyridin-3-yl)bicyclo[2.2.2]octan-1-yl)methyl)carbamoyl)(trans-cyclohexyl) 3-hydroxyazetidine-1-carboxylate | 684.6 |
| 3.07 | 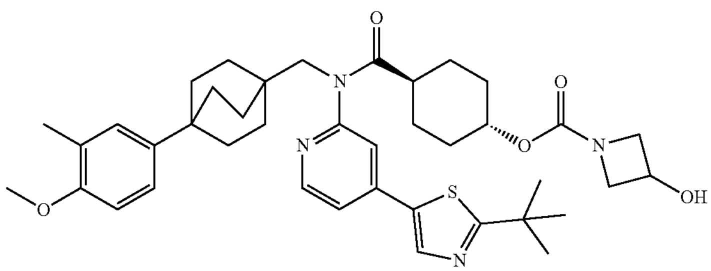 [SMILES: COc1ccc(C23CCC(CN(c4cc(-c5cnc(C(C)(C)C)s5)ccn4)C(=O)[C@H]4CC[C@H](OC(=O)N5CC(O)C5)CC4)(CC2)CC3)cc1C] | 4-((4-(2-(tert-Butyl)thiazol-5-yl)pyridin-2-yl)((4-(4-methoxy-3-methyphenyl)bicyclo[2.2.2]octan-1-yl)methyl)carbamoyl)cyclohexyl trans-3-hydroxyazetidine-1-carboxylate | 701.8 |
| 3.08 | 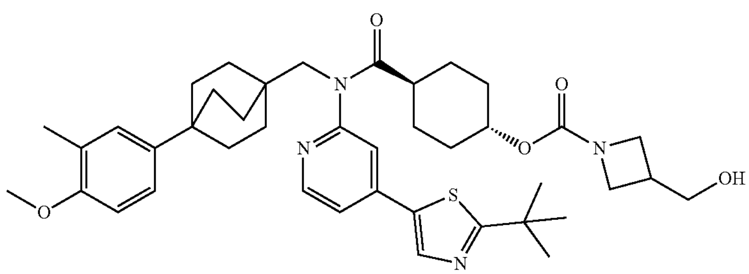 [SMILES: COc1ccc(C23CCC(CN(c4cc(-c5cnc(C(C)(C)C)s5)ccn4)C(=O)[C@H]4CC[C@H](OC(=O)N5CC(CO)C5)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)(trans-cyclohexyl) 3-(hydroxymethyl)azetidine-1-carboxylate | 715.2 |
| 3.09 | 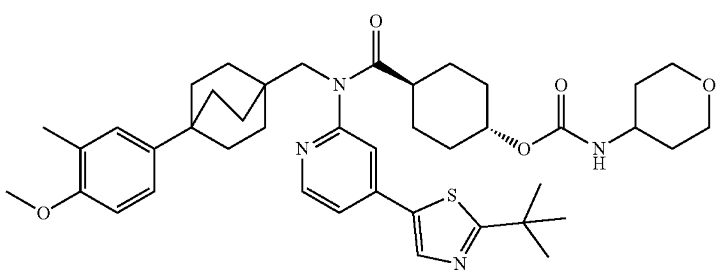 [SMILES: COc1ccc(C23CCC(CN(c4cc(-c5cnc(C(C)(C)C)s5)ccn4)C(=O)[C@H]4CC[C@H](OC(=O)NC5CCOCC5)CC4)(CC2)CC3)cc1C] | 4-((4-(2-(tert-Butyl)thiazol-5-yl)pyridin-2-yl)((4-(4-methoxy-3-methylphenyl)bicyclo[2.2.2]octan-1-yl)methyl)carbamoyl)cyclohexyl (tetrahydro-2H-pyran-4-yl)trans-carbamate | 729.9 |
| 3.10 | 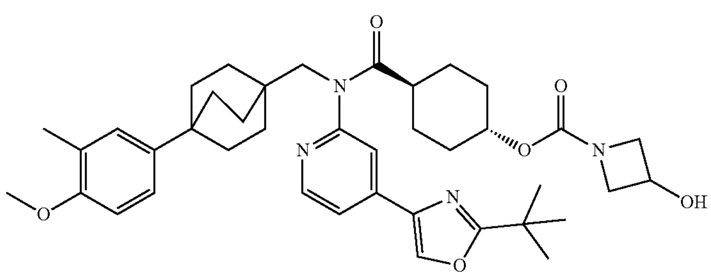 [SMILES: COc1ccc(C23CCC(CN(c4cc(-c5coc(C(C)(C)C)n5)ccn4)C(=O)[C@H]4CC[C@H](OC(=O)N5CC(O)C5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl 3-hydroxyazetidine-trans-1-carboxylate | 685.3 |

-continued

| Cmpd | Structure | Name | [M + H]+ |
|---|---|---|---|
| 3.11 | 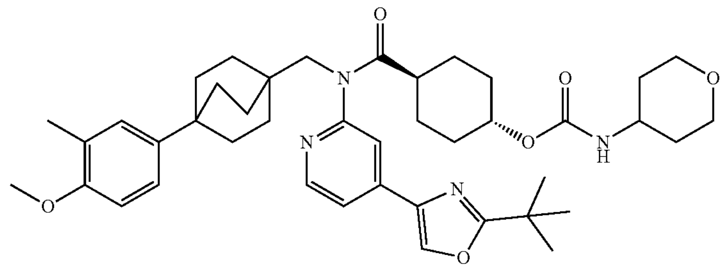 [SMILES: COc1ccc(C23CCC(CN(c4cc(-c5coc(C(C)(C)C)n5)ccn4)C(=O)[C@H]4CC[C@H](OC(=O)NC5CCOCC5)CC4)(CC2)CC3)cc1C] | 4-((4-(2-(tert-Butyl)oxazol-4-yl)pyridin-2-yl)((4-(4-methoxy-3-methylphenyl)bicyclo[2.2.2]octan-1-yl)methyl)carbamoyl)cyclohexyl (tetrahydro-2H-pyran-4-yl)trans-carbamate | 713.1 |
| 3.12 | 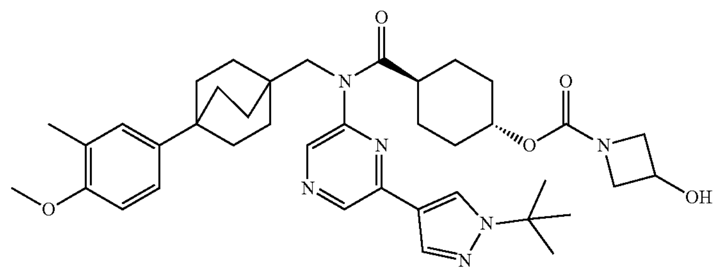 [SMILES: COc1ccc(C23CCC(CN(c4cncc(-c5cnn(C(C)(C)C)c5)n4)C(=O)[C@H]4CC[C@H](OC(=O)N5CC(O)C5)CC4)(CC2)CC3)cc1C] | 4-((6-(1-(tert-Butyl)-1H-pyrazol-4-yl)pyrazin-2-yl)((4-(4-methoxy-3-methylphenyl)bicyclo[2.2.2]octan-1-yl)methyl)carbamoyl)(trans-cyclohexyl) 3-hydroxyazetidine-1-carboxylate | 685.5 |
| 3.13 | 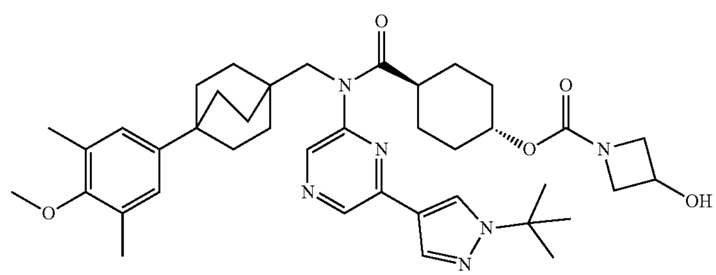 [SMILES: COc1c(C)cc(C23CCC(CN(c4nccc(-c5cnn(C(C)(C)C)c5)n4)C(=O)[C@H]4CC[C@H](OC(=O)N5CC(O)C5)CC4)(CC2)CC3)cc1C] | 4-((6-(1-(tert-Butyl)-1H-pyrazol-4-yl)pyrazin-2-yl)((4-(4-methoxy-3,5-dimethylphenyl)bicyclo[2.2.2]octan-1-yl)methyl)carbamoyl)(trans-cyclohexyl) 3-hydroxyazetidine-1-carboxylate | 699.2 |
| 3.14 | 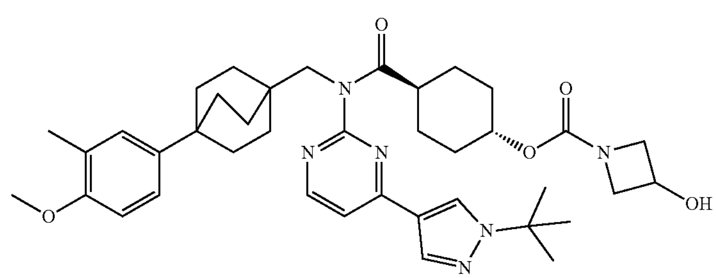 | 4-((4-(1-(tert-Butyl)-1H-pyrazol-4-yl)pyrimidin-2-yl)((4-(4-methoxy-3-methylphenyl)bicyclo[2.2.2]octan-1-yl)methyl)carbamoyl)(trans-cyclohexyl) 3-hydroxyazetidine-1-carboxylate | 685.6 |
| 3.15 | 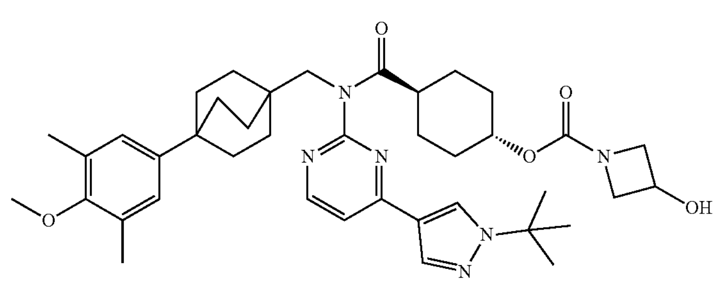 | 4-((4-(1-(tert-Butyl)-1H-pyrazol-4-yl)pyrimidin-2-yl)((4-(4-methoxy-3,5-dimethylphenyl)bicyclo[2.2.2]octan-1-yl)methyl)carbamoyl)(trans-cyclohexyl) 3-hydroxyazetidine-1-carboxylate | 699.6 |

Alternative conditions: Step 1a: rt-60° C.; 3-24 h; In some instances, 1 equiv AcOH was used. Step 1b: rt-30° C.; 16 h-4 days. Step 2: toluene/CH$_2$Cl$_2$ (2:1) as solvent; 0-80° C.; 15 min-5 h; In some instances, no DMAP was used. Step 3: 1-5 h; In some instances, 6 equiv aq. HCl was used. Step 4a: In some instances, more than 1.5 equiv CDI needed for full conversion to acyl imidazole; rt-80° C.; 1-18 h. Step 4b: 1.5 h-5 days; iPr$_2$NEt typically added prior to amine; No iPr$_2$NEt used when amine was a free base.

Compound 4

4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl trans-3-hydroxyazetidine-1-carboxylate

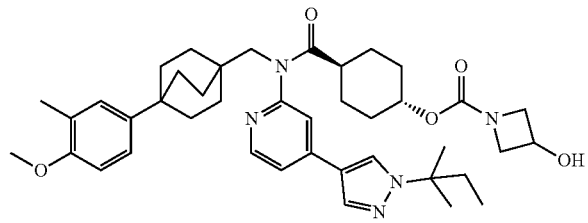 [SMILES: CCC(C)(C)n1cc(-c2ccnc(N(CC34CCC(c5ccc(OC)c(C)c5)(CC3)CC4)C(=O)[C@H]3CC[C@H](OC(=O)N4CC(O)C4)CC3)c2)cn1]

Step 1: 7V-((4-(4-Methoxy-3-methylphenyl)bicyclo[2.2.2]octan-1-yl)methyl)-4-(1-(tert-pentyl)-1H-pyrazol-4-yl)pyridin-2-amine Sodium triacetoxyborohydride (689.1 mg, 3.25 mmol) was added to a solution of Intermediate 2 (420.0 mg, 1.63 mmol), Intermediate 9 (449.3 mg, 1.95 mmol), and 1,2-dichloroethane (10 mL) at 0° C. under $N_2$. The mixture was allowed to stir at rt overnight, diluted with sat'd $NaHCO_3$ (20 mL), and then extracted with $CH_2Cl_2$ (20 mL×3). The combined organic layers were washed with brine (20 mL), dried over $Na_2SO_4$, filtered, concentrated, and then purified by silica gel chromatography ($CH_2Cl_2/CH_3OH$=80/1→50/1) to give N-(4-(4-methoxy-3-methylphenyl)bicyclo[2.2.2]octan-1-yl)methyl)-4-(1-(tert-pentyl)-1H-pyrazol-4-yl)pyridin-2-amine (600 mg, 78%) as a red solid. $^1$H NMR (400 MHz, $CDCl_3$): δ 7.86-7.82 (m, 3H), 7.11 (s, 1H), 7.09 (s, 1H), 6.80-6.63 (m, 3H), 6.60-6.55 (m, 1H), 3.81 (s, 3H), 3.10 (d, 2H), 2.22 (s, 3H), 1.98-1.90 (m, 2H), 1.84-1.83 (m, 5H), 1.65-1.62 (m, 13H), 0.76-0.67 (m, 3H).

Step 2: tert-4-((tert-Butyldimethylsilyl)oxy)-N-((4-(4-methoxy-3-methylphenyl)bicyclo[2.2.2]octan-1-yl)methyl)-N-(4-(1-(tert-pentyl)-1H-pyrazol-4-yl)pyridin-2-yl)cyclohexanecarboxamide Propylphosphonic anhydride solution (50% purity in EtOAc, 1.4 mL, 2.28 mmol) was added to a mixture of N-((4-(4-methoxy-3-methylphenyl)bicyclo[2.2.2]octan-1-yl)methyl)-4-(1-(tert-pentyl)-1H-pyrazol-4-yl)pyridin-2-amine (400.0 mg, 0.85 mmol), $Et_3N$ (0.48 mL, 3.39 mmol), DMAP (31.0 mg, 0.25 mmol), Intermediate 10 (415.5 mg, 4.61 mmol), and $CH_2Cl_2$ (10 mL). The mixture was stirred at 40° C. for 3 h, poured into water (10 mL), and then extracted with $CH_2Cl_2$ (10 mL×4). The combined organic layers were washed with brine (10 mL), dried over $Na_2SO_4$, filtered, and then purified by silica gel chromatography ($CH_2Cl_2/CH_3OH$=200/1→150/1) to give tert-4-((tert-butyldimethylsilyl)oxy)-N-((4-(4-methoxy-3-methylphenyl)bicycle[2.2.2]octan-1-yl)methyl)-N-(4-(1-(tert-pentyl)-1H-pyrazol-4-yl)pyridin-2-yl)cyclohexanecarboxamide (700 mg, 77%) as a red solid. $^1$H NMR (400 MHz, $CDCl_3$): δ 8.43 (d, 1H), 7.91 (s, 1H), 7.88 (s, 1H), 7.30-7.27 (m, 2H), 7.04-7.02 (m, 2H), 7.72 (d, 1H), 3.80-3.79 (m, 1H), 3.78 (s, 3H), 3.60-3.55 (m, 2H), 2.32-2.18 (m, 2H), 2.05 (s, 3H), 2.00-1.96 (m, 15H), 1.82 (s, 6H), 1.73-1.64 (m, 4H), 1.04-1.12 (m, 2H), 0.89-0.87 (m, 9H), 0.79-0.75 (m, 3H), 0.064 (s, 6H); LCMS: 713.6 [M+H]$^+$.

Step 3: tert-4-Hydroxy-7V-((4-(4-methoxy-3-methylphenyl)bicyclo[2.2.2]octan-1-yl)methyl)-N-(4-(1-(tert-pentyl)-1H-pyrazol-4-yl)pyridin-2-yl)cyclohexanecarboxamide Aqueous hydrochloric acid (1 M, 0.56 mL, 0.56 mmol) was added dropwise to a solution of tert-((tert-butyldimethylsilyl)oxy)-N-((4-(4-methoxy-3-methylphenyl)bicycle[2.2.2]octan-1-yl)methyl)-N-(4-(1-(tert-pentyl)-1H-pyrazol-4-yl)pyridin-2-yl)cyclohexanecarboxamide (400 mg, 0.56 mmol), THF (5 mL), and $CH_3OH$ (5 mL) at 0° C. The mixture was stirred at rt for 4 h, poured into sat'd $NaHCO_3$ (20 mL), and then extracted with ethyl acetate (20 mL×3). The combined organic layers were washed with brine (20 mL), dried over $Na_2SO_4$, filtered, concentrated, and then purified by silica gel chromatography (petroleum ether/ethyl acetate=10/0→3/1) to give tert-4-hydroxy-N-((4-(4-methoxy-3-methyl phenyl)bicyclo[2.2.2]octan-1-yl)methyl)-N-(4-(1-(tert-pentyl)-1H-pyrazol-4-yl)pyridin-2-yl)cyclohexanecarboxamide (370 mg, 63%) as a white solid. $^1$H NMR (400 MHz, DMSO-$d_6$): δ 8.59 (s, 1H), 8.41 (d, 1H), 8.16 (s, 1H), 7.73 (s, 1H), 7.58 (d, 1H), 7.01-6.95 (m, 2H), 6.72 (d, 1H), 4.41 (d, 1H), 3.71-3.70 (m, 5H), 3.33-3.32 (m, 1H), 2.24-2.22 (m, 1H), 2.08 (s, 3H), 1.88-1.86 (m, 2H), 1.62-1.60 (m, 4H), 1.58-1.54 (m, 12H), 1.37-1.34 (m, 8H), 0.83-0.80 (m, 2H), 0.65 (t, 3H); LCMS: 599.4 [M+H]$^+$.

Step 4: tert-4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl 3-hydroxy azetidine-1-carboxylate 1,1'-Carbonyldiimidazole (60.9 mg, 0.37 mmol) was added at rt to a solution of tert-4-hydroxy-N-((4-(4-methoxy-3-methylphenyl)bicyclo[2.2.2]octan-1-yl)methyl)-N-(4-(1-(tert-pentyl)-1H-pyrazol-4-yl)pyridin-2-yl)cyclohexanecarboxamide (150.0 mg, 0.25 mmol) and $CH_3CN$ (5 mL). The mixture was stirred at 80° C. overnight and cooled to rt. N,N-Diisopropylethylamine (71.2 mg, 0.55 mmol) and then azetidin-3-ol hydrochloride (54.9 mg, 0.50 mmol) and were added. The mixture was stirred at rt overnight, poured into $H_2O$ (10 mL), and then extracted with ethyl acetate (10 mL×4). The organic layer was washed with brine (10 mL), dried over $Na_2SO_4$, filtered, concentrated, and then purified by prep-HPLC (water (0.04% HCl)—$CH_3CN$) to give tert-4-(((4-(4-methoxy-3-methylphenyl)bicyclo[2.2.2]octan-1-yl)methyl)(4-(1-(tert-pentyl)-1H-pyrazol-4-yl)pyri din-2-yl)carbamoyl)cyclohexyl 3-hydroxyazetidine-1-carboxylate (80.5 mg, 45%). $^1$H NMR (400 MHz, DMSO-$d_6$): δ 8.59 (s, 1H), 8.40 (d, 1H), 8.16 (s, 1H), 7.74 (s, 1H), 7.58 (d, 1H), 7.00-6.97 (m, 2H), 6.76 (d, 1H), 5.75-5.73 (m, 1H), 4.74-4.35 (m, 2H), 3.99-3.95 (m, 2H), 3.72-3.70 (m, 5H), 3.57-3.54 (m, 2H), 2.33-2.22 (m, 1H), 2.08 (s, 3H), 2.88-2.84 (m, 6H), 1.62-1.57 (m, 7H), 1.54 (s, 6H), 1.38-1.37 (m, 1H), 1.36-1.34 (m, 6H), 1.07-0.91 (m, 2H), 0.65 (t, 3H); LCMS: 698.5 [M+H]$^+$ The Compounds below were synthesized from the appropriate Intermediates following the procedures described for Compound 4.

| Cmpd | Structure | Name | [M + H]+ |
|---|---|---|---|
| 4.01 | 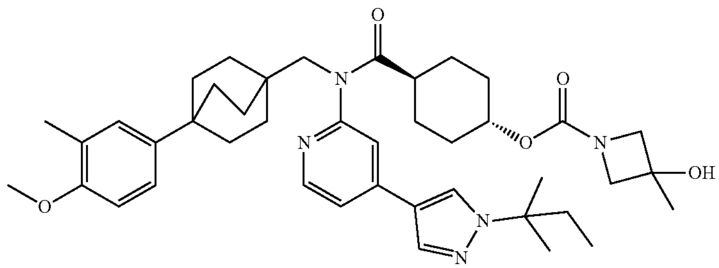 [SMILES: CCC(C)(C)n1cc(-c2ccnc(N(CC34CCC(c5ccc(OC)c(C)c5)(CC3)CC4)C(=O)[C@H]3CC[C@H](OC(=O)N4CC(C)(O)C4)CC3)c2)cn1] | 4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl trans-3-hydroxy-3-methylazetidine-1-carboxylate | 712.4 |
| 4.02 | 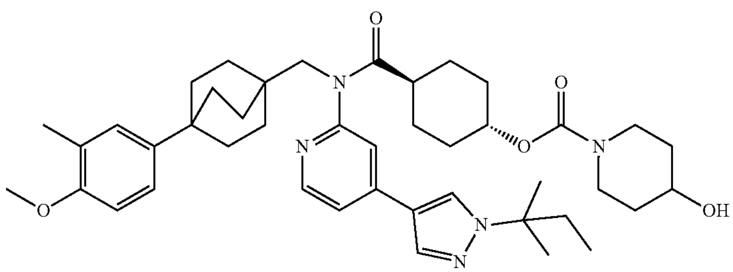 | 4-(((4-(4-Methoxy-3-methylphenyl)bicyclo[2.2.2]octan-1-yl)methyl)(4-(1-(tert-pentyl)-1H-pyrazol-4-yl)pyridin-2-yl)carbamoyl)cyclohexyl trans-4-hydroxypiperidine-1-carboxylate | 726.5 |
| 4.03 | 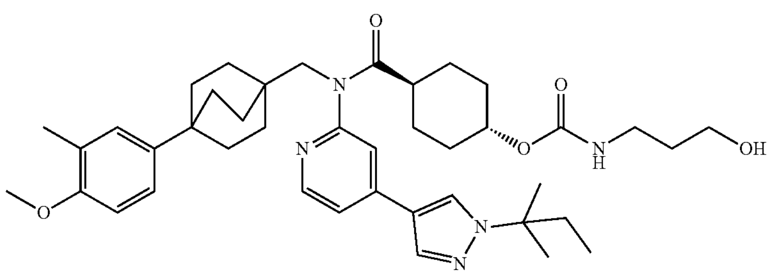 [SMILES: CCC(C)(C)n1cc(-c2ccnc(N(CC34CCC(c5ccc(OC)c(C)c5)(CC3)CC4)C(=O)[C@H]3CC[C@H](OC(=O)NCCCO)CC3)c2)cn1] | 4-(((4-(4-Methoxy-3-methylphenyl)bicyclo[2.2.2]octan-1-yl)methyl)(4-(1-(tert-pentyl)-1H-pyrazol-4-yl)pyridin-2-yl))carbamoyl)cyclohexyl trans-(3-hydroxypropyl)carbamate | 700.5 |
| 4.04 | 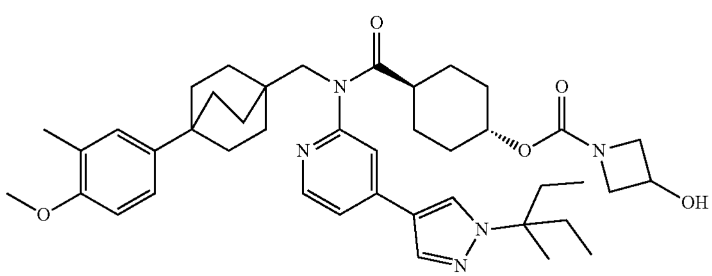 [SMILES: CCC(C)(CC)n1cc(-c2ccnc(N(CC34CCC(c5ccc(OC)c(C)c5)(CC3)CC4)C(=O)[C@H]3CC[C@H](OC(=O)N4CC(O)C4)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-3-hydroxyazetidine-1-carboxylate | 712.5 |
| 4.05 | 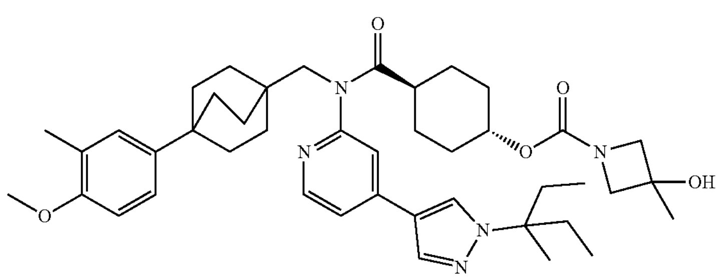 [SMILES: CCC(C)(CC)n1cc(-c2ccnc(N(CC34CCC(c5ccc(OC)c(C)c5)(CC3)CC4)C(=O)[C@H]3CC[C@H](OC(=O)N4CC(C)(O)C4)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-3-hydroxy-3-methylazetidine-1-carboxylate | 726.2 |

-continued

| Cmpd | Structure | Name | [M + H]+ |
|---|---|---|---|
| 4.06 | 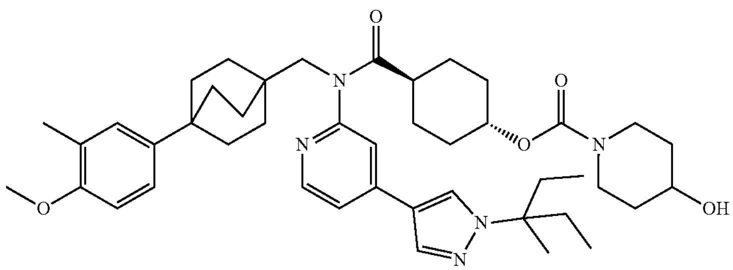 [SMILES: CCC(C)(CC)n1cc(-c2ccnc(N(CC34CCC(c5ccc(OC)c(C)c5)(CC3)CC4)C(=O)[C@H]3CC[C@H](OC(=O)N4CCC(O)CC4)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-4-hydroxypiperidine-1-carboxylate | 740.2 |
| 4.07 | 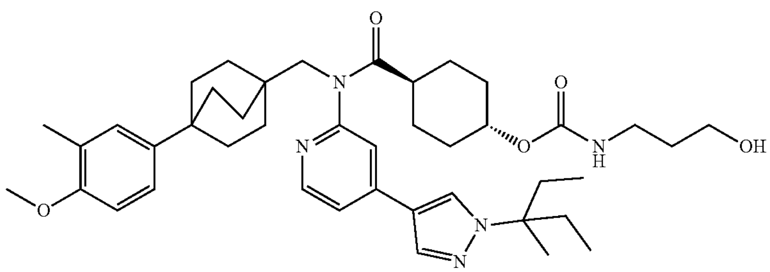 [SMILES: CCC(C)(CC)n1cc(-c2ccnc(N(CC34CCC(c5ccc(OC)c(C)c5)(CC3)CC4)C(=O)[C@H]3CC[C@H](OC(=O)NCCCO)CC3)c2)cn1] | 4-(((4-(4-Methoxy-3-methylphenyl)bicyclo[2.2.2]octan-1-yl)methyl)(4-(1-(3-methylpentan-3-yl)-1H-pyrazol-4-yl)pyridin-2-yl)carbamoyl)cyclohexyl trans-(3-hydroxypropyl)carbamate | 714.5 |
| 4.08 | 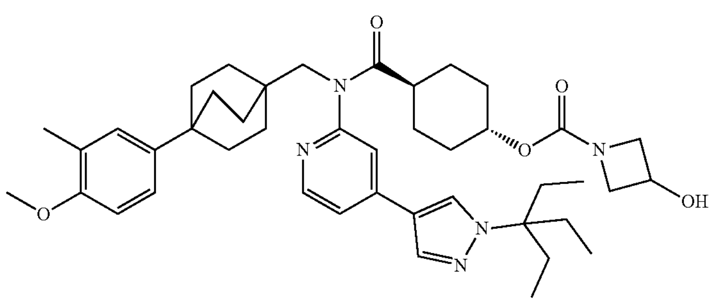 [SMILES: CCC(CC)(CC)n1cc(-c2ccnc(N(CC34CCC(c5ccc(OC)c(C)c5)(CC3)CC4)C(=O)[C@H]3CC[C@H](OC(=O)N4CC(O)C4)CC3)c2)cn1] | 4-((4-(1-(3-Ethylpentan-3-yl)-1H-pyrazol-4-yl)pyridin-2-yl)((4-(4-methoxy-3-methylphenyl)bicyclo[2.2.2]octan-1-yl)methyl)carbamoyl)cyclohexyl trans-3-hydroxyazetidine-1-carboxylate | 726.2 |
| 4.09 | 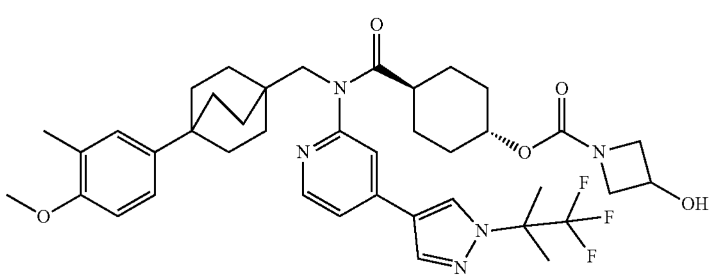 [SMILES: COc1ccc(C23CCC(CN(c4cc(-c5cnn(C(C)(C)C(F)(F)F)c5)ccn4)C(=O)[C@H]4CC[C@H](OC(=O)N5CC(O)C5)CC4)(CC2)CC3)cc1C] | 4-(((4-(4-Methoxy-3-methylphenyl)bicyclo[2.2.2]octan-1-yl)methyl)(4-(1-(1,1,1-trifluoro-2-methylpropan-2-yl)-1H-pyrazol-4-yl)pyridin-2-yl)carbamoyl)cyclohexyl trans-3-hydroxyazetidine-1-carboxylate | 738.5 |
| 4.10[1] | 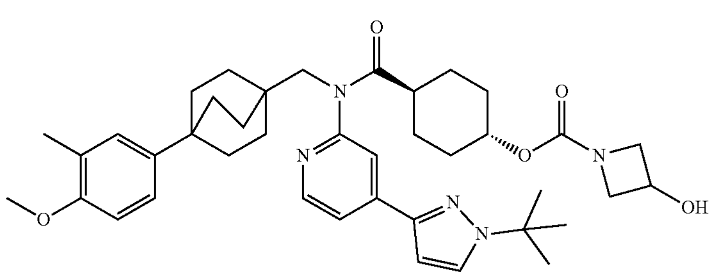 [SMILES: COc1ccc(C23CCC(CN(c4cc(-c5ccn(C(C)(C)C)n5)ccn4)C(=O)[C@H]4CC[C@H](OC(=O)N5CC(O)C5)CC4)(CC2)CC3)cc1C] | 4-((4-(1-(tert-Butyl)-1H-pyrazol-3-yl)pyridin-2-yl)((4-(4-methoxy-3-methylphenyl)bicyclo[2.2.2]octan-1-yl)methyl)carbamoyl)cyclohexyl trans-3-hydroxyazetidine-1-carboxylate | 684.6 |

| Cmpd | Structure | Name | [M + H]+ |
|---|---|---|---|
| 4.11[1] | 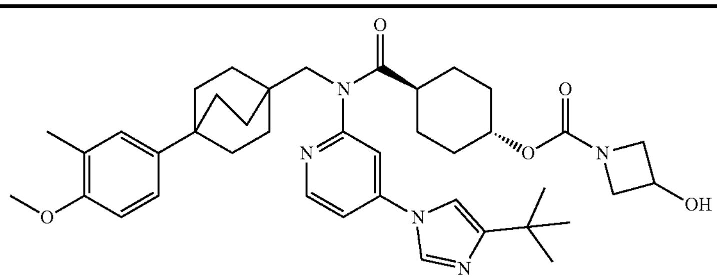 | 4-((4-(4-(tert-Butyl)-1H-imidazol-1-yl)pyridin-2-yl)((4-(4-methoxy-3-methylphenyl)bicyclo[2.2.2]octan-1-yl)methyl)carbamoyl)cyclohexyl trans-3-hydroxyazetidine-1-carboxylate | 684.6 |

Alternate conditions: Step 2: [1]No DMAP was used; overnight. Step 3: 1-4 h. Step 4a: 3.5 h-overnight; 50-80° C.; In some instances, more than 1.5 equiv CDI needed for full conversion to acyl imidazole; Step 4b: 1 h-overnight: No iPr2NEt used when amine was a free base.

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example A-2: Oral Solution

To prepare a pharmaceutical composition for oral delivery, a sufficient amount of a compound described herein, or a pharmaceutically acceptable salt thereof, is added to water (with optional solubibzer(s), optional buffer(s), and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Example B-1: In Vitro FXR Assay (TK)

Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 μL OptiMEM (Life Technologies, Cat #31985-062) was combined with expression plasmids for hFXR, hRXR, TK-ECRE-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Representative data for exemplary compounds disclosed herein is presented in Table 2.

TABLE 2

| Cmpd | TK hFXR: EC50 |
|---|---|
| 1 | ++ |
| 1.01 | ++ |
| 1.02 | ++ |
| 1.03 | ++ |
| 1.04 | ++ |
| 1.05 | ++ |
| 1.06 | ++ |
| 1.07 | ++ |
| 1.08 | ++ |
| 1.09 | +++ |
| 1.10 | ++ |
| 1.11 | ++ |
| 1.12 | +++ |

TABLE 2-continued

| Cmpd | TK hFXR: EC50 |
|---|---|
| 1.13 | ++ |
| 1.14 | +++ |
| 1.15 | ++ |
| 2 | +++ |
| 2.01 | +++ |
| 2.02 | +++ |
| 2.03 | +++ |
| 2.04 | +++ |
| 2.05 | +++ |
| 2.06 | +++ |
| 2.07 | +++ |
| 2.08 | +++ |
| 2.09 | ++ |
| 2.10 | +++ |
| 2.11 | +++ |
| 2.12 | +++ |
| 2.13 | +++ |
| 2.14 | +++ |
| 2.15 | +++ |
| 2.16 | ++ |
| 2.17 | +++ |
| 2.18 | ++ |
| 2.19 | +++ |
| 2.20 | +++ |
| 2.21 | +++ |
| 2.22 | +++ |
| 2.23 | +++ |
| 2.24 | +++ |
| 2.25 | +++ |
| 2.26 | +++ |
| 2.27 | +++ |
| 2.28 | +++ |
| 2.29 | ++ |
| 2.30 | +++ |
| 2.31 | +++ |
| 2.32 | +++ |
| 2.33 | +++ |
| 2.34 | +++ |
| 2.35 | ++ |
| 2.36 | ++ |
| 2.37 | ++ |
| 2.38 | ++ |
| 2.39 | ++ |
| 3 | +++ |
| 3.01 | +++ |
| 3.02 | +++ |
| 3.03 | +++ |
| 3.04 | +++ |
| 3.05 | +++ |
| 3.06 | ++ |
| 3.07 | +++ |
| 3.08 | +++ |
| 3.09 | ++ |
| 3.10 | +++ |
| 3.11 | +++ |
| 3.12 | ++ |
| 3.13 | ++ |
| 3.14 | ++ |
| 3.15 | ++ |
| 4 | +++ |
| 4.01 | +++ |
| 4.02 | +++ |
| 4.03 | +++ |
| 4.04 | +++ |
| 4.05 | +++ |
| 4.06 | +++ |
| 4.07 | +++ |
| 4.08 | ++ |
| 4.09 | +++ |
| 4.10 | ++ |
| 4.11 | ++ |

'+++' means $EC_{50} \leq 0.01$ μM;
'++' means $EC_{50} > 0.01$ μM & <1 μM.

Example B-2: In Vitro FXR Assay (hSHP)

Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 μL OptiMEM (Life Technologies, Cat #31985-062) was combined with expression plasmids for hFXR, hRXR, hSHP-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Example B-3: NASH Activity Study (STZ Model)

NASH can be induced in male C57BL/6 by a single subcutaneous injection of 200 ug STZ 2 days after birth followed by feeding high fat diet (HFD) ad libitum after 4 weeks of age. While continuing HFD, compounds can be dosed for 4-8 weeks to determine the effects on NASH. Fasting glucose can be measured throughout the study with a hand-held glucose meter. Serum alanine aminotransferase (ALT), aspartate aminotransferase (AST) and triglyceride (TG) can be measured by a clinical chemistry analyzer. The contents of TG in the liver tissue can be measured using the Triglyceride E-test kit (Wako, Tokyo, Japan). Histological analysis of liver sections can be performed on tissue embedded in Tissue-TEK O.C.T. compound, snap frozen in liquid nitrogen, and stored at −80° C. The sections can be cut (5 um), air dried and fixed in acetone. For hematoxylin and eosin staining, liver sections can be prefixed by Bouin's solution and then stained with hematoxylin and eosin solution. The degree of (zone-3) liver fibrosis can be assessed with Sirius red staining.

Example B-4: NASH Activity Study (AMLN Model)

NASH is induced in male C57BL/6 mice by diet-induction with AMLN diet (DIO-NASH) (D09100301, Research Diet, USA) (40% fat (18% trans-fat), 40% carbohydrates (20% fructose) and 2% cholesterol). The animals are kept on the diet for 29 weeks. After 26 weeks of diet induction, liver biopsies are performed for base line histological assessment of disease progression (hepatosteatosis and fibrosis), stratified and randomized into treatment groups according to liver fibrosis stage, steatosis score, and body weight. Three weeks after biopsy the mice are stratified into treatment groups and dosed daily by oral gavage with FXR agonists for 8 weeks. At the end of the study liver biopsies are performed to assess hepatic steatosis and fibrosis by examining tissue sections stained with H&E and Sirius Red, respectively. Total collagen content in the liver is measured by colorimetric determination of hydroxyproline residues by acid hydrolysis of collagen. Triglycerides and total cholesterol content in liver homogenates are measured in single determinations using

Example B-5: CCl₄ Fibrosis Model

Fibrosis can be induced in BALB/c male mice by biweekly administration of CCl₄ administered by intraperitoneal injection. CCl₄ is formulated 1:1 in oil and is injected IP at 1 mL/kg. After 2-4 weeks of fibrosis induction the compounds can be administered daily by oral gavage for 2-6 weeks of treatment while continuing CCl₄ administration. At study termination livers can be formalin fixed and stained with Sirius Red stain for histopathological evaluation of fibrosis. Total collagen content can be measured by colorimetric determination of hydroxyproline residues by acid hydrolysis of collagen. Serum alanine aminotransferase (ALT) and aspartate aminotransferase (AST) can be measured by a clinical chemistry analyzer.

Example B-6: Intrahepatic Cholestasis Model

Experimental intrahepatic cholestasis induced by 17a-ethynylestradiol (EE2) treatment in rodents is a widely used in vivo model to examine the mechanisms involved in estrogen-induced cholestasis. Intrahepatic cholestasis can be induced in adult male mice by subcutaneous injection of 10 mg/kg 17a-ethynylestradiol (E2) daily for 5 days. Testing of FXR ligands can be performed by administration of compounds during E2 induction of cholestasis. Cholestatic effects can be quantitated by assessing liver/body weight ratio and measuring serum total bile acids and alkaline phosphatase levels can be measured using reagents and controls from Diagnostic Chemicals Ltd. and the Cobas Mira plus CC analyzer (Roche Diagnostics). For histology and mitosis measurements, liver samples from each mouse can be fixed in 10% neutral buffered formalin. Slides are stained with hematoxylin and eosin using standard protocols and examined microscopically for structural changes. Hepatocyte proliferation is evaluated by immunohistochemical staining for Ki67.

Example B-7: Direct Target Gene Regulation

Direct target gene regulation by FXR ligands can be assessed by dosing mice either acutely or chronically with compounds and collecting tissues at various time points after dosing. RNA can be isolated from tissues such as the ileum and liver, and reverse transcribed to cDNA for quantitative PCR analysis of genes known in the literature to be directly and indirectly regulated by FXR such as SHP, BSEP, IBABP, FGF15, CYP7A1, CYP8B1 and $C_3$.

Example B-8: Mouse PK Study

The plasma pharmacokinetics of any one of the compounds disclosed herein as a test article is measured following a single bolus intravenous and oral administration to mice (CD-1, C57BL, and diet induced obesity mice). Test article is formulated for intravenous administration in a vehicle solution of DMSO, PEG400, hydroxypropyl-β-cyclodextrin (HPβCD) and is administered (for example at a dose volume of 3 mL/kg) at selected dose levels. An oral dosing formulation is prepared in appropriate oral dosing vehicles (vegetable oils, PEG400, Solutol, citrate buffer, or carboxymethyl cellulose) and is administered at a dose volume of 5~10 mL/kg at selected dose levels. Blood samples (approximately 0.15 mL) are collected by cheek pouch method at pre-determined time intervals post intravenous or oral doses into tubes containing EDTA. Plasma is isolated by centrifugation of blood at 10,000 g for 5 minutes, and aliquots are transferred into a 96-well plate and stored at −60° C., or below until analysis.

Calibration standards of test article are prepared by diluting DMSO stock solution with DMSO in a concentration range. Aliquots of calibration standards in DMSO are combined with plasma from naïve mouse so that the final concentrations of calibration standards in plasma are 10-fold lower than the calibration standards in DMSO. PK plasma samples are combined with blank DMSO to match the matrix. The calibration standards and PK samples are combined with ice-cold acetonitrile containing an analytical internal standard and centrifuged at 1850 g for 30 minutes at 4° C. The supernatant fractions are analyzed by LC/MS/MS and quantitated against the calibration curve. Pharmacokinetic parameters (area under the curve (AUC), $C_{max}$, $T_{max}$, elimination half-life ($T_{1/2}$), clearance (CL), steady state volume of distribution ($V_{dss}$), and mean residence time (MRT)) are calculated via non-compartmental analysis using Microsoft Excel (version 2013).

Example B-9: Rat ANIT Model

A compound described herein is evaluated in a chronic treatment model of cholestasis over a range of doses (for example, doses in the range of 0.01 to 100 mg/kg). This model is used to evaluate the suitability of the use of FXR agonists, e.g., a compound described herein, for the treatment of cholestatic liver disorders such as bile acid malabsorption (e.g, primary or secondary bile acid diarrhea), bile reflux gastritis, collagenous colitis, lymphocytic colitis, diversion colitis, indeterminate colitis, Alagille syndrome, biliary atresia, ductopenic liver transplant rejection, bone marrow or stem cell transplant associated graft versus host disease, cystic fibrosis liver disease, and parenteral nutrition-associated liver disease.

Rats are treated with alpha-naphthylisothiocyanate (ANIT) (0.1% w/w) in food for 3 days prior to treatment with a compound described herein, at a range of doses (for example, doses in the range of 0.01 to 100 mg/kg). A noncholestatic control group is fed standard chow diet without ANIT and serves as the noncholestatic control animals ("Control"). After 14 days of oral dosing, rat serum is analyzed for levels of analytes. LLQ, lower limit of quantitation. Mean±SEM; n=5.

Levels of hepatobiliary injury indicators are measured in rat serum, such as elevated levels of circulating aspartate aminotransferase (AST), alanine aminotransferase (ALT), bilirubin and bile acids. ANIT exposure induces profound cholestasis and hepatocellular damage. A compound that improves many of these indicators is useful in the treatment of the aforementioned diseases or conditions.

Reductions in the accumulation of bile acids in the liver, enhancements in bile acid excretion in the biliary tract and inhibition of bile acid synthesis is consistent with the pharmacological action of an FXR agonist. An improvement in the serum conjugated bilirubin (a direct indicator for hepatic function) implies recovery from cholestasis with improved bile excretion.

Furthermore, an analysis is made to ascertain the effects of the compound described herein on serum FGF15 fibroblast growth factor 15 (FGF15 in rodent; FGF19 in human) expression, a hormone that is secreted in the portal blood and signals to the liver to repress CYP7A1 expression synergistically with SHP. The direct FXR-dependent induction of FGF15/19 along with FGF15/19's anti-cholestatic properties makes it a convenient serum biomarker for detecting target engagement of FXR agonists.

Serum FGF15 levels are quantified using an FGF15 Meso Scale Discovery (MSD) assay. For example, Mouse FGF15 antibody from R&D Systems (AF6755) is used both as capture and detection antibody in the assay. MSD SULFO-TAG NHS-Ester is used to label the FGF15 antibody. MSD standard 96-well plates are coated with the FGF15 capture antibody and the plates are blocked with MSD Blocker A (R93AA-2). After washing the plate with PBS+0.05% Tween 20, MSD diluent 4 is dispensed into each well and incubated for 30 min. 25 pi of calibrator dilutions or samples (serum or EDTA plasma) are dispensed into each well and incubated with shaking at RT.

After washing, detection antibody is added and incubated with shaking for 1 h at RT. After washing and the addition of MSD Read buffer (R92TC-2), the plate is read on an MSD SECTOR Imager 6000. Plots of the standard curve and unknown samples are calculated using MSD data analysis software.

The examples and embodiments described herein are for illustrative purposes only and various modifications or changes suggested to persons skilled in the art are to be included within the spirit and purview of this application and scope of the appended claims.

Example B-10: Mouse Chronic DSS Colitis Model

The chronic Dextran Sodium Sulfate (DSS)-induced mouse can be used to test the therapeutic potential of compounds against inflammatory bowel disease (IBD). Chronic colitis can be induced by feeding mice DSS in drinking water. For example, 2% DSS in drinking water for 5 days and regular drinking water for 5 days, then this feeding cycle can be repeated two more times with higher concentrations of DSS, 2.5% and 3%, respectively for a total of three cycles. Colitis develops approximately after the first cycle of DSS feeding, which can be monitored by loss of body weight, stool consistency and rectal bleeding. An FXR agonist can be tested by administering to mice at the same time of starting 2% DSS water feeding. Alternatively, testing of an FXR agonist can be performed post the first feeding cycle of 2% DSS water and regular water. During the period of administering the FXR agonist to mice, the therapeutic effects can be monitored by observations on body weights, stool consistency and rectal bleeding. After euthanasia, the disease development and effects of the FXR agonist can be further quantified by measuring colon weight and length, colon histology by H&E staining for inflammation and structural changes in mucosa, and protein and RNA expression of genes related to the disease.

Example B-11: Adoptive T-cell Transfer Colitis Mouse Model

The adoptive T-cell transfer colitis model is accepted as a relevant mouse model for human inflammatory bowel disease (IBD). To induce colitis in this model, the CD4 T-lymphocyte population is isolated from the spleens of donor mice, subsequently a subpopulation of CD4+CD45RB high T-cells is purified by cell sorting using flow cytometry. The purified CD4+CD45RB high T-cells are injected into the peritoneal cavity of the recipient SCID mice. Colitis develops approximately three to six weeks after T-cell transfer, which can be monitored by loss of body weight (although loss of body weight can be variable), inconsistent stool or bloody diarrhea. Testing of an FXR agonist can be initiated at the same time of injecting purified CD4+CD45RB high T-cells to the recipient SCID mice. Alternatively, the FXR agonist can be administered two or three weeks post T-cell transfer, when colitis has already developed in the model. During the period of administering the FXR agonist to mice, the therapeutic effects can be monitored by observations on body weights, stool consistency and rectal bleeding. After euthanasia, the disease development and effects of the FXR agonist can be further quantified by measuring colon weight and length, colon and ileum histology by H&E staining for inflammation and structural changes in mucosa, and protein and RNA expression of genes related to the disease.

Example B-12: Mdr1a−/− Mouse Model

The Mdr1a−/− mouse model is a spontaneous colitis model that has been used in testing new therapies for human IBD. Loss of the Mdr1a gene in this model leads to impaired intestinal barrier function, which results in increased infiltration of gut bacteria and subsequent colitis. Under proper housing conditions, Mdr1a−/− mice can develop colitis at about 8 to 13 weeks of age. During disease progression, a disease activity index (DAI) summing the clinical observation scores on rectal prolapse, stool consistency and rectal bleeding can be used to monitor the disease. Testing of an FXR agonist can be started at the initial stage of disease, generally with DAI score less than 1.0. Alternatively, administration of an FXR agonist can be initiated when colitis has developed, typically with a DAI score above 2.0. Therapeutic effects of the FXR agonist can be monitored by measuring the DAI, and testing can be terminated when desired disease severity has been achieved, generally with a DAI score around 5.0. After euthanasia, the disease development and effects of the FXR agonist can be further quantified by measuring colon weight and length, colon histology by H&E staining for inflammation and structural changes in mucosa, and protein and RNA expression of genes related to the disease.

The examples and embodiments described herein are for illustrative purposes only and various modifications or changes suggested to persons skilled in the art are to be included within the spirit and purview of this application and scope of the appended claims.

What is claimed is:
1. A method of treating a gastrointestinal disease or condition in a mammal, comprising administering to the mammal a compound of Formula (I'), or a pharmaceutically acceptable salt thereof:

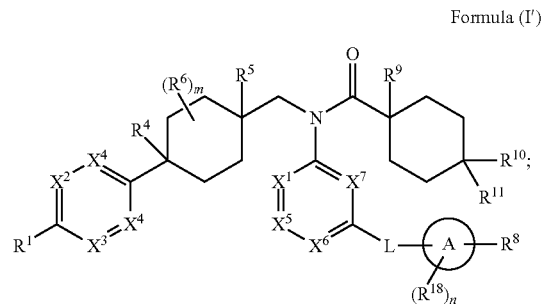

Formula (I')

wherein:
ring A is

[chemical structures of thiazole, oxazole, and pyrazole rings with R⁸ substituents]

$X^1$ is N;
$X^5$, $X^6$, and $X^7$ are each $CR^7$;
$R^1$ is selected from H, halogen, —CN, —OH, —N($R^{17}$)$_2$, —N$R^{17}$S(=O)$_2$(C$_1$-C$_4$alkyl), —S(=O)$_2$N($R^{17}$)$_2$, —OC(=O)(C$_1$-C$_4$alkyl), —CO$_2$H, —CO$_2$(C$_1$-C$_4$alkyl), —C(=O)N($R^{17}$)$_2$, —NR$^{17}$C(=O)(C$_1$-C$_4$alkyl), —NR$^{17}$C(=O)O(C$_1$-C$_4$alkyl), —OC(=O)N($R^{17}$)$_2$, —NR$^{15}$C(=O)N($R^{17}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, and monocyclic C$_2$-C$_5$heterocycloalkyl;
$X^2$ is $CR^2$;
$R^2$ is H, halogen, —CN, —OH, —N($R^{17}$)$_2$, —NR$^{17}$S(=O)$_2$(C$_1$-C$_4$alkyl), —S(=O)$_2$N($R^{17}$)$_2$, —OC(=O)(C$_1$-C$_4$alkyl), —CO$_2$H, —CO$_2$(C$_1$-C$_4$alkyl), —C(=O)N($R^{17}$)$_2$, —NR$^{17}$C(=O)(C$_1$-C$_4$alkyl), —NR$^{17}$C(=O)O(C$_1$-C$_4$alkyl), —OC(=O)N($R^{17}$)$_2$, —NR$_{17}$C(=O)N($R^{17}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, or monocyclic C$_2$-C$_5$heterocycloalkyl;
$X^3$ is $CR^3$;
$R^3$ is H, halogen, —CN, —OH, —N($R^{17}$)$_2$, —NR$^{17}$S(=O)$_2$(C$_1$-C$_4$alkyl), —OC(=O)(C$_1$-C$_4$alkyl), —CO$_2$H, —CO$_2$(C$_1$-C$_4$alkyl), —C(=O)N($R^{17}$)$_2$, —NR$^{17}$C(=O)(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, or C$_1$-C$_4$heteroalkyl;
each $X^4$ is independently CH or CF;
$R^4$ and $R^5$ are taken together to form a bridge that is —CH$_2$— or —CH$_2$CH$_2$—;
each $R^6$ is independently H, F, —OH, or —CH$_3$;
L is absent;
each $R^7$ is independently selected from H, halogen, —CN, —OH, C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_3$-C$_6$cycloalkyl, and C$_1$-C$_4$heteroalkyl;
$R^8$ is C$_4$-C$_8$alkyl or C$_4$-C$_8$haloalkyl;
$R^9$ is H, F, or —CH$_3$;
$R^{10}$ is —OC(=O)N($R^{12}$)($R^{13}$);
$R^{11}$ is H F or —CH$_3$.
$R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N(C$_1$-C$_4$alkyl)$_2$, C$_1$-C$_6$alkyl, C$_1$-C$_6$alkoxy, —S(C$_1$-C$_4$alkyl), —S(=O)(C$_1$-C$_4$alkyl), —S(=O)$_2$(C$_1$-C$_4$alkyl), —C$_1$-C$_4$alkyl-S(=O)$_2$(C$_1$-C$_4$alkyl), —C$_1$-C$_6$alkyl-OR$^{17}$, and —O—C$_1$-C$_6$alkyl-OR$^{17}$;

each $R^{17}$ is independently H or C$_1$-C$_6$alkyl;
each $R^{18}$ is independently halogen, —CN, —OH, —N($R^{17}$)$_2$, —NR$_{17}$S(=O)$_2$(C$_1$-C$_4$alkyl), —S(C$_1$-C$_4$alkyl), —S(=O)(C$_1$-C$_4$alkyl), —S(=O)$_2$(C$_1$-C$_4$alkyl), —S(=O)$_2$N($R^{17}$)$_2$, —C(=O)(C$_1$-C$_4$alkyl), —OC(=O)(C$_1$-C$_4$alkyl), —CO$_2$H, —CO$_2$(C$_1$-C$_4$alkyl), —NR$^{17}$C(=O)(C$_1$-C$_4$alkyl), —C(=O)N($R^{17}$)$_2$, —NR$^{17}$C(=O)O(C$_1$-C$_4$alkyl), —OC(=O)N($R^{17}$)$_2$, C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, C$_1$-C$_4$heteroalkyl, C$_3$-C$_6$cycloalkyl, monocyclic C$_2$-C$_6$heterocycloalkyl, phenyl, or monocyclic heteroaryl;
m is 0, 1, or 2; and
n is 0, 1, or 2.

2. The method of claim 1, or a pharmaceutically acceptable salt thereof, wherein the compound has the structure of Formula (Ia'), or a pharmaceutically acceptable salt thereof:

[chemical structure of Formula (Ia')]

Formula (Ia')

3. The method of claim 1, wherein $R^{12}$ and $R^{13}$ are taken together to form a 4-, 5-, or 6-membered heterocycloalkyl ring optionally containing an additional heteroatom selected from O, S, and N and optionally substituted with 1, 2, or 3 groups selected from —OH, —N(C$_1$-C$_4$alkyl)$_2$, C$_1$-C$_6$alkyl, C$_1$-C$_6$alkoxy, —S(=O)$_2$(C$_1$-C$_4$alkyl), —C$_1$-C$_4$alkyl-S(=O)$_2$(C$_1$-C$_4$alkyl), —C$_1$-C$_6$alkyl-OR$^{17}$, and —O—C$_1$-C$_6$alkyl-OR$^{17}$.

4. The method of claim 3, wherein $R^8$ is C$_4$-C$_8$alkyl.

5. The method of claim 4, wherein $R^4$ and $R^5$ are taken together to form a bridge that is —CH$_2$CH$_2$—.

6. The method of claim 5, wherein $R^{12}$ and $R^{13}$ are taken together to form a 4-membered or 5-membered heterocycloalkyl ring optionally containing an additional heteroatom selected from O, S, and N and optionally substituted with 1 or 2 groups selected from —OH, —N(C$_1$-C$_4$alkyl)$_2$, C$_1$-C$_6$alkyl, and C$_1$-C$_6$alkoxy.

7. The method of claim 6, wherein each $X^4$ is CH.

8. The method of claim 7, wherein $X^3$ is CH.

9. The method of claim 8, wherein $X^2$ is $CR^2$ and $R^2$ is C$_1$-C$_4$alkyl.

10. The method of claim 9, wherein $R^1$ is C$_1$-C$_4$alkoxy.

11. The method of claim 10, wherein m is 0.

12. The method of claim 11, wherein $R^9$ is H, $R^{11}$ is H, and $R^7$ is H.

13. A method of treating a gastrointestinal disease or condition in a mammal, comprising administering to the mammal a compound selected from:

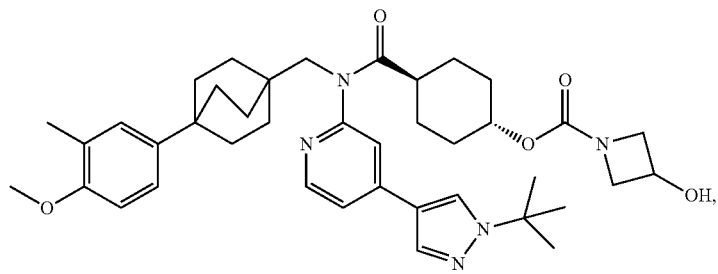
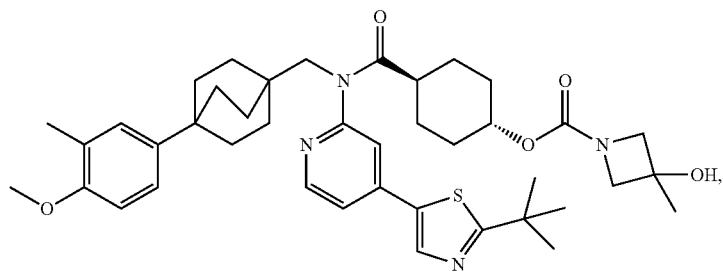
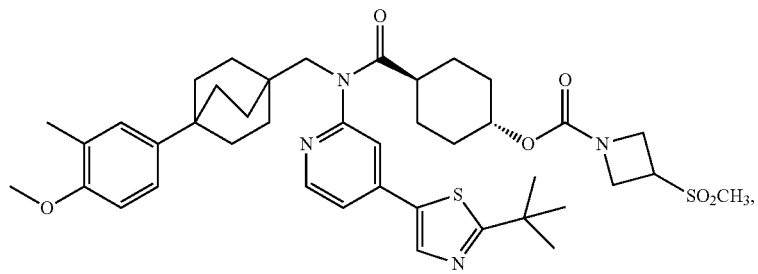
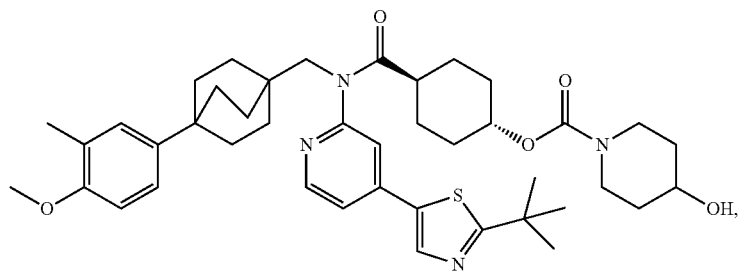
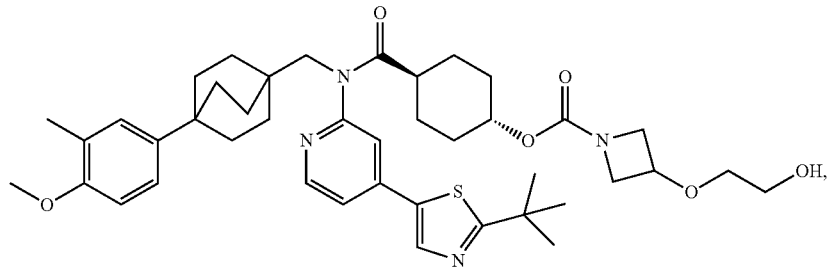
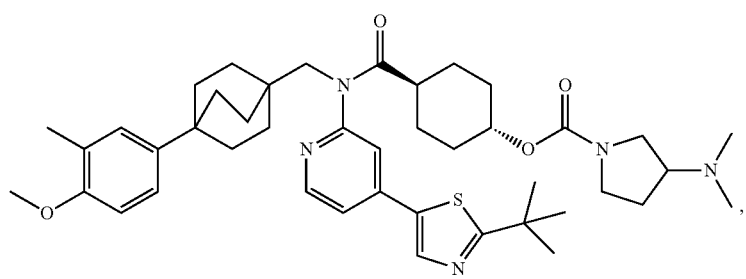

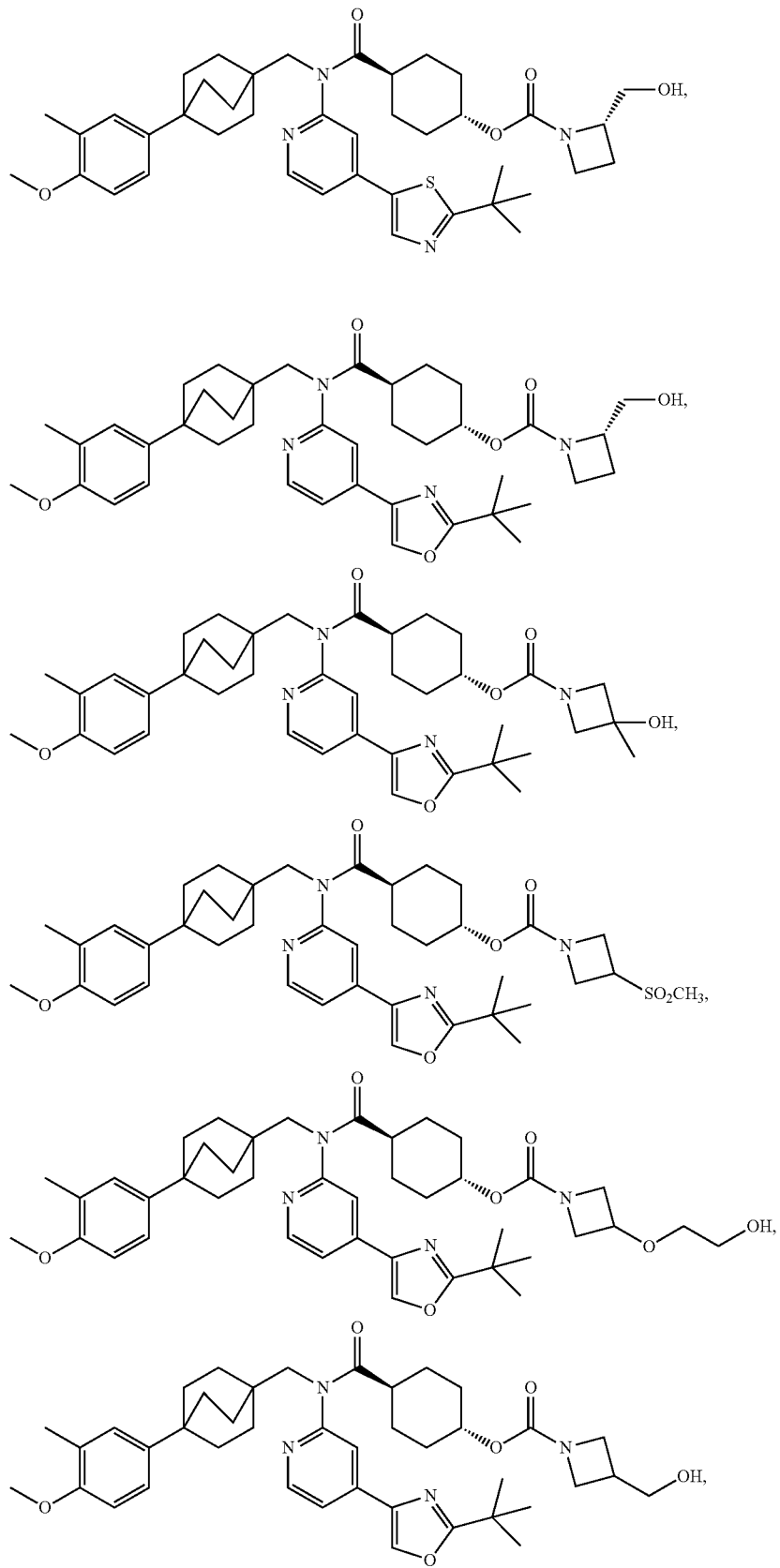

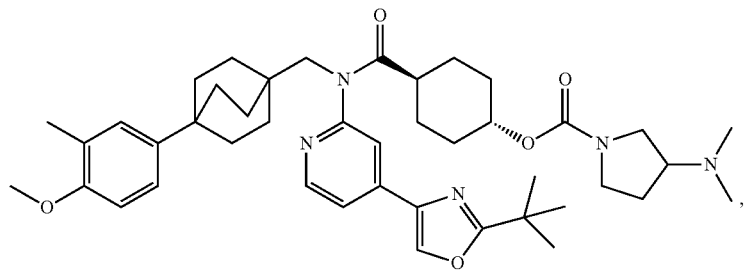
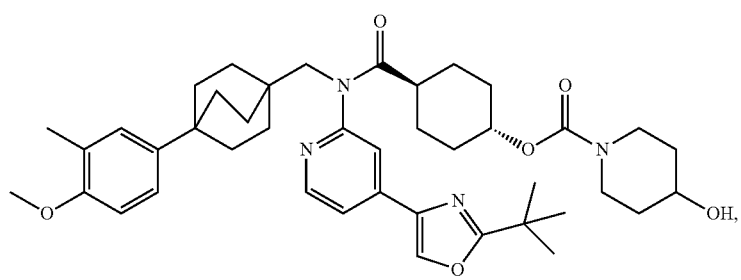
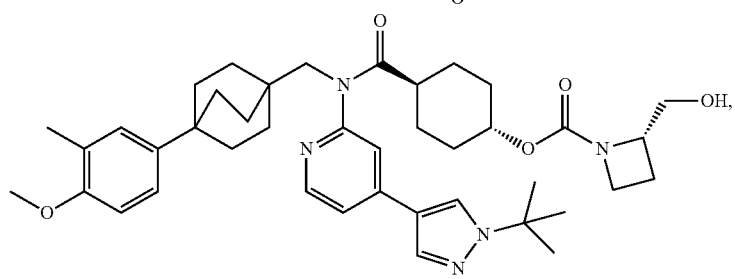
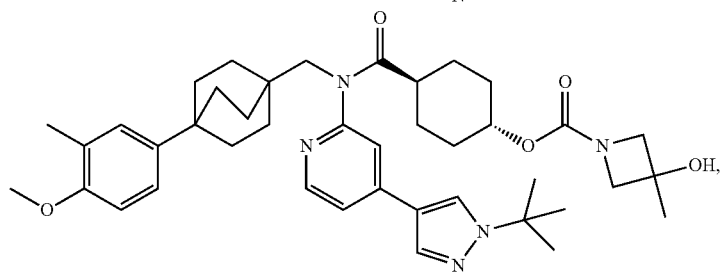
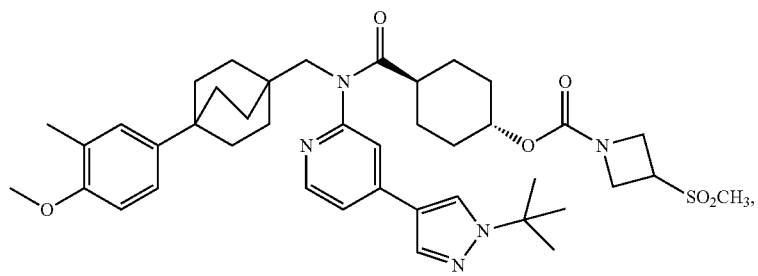
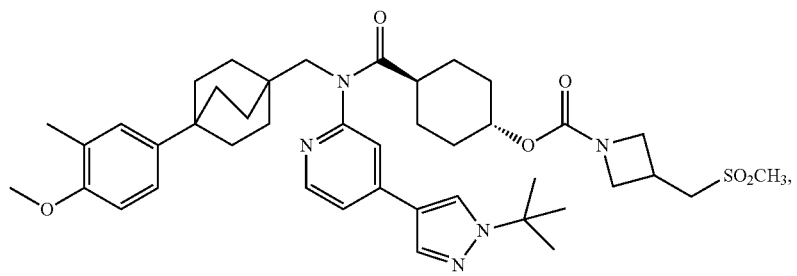

-continued
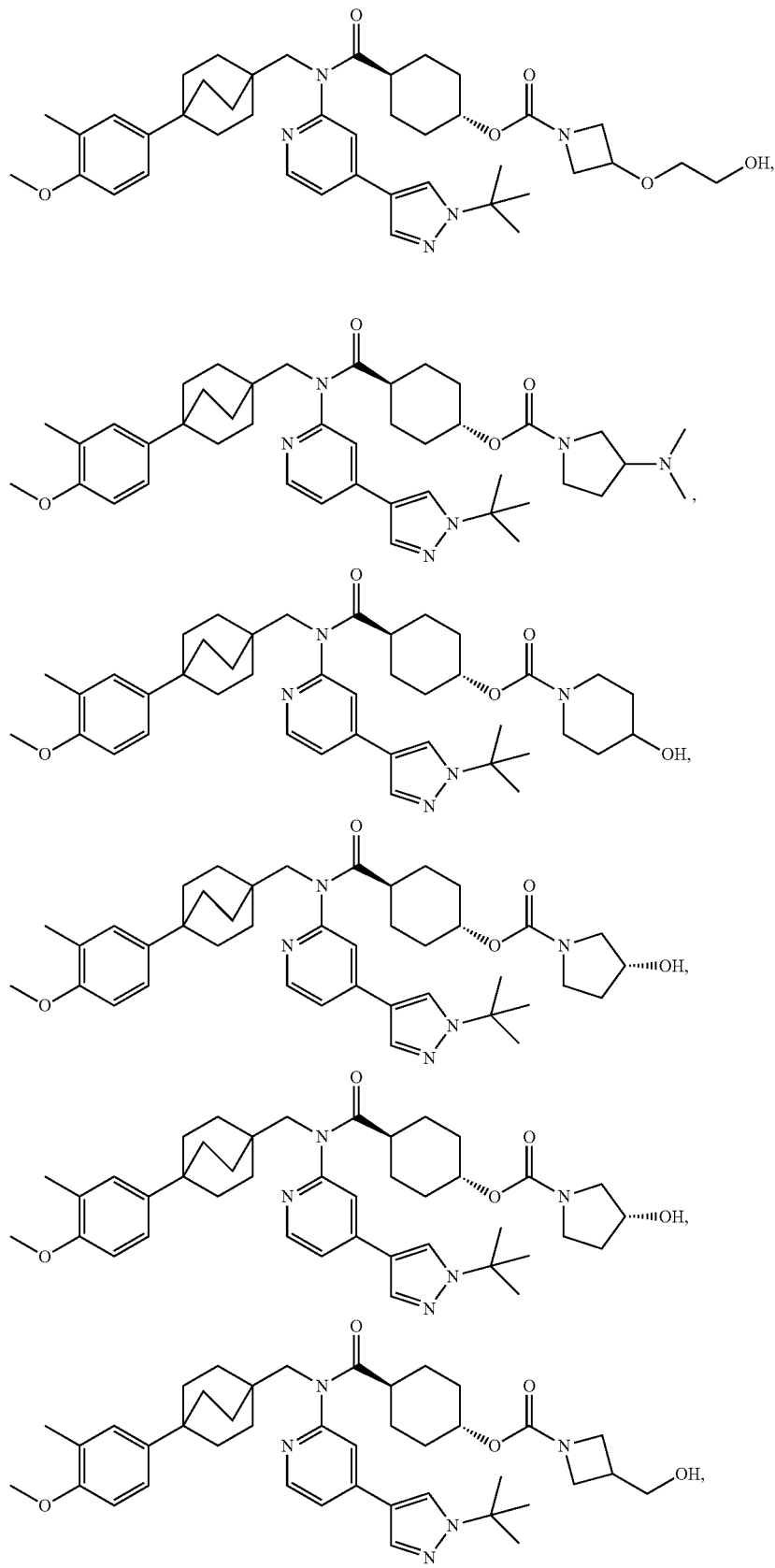

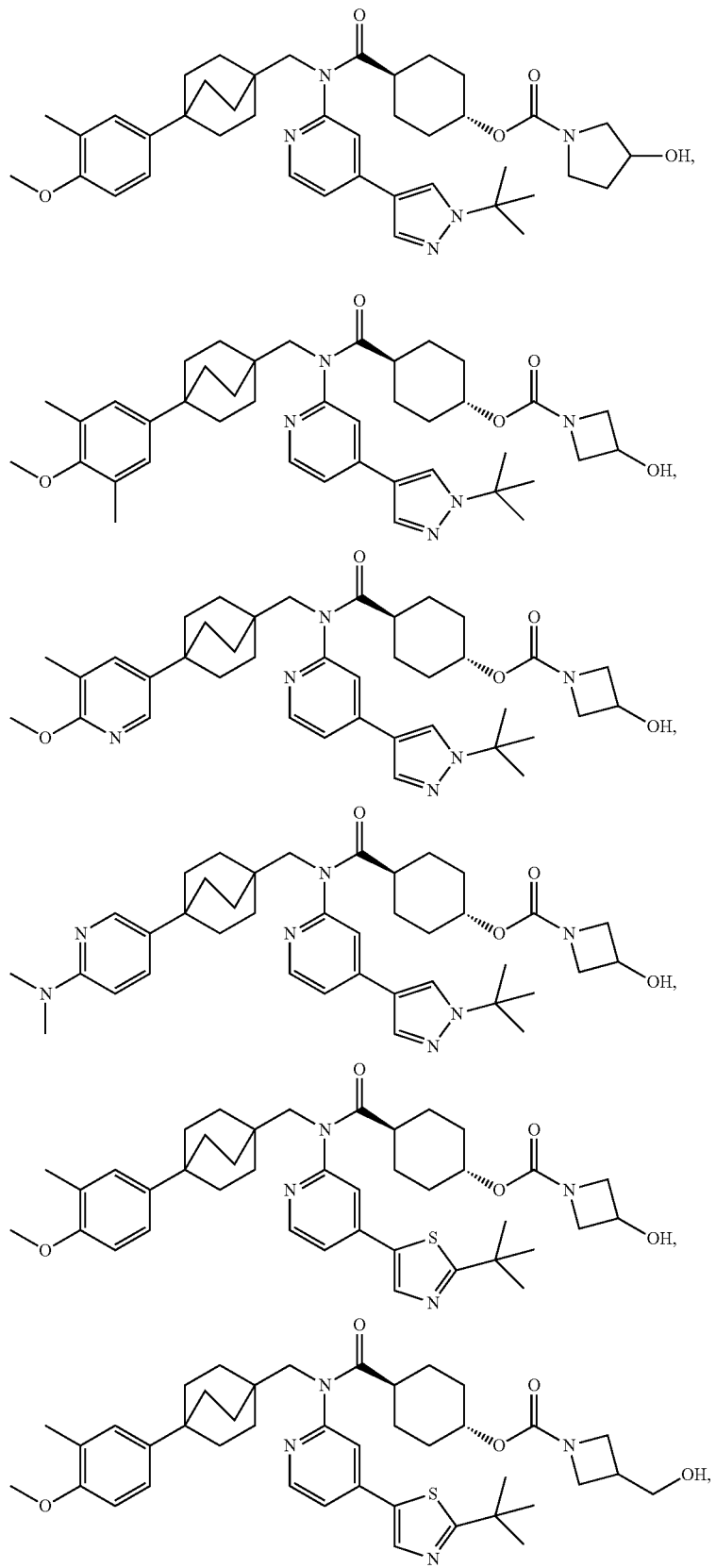

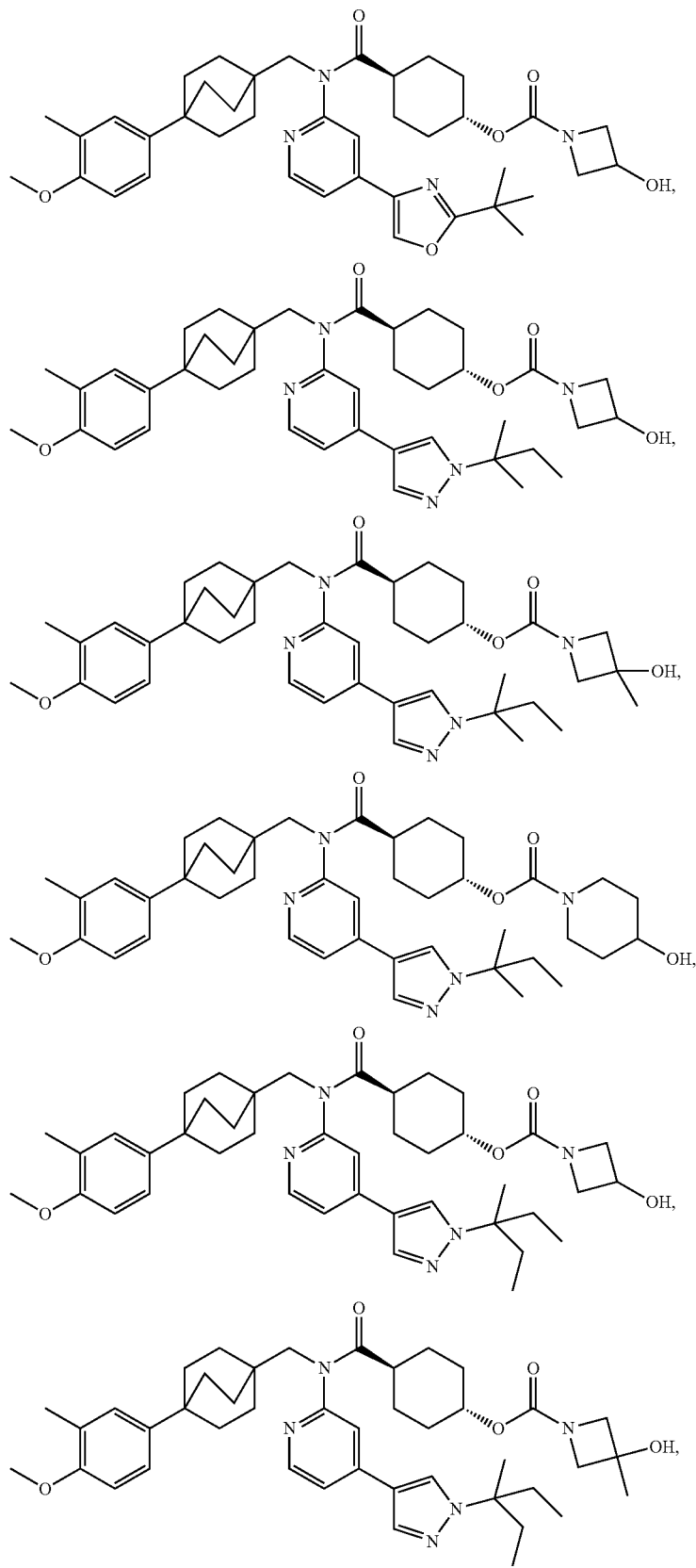

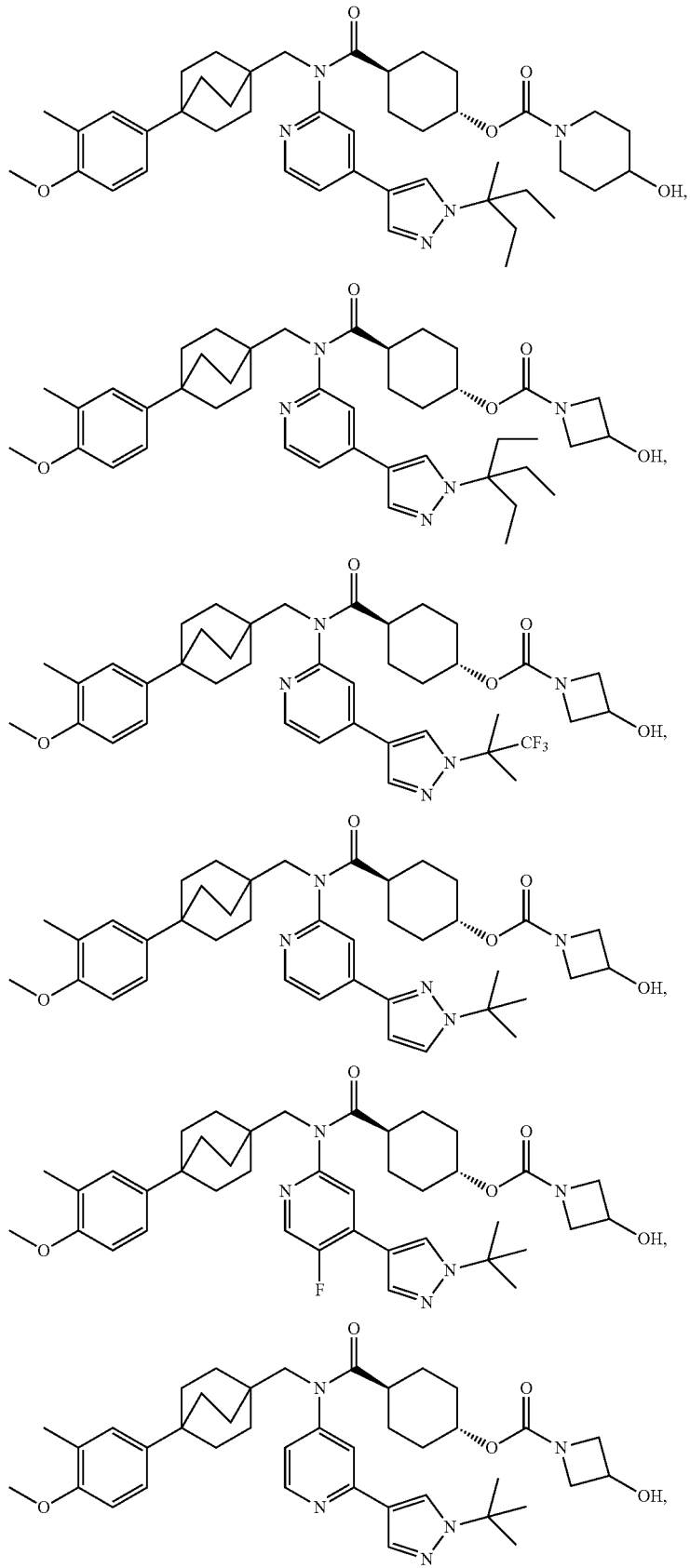

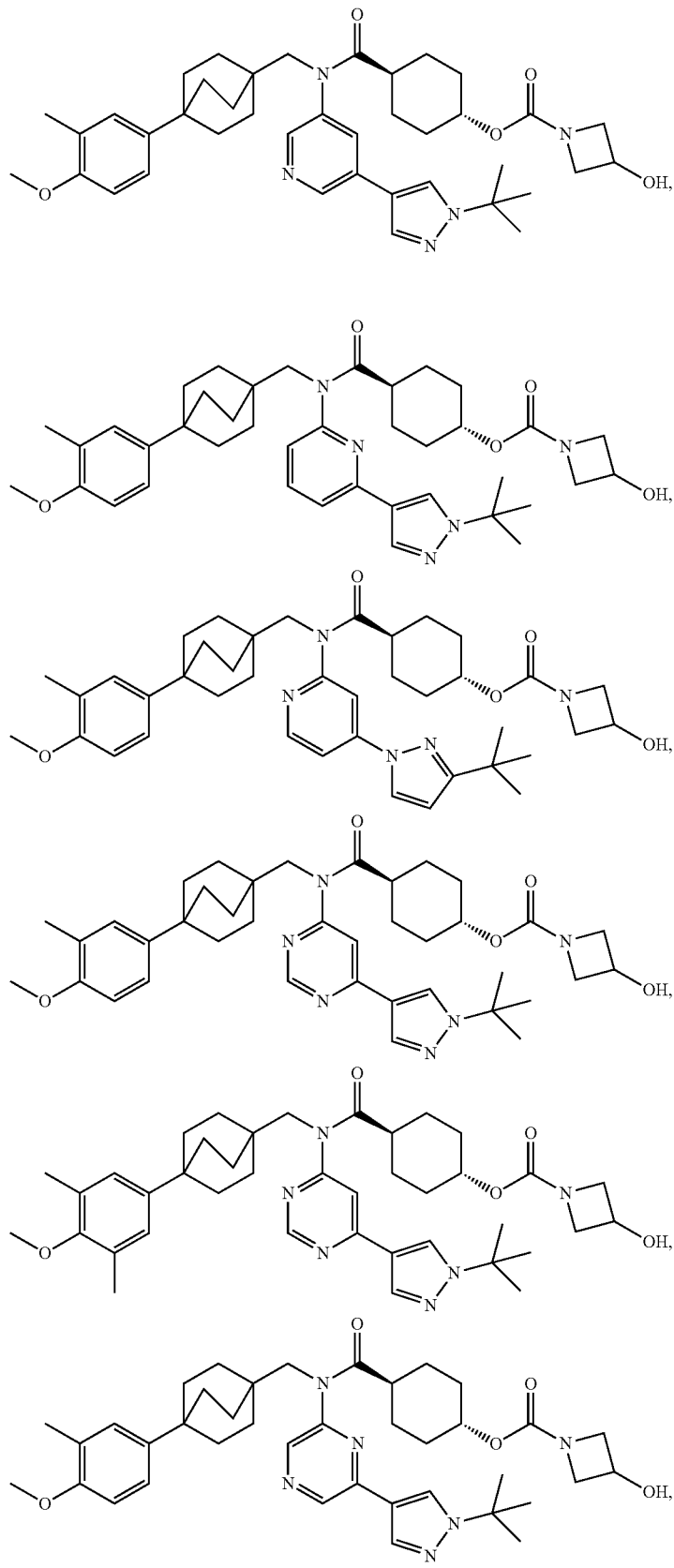

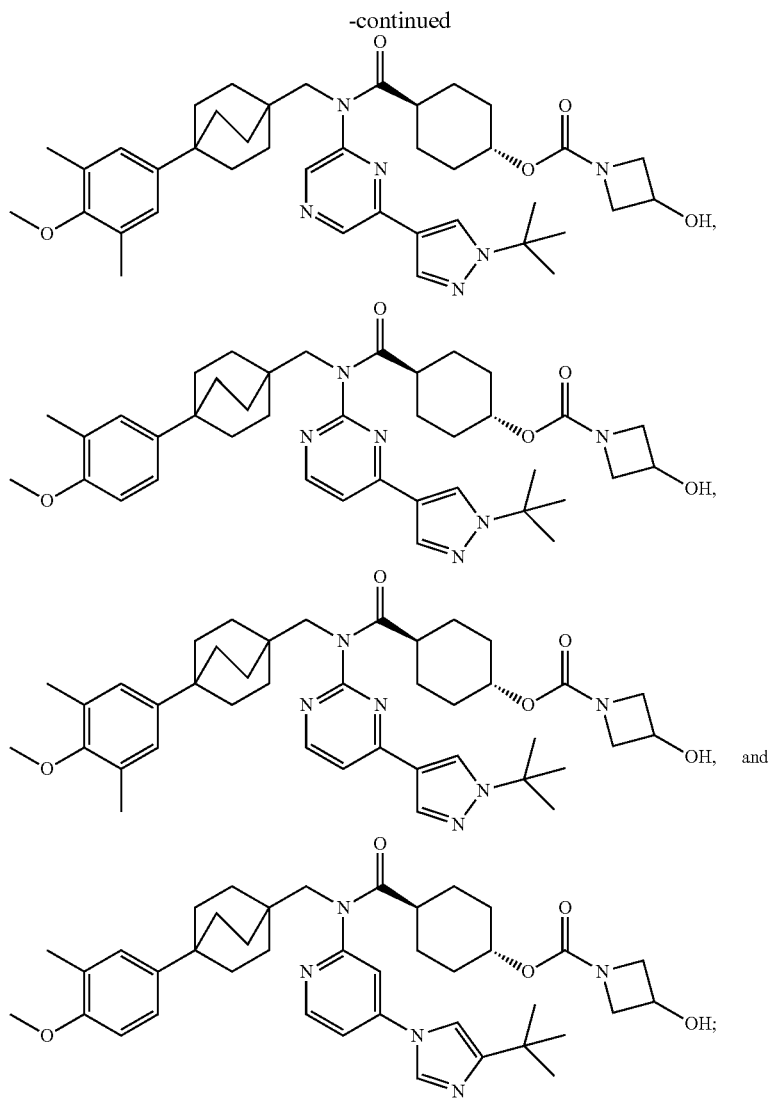

or a pharmaceutically acceptable salt thereof.

14. A method of treating primary biliary cirrhosis (PBC), primary sclerosing cholangitis (PSC), nonalcoholic steatohepatitis (NASH), nonalcoholic fatty liver disease (NAFLD), intrahepatic cholestasis, Ala ille syndrome, or biliary atresia in a mammal, comprising administering to the mammal a compound of Formula (I'), or a pharmaceutically acceptable salt thereof:

Formula (I')

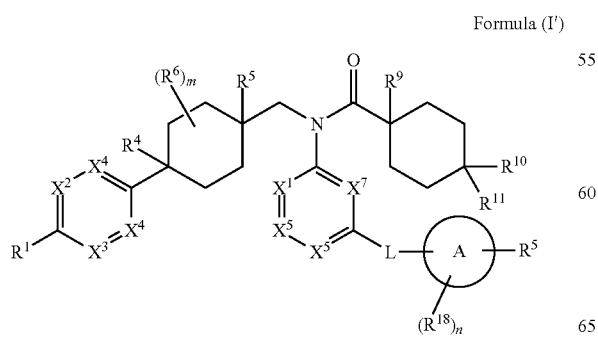

wherein:
ring A is

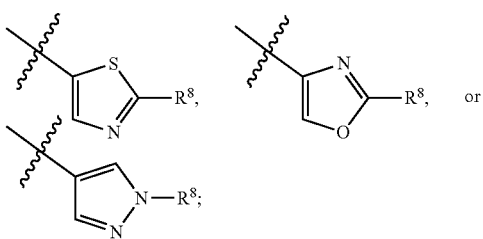

$X^1$ is N;
$X^5$, $X^6$, and $X^7$ are each $CR^7$;
$R^1$ is selected from H, halogen, —CN, —OH, —N($R^{17}$)$_2$, —N$R^{17}$S(=O)$_2$($C_1$-$C_4$alkyl), —S(=O)$_2$N($R^{17}$)$_2$, —OC(=O)($C_1$-$C_4$alkyl), —CO$_2$H, —CO$_2$($C_1$-$C_4$alkyl), —C(=O)N($R^{17}$)$_2$, —N$R^{17}$C(=O)($C_1$-$C_4$alkyl), —N$R^{17}$C(=O)O($C_1$-$C_4$alkyl), —OC(=O)N($R^{17}$)$_2$, —N$R^{15}$C(=O)N($R^{17}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, C₁-C₄alkoxy, C₁-C₄fluoroalkyl, C₁-C₄fluoroalkoxy, C₁-C₄heteroalkyl, C₃-C₆cycloalkyl, and monocyclic C₂-C₅heterocycloalkyl;

X² is CR²;

R² is H, halogen, —CN, —OH, —N(R¹⁷)₂, —NR¹⁷S(=O)₂(C₁-C₄alkyl), —S(=O)₂N(R¹⁷)₂, —OC(=O)(C₁-C₄alkyl), —CO₂H, —CO₂(C₁-C₄alkyl), —C(=O)N(R¹⁷)₂, —NR¹⁷C(=O)(C₁-C₄alkyl), —NR¹⁷C(=O)O(C₁-C₄alkyl), —OC(=O)N(R¹⁷)₂, —NR¹⁷C(=O)N(R¹⁷)₂, —SH, —S(C₁-C₄alkyl), —S(=O)(C₁-C₄alkyl), —S(=O)₂(C₁-C₄alkyl), C₁-C₄alkyl, C₂-C₄alkenyl, C₂-C₄alkynyl, C₁-C₄alkoxy, C₁-C₄fluoroalkyl, C₁-C₄fluoroalkoxy, C₁-C₄heteroalkyl, C₃-C₆cycloalkyl, or monocyclic C₂-C₅heterocycloalkyl;

X³ is CR³;

R³ is H, halogen, —CN, —OH, —N(R¹⁷)₂, —NR¹⁷S(=O)₂(C₁-C₄alkyl), —OC(=O)(C₁-C₄alkyl), —CO₂H, —CO₂(C₁-C₄alkyl), —C(=O)N(R¹⁷)₂, —NR¹⁷C(=O)(C₁-C₄alkyl), C₁-C₄alkyl, C₂-C₄alkenyl, C₂-C₄alkynyl, C₁-C₄alkoxy, C₁-C₄fluoroalkyl, C₁-C₄fluoroalkoxy, or C₁-C₄heteroalkyl;

each X⁴ is independently CH or CF;

R⁴ and R⁵ are taken together to form a bridge that is —CH₂— or —CH₂CH₂—;

each R⁶ is independently H, F, —OH, or —CH₃;

L is absent;

each R⁷ is independently selected from H, halogen, —CN, —OH, C₁-C₄alkyl, C₂-C₄alkenyl, C₂-C₄alkynyl, C₁-C₄alkoxy, C₁-C₄fluoroalkyl, C₁-C₄fluoroalkoxy, C₃-C₆cycloalkyl, and C₁-C₄heteroalkyl;

R⁸ is C₄-C₈alkyl or C₄-C₈haloalkyl;

R⁹ is H, F, or —CH₃;

R¹⁰ is —OC(=O)N(R¹²)(R¹³);

R¹¹ is H, F, or —CH₃;

R¹² and R¹³ are taken together to form a 4-, 5-, or 6-membered heterocycloalkyl ring optionally containing an additional heteroatom selected from O, S, and N and optionally substituted with 1, 2, or 3 groups selected from —OH, —N(C₁-C₄alkyl)₂, C₁-C₆alkyl, C₁-C₆alkoxy, —S(C₁-C₄alkyl), —S(=O)(C₁-C₄alkyl), —S(=O)₂(C₁-C₄alkyl), —C₁-C₄alkyl-S(=O)₂(C₁-C₄alkyl), —C₁-C₆alkyl-OR¹⁷, and —O—C₁-C₆alkyl-OR¹⁷;

each R¹⁷ is independently H or C₁-C₆alkyl;

each R¹⁸ is independently halogen, —CN, —OH, —N(R¹⁷)₂, —NR¹⁷S(=O)₂(C₁-C₄alkyl), —S(C₁-C₄alkyl), —S(=O)(C₁-C₄alkyl), —S(=O)₂(C₁-C₄alkyl), —S(=O)₂N(R¹⁷)₂, —C(=O)(C₁-C₄alkyl), —OC(=O)(C₁-C₄alkyl), —CO₂H, —CO₂(C₁-C₄alkyl), —NR¹⁷C(=O)(C₁-C₄alkyl), —C(=O)N(R¹⁷)₂, —NR¹⁷C(=O)O(C₁-C₄alkyl), —OC(=O)N(R¹⁷)₂, C₁-C₄alkyl, C₂-C₄alkenyl, C₂-C₄alkynyl, C₁-C₄alkoxy, C₁-C₄fluoroalkyl, C₁-C₄fluoroalkoxy, C₁-C₄heteroalkyl, C₃-C₆cycloalkyl, monocyclic C₂-C₆heterocycloalkyl, phenyl, or monocyclic heteroaryl;

m is 0, 1, or 2; and n is 0, 1, or 2.

15. The method of claim 1, wherein the gastrointestinal disease or condition is necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, graft versus host disease, or any combination thereof.

16. The method of claim 15, wherein the gastrointestinal disease or condition is inflammatory bowel disease or irritable bowel syndrome.

17. The method of claim 13, wherein the gastrointestinal disease or condition is necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, graft versus host disease, or any combination thereof.

18. The method of claim 17, wherein the gastrointestinal disease or condition is inflammatory bowel disease or irritable bowel syndrome.

19. The method of claim 14, wherein the compound of Formula (I') is selected from:

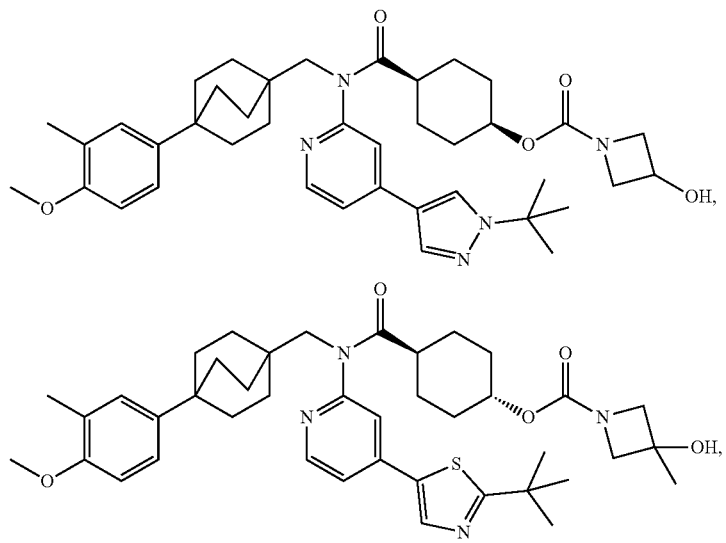

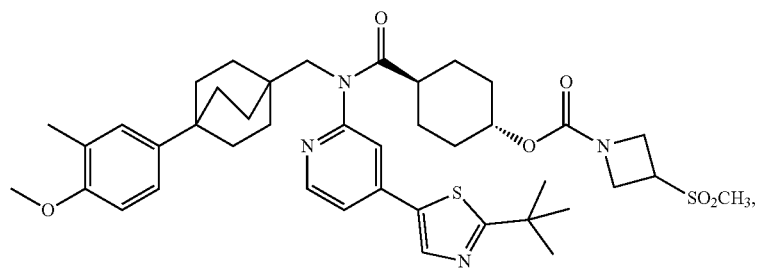
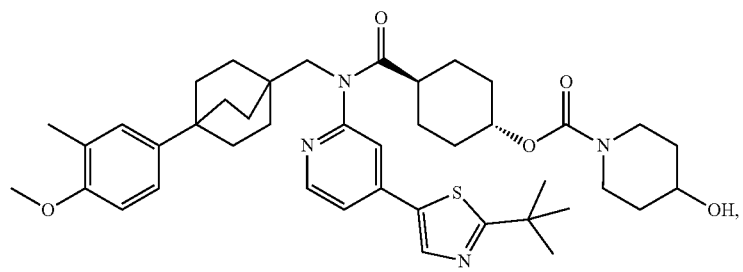
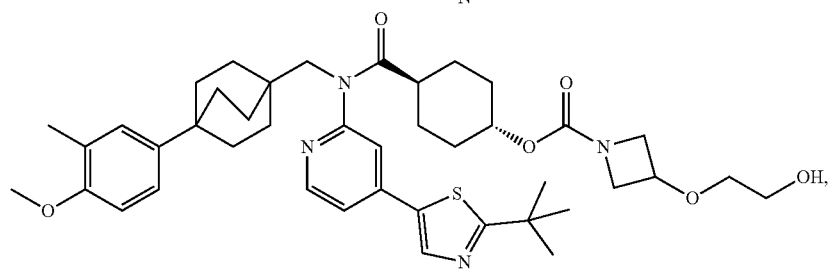
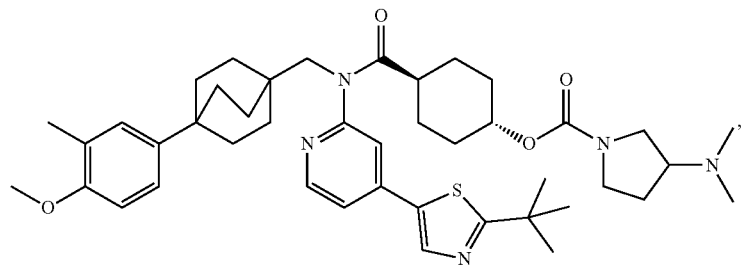
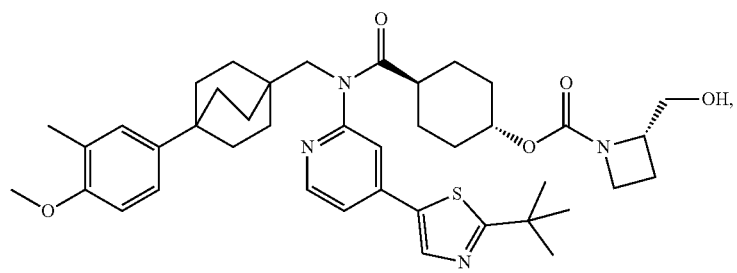
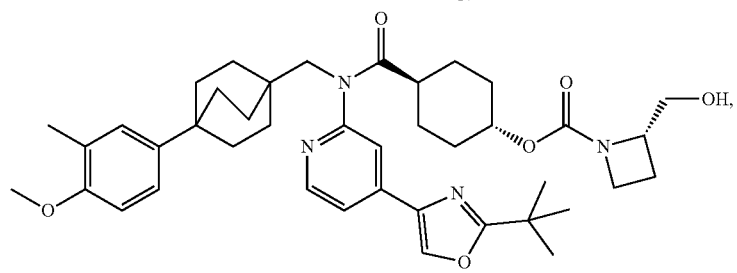

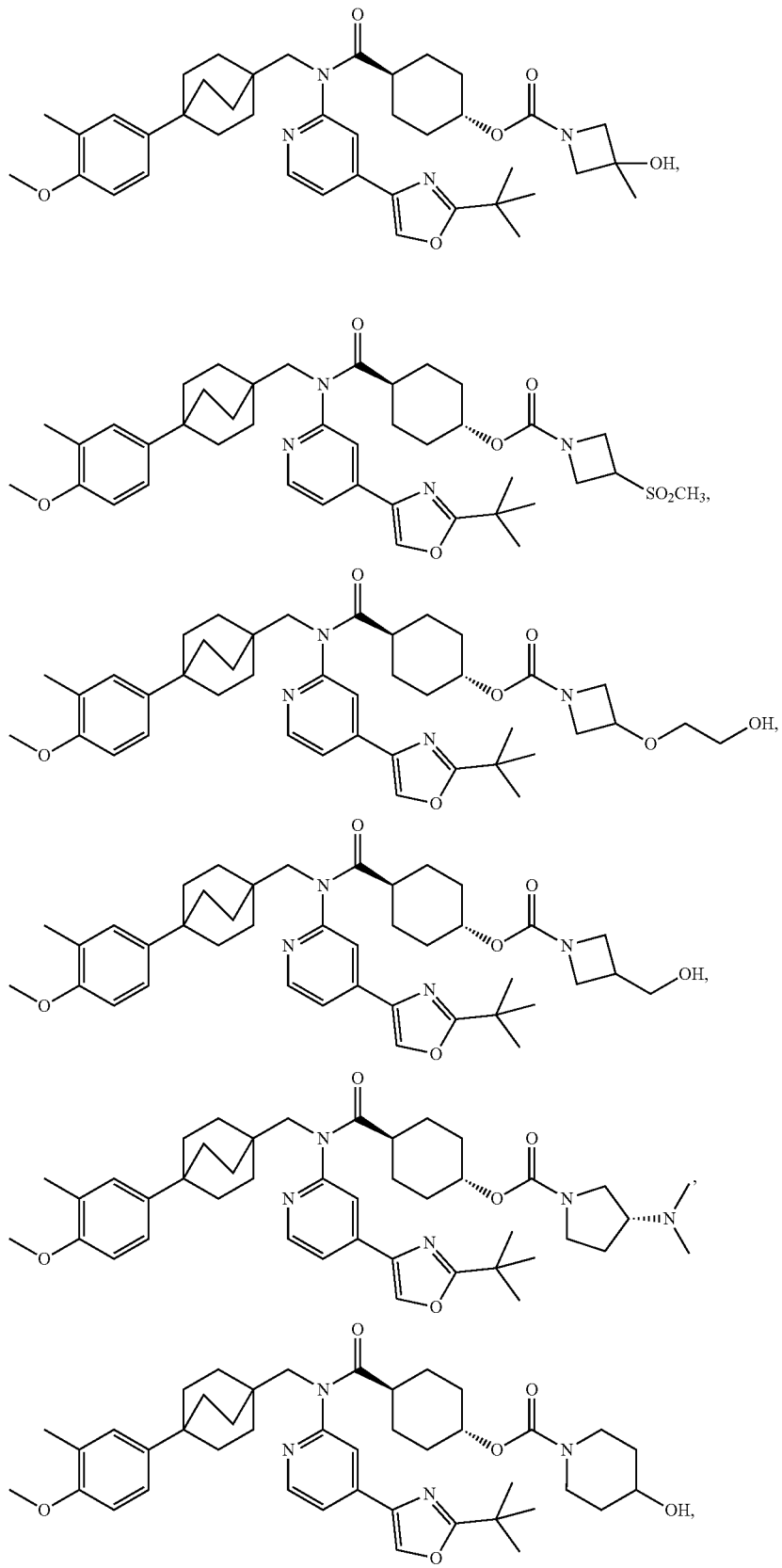

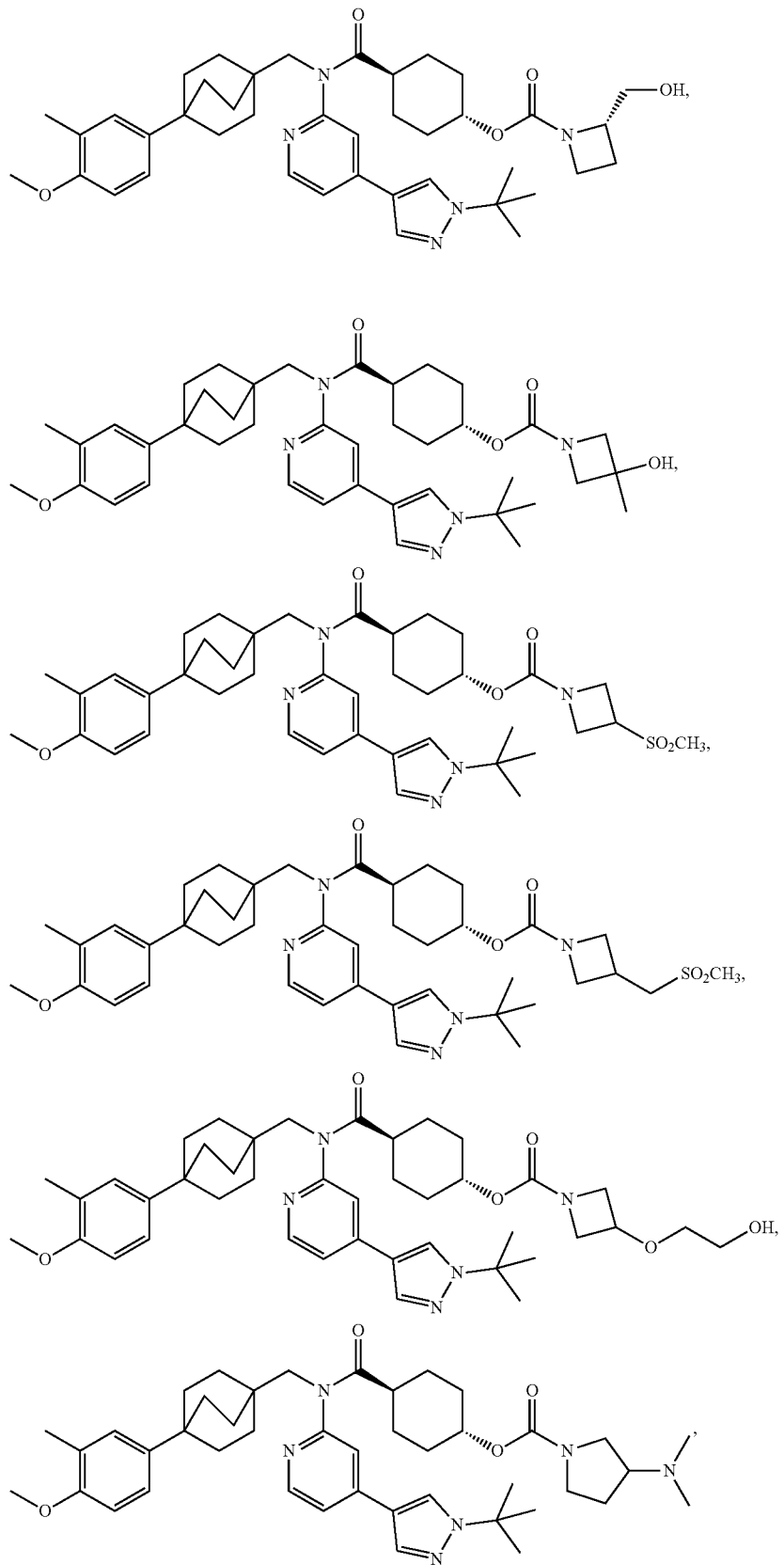

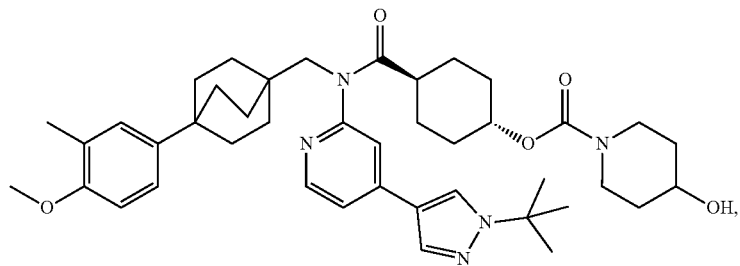
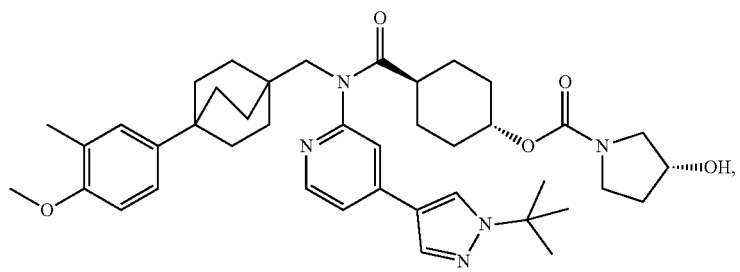
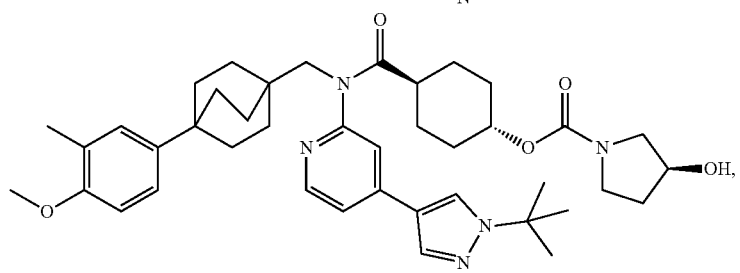
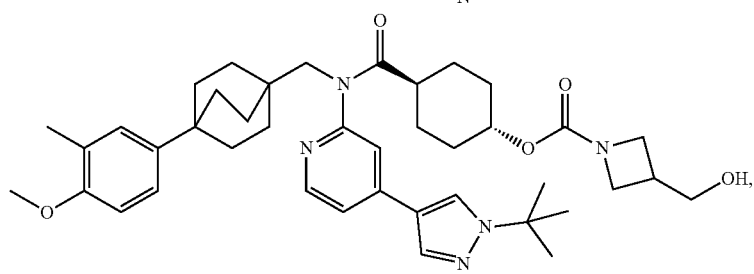
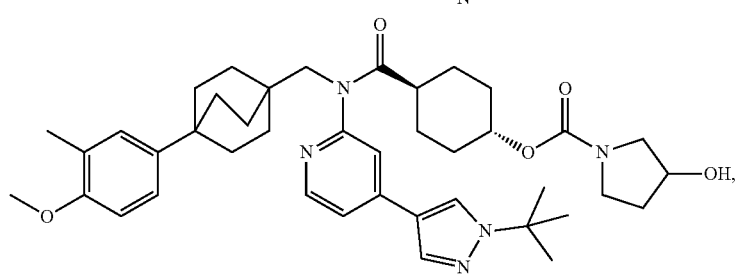
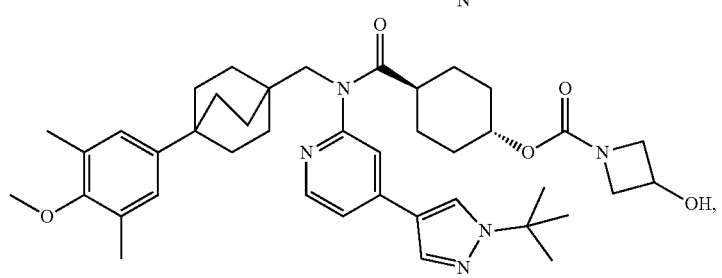

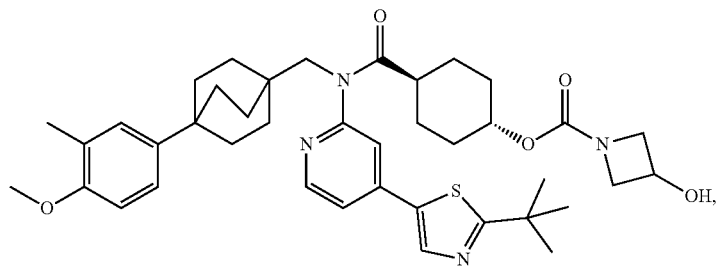
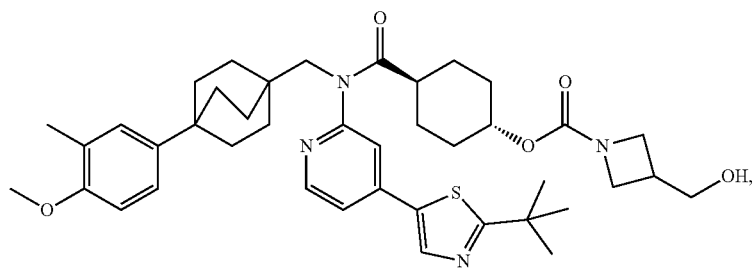
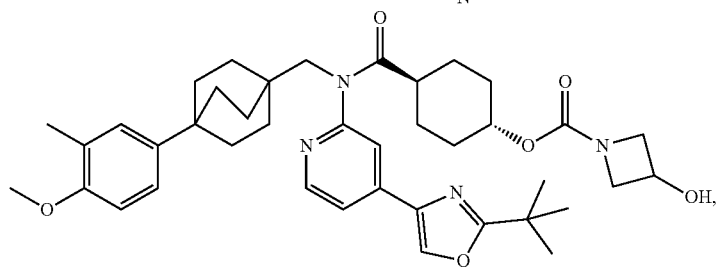
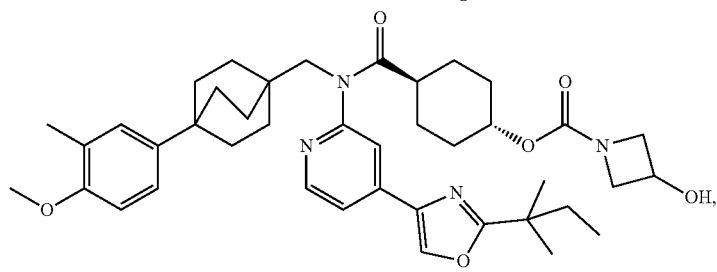
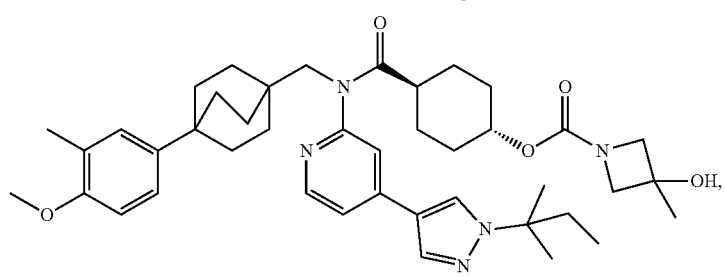
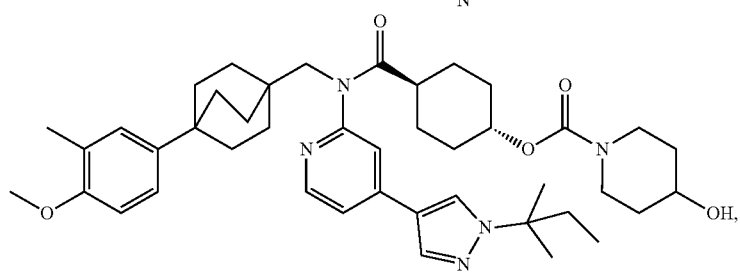

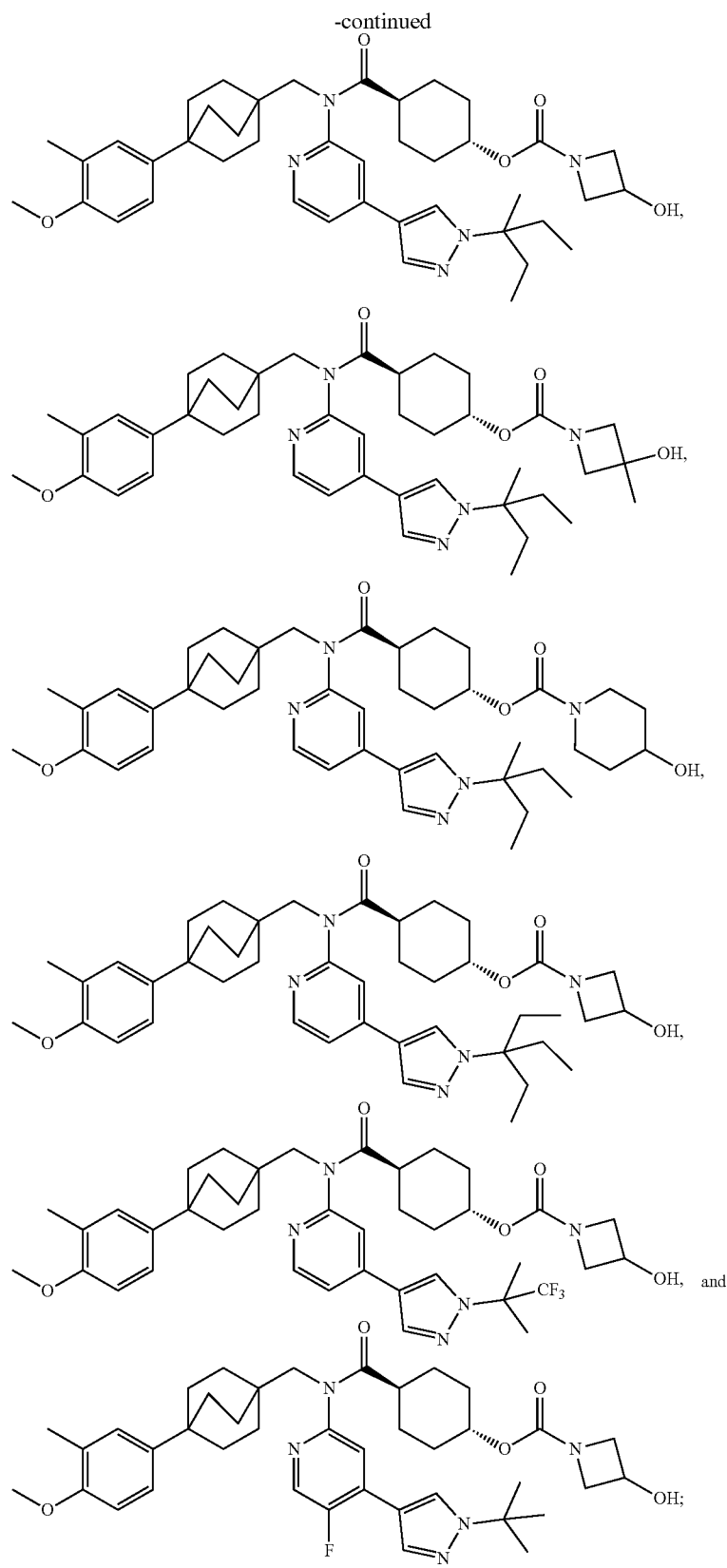
or a pharmaceutically acceptable salt thereof.
* * * * *

UNITED STATES PATENT AND TRADEMARK OFFICE
CERTIFICATE OF CORRECTION

PATENT NO. : 11,773,094 B2
APPLICATION NO. : 17/349757
DATED : October 3, 2023
INVENTOR(S) : Nicholas D. Smith et al.

Page 1 of 1

It is certified that error appears in the above-identified patent and that said Letters Patent is hereby corrected as shown below:

In the Claims

Claim 14, Column 229, Lines 55-65, delete " 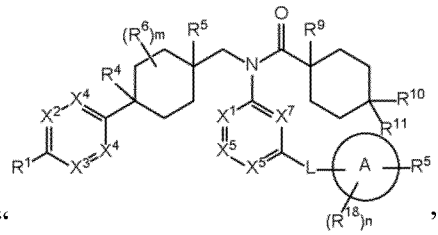 " and replace with

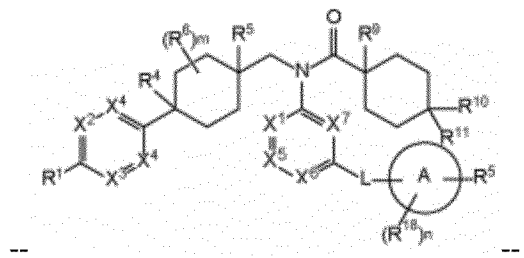 --

Claim 19, Column 232, Line 1, delete " 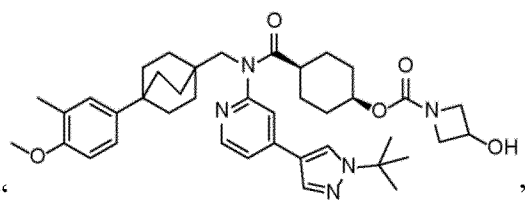 " and replace with -

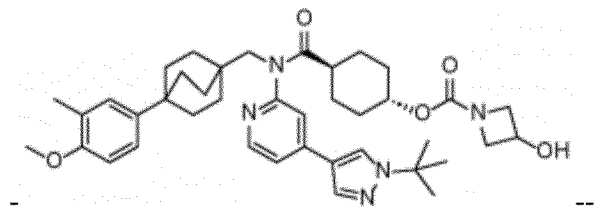 --

Signed and Sealed this
Tenth Day of December, 2024

Katherine Kelly Vidal
*Director of the United States Patent and Trademark Office*